US009127287B2

(12) United States Patent
Hall et al.

(10) Patent No.: US 9,127,287 B2
(45) Date of Patent: Sep. 8, 2015

(54) COMPOSITIONS AND METHODS FOR PRODUCING FERMENTABLE CARBOHYDRATES

(75) Inventors: Richard J. Hall, Durham, NC (US); Simon Warner, Chapel Hill, NC (US); Rogerio Prata, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 518 days.

(21) Appl. No.: 12/997,581

(22) PCT Filed: Jun. 11, 2009

(86) PCT No.: PCT/US2009/046968

§ 371 (c)(1), (2), (4) Date: Mar. 4, 2011

(87) PCT Pub. No.: WO2009/152285

PCT Pub. Date: Dec. 17, 2009

(65) Prior Publication Data

US 2011/0201059 A1 Aug. 18, 2011

Related U.S. Application Data

(60) Provisional application No. 61/060,789, filed on Jun. 11, 2008.

(51) Int. Cl.
*C12N 15/82* (2006.01)
*A01H 5/00* (2006.01)

(52) U.S. Cl.
CPC ........ *C12N 15/8245* (2013.01); *C12N 15/8246* (2013.01)

(58) Field of Classification Search
None
See application file for complete search history.

(56) References Cited

U.S. PATENT DOCUMENTS

| | | | | |
|---|---|---|---|---|
| 4,902,622 | A | 2/1990 | Nakai et al. | |
| 5,750,875 | A | 5/1998 | Stalker et al. | |
| 5,786,140 | A | 7/1998 | Mattes et al. | |
| 6,127,603 | A | 10/2000 | Nicholas | |
| 6,235,971 | B1 | 5/2001 | Barry et al. | |
| 6,664,444 | B1 | 12/2003 | Koops et al. | |
| 7,208,307 | B2 | 4/2007 | Mattes et al. | |
| 7,235,712 | B1 | 6/2007 | Zhang et al. | |
| 7,655,836 | B2 * | 2/2010 | Birch et al. | 800/284 |
| 2007/0077569 | A1 | 4/2007 | Birch et al. | |
| 2007/0240240 | A1 | 10/2007 | Birch et al. | |

FOREIGN PATENT DOCUMENTS

| | | | |
|---|---|---|---|
| JP | 63-129990 | A | 6/1988 |
| WO | WO 89/12386 | A1 | 12/1989 |
| WO | WO 91/19808 | A1 | 12/1991 |
| WO | WO 95/13389 | A1 | 5/1995 |
| WO | WO 01/59131 | A2 | 8/2001 |
| WO | WO 02/18603 | A1 | 3/2002 |
| WO | WO 02/27003 | A1 | 4/2002 |
| WO | WO 03/018766 | A2 | 3/2003 |
| WO | WO 2004/099403 | A1 | 11/2004 |
| WO | WO 2005/096804 | A2 | 10/2005 |

OTHER PUBLICATIONS

Börnke et al, 2001, J. Bacteriol., 183:2425-2430.*

Birch et al, 2007, Plant Biotech., 5:109-117.*

Bornke, F., et al., "Cloning and Characterization of the Gene Cluster for Palatinose Metabolism from Phytopathogenic Bacterium *Erwinia rhapontici*," *J. Bacteriology*, Apr. 2001, pp. 2425-2430, vol. 183, No. 8.

Cheetham, P.S.J., "The Extraction and Mechanism of a Novel Isomaltulose-synthesizing Enzyme from *Erwiniav rhapontici*," *Biochem. J.* (1984), pp. 213-220, vol. 220.

Galvez-Mariscal, A., and A. Lopez-Munguia, "Production and Characterization of a Dextranase from an Isolated *Paecilomyces lilacinus* Strain," *Appl. Microbiol Biotechnol*, 1992, pp. 327-331, vol. 36.

Jimenez, E.F., "The Dextranase Along Sugar-making Industry,"*Biotecnologia Aplicada*, 2005, pp. 20-27, vol. 22.

Loreti, E., et al., "Glucose and Disaccharide-Sending Mechanisms Modulate the Expression of *a-amylase* in Barley Embryos," *Plant Physiology*, Jul. 2000, pp. 938-948.

Ohta, K. et. Al., "Production of High Concentrations of Ethanol from Inulin by Simultaneous Saccarification and Fermentation Using *Aspergillus niger* and *Saccharomyces cerevisiae*," *Applied and Environmental Microbiology*, Mar. 1993, pp. 729-733, vol. 59, No. 3.

Salvucci, M.E., Distinct Sucrose Isomerases Catalyze Trehalulose Synthesis in Whiteflies, *Besmisia argentifolii*, and *Erwinia rhapontici, Comperative Biochemistry and Physiology*, 2003, pp. 385-395, Part B, No. 135.

Watanabe, K., et al., "Proline Residues Responsible for Thermostability Occur with High Frequency in the Loop Regions of an Extremely Thermostable Oligo-1,6-glucosidase from *Bacillus thermoglucosidasius* KP1006," *J. Biolog. Chem.*, Dec. 25, 1991, pp. 24287-24294, vol. 266, No. 36.

(Continued)

*Primary Examiner* — Ashwin Mehta
*Assistant Examiner* — Jason Deveau Rosen
(74) *Attorney, Agent, or Firm* — Joshua L. Price

(57) ABSTRACT

Provided herein are methods for producing fermentable sugar obtained from a plant tissue. The methods include providing transgenic plant material comprising one or more locked carbohydrates and contacting plant material with an enzyme capable of converting the locked carbohydrate into a fermentable sugar. The methods are useful for providing sugar or sugar pre-cursors for several industrial purposes including ethanol production. The invention also encompasses plants and plant parts that produce a lock enzyme to yield a locked carbohydrate, with the consequence of accumulating the locked carbohydrate in the plant. The invention also encompasses providing a key enzyme able to convert locked carbohydrates to fermentable sugars. Key enzymes can be provided by transgenic plants or plant parts, transgenic microbes, transgenic yeast, microbes or yeast.

22 Claims, No Drawings

(56) References Cited

OTHER PUBLICATIONS

Wu, L., and R.G. Birch, "Doubled Sugar Content in Sugarcane Plants Modified to Produce a Sucrose Isomer," *Plant Biotechnology Journal* , 2007, pp. 109-117. vol. 5.

Zhang, D., et al., "Isomaltulose Synthase from *Klebsiella* sp. Strain LX3: Gene Cloning and Characterization and Engineering of Thermostability," *Applied and Environmental Microbiology*, Jun. 2002, pp. 2676-2682, vol. 68, No. 6.

Form PCT/ISA/220 Transmittal of International Search Report dated Sep. 17, 2009, for parent PCT Application No. PCT/US2009/046968.

* cited by examiner

SEQUENCE LISTING

```
<160> NUMBER OF SEQ ID NOS: 58

<210> SEQ ID NO 1
<211> LENGTH: 562
<212> TYPE: PRT
<213> ORGANISM: (Geo)Bacillus thermoglucosidasius KP1006
<220> FEATURE:
<221> NAME/KEY: enzyme
<222> LOCATION: (1)..(562)
<223> OTHER INFORMATION: alpha-1,6-glucosidase

<400> SEQUENCE: 1

Met Glu Arg Val Trp Trp Lys Glu Ala Val Val Tyr Gln Ile Tyr Pro
1               5                   10                  15

Arg Ser Phe Tyr Asp Ser Asn Gly Asp Gly Ile Gly Asp Ile Arg Gly
            20                  25                  30

Ile Ile Ala Lys Leu Asp Tyr Leu Lys Glu Leu Gly Val Asp Val Val
        35                  40                  45

Trp Leu Ser Pro Val Tyr Lys Ser Pro Asn Asp Asp Asn Gly Tyr Asp
    50                  55                  60

Ile Ser Asp Tyr Arg Asp Ile Met Asp Glu Phe Gly Thr Met Ala Asp
65                  70                  75                  80

Trp Lys Thr Met Leu Glu Glu Met His Lys Arg Gly Ile Lys Leu Val
                85                  90                  95

Met Asp Leu Val Val Asn His Thr Ser Asp Glu His Pro Trp Phe Ile
            100                 105                 110

Glu Ser Arg Lys Ser Lys Asp Asn Pro Tyr Arg Asp Tyr Tyr Ile Trp
        115                 120                 125

Arg Pro Gly Lys Asn Gly Lys Glu Pro Asn Asn Trp Glu Ser Val Phe
    130                 135                 140

Ser Gly Ser Ala Trp Glu Tyr Asp Glu Met Thr Gly Glu Tyr Tyr Leu
145                 150                 155                 160

His Leu Phe Ser Lys Lys Gln Pro Asp Leu Asn Trp Glu Asn Pro Lys
                165                 170                 175

Val Arg Arg Glu Val Tyr Glu Met Met Lys Phe Trp Leu Asp Lys Gly
            180                 185                 190

Val Asp Gly Phe Arg Met Asp Val Ile Asn Met Ile Ser Lys Val Pro
        195                 200                 205
```

```
Glu Leu Pro Asp Gly Glu Pro Gln Ser Gly Lys Lys Tyr Ala Ser Gly
    210                 215                 220

Ser Arg Tyr Tyr Met Asn Gly Pro Arg Val His Glu Phe Leu Gln Glu
225                 230                 235                 240

Met Asn Arg Glu Val Leu Ser Lys Tyr Asp Ile Met Thr Val Gly Glu
                245                 250                 255

Thr Pro Gly Val Thr Pro Lys Glu Gly Ile Leu Tyr Thr Asp Pro Ser
            260                 265                 270

Arg Arg Glu Leu Asn Met Val Phe Gln Phe Glu His Met Asp Leu Asp
        275                 280                 285

Ser Gly Pro Gly Gly Lys Trp Asp Ile Arg Pro Trp Ser Leu Ala Asp
    290                 295                 300

Leu Lys Lys Thr Met Thr Lys Trp Gln Lys Glu Leu Glu Gly Lys Gly
305                 310                 315                 320

Trp Asn Ser Leu Tyr Leu Asn Asn His Asp Gln Pro Arg Ala Val Ser
                325                 330                 335

Arg Phe Gly Asp Asp Gly Lys Tyr Arg Val Glu Ser Ala Lys Met Leu
            340                 345                 350

Ala Thr Phe Leu His Met Met Gln Gly Thr Pro Tyr Ile Tyr Gln Gly
        355                 360                 365

Glu Glu Ile Gly Met Thr Asn Val Arg Phe Pro Ser Ile Glu Asp Tyr
    370                 375                 380

Arg Asp Ile Glu Thr Leu Asn Met Tyr Lys Glu Arg Val Glu Glu Tyr
385                 390                 395                 400

Gly Glu Asp Pro Gln Glu Val Met Glu Lys Ile Tyr Tyr Lys Gly Arg
                405                 410                 415

Asp Asn Ala Arg Thr Pro Met Gln Trp Asp Asp Ser Glu Asn Ala Gly
            420                 425                 430

Phe Thr Ala Gly Thr Pro Trp Ile Pro Val Asn Pro Asn Tyr Lys Glu
        435                 440                 445

Ile Asn Val Lys Ala Ala Leu Glu Asp Pro Asn Ser Val Phe His Tyr
    450                 455                 460

Tyr Lys Lys Leu Ile Gln Leu Arg Lys Gln His Asp Ile Ile Val Tyr
465                 470                 475                 480

Gly Thr Tyr Asp Leu Ile Leu Glu Asp Asp Pro Tyr Ile Tyr Arg Tyr
                485                 490                 495

Thr Arg Thr Leu Gly Asn Glu Gln Leu Ile Val Ile Thr Asn Phe Ser
            500                 505                 510

Glu Lys Thr Pro Val Phe Arg Leu Pro Asp His Ile Ile Tyr Lys Thr
        515                 520                 525

Lys Glu Leu Leu Ile Ser Asn Tyr Asp Val Asp Glu Ala Glu Glu Leu
    530                 535                 540

Lys Glu Ile Arg Leu Arg Pro Trp Glu Ala Arg Val Tyr Lys Ile Arg
545                 550                 555                 560

Leu Pro


<210> SEQ ID NO 2
<211> LENGTH: 551
<212> TYPE: PRT
<213> ORGANISM: Erwinia rhapontici DSM 4484
<220> FEATURE:
<221> NAME/KEY: enzyme
<222> LOCATION: (1)..(551)
<223> OTHER INFORMATION: alpha-1,6-glucosidase Genebank AAK28737
```

-continued

<400> SEQUENCE: 2

Met Arg Ser Thr Pro His Trp Lys Glu Ala Val Val Tyr Gln Val Tyr
1 5 10 15

Pro Arg Ser Phe Met Asp Ser Asn Gly Asp Gly Thr Gly Asp Leu Asn
20 25 30

Gly Ile Ile Ser Lys Leu Asp Tyr Leu Gln Gln Leu Gly Ile Thr Leu
35 40 45

Leu Trp Leu Ser Pro Val Tyr Arg Ser Pro Met Asp Asp Asn Gly Tyr
50 55 60

Asp Ile Ser Asp Tyr Glu Glu Ile Ala Asp Ile Phe Gly Ser Met Ser
65 70 75 80

Asp Met Glu Arg Leu Ile Ala Glu Ala Lys Ala Arg Asp Ile Gly Ile
85 90 95

Leu Met Asp Leu Val Val Asn His Thr Ser Asp Glu His Pro Trp Phe
100 105 110

Ile Asp Ala Leu Ser Ser Lys Asn Ser Ala Tyr Arg Asp Phe Tyr Ile
115 120 125

Trp Arg Ala Pro Ala Ala Asp Gly Gly Pro Pro Asp Asp Ser Arg Ser
130 135 140

Asn Phe Gly Gly Ser Ala Trp Thr Leu Asp Glu Ala Ser Gly Glu Tyr
145 150 155 160

Tyr Leu His Gln Phe Ser Thr Arg Gln Pro Asp Leu Asn Trp Glu Asn
165 170 175

Pro Arg Val Arg Glu Ala Ile His Ala Met Met Asn Arg Trp Leu Asp
180 185 190

Lys Gly Ile Gly Gly Phe Arg Met Asp Val Ile Asp Leu Ile Gly Lys
195 200 205

Glu Val Asp Pro Gln Ile Met Ala Asn Gly Arg His Pro His Leu Tyr
210 215 220

Leu Gln Gln Met Asn Arg Ala Thr Phe Gly Pro Arg Gly Ser Val Thr
225 230 235 240

Val Gly Glu Thr Trp Ser Ala Thr Pro Glu Asp Ala Leu Leu Tyr Ser
245 250 255

Ala Glu Glu Arg Gln Glu Arg Gln Glu Leu Thr Met Val Phe Gln Phe
260 265 270

Glu His Ile Lys Leu Phe Trp Asp Glu Gln Tyr Gly Lys Trp Cys Asn
275 280 285

Gln Pro Phe Asp Leu Leu Arg Phe Lys Ala Val Ile Asp Lys Trp Gln
290 295 300

Thr Ala Leu Ala Asp His Gly Trp Asn Ser Leu Phe Trp Ser Asn His
305 310 315 320

Asp Leu Pro Arg Ala Val Ser Lys Phe Gly Asp Asp Gly Glu Tyr Arg
325 330 335

Val Val Ser Ala Lys Met Leu Ala Thr Ala Leu His Cys Leu Lys Gly
340 345 350

Thr Pro Tyr Ile Tyr Gln Gly Glu Glu Ile Gly Met Thr Asn Val Asn
355 360 365

Phe Ala Asp Ile Asp Asp Tyr Arg Asp Ile Glu Ser Leu Asn Leu Tyr
370 375 380

Gln Glu Arg Ile Ala Glu Gly Met Ser His Glu Ala Met Met Arg Gly
385 390 395 400

Ile His Ala Asn Gly Pro Asp Asn Ala Arg Thr Pro Met Gln Trp Thr
405 410 415

```
Ala Val His Met Pro Gly Leu Pro Pro Val Ser Pro Gly Leu Arg Leu
            420                 425                 430

Ile Leu Thr Ser Gly Gln Trp Asn Val Ala Ala Ala Leu Asp Asp Pro
        435                 440                 445

Asp Ser Val Phe Tyr His Tyr Gln Lys Leu Val Ala Leu Arg Lys Gln
    450                 455                 460

Leu Pro Leu Leu Val His Gly Asp Phe Arg Gln Ile Val Val Glu His
465                 470                 475                 480

Pro Gln Val Phe Ala Trp Leu Arg Thr Leu Gly Glu Gln Thr Leu Val
                485                 490                 495

Val Ile Asn Asn Phe Thr Arg Asp Ala Val Met Leu Ala Ile Pro Asp
            500                 505                 510

Asn Leu Gln Ser Gln Gln Gly Arg Cys Leu Ile Asn Asn Tyr Ala Pro
        515                 520                 525

Arg Glu Gln Leu Glu Pro Ile Met Glu Leu Gln Pro Tyr Glu Ser Phe
    530                 535                 540

Ala Leu Leu Ile Glu Arg Leu
545                 550


<210> SEQ ID NO 3
<211> LENGTH: 564
<212> TYPE: PRT
<213> ORGANISM: Bacillus thuringiensis str. Al Hakam
<220> FEATURE:
<221> NAME/KEY: enzyme
<222> LOCATION: (1)..(564)
<223> OTHER INFORMATION: alpha-1,6-glucosidase

<400> SEQUENCE: 3

Met Lys Trp Gly Ser Ile Met Glu Lys Gln Trp Trp Lys Glu Ser Val
1               5                   10                  15

Val Tyr Gln Ile Tyr Pro Arg Ser Phe Met Asp Ser Asn Gly Asp Gly
            20                  25                  30

Ile Gly Asp Leu Arg Gly Ile Ile Ser Lys Leu Asp Tyr Leu Lys Glu
        35                  40                  45

Leu Gly Ile Asp Val Ile Trp Leu Ser Pro Val Tyr Glu Ser Pro Asn
    50                  55                  60

Asp Asp Asn Gly Tyr Asp Ile Ser Asp Tyr Cys Lys Ile Met Asn Glu
65                  70                  75                  80

Phe Gly Thr Met Glu Asp Trp Asp Glu Leu Leu His Glu Met His Glu
                85                  90                  95

Arg Asn Met Lys Leu Met Met Asp Leu Val Val Asn His Thr Ser Asp
            100                 105                 110

Glu His Asn Trp Phe Ile Glu Ser Arg Lys Ser Lys Asp Asn Lys Tyr
        115                 120                 125

Arg Asp Tyr Tyr Ile Trp Arg Pro Gly Lys Glu Gly Lys Glu Pro Asn
    130                 135                 140

Asn Trp Gly Ala Ala Phe Ser Gly Ser Ala Trp Gln Tyr Asp Glu Met
145                 150                 155                 160

Thr Asp Glu Tyr Tyr Leu His Leu Phe Ser Lys Lys Gln Pro Asp Leu
                165                 170                 175

Asn Trp Asp Asn Glu Lys Val Arg Gln Asp Val Tyr Glu Met Met Lys
            180                 185                 190

Phe Trp Leu Glu Lys Gly Ile Asp Gly Phe Arg Met Asp Val Ile Asn
        195                 200                 205
```

-continued

```
Phe Ile Ser Lys Glu Glu Gly Leu Pro Thr Val Glu Thr Glu Glu Glu
    210                 215                 220

Gly Tyr Val Ser Gly His Lys His Phe Met Asn Gly Pro Asn Ile His
225                 230                 235                 240

Lys Tyr Leu His Glu Met Asn Glu Glu Val Leu Ser His Tyr Asp Ile
                245                 250                 255

Met Thr Val Gly Glu Met Pro Gly Val Thr Thr Glu Glu Ala Lys Leu
            260                 265                 270

Tyr Thr Gly Glu Glu Arg Lys Glu Leu Gln Met Val Phe Gln Phe Glu
        275                 280                 285

His Met Asp Leu Asp Ser Gly Glu Gly Gly Lys Trp Asp Val Lys Pro
    290                 295                 300

Cys Ser Leu Leu Thr Leu Lys Glu Asn Leu Thr Lys Trp Gln Lys Ala
305                 310                 315                 320

Leu Glu His Thr Gly Trp Asn Ser Leu Tyr Trp Asn Asn His Asp Gln
                325                 330                 335

Pro Arg Val Val Ser Arg Phe Gly Asn Asp Gly Met Tyr Arg Ile Glu
            340                 345                 350

Ser Ala Lys Met Leu Ala Thr Val Leu His Met Met Lys Gly Thr Pro
        355                 360                 365

Tyr Ile Tyr Gln Gly Glu Glu Ile Gly Met Thr Asn Val Arg Phe Glu
    370                 375                 380

Ser Ile Asp Glu Tyr Arg Asp Ile Glu Thr Leu Asn Met Tyr Lys Glu
385                 390                 395                 400

Lys Val Met Glu Arg Gly Glu Asp Ile Glu Lys Val Met Gln Ser Ile
                405                 410                 415

Tyr Ile Lys Gly Arg Asp Asn Ala Arg Thr Pro Met Gln Trp Asp Asp
            420                 425                 430

Gln Asn His Ala Gly Phe Thr Thr Gly Glu Pro Trp Ile Thr Val Asn
        435                 440                 445

Pro Asn Tyr Lys Glu Ile Asn Val Lys Gln Ala Ile Gln Asn Lys Asp
    450                 455                 460

Ser Ile Phe Tyr Tyr Tyr Lys Lys Leu Ile Glu Leu Arg Lys Asn Asn
465                 470                 475                 480

Glu Ile Val Val Tyr Gly Ser Tyr Asp Leu Ile Leu Glu Asn Asn Pro
                485                 490                 495

Ser Ile Phe Ala Tyr Val Arg Thr Tyr Gly Val Glu Lys Leu Leu Val
            500                 505                 510

Ile Ala Asn Phe Thr Ala Glu Glu Cys Ile Phe Glu Leu Pro Glu Asp
        515                 520                 525

Ile Ser Tyr Ser Glu Val Glu Leu Leu Ile His Asn Tyr Asp Val Glu
    530                 535                 540

Asn Gly Pro Ile Glu Asn Ile Thr Leu Arg Pro Tyr Glu Ala Met Val
545                 550                 555                 560

Phe Lys Leu Lys
```

<210> SEQ ID NO 4
<211> LENGTH: 576
<212> TYPE: PRT
<213> ORGANISM: Arthrobacter globiformis
<220> FEATURE:
<221> NAME/KEY: enzyme
<222> LOCATION: (1)..(576)
<223> OTHER INFORMATION: alpha-1,6-glucosidase Genebank AB113246

<400> SEQUENCE: 4

-continued

```
Met Thr Ile Glu Glu Thr Glu Glu Glu Ala Thr Tyr Arg Ala Gly Arg
1               5                   10                  15

Glu Trp Phe Lys Ser Ala Val Val Tyr Gln Ile Tyr Pro Arg Ser Phe
            20                  25                  30

Ala Asp Ser Asp Gly Asp Gly Val Gly Asp Leu Arg Gly Ile Ile Gly
        35                  40                  45

Lys Leu Asp Tyr Leu Gln Lys Leu Gly Val Asp Val Val Trp Leu Ser
    50                  55                  60

Pro Val Tyr Arg Ser Pro Gln Asp Asp Asn Gly Tyr Asp Ile Ser Asp
65                  70                  75                  80

Tyr Arg Glu Ile Asp Pro Val Phe Gly Gly Leu Glu Thr Leu Asp Glu
                85                  90                  95

Leu Leu Asp Gly Leu His Ala Arg Gly Met Lys Leu Val Met Asp Leu
            100                 105                 110

Val Val Asn His Thr Ser Asp Glu His Pro Trp Phe Val Glu Ser Arg
        115                 120                 125

Ser Ser Lys Asp Ser Pro Lys Arg Asp Trp Tyr Trp Trp Arg Pro Ala
    130                 135                 140

Arg Glu Gly Ala Glu Pro Gly Thr Ala Gly Ala Glu Pro Asn Asn Trp
145                 150                 155                 160

Gly Ser Ala Phe Ser Gly Pro Ala Trp Glu Tyr Asp Ala Ala Thr Gly
                165                 170                 175

Glu Tyr Tyr Leu His Leu Phe Ser Arg Lys Gln Pro Asp Leu Asn Trp
            180                 185                 190

Glu Asn Pro Glu Val Arg Ala Ala Val Tyr Asp Met Met Asn Trp Trp
        195                 200                 205

Leu Asp Arg Gly Val Asp Gly Phe Arg Met Asp Val Ile Asn Phe Ile
    210                 215                 220

Ser Lys Asp Gln Thr Leu Pro Asp Gly Pro Arg Ala Asp Gly Met Leu
225                 230                 235                 240

Phe Gly Asp Gly Gly Pro His Tyr Ile Cys Gly Pro Arg Ile His Glu
                245                 250                 255

Phe Leu Gln Glu Met His Gln Glu Val Phe Ala Gly Arg Asp Lys Asp
            260                 265                 270

Leu Leu Thr Val Gly Glu Met Pro Gly Val Thr Val Asp Glu Ala Val
        275                 280                 285

Leu Phe Thr Asp Pro Gly Arg Arg Glu Val Asp Met Val Phe Gln Phe
    290                 295                 300

Glu His Val Ala Leu Asp Gln Glu Gly Gly Asn Lys Trp Arg Pro Lys
305                 310                 315                 320

Lys Leu Leu Leu Thr Asp Leu Lys Lys Ser Leu Gly Arg Trp Gln Glu
                325                 330                 335

Ala Leu Gly Glu Arg Gly Trp Asn Ser Leu Tyr Trp Gly Asn His Asp
            340                 345                 350

Gln Ala Arg Ala Val Ser Arg Phe Gly Asp Asp Gly Glu Tyr Arg Glu
        355                 360                 365

Gln Ser Ala Lys Met Leu Ala Ala Val Leu His Leu His Arg Gly Thr
    370                 375                 380

Pro Tyr Val Tyr Gln Gly Glu Glu Leu Gly Met Thr Asn Met Ala Phe
385                 390                 395                 400

Gly Ala Ile Ser Asp Tyr Arg Asp Ile Glu Val Leu Asn His His Arg
                405                 410                 415
```

```
Glu Ala Thr Thr His Leu Gly His Thr Asp Ala Glu Val Leu Ala Ala
            420                 425                 430

Leu Ala Pro Leu Asn Arg Asp Asn Ala Arg Thr Pro Val Gln Trp Asp
        435                 440                 445

Ala Ser Arg His Gly Gly Phe Thr Thr Gly Ala Pro Trp Ile Ala Val
    450                 455                 460

Asn Pro Asn Ala Asn Thr Ile Asn Ala Ala Ala Gln Val Asp Asp Pro
465                 470                 475                 480

Asp Ser Val Phe Ser Phe Tyr Arg Arg Val Ile Ala Leu Arg His Ala
                485                 490                 495

Asp Pro Val Val Ala Tyr Gly Asp Phe Thr Met Leu Leu Pro Asp Asp
            500                 505                 510

Glu His Val Tyr Ala Phe Arg Arg Ser Leu Pro Asp Ala Glu Leu Leu
        515                 520                 525

Val Leu Gly Asn Phe Ser Gly Thr Gly Gln Ser Ala Gly Val Asp Gly
    530                 535                 540

Ser Trp Gly Asp Ala Glu Leu Val Leu Gly Asn Tyr Pro Ala Ala Pro
545                 550                 555                 560

Gly Leu Gly Leu Arg Pro Trp Glu Val Lys Val Phe Arg Arg Asn Leu
                565                 570                 575


<210> SEQ ID NO 5
<211> LENGTH: 787
<212> TYPE: PRT
<213> ORGANISM: Bacillus thermoamyloliquefaciens
<220> FEATURE:
<221> NAME/KEY: enzyme
<222> LOCATION: (1)..(787)
<223> OTHER INFORMATION: alpha-1,6-glucosidase Q9F234

<400> SEQUENCE: 5

Met Leu Glu Asp Thr Ser Phe Ala Ile Gln Pro Glu Gln Asp Asp Lys
1               5                   10                  15

Thr Gln Glu Thr His Arg Ile Asp Ile Gly Asn Met His Thr Phe Ser
            20                  25                  30

His Thr Glu His Val Phe Ser Phe His Cys Asp Thr Gly Ile Val Lys
        35                  40                  45

Ile Arg Phe Tyr Arg Glu Asp Ile Val Arg Ile Ala Phe Asn Pro Phe
    50                  55                  60

Gly Glu Thr Ser Leu Ser Thr Ser Val Ala Val Val Lys Glu Pro Glu
65                  70                  75                  80

Lys Val Asp Ala Ser Val His Glu Thr Glu Glu Val Thr Leu Thr
                85                  90                  95

Ser Ala Lys Gln Thr Val Val Leu Gln Lys Arg Pro Phe Arg Val Arg
            100                 105                 110

Ile Tyr Asp Asn His Gly Arg Leu Leu Val Ala Glu Gly Lys Lys Gly
        115                 120                 125

Met Ala Phe Thr Tyr Gln Gly Glu Val Cys Cys Phe Lys Met Met Asp
    130                 135                 140

Glu Ala Asp His Phe Tyr Gly Phe Gly Glu Lys Thr Gly Phe Leu Asp
145                 150                 155                 160

Lys Arg Gly Glu Thr Met Thr Met Trp Asn Thr Asp Val Tyr Ala Pro
                165                 170                 175

His Asn Pro Glu Thr Asp Pro Leu Tyr Gln Ser His Pro Tyr Phe Met
            180                 185                 190

Thr Val Arg Asn Gly Ser Ala His Gly Ile Phe Phe Asp Asn Thr Tyr
```

```
        195                 200                 205

Lys Thr Thr Phe Asp Phe Gln Thr Ala Thr Asp Glu Tyr Cys Phe Ser
    210                 215                 220

Ala Glu Gly Gly Ala Ile Asp Tyr Tyr Val Phe Ala Gly Pro Thr Pro
225                 230                 235                 240

Lys Asp Val Leu Glu Gln Tyr Thr Asp Leu Thr Gly Arg Met Pro Leu
                245                 250                 255

Pro Pro Lys Trp Ala Leu Gly Tyr His Gln Ser Arg Tyr Ser Tyr Glu
            260                 265                 270

Thr Glu Gln Glu Val Arg Glu Ile Ala Gln Thr Phe Ile Glu Lys Asp
        275                 280                 285

Ile Pro Leu Asp Val Ile Tyr Leu Asp Ile His Tyr Met Asn Gly Tyr
    290                 295                 300

Arg Val Phe Thr Phe Asp Arg Asn Arg Phe Pro Asn Leu Lys Gln Leu
305                 310                 315                 320

Ile Ala Asp Leu Lys Gln Lys Gly Ile Arg Val Val Pro Ile Val Asp
                325                 330                 335

Pro Gly Val Lys Glu Asp Pro Glu Tyr Val Ile Tyr Gln Glu Gly Ile
            340                 345                 350

Arg His Asp Tyr Phe Cys Lys Tyr Ile Glu Gly Asn Val Tyr Phe Gly
        355                 360                 365

Glu Val Trp Pro Gly Lys Ser Ala Phe Pro Asp Phe Thr Asn Lys Lys
    370                 375                 380

Val Arg Lys Trp Trp Gly Glu Lys His Gln Phe Tyr Thr Asp Leu Gly
385                 390                 395                 400

Ile Glu Gly Ile Trp Asn Asp Met Asn Glu Pro Ser Val Phe Asn Glu
                405                 410                 415

Thr Lys Thr Met Asp Val Lys Val Ile His Asp Asn Asp Gly Asp Pro
            420                 425                 430

Lys Thr His Arg Glu Leu His Asn Val Tyr Gly Phe Met Met Gly Glu
        435                 440                 445

Ala Thr Tyr Lys Gly Met Lys Lys Leu Leu Asn Gly Lys Arg Pro Phe
    450                 455                 460

Leu Leu Thr Arg Ala Gly Phe Ser Gly Ile Gln Arg Tyr Ala Ala Val
465                 470                 475                 480

Trp Thr Gly Asp Asn Arg Ser Phe Trp Glu His Leu Gln Met Ser Leu
                485                 490                 495

Pro Met Cys Met Asn Leu Gly Leu Ser Gly Val Ala Phe Cys Gly Pro
            500                 505                 510

Asp Val Gly Gly Phe Ala His Asn Thr Asn Gly Glu Leu Leu Thr Arg
        515                 520                 525

Trp Met Gln Val Gly Ala Phe Thr Pro Tyr Phe Arg Asn His Cys Ala
    530                 535                 540

Ile Gly Phe Arg Arg Gln Glu Pro Trp Ala Phe Gly Glu Lys Tyr Glu
545                 550                 555                 560

Arg Ile Ile Lys Lys Tyr Ile Arg Leu Arg Tyr Gln Trp Leu Pro His
                565                 570                 575

Leu Tyr Thr Leu Phe Ala Glu Ala His Glu Thr Gly Ala Pro Val Met
            580                 585                 590

Arg Pro Leu Phe Phe Glu Tyr Pro Asp Asp Glu Asn Thr Tyr Asn Leu
        595                 600                 605

Tyr Asp Glu Phe Leu Val Gly Ala Asn Val Leu Ile Ala Pro Ile Met
    610                 615                 620
```

```
Thr Pro Ser Thr Thr Arg Arg Val Ala Tyr Phe Pro Lys Gly Asn Trp
625                 630                 635                 640

Val Asp Tyr Trp Thr Gly Glu Val Leu Glu Gly Gly Gln Tyr His Leu
                645                 650                 655

Ile Ser Ala Asp Leu Glu Thr Leu Pro Ile Phe Ile Lys Gln Gly Ser
            660                 665                 670

Ala Ile Ala Leu Gly Asp Val Lys Arg Ser Thr Glu Met Pro Asp Glu
        675                 680                 685

His Arg Thr Val His Ile Tyr Lys Ala Asn Gly Gly Lys Ala Thr Tyr
    690                 695                 700

Val Leu Tyr Asp Asp Asp Gly Gln Thr Phe Ser Tyr Glu Lys Gly Asp
705                 710                 715                 720

Tyr Leu Arg Met Tyr Ile Glu Val Glu Tyr Gly Glu Asn Ser Val His
                725                 730                 735

Ile Val Thr Lys Ser Glu Gly Thr Tyr Gln Pro Ser Trp Lys Leu Ser
            740                 745                 750

Phe Ala Ile His His Ala Thr Glu Gln Thr Lys Val Thr Ile Asp Gly
        755                 760                 765

Asn Glu Gln Asn Ala Ile Phe Asp Pro His Gln Arg Ile Leu Leu Ile
    770                 775                 780

Gln Ser Glu
785


<210> SEQ ID NO 6
<211> LENGTH: 752
<212> TYPE: PRT
<213> ORGANISM: Thermoanaerobacter ethanolicus
<220> FEATURE:
<221> NAME/KEY: enzyme
<222> LOCATION: (1)..(752)
<223> OTHER INFORMATION: alpha-1,6-glucosidase ABR26230

<400> SEQUENCE: 6

Met Tyr Gln Lys Thr Ser Glu Lys Ile Val Val Arg Asn Glu Gly Lys
1               5                   10                  15

Lys Leu Glu Leu Arg Val Leu Gly Asp Lys Ile Ile Asn Val Phe Val
            20                  25                  30

Ser Asn Lys Glu Glu Lys Arg Lys Asp Thr Ile Ala Ile Glu Arg Lys
        35                  40                  45

Glu Tyr Asp Thr Pro Glu Phe Ser Ile Ser Asp Glu Leu Glu Ser Ile
    50                  55                  60

Leu Ile Glu Thr Asn Ser Leu Lys Val Lys Ile Asn Lys Asn Asp Leu
65                  70                  75                  80

Ser Val Ser Phe Leu Asp Lys Asn Gly Asn Ile Ile Asn Glu Asp Tyr
                85                  90                  95

Asn Gly Gly Ala Lys Phe Asn Glu Thr Asp Val Arg Cys Tyr Lys Lys
            100                 105                 110

Leu Arg Glu Asp His Phe Tyr Gly Phe Gly Glu Lys Ala Gly Tyr Leu
        115                 120                 125

Asp Lys Lys Gly Glu Arg Leu Glu Met Trp Asn Thr Asp Glu Phe Met
    130                 135                 140

Thr His Asn Gln Thr Thr Lys Leu Leu Tyr Glu Ser Tyr Pro Phe Phe
145                 150                 155                 160

Ile Gly Met Asn Asp Tyr His Thr Tyr Gly Ile Phe Leu Asp Asn Ser
                165                 170                 175
```

-continued

```
Phe Arg Ser Phe Phe Asp Met Gly Gln Glu Ser Gln Glu Tyr Tyr Phe
            180                 185                 190

Phe Gly Ala Tyr Gly Gly Gln Met Asn Tyr Tyr Phe Ile Tyr Gly Glu
        195                 200                 205

Asp Ile Lys Glu Val Val Glu Asn Tyr Thr Tyr Leu Thr Gly Arg Ile
    210                 215                 220

Ser Leu Pro Pro Leu Trp Val Leu Gly Asn Gln Gln Ser Arg Tyr Ser
225                 230                 235                 240

Tyr Thr Pro Gln Glu Arg Val Leu Glu Val Ala Lys Thr Phe Arg Glu
                245                 250                 255

Lys Asp Ile Pro Cys Asp Val Ile Tyr Leu Asp Ile Asp Tyr Met Glu
            260                 265                 270

Gly Tyr Arg Val Phe Thr Trp Asn Lys Glu Thr Phe Lys Asn His Lys
        275                 280                 285

Glu Met Leu Lys Gln Leu Lys Glu Met Gly Phe Lys Val Val Thr Ile
    290                 295                 300

Val Asp Pro Gly Val Lys Arg Asp Tyr Asp Tyr His Val Tyr Arg Glu
305                 310                 315                 320

Gly Ile Glu Lys Gly Tyr Phe Val Lys Asp Lys Tyr Gly Ile Thr Tyr
                325                 330                 335

Val Gly Lys Val Trp Pro Gly Glu Ala Cys Phe Pro Asp Phe Leu Gln
            340                 345                 350

Glu Glu Val Arg Tyr Trp Trp Gly Glu Lys His Arg Glu Phe Ile Asn
        355                 360                 365

Asp Gly Ile Asp Gly Ile Trp Asn Asp Met Asn Glu Pro Ala Val Phe
    370                 375                 380

Glu Thr Pro Thr Lys Thr Met Pro Glu Asp Asn Ile His Ile Leu Asp
385                 390                 395                 400

Gly Glu Lys Val Leu His Lys Glu Ala His Asn Val Tyr Ala Asn Tyr
                405                 410                 415

Met Ala Met Ala Thr Arg Asp Gly Phe Leu Arg Ile Arg Pro Asn Glu
            420                 425                 430

Arg Pro Phe Val Leu Thr Arg Ala Ala Phe Ser Gly Ile Gln Arg Tyr
        435                 440                 445

Ala Ala Met Trp Thr Gly Asp Asn Arg Ser Leu Tyr Glu His Leu Leu
    450                 455                 460

Met Met Met Pro Met Leu Met Asn Ile Gly Leu Ser Gly Gln Pro Phe
465                 470                 475                 480

Val Gly Ala Asp Val Gly Gly Phe Glu Gly Asp Cys His Glu Glu Leu
                485                 490                 495

Phe Ile Arg Trp Ile Glu Ala Ala Val Phe Thr Pro Phe Leu Arg Val
            500                 505                 510

His Ser Ala Ile Gly Thr Lys Asp Gln Glu Pro Trp Ser Phe Gly Lys
        515                 520                 525

Arg Ala Glu Asp Ile Ser Arg Lys Tyr Ile Lys Met Arg Tyr Glu Leu
    530                 535                 540

Leu Pro Tyr Leu Tyr Asp Leu Phe Tyr Ile Ala Ser Gln Lys Gly Tyr
545                 550                 555                 560

Pro Ile Met Arg Pro Leu Val Phe Glu Tyr Gln Lys Asp Glu Asn Thr
                565                 570                 575

His Lys Ile Tyr Asp Glu Phe Met Phe Gly Glu Gly Leu Leu Val Ala
            580                 585                 590

Pro Val Tyr Leu Pro Ser Lys Glu Arg Arg Glu Val Tyr Leu Pro Glu
```

-continued

```
        595                 600                 605

Gly Ile Trp Tyr Asp Tyr Trp Thr Gly Lys Gly Phe Lys Gly Lys Asn
    610                 615                 620

Tyr Tyr Leu Val Asp Ala Pro Ile Glu Val Ile Pro Leu Phe Val Lys
625                 630                 635                 640

Glu Gly Gly Ile Leu Leu Lys Gln Gln Pro Gln Ser Phe Ile Gly Glu
                645                 650                 655

Lys Lys Leu Glu Glu Leu Thr Val Glu Ile Tyr Lys Gly Lys Glu Gly
            660                 665                 670

His Tyr Leu His Tyr Glu Asp Asp Gly Lys Ser Phe Asp Tyr Thr Lys
        675                 680                 685

Gly Val Tyr Asn Leu Phe Asp Ile Ser Phe Cys Tyr Lys Glu Gly Arg
    690                 695                 700

Met Asp Ile Lys Phe Asp Lys Ile His Phe Gly Tyr Asp Lys Gly Val
705                 710                 715                 720

Lys Lys Tyr Lys Phe Ile Phe Lys Asn Phe Asp Asp Ile Lys Glu Ile
                725                 730                 735

Lys Ile Asn Gly Glu Lys Val Glu Lys Glu Ser Cys Glu Ile Glu Leu
            740                 745                 750
```

<210> SEQ ID NO 7
<211> LENGTH: 1717
<212> TYPE: DNA
<213> ORGANISM: Arabidopsis
<220> FEATURE:
<221> NAME/KEY: promoter
<222> LOCATION: (1)..(1717)
<223> OTHER INFORMATION: UBQ promoter

<400> SEQUENCE: 7

```
ggagccaagt ctcataaacg ccattgtgga agaaagtctt gagttggtgg taatgtaaca     60

gagtagtaag aacagagaag agagagagtg tgagatacat gaattgtcgg gcaacaaaaa    120

tcctgaacat cttattttag caaagagaaa gagttccgag tctgtagcag aagagtgagg    180

agaaatttaa gctcttggac ttgtgaattg ttccgcctct tgaatacttc ttcaatcctc    240

atatattctt cttctatgtt acctgaaaac cggcatttaa tctcgcgggt ttattccggt    300

tcaacatttt ttttgttttg agttattatc tgggcttaat aacgcaggcc tgaaataaat    360

tcaaggccca actgtttttt tttttaagaa gttgctgtta aaaaaaaaaa aagggaatta    420

acaacaacaa caaaaaaaga taaagaaaat aataacaatt actttaattg tagactaaaa    480

aaacatagat tttatcatga aaaaaagaga aaagaaataa aaacttggat caaaaaaaaa    540

acatacagat cttctaatta ttaacttttc ttaaaaatta ggtccttttt cccaacaatt    600

aggtttagag ttttggaatt aaaccaaaaa gattgttcta aaaaatactc aaatttggta    660

gataagtttc cttattttaa ttagtcaatg gtagatactt ttttttcttt tctttattag    720

agtagattag aatcttttat gccaagtatt gataaattaa atcaagaaga taaactatca    780

taatcaacat gaaattaaaa gaaaaatctc atatatagta ttagtattct ctatatatat    840

tatgattgct tattcttaat gggttgggtt aaccaagaca tagtcttaat ggaaagaatc    900

tttttgaac tttttcctta ttgattaaat tcttctatag aaaagaaaga aattatttga    960

ggaaaagtat atacaaaaag aaaaatagaa aaatgtcagt gaagcagatg taatggatga   1020

cctaatccaa ccaccaccat aggatgtttc tacttgagtc ggtcttttaa aaacgcacgg   1080

tggaaaatat gacacgtatc atatgattcc ttcctttagt ttcgtgataa taatcctcaa   1140
```

```
ctgatatctt cctttttttg ttttggctaa agatatttta ttctcattaa tagaaaagac   1200

ggttttgggc ttttggtttg cgatataaag aagaccttcg tgtggaagat aataattcat   1260

cctttcgtct ttttctgact cttcaatctc tcccaaagcc taaagcgatc tctgcaaatc   1320

tctcgcgact ctctctttca aggtatattt tctgattctt tttgtttttg attcgtatct   1380

gatctccaat ttttgttatg tggattattg aatcttttgt ataaattgct tttgacaata   1440

ttgttcgttt cgtcaatcca gcttctaaat tttgtcctga ttactaagat atcgattcgt   1500

agtgtttaca tctgtgtaat ttcttgcttg attgtgaaat taggattttc aaggacgatc   1560

tattcaattt ttgtgttttc tttgttcgat tctctctgtt ttaggtttct tatgtttaga   1620

tccgtttctc tttggtgttg ttttgatttc tcttacggct tttgatttgg tatatgttcg   1680

ctgattggtt tctacttgtt ctattgtttt atttcag                            1717
```

<210> SEQ ID NO 8
<211> LENGTH: 158
<212> TYPE: DNA
<213> ORGANISM: beet curly top virus
<220> FEATURE:
<221> NAME/KEY: rep_origin
<222> LOCATION: (1)..(158)

<400> SEQUENCE: 8

```
attgaatcgg gctctcttca aatcccctat caattgggtg ctttgggtgc tcttaaatac     60

caccaagggg ccatccgcat taatattacc ggatggcccc caaaaaatac gtggcccaat    120

gaaaatatgc cacgtggaaa gctaaagatg ttgatgtg                            158
```

<210> SEQ ID NO 9
<211> LENGTH: 1546
<212> TYPE: DNA
<213> ORGANISM: beet curly top virus
<220> FEATURE:
<221> NAME/KEY: misc_feature
<222> LOCATION: (1)..(1546)
<223> OTHER INFORMATION: BCTV replicase

<400> SEQUENCE: 9

```
tcaatatgcc tttttacaaa aaagccaaaa attttttcct tacataccct caatgttcag     60

taaccaaaga agacgcctta gaacagctcc tcgctataaa tacaccttcg aataaaaaat    120

atattcgcat ctgcagagaa ttacatgaaa atggggaacc acatctgcat gcccttattc    180

aattcgaagg aaaagtccag atccgtaatg cccgttactt cgatctgcaa catcgaagta    240

ccagcaaaca attccactgc aatattcagg gagctaaatc cagttccgac gtcaagtcct    300

acgtctcaaa ggacggagat cacatcgact ggggtgaatt tcaggtcgat ggaagatctg    360

cacgcggagg tcaacagacg gctaatgatg ctgcagcaga ggcattaaat gcaggtaatg    420

cattagaagc tctgcagata ataagggaga aactcccaga aaaatatatt tttcagtatc    480

acaacctcaa acctaactta gaggctattt ttcttcctcc tccagatctt tatcaaccac    540

cttttcctct ttcttctttc actagagttc cagaaattat tcaagagtgg gccgattctt    600

attttggttt ggatcccgct gcgcggcctt ttagatataa tagtttaatc atagagggtg    660

attcaagaac tggtaaaaca atgtgggcca ggtgtttagg tccacataat tatattactg    720

gtcatttaga ttttagttta aaaacttata atgataatgt tctgtataac gtcattgatg    780

acgtagatcc caattactta aagatgaagc attggaagca ccttataggc gcacaaagag    840

agtggcagac aaacttaaag tatggaaaac cacgtgtcat taaaggtggt attcccagta    900
```

```
ttatattatg caatccaggc gaaggcagct cttaccagga cttcctcaat aaatcagaaa    960

atgaagccct taggtcctgg acattacaaa attcagtctt cgccaaactc acaagtcctc   1020

tctttgataa caatcaagaa gcgtcctcgc aagatcaaac ttccttgtaa gtgtcatttc   1080

acaattcatc atgaatgtaa tcagggattt tcgcacagag gaacccatca cgctgcaaca   1140

agcgacgaat tccatacccg tggacttggt accgaatcca ttgtacctca aactccagga   1200

cttcttccgt tccgggccag tttatcaact gaaagtccag ataagattca accacaacct   1260

ccgcaaatac ttgaatcttc acaagtgctg gatagatttg acgatcactg gatcgcacag   1320

gacattaact ggggaccgtt ttttgaaagt cttgaaaaag agactagaga tatacttgga   1380

taatttaggt ttaatttgta ttaataatgt aattagaggt ttaaatcatg tcctgtatga   1440

agaatttaat tttgtatcta gtgtaattca gaaccagagt gttgcaatga aattgtatta   1500

aaaaaataat atttttatta ataaaaataa catctacaat tgccaa                  1546


<210> SEQ ID NO 10
<211> LENGTH: 181
<212> TYPE: DNA
<213> ORGANISM: Agrobacterium
<220> FEATURE:
<221> NAME/KEY: promoter
<222> LOCATION: (1)..(181)
<223> OTHER INFORMATION: NOS promoter

<400> SEQUENCE: 10

tttctggagt ttaatgagct aagcacatac gtcagaaacc attattgcgc gttcaaaagt     60

cgcctaaggt cactatcagc tagcaaatat ttcttgtcaa aaatgctcca ctgacgttcc    120

ataaattccc ctcggtatcc aattagagtc tcatattcac tctcaatcca aataatctgc    180

a                                                                    181


<210> SEQ ID NO 11
<211> LENGTH: 2259
<212> TYPE: DNA
<213> ORGANISM: T. ethanolicus
<220> FEATURE:
<221> NAME/KEY: CDS
<222> LOCATION: (1)..(2259)
<223> OTHER INFORMATION: dicot optimized alpha-1,6-glucosidase

<400> SEQUENCE: 11

atg tac caa aag act tct gag aag atc gtt gtt agg aac gag gga aag      48
Met Tyr Gln Lys Thr Ser Glu Lys Ile Val Val Arg Asn Glu Gly Lys
1               5                   10                  15

aag ttg gag ctt agg gtt ctc gga gat aag atc atc aac gtg ttc gtg      96
Lys Leu Glu Leu Arg Val Leu Gly Asp Lys Ile Ile Asn Val Phe Val
            20                  25                  30

tcc aac aaa gaa gag aag agg aag gat aca att gct atc gag agg aaa     144
Ser Asn Lys Glu Glu Lys Arg Lys Asp Thr Ile Ala Ile Glu Arg Lys
        35                  40                  45

gag tac gat act cca gag ttc tct atc tct gat gag ctt gag tct atc     192
Glu Tyr Asp Thr Pro Glu Phe Ser Ile Ser Asp Glu Leu Glu Ser Ile
    50                  55                  60

ctc att gag act aac tcc ctc aag gtg aag atc aac aag aac gat ctt     240
Leu Ile Glu Thr Asn Ser Leu Lys Val Lys Ile Asn Lys Asn Asp Leu
65                  70                  75                  80

tct gtg tcc ttc ttg gat aag aac gga aac atc atc aac gag gat tac     288
Ser Val Ser Phe Leu Asp Lys Asn Gly Asn Ile Ile Asn Glu Asp Tyr
                85                  90                  95

aat ggt gga gct aag ttc aac gag act gat gtt agg tgc tac aag aag     336
```

-continued

```
Asn Gly Gly Ala Lys Phe Asn Glu Thr Asp Val Arg Cys Tyr Lys Lys
            100                 105                 110

ttg aga gag gat cac ttt tac gga ttt gga gag aag gct gga tac ctt      384
Leu Arg Glu Asp His Phe Tyr Gly Phe Gly Glu Lys Ala Gly Tyr Leu
        115                 120                 125

gat aag aag ggt gaa agg ctt gag atg tgg aac act gat gag ttc atg      432
Asp Lys Lys Gly Glu Arg Leu Glu Met Trp Asn Thr Asp Glu Phe Met
    130                 135                 140

act cac aac cag act act aag ctc ctt tac gag tcc tac cca ttc ttc      480
Thr His Asn Gln Thr Thr Lys Leu Leu Tyr Glu Ser Tyr Pro Phe Phe
145                 150                 155                 160

atc gga atg aac gat tac cac act tac gga atc ttt ctc gat aac tcc      528
Ile Gly Met Asn Asp Tyr His Thr Tyr Gly Ile Phe Leu Asp Asn Ser
                165                 170                 175

ttc cgt tcc ttc ttt gat atg gga caa gag tcc caa gag tac tac ttt      576
Phe Arg Ser Phe Phe Asp Met Gly Gln Glu Ser Gln Glu Tyr Tyr Phe
            180                 185                 190

ttc gga gct tac ggt gga caa atg aac tac tac ttc atc tac ggt gaa      624
Phe Gly Ala Tyr Gly Gly Gln Met Asn Tyr Tyr Phe Ile Tyr Gly Glu
        195                 200                 205

gat atc aaa gaa gtg gtg gag aac tac act tat ctc act gga agg att      672
Asp Ile Lys Glu Val Val Glu Asn Tyr Thr Tyr Leu Thr Gly Arg Ile
    210                 215                 220

tct ctt cca cca ctt tgg gtt ttg gga aat cag cag tct agg tac tct      720
Ser Leu Pro Pro Leu Trp Val Leu Gly Asn Gln Gln Ser Arg Tyr Ser
225                 230                 235                 240

tat act cca caa gag agg gtt ttg gag gtt gca aag act ttc aga gag      768
Tyr Thr Pro Gln Glu Arg Val Leu Glu Val Ala Lys Thr Phe Arg Glu
                245                 250                 255

aag gat atc cct tgc gat gtg atc tac ctc gat atc gat tac atg gaa      816
Lys Asp Ile Pro Cys Asp Val Ile Tyr Leu Asp Ile Asp Tyr Met Glu
            260                 265                 270

gga tac cgt gtt ttc act tgg aac aaa gag act ttc aag aac cac aaa      864
Gly Tyr Arg Val Phe Thr Trp Asn Lys Glu Thr Phe Lys Asn His Lys
        275                 280                 285

gag atg ctt aag cag ctc aaa gag atg ggt ttc aag gtt gtg act atc      912
Glu Met Leu Lys Gln Leu Lys Glu Met Gly Phe Lys Val Val Thr Ile
    290                 295                 300

gtt gat cca ggt gtt aag agg gat tac gat tac cat gtg tac cgt gaa      960
Val Asp Pro Gly Val Lys Arg Asp Tyr Asp Tyr His Val Tyr Arg Glu
305                 310                 315                 320

ggt att gag aag gga tac ttc gtg aag gat aag tac gga atc act tat     1008
Gly Ile Glu Lys Gly Tyr Phe Val Lys Asp Lys Tyr Gly Ile Thr Tyr
                325                 330                 335

gtg gga aaa gtt tgg cct ggc gag gct tgt ttt cca gat ttc ctc caa     1056
Val Gly Lys Val Trp Pro Gly Glu Ala Cys Phe Pro Asp Phe Leu Gln
            340                 345                 350

gag gaa gtt aga tat tgg tgg gga gaa aag cac aga gag ttc atc aac     1104
Glu Glu Val Arg Tyr Trp Trp Gly Glu Lys His Arg Glu Phe Ile Asn
        355                 360                 365

gac gga atc gat ggt atc tgg aac gat atg aac gag cca gct gtt ttt     1152
Asp Gly Ile Asp Gly Ile Trp Asn Asp Met Asn Glu Pro Ala Val Phe
    370                 375                 380

gaa act cca act aag act atg cca gag gat aac atc cac att ctc gat     1200
Glu Thr Pro Thr Lys Thr Met Pro Glu Asp Asn Ile His Ile Leu Asp
385                 390                 395                 400

ggt gaa aag gtt ctc cac aaa gag gct cat aac gtt tac gct aac tac     1248
Gly Glu Lys Val Leu His Lys Glu Ala His Asn Val Tyr Ala Asn Tyr
                405                 410                 415
```

```
atg gct atg gct act agg gat gga ttt ctc agg att agg cca aat gag      1296
Met Ala Met Ala Thr Arg Asp Gly Phe Leu Arg Ile Arg Pro Asn Glu
            420                 425                 430

agg cca ttt gtg ctt act agg gct gct ttc tct gga att cag cgt tat      1344
Arg Pro Phe Val Leu Thr Arg Ala Ala Phe Ser Gly Ile Gln Arg Tyr
        435                 440                 445

gct gct atg tgg act ggt gat aac aga tct ctt tac gag cac ctc ctt      1392
Ala Ala Met Trp Thr Gly Asp Asn Arg Ser Leu Tyr Glu His Leu Leu
    450                 455                 460

atg atg atg cct atg ctc atg aac atc gga ctt tct gga caa cca ttc      1440
Met Met Met Pro Met Leu Met Asn Ile Gly Leu Ser Gly Gln Pro Phe
465                 470                 475                 480

gtt ggt gct gat gtt gga gga ttt gag ggc gat tgc cac gag gaa ctt      1488
Val Gly Ala Asp Val Gly Gly Phe Glu Gly Asp Cys His Glu Glu Leu
                485                 490                 495

ttc att aga tgg atc gag gct gct gtt ttt act cca ttc ctt agg gtg      1536
Phe Ile Arg Trp Ile Glu Ala Ala Val Phe Thr Pro Phe Leu Arg Val
            500                 505                 510

cac tct gct att gga act aag gat caa gag cct tgg tct ttt gga aag      1584
His Ser Ala Ile Gly Thr Lys Asp Gln Glu Pro Trp Ser Phe Gly Lys
        515                 520                 525

agg gct gag gat att tcc cgt aag tac atc aag atg cgt tac gag ctt      1632
Arg Ala Glu Asp Ile Ser Arg Lys Tyr Ile Lys Met Arg Tyr Glu Leu
    530                 535                 540

ctt cca tac ctt tac gat ctc ttc tac att gct tcc caa aag gga tac      1680
Leu Pro Tyr Leu Tyr Asp Leu Phe Tyr Ile Ala Ser Gln Lys Gly Tyr
545                 550                 555                 560

cca att atg agg cca ctt gtg ttt gag tac cag aag gat gag aac act      1728
Pro Ile Met Arg Pro Leu Val Phe Glu Tyr Gln Lys Asp Glu Asn Thr
                565                 570                 575

cac aag atc tac gat gag ttt atg ttc gga gag gga ctt ctt gtt gct      1776
His Lys Ile Tyr Asp Glu Phe Met Phe Gly Glu Gly Leu Leu Val Ala
            580                 585                 590

cca gtg tac ctt cca tct aaa gag cgt aga gag gtt tac ctt cca gag      1824
Pro Val Tyr Leu Pro Ser Lys Glu Arg Arg Glu Val Tyr Leu Pro Glu
        595                 600                 605

gga atc tgg tat gat tac tgg act gga aag gga ttc aag gga aag aac      1872
Gly Ile Trp Tyr Asp Tyr Trp Thr Gly Lys Gly Phe Lys Gly Lys Asn
    610                 615                 620

tac tac ctt gtg gat gct cca att gag gtt atc cca ctc ttt gtg aaa      1920
Tyr Tyr Leu Val Asp Ala Pro Ile Glu Val Ile Pro Leu Phe Val Lys
625                 630                 635                 640

gag ggt gga att ctt ctt aag cag cag cca cag tct ttt att gga gag      1968
Glu Gly Gly Ile Leu Leu Lys Gln Gln Pro Gln Ser Phe Ile Gly Glu
                645                 650                 655

aag aag ctc gag gaa ctt act gtt gag atc tac aag gga aaa gag gga      2016
Lys Lys Leu Glu Glu Leu Thr Val Glu Ile Tyr Lys Gly Lys Glu Gly
            660                 665                 670

cat tac ctc cat tat gag gat gat gga aag tcc ttc gat tac act aag      2064
His Tyr Leu His Tyr Glu Asp Asp Gly Lys Ser Phe Asp Tyr Thr Lys
        675                 680                 685

ggc gtg tac aac ctc ttc gat atc tca ttc tgc tac aaa gag gga agg      2112
Gly Val Tyr Asn Leu Phe Asp Ile Ser Phe Cys Tyr Lys Glu Gly Arg
    690                 695                 700

atg gat atc aag ttc gat aag atc cac ttc gga tac gat aag ggt gtt      2160
Met Asp Ile Lys Phe Asp Lys Ile His Phe Gly Tyr Asp Lys Gly Val
705                 710                 715                 720

aag aag tac aag ttc atc ttc aag aac ttc gat gat atc aaa gag atc      2208
Lys Lys Tyr Lys Phe Ile Phe Lys Asn Phe Asp Asp Ile Lys Glu Ile
                725                 730                 735
```

```
aag atc aac ggc gag aag gtt gag aaa gag tct tgc gag att gag ctt      2256
Lys Ile Asn Gly Glu Lys Val Glu Lys Glu Ser Cys Glu Ile Glu Leu
            740                 745                 750

taa                                                                  2259


<210> SEQ ID NO 12
<211> LENGTH: 752
<212> TYPE: PRT
<213> ORGANISM: T. ethanolicus

<400> SEQUENCE: 12

Met Tyr Gln Lys Thr Ser Glu Lys Ile Val Val Arg Asn Glu Gly Lys
1               5                   10                  15

Lys Leu Glu Leu Arg Val Leu Gly Asp Lys Ile Ile Asn Val Phe Val
            20                  25                  30

Ser Asn Lys Glu Glu Lys Arg Lys Asp Thr Ile Ala Ile Glu Arg Lys
        35                  40                  45

Glu Tyr Asp Thr Pro Glu Phe Ser Ile Ser Asp Glu Leu Glu Ser Ile
    50                  55                  60

Leu Ile Glu Thr Asn Ser Leu Lys Val Lys Ile Asn Lys Asn Asp Leu
65                  70                  75                  80

Ser Val Ser Phe Leu Asp Lys Asn Gly Asn Ile Ile Asn Glu Asp Tyr
                85                  90                  95

Asn Gly Gly Ala Lys Phe Asn Glu Thr Asp Val Arg Cys Tyr Lys Lys
            100                 105                 110

Leu Arg Glu Asp His Phe Tyr Gly Phe Gly Glu Lys Ala Gly Tyr Leu
        115                 120                 125

Asp Lys Lys Gly Glu Arg Leu Glu Met Trp Asn Thr Asp Glu Phe Met
    130                 135                 140

Thr His Asn Gln Thr Thr Lys Leu Leu Tyr Glu Ser Tyr Pro Phe Phe
145                 150                 155                 160

Ile Gly Met Asn Asp Tyr His Thr Tyr Gly Ile Phe Leu Asp Asn Ser
                165                 170                 175

Phe Arg Ser Phe Phe Asp Met Gly Gln Glu Ser Gln Glu Tyr Tyr Phe
            180                 185                 190

Phe Gly Ala Tyr Gly Gly Gln Met Asn Tyr Tyr Phe Ile Tyr Gly Glu
        195                 200                 205

Asp Ile Lys Glu Val Val Glu Asn Tyr Thr Tyr Leu Thr Gly Arg Ile
    210                 215                 220

Ser Leu Pro Pro Leu Trp Val Leu Gly Asn Gln Gln Ser Arg Tyr Ser
225                 230                 235                 240

Tyr Thr Pro Gln Glu Arg Val Leu Glu Val Ala Lys Thr Phe Arg Glu
                245                 250                 255

Lys Asp Ile Pro Cys Asp Val Ile Tyr Leu Asp Ile Asp Tyr Met Glu
            260                 265                 270

Gly Tyr Arg Val Phe Thr Trp Asn Lys Glu Thr Phe Lys Asn His Lys
        275                 280                 285

Glu Met Leu Lys Gln Leu Lys Glu Met Gly Phe Lys Val Val Thr Ile
    290                 295                 300

Val Asp Pro Gly Val Lys Arg Asp Tyr Asp Tyr His Val Tyr Arg Glu
305                 310                 315                 320

Gly Ile Glu Lys Gly Tyr Phe Val Lys Asp Lys Tyr Gly Ile Thr Tyr
                325                 330                 335

Val Gly Lys Val Trp Pro Gly Glu Ala Cys Phe Pro Asp Phe Leu Gln
```

```
            340                 345                 350

Glu Glu Val Arg Tyr Trp Trp Gly Glu Lys His Arg Glu Phe Ile Asn
        355                 360                 365

Asp Gly Ile Asp Gly Ile Trp Asn Asp Met Asn Glu Pro Ala Val Phe
    370                 375                 380

Glu Thr Pro Thr Lys Thr Met Pro Glu Asp Asn Ile His Ile Leu Asp
385                 390                 395                 400

Gly Glu Lys Val Leu His Lys Glu Ala His Asn Val Tyr Ala Asn Tyr
                405                 410                 415

Met Ala Met Ala Thr Arg Asp Gly Phe Leu Arg Ile Arg Pro Asn Glu
            420                 425                 430

Arg Pro Phe Val Leu Thr Arg Ala Ala Phe Ser Gly Ile Gln Arg Tyr
        435                 440                 445

Ala Ala Met Trp Thr Gly Asp Asn Arg Ser Leu Tyr Glu His Leu Leu
    450                 455                 460

Met Met Met Pro Met Leu Met Asn Ile Gly Leu Ser Gly Gln Pro Phe
465                 470                 475                 480

Val Gly Ala Asp Val Gly Gly Phe Glu Gly Asp Cys His Glu Glu Leu
                485                 490                 495

Phe Ile Arg Trp Ile Glu Ala Ala Val Phe Thr Pro Phe Leu Arg Val
            500                 505                 510

His Ser Ala Ile Gly Thr Lys Asp Gln Glu Pro Trp Ser Phe Gly Lys
        515                 520                 525

Arg Ala Glu Asp Ile Ser Arg Lys Tyr Ile Lys Met Arg Tyr Glu Leu
    530                 535                 540

Leu Pro Tyr Leu Tyr Asp Leu Phe Tyr Ile Ala Ser Gln Lys Gly Tyr
545                 550                 555                 560

Pro Ile Met Arg Pro Leu Val Phe Glu Tyr Gln Lys Asp Glu Asn Thr
                565                 570                 575

His Lys Ile Tyr Asp Glu Phe Met Phe Gly Glu Gly Leu Leu Val Ala
            580                 585                 590

Pro Val Tyr Leu Pro Ser Lys Glu Arg Arg Glu Val Tyr Leu Pro Glu
        595                 600                 605

Gly Ile Trp Tyr Asp Tyr Trp Thr Gly Lys Gly Phe Lys Gly Lys Asn
    610                 615                 620

Tyr Tyr Leu Val Asp Ala Pro Ile Glu Val Ile Pro Leu Phe Val Lys
625                 630                 635                 640

Glu Gly Gly Ile Leu Leu Lys Gln Gln Pro Gln Ser Phe Ile Gly Glu
                645                 650                 655

Lys Lys Leu Glu Glu Leu Thr Val Glu Ile Tyr Lys Gly Lys Glu Gly
            660                 665                 670

His Tyr Leu His Tyr Glu Asp Asp Gly Lys Ser Phe Asp Tyr Thr Lys
        675                 680                 685

Gly Val Tyr Asn Leu Phe Asp Ile Ser Phe Cys Tyr Lys Glu Gly Arg
    690                 695                 700

Met Asp Ile Lys Phe Asp Lys Ile His Phe Gly Tyr Asp Lys Gly Val
705                 710                 715                 720

Lys Lys Tyr Lys Phe Ile Phe Lys Asn Phe Asp Asp Ile Lys Glu Ile
                725                 730                 735

Lys Ile Asn Gly Glu Lys Val Glu Lys Glu Ser Cys Glu Ile Glu Leu
            740                 745                 750

<210> SEQ ID NO 13
```

<211> LENGTH: 19
<212> TYPE: PRT
<213> ORGANISM: soybean
<220> FEATURE:
<221> NAME/KEY: targeting
<222> LOCATION: (1)..(19)
<223> OTHER INFORMATION: ER targeting sequence

<400> SEQUENCE: 13

```
Met Ala Lys Leu Val Phe Ser Leu Cys Phe Leu Leu Phe Ser Gly Cys
1               5                   10                  15

Cys Phe Ala
```

<210> SEQ ID NO 14
<211> LENGTH: 566
<212> TYPE: PRT
<213> ORGANISM: Erwinia carotovora
<220> FEATURE:
<221> NAME/KEY: enzyme
<222> LOCATION: (1)..(566)
<223> OTHER INFORMATION: sucrose isomerase YP 049947

<400> SEQUENCE: 14

```
Met Val Ala Val Asn Asp Gly Val Ser Ala His Pro Val Trp Trp Lys
1               5                   10                  15

Glu Ala Val Phe Tyr Gln Val Tyr Pro Arg Ser Phe Lys Asp Ser Asp
            20                  25                  30

Gly Asp Gly Ile Gly Asp Leu Lys Gly Leu Thr Glu Lys Leu Asp Tyr
        35                  40                  45

Leu Lys Ala Leu Gly Ile Asn Ala Ile Trp Ile Asn Pro His Tyr Asp
    50                  55                  60

Ser Pro Asn Thr Asp Asn Gly Tyr Asp Ile Arg Asp Tyr Arg Lys Ile
65                  70                  75                  80

Met Lys Glu Tyr Gly Thr Met Asp Asp Phe Asp Arg Leu Ile Ala Glu
                85                  90                  95

Met Lys Lys Arg Asp Met Arg Leu Met Ile Asp Val Val Val Asn His
            100                 105                 110

Thr Ser Asp Glu His Glu Trp Phe Val Glu Ser Lys Lys Ser Lys Asp
        115                 120                 125

Asn Pro Tyr Arg Asp Tyr Tyr Ile Trp Arg Asp Gly Lys Asp Gly Thr
    130                 135                 140

Gln Pro Asn Asn Tyr Pro Ser Phe Phe Gly Gly Ser Ala Trp Gln Lys
145                 150                 155                 160

Asp Asn Ala Thr Gln Gln Tyr Tyr Leu His Tyr Phe Gly Val Gln Gln
                165                 170                 175

Pro Asp Leu Asn Trp Asp Asn Pro Lys Val Arg Glu Glu Val Tyr Asp
            180                 185                 190

Met Leu Arg Phe Trp Ile Asp Lys Gly Val Ser Gly Leu Arg Met Asp
        195                 200                 205

Thr Val Ala Thr Phe Ser Lys Asn Pro Ala Phe Pro Asp Leu Thr Pro
    210                 215                 220

Lys Gln Leu Gln Asn Phe Ala Tyr Thr Tyr Thr Gln Gly Pro Asn Leu
225                 230                 235                 240

His Arg Tyr Ile Gln Glu Met His Gln Lys Val Leu Ala Lys Tyr Asp
                245                 250                 255

Val Val Ser Ala Gly Glu Ile Phe Gly Val Pro Leu Glu Glu Ala Ala
            260                 265                 270

Pro Phe Ile Asp Gln Arg Arg Lys Glu Leu Asp Met Ala Phe Ser Phe
```

-continued

```
        275                 280                 285

Asp Leu Ile Arg Leu Asp Arg Ala Val Glu Glu Arg Trp Arg Arg Asn
    290                 295                 300

Asp Trp Thr Leu Ser Gln Phe Arg Gln Ile Asn Asn Arg Leu Val Asp
305                 310                 315                 320

Met Ala Gly Gln His Gly Trp Asn Thr Phe Phe Leu Ser Asn His Asp
                325                 330                 335

Asn Pro Arg Ala Val Ser His Phe Gly Asp Asp Arg Pro Glu Trp Arg
            340                 345                 350

Thr Arg Ser Ala Lys Ala Leu Ala Thr Leu Ala Leu Thr Gln Arg Ala
        355                 360                 365

Thr Pro Phe Ile Tyr Gln Gly Asp Glu Leu Gly Met Thr Asn Tyr Pro
    370                 375                 380

Phe Thr Ser Leu Ser Glu Phe Asp Asp Ile Glu Val Lys Gly Phe Trp
385                 390                 395                 400

Gln Asp Phe Val Glu Thr Gly Lys Val Lys Pro Asp Val Phe Leu Glu
                405                 410                 415

Asn Val Lys Gln Thr Ser Arg Asp Asn Ser Arg Thr Pro Phe Gln Trp
            420                 425                 430

Ser Asn Thr Ala Gln Ala Gly Phe Thr Thr Gly Thr Pro Trp Phe Arg
        435                 440                 445

Ile Asn Pro Asn Tyr Lys Asn Ile Asn Ala Glu Glu Gln Thr Gln Asn
    450                 455                 460

Pro Asp Ser Ile Phe His Phe Tyr Arg Gln Leu Ile Glu Leu Arg His
465                 470                 475                 480

Ala Thr Pro Ala Phe Thr Tyr Gly Thr Tyr Gln Asp Leu Asp Pro Asn
                485                 490                 495

Asn Asn Glu Val Leu Ala Tyr Thr Arg Glu Leu Asn Gln Gln Arg Tyr
            500                 505                 510

Leu Val Val Val Asn Phe Lys Glu Lys Pro Val His Tyr Val Leu Pro
        515                 520                 525

Lys Thr Leu Ser Ile Lys Gln Ser Leu Leu Glu Ser Gly Gln Lys Asp
    530                 535                 540

Lys Val Glu Pro Asn Ala Thr Thr Leu Glu Leu Gln Pro Trp Gln Ser
545                 550                 555                 560

Gly Ile Tyr Gln Leu Asn
                565


<210> SEQ ID NO 15
<211> LENGTH: 16
<212> TYPE: PRT
<213> ORGANISM: sweet potato
<220> FEATURE:
<221> NAME/KEY: SIGNAL
<222> LOCATION: (1)..(16)
<223> OTHER INFORMATION: sporamin vacuolar targeting sequence

<400> SEQUENCE: 15

His Ser Arg Phe Asn Pro Ile Arg Leu Pro Thr Thr His Glu Pro Ala
1               5                   10                  15


<210> SEQ ID NO 16
<211> LENGTH: 1701
<212> TYPE: DNA
<213> ORGANISM: unknown
<220> FEATURE:
<223> OTHER INFORMATION: artificial sequence
<220> FEATURE:
```

```
<221> NAME/KEY: CDS
<222> LOCATION: (1)..(1701)
<223> OTHER INFORMATION: sucrose isomerase dicot optimized

<400> SEQUENCE: 16

atg gtt gct gtt aac gat ggt gtt tct gct cat cca gtt tgg tgg aaa       48
Met Val Ala Val Asn Asp Gly Val Ser Ala His Pro Val Trp Trp Lys
1               5                   10                  15

gag gct gtt ttc tac caa gtt tac cca cgt tct ttc aag gat tcc gat       96
Glu Ala Val Phe Tyr Gln Val Tyr Pro Arg Ser Phe Lys Asp Ser Asp
            20                  25                  30

ggt gat gga att gga gat ctc aag gga ctt act gag aag ctc gat tac      144
Gly Asp Gly Ile Gly Asp Leu Lys Gly Leu Thr Glu Lys Leu Asp Tyr
        35                  40                  45

ctt aag gct ctc ggt att aac gct atc tgg atc aac cca cac tac gat      192
Leu Lys Ala Leu Gly Ile Asn Ala Ile Trp Ile Asn Pro His Tyr Asp
    50                  55                  60

tct cca aac act gat aac gga tac gat atc agg gat tac cgt aaa atc      240
Ser Pro Asn Thr Asp Asn Gly Tyr Asp Ile Arg Asp Tyr Arg Lys Ile
65                  70                  75                  80

atg aag gaa tac gga act atg gat gat ttc gat agg ctt atc gct gaa      288
Met Lys Glu Tyr Gly Thr Met Asp Asp Phe Asp Arg Leu Ile Ala Glu
                85                  90                  95

atg aag aaa agg gat atg agg ctc atg att gat gtt gtg gtg aac cac      336
Met Lys Lys Arg Asp Met Arg Leu Met Ile Asp Val Val Val Asn His
            100                 105                 110

act tct gat gag cat gag tgg ttc gtt gag tct aag aag tcc aag gat      384
Thr Ser Asp Glu His Glu Trp Phe Val Glu Ser Lys Lys Ser Lys Asp
        115                 120                 125

aac cca tac cgt gat tac tac atc tgg cgt gat gga aag gat gga act      432
Asn Pro Tyr Arg Asp Tyr Tyr Ile Trp Arg Asp Gly Lys Asp Gly Thr
    130                 135                 140

cag cca aat aac tac cca tct ttc ttc ggt gga tct gct tgg caa aag      480
Gln Pro Asn Asn Tyr Pro Ser Phe Phe Gly Gly Ser Ala Trp Gln Lys
145                 150                 155                 160

gat aat gct act cag cag tac tac ctt cac tac ttc gga gtt caa cag      528
Asp Asn Ala Thr Gln Gln Tyr Tyr Leu His Tyr Phe Gly Val Gln Gln
                165                 170                 175

cca gat ctc aat tgg gat aac cca aaa gtt agg gaa gag gtg tac gat      576
Pro Asp Leu Asn Trp Asp Asn Pro Lys Val Arg Glu Glu Val Tyr Asp
            180                 185                 190

atg ctt agg ttc tgg atc gat aag ggt gtt agt gga ctc aga atg gat      624
Met Leu Arg Phe Trp Ile Asp Lys Gly Val Ser Gly Leu Arg Met Asp
        195                 200                 205

act gtg gct act ttc tct aag aat cca gct ttc cca gat ctt act cca      672
Thr Val Ala Thr Phe Ser Lys Asn Pro Ala Phe Pro Asp Leu Thr Pro
    210                 215                 220

aag cag ctt cag aac ttc gct tac act tac act cag gga cca aat ctt      720
Lys Gln Leu Gln Asn Phe Ala Tyr Thr Tyr Thr Gln Gly Pro Asn Leu
225                 230                 235                 240

cac cgt tac atc caa gag atg cac caa aag gtt ctc gct aag tac gat      768
His Arg Tyr Ile Gln Glu Met His Gln Lys Val Leu Ala Lys Tyr Asp
                245                 250                 255

gtt gtt tcc gct ggt gaa att ttc gga gtg cca ctt gaa gaa gct gct      816
Val Val Ser Ala Gly Glu Ile Phe Gly Val Pro Leu Glu Glu Ala Ala
            260                 265                 270

cca ttc att gat cag agg cgt aaa gaa ctc gat atg gct ttc tcc ttc      864
Pro Phe Ile Asp Gln Arg Arg Lys Glu Leu Asp Met Ala Phe Ser Phe
        275                 280                 285

gat ctt atc cgt ctt gat agg gct gtt gaa gaa agg tgg agg cgt aat      912
```

```
Asp Leu Ile Arg Leu Asp Arg Ala Val Glu Glu Arg Trp Arg Arg Asn
    290                 295                 300

gat tgg act ttg tcc cag ttc agg cag att aac aac agg ctt gtg gat      960
Asp Trp Thr Leu Ser Gln Phe Arg Gln Ile Asn Asn Arg Leu Val Asp
305                 310                 315                 320

atg gct gga caa cat gga tgg aat act ttc ttc ctc tcc aac cat gat     1008
Met Ala Gly Gln His Gly Trp Asn Thr Phe Phe Leu Ser Asn His Asp
                325                 330                 335

aat cca agg gct gtt tct cat ttc gga gat gat aga cca gag tgg aga     1056
Asn Pro Arg Ala Val Ser His Phe Gly Asp Asp Arg Pro Glu Trp Arg
            340                 345                 350

act aga tct gct aag gct ctt gct act ctt gct ctt act caa agg gct     1104
Thr Arg Ser Ala Lys Ala Leu Ala Thr Leu Ala Leu Thr Gln Arg Ala
        355                 360                 365

act cca ttc atc tat cag ggt gat gag ctt gga atg act aac tac cca     1152
Thr Pro Phe Ile Tyr Gln Gly Asp Glu Leu Gly Met Thr Asn Tyr Pro
    370                 375                 380

ttc act tca ctt tcc gag ttc gat gat att gag gtg aag gga ttc tgg     1200
Phe Thr Ser Leu Ser Glu Phe Asp Asp Ile Glu Val Lys Gly Phe Trp
385                 390                 395                 400

caa gat ttt gtg gag act gga aag gtt aag cca gat gtg ttc ctt gag     1248
Gln Asp Phe Val Glu Thr Gly Lys Val Lys Pro Asp Val Phe Leu Glu
                405                 410                 415

aac gtg aag caa act tct agg gat aac tcc agg act cca ttc caa tgg     1296
Asn Val Lys Gln Thr Ser Arg Asp Asn Ser Arg Thr Pro Phe Gln Trp
            420                 425                 430

tct aat act gct cag gct gga ttc act act gga aca cct tgg ttt agg     1344
Ser Asn Thr Ala Gln Ala Gly Phe Thr Thr Gly Thr Pro Trp Phe Arg
        435                 440                 445

atc aac cct aac tac aag aac atc aac gct gag gaa caa act cag aac     1392
Ile Asn Pro Asn Tyr Lys Asn Ile Asn Ala Glu Glu Gln Thr Gln Asn
    450                 455                 460

cca gat tcc atc ttc cat ttc tac cgt cag ttg att gaa ctt agg cat     1440
Pro Asp Ser Ile Phe His Phe Tyr Arg Gln Leu Ile Glu Leu Arg His
465                 470                 475                 480

gct act cca gct ttt act tac gga act tac cag gat ctt gat cca aac     1488
Ala Thr Pro Ala Phe Thr Tyr Gly Thr Tyr Gln Asp Leu Asp Pro Asn
                485                 490                 495

aac aac gag gtt ctc gct tac act aga gag ctt aac cag cag aga tac     1536
Asn Asn Glu Val Leu Ala Tyr Thr Arg Glu Leu Asn Gln Gln Arg Tyr
            500                 505                 510

ctt gtt gtt gtg aac ttc aaa gag aag cca gtt cac tac gtt ctt cca     1584
Leu Val Val Val Asn Phe Lys Glu Lys Pro Val His Tyr Val Leu Pro
        515                 520                 525

aag act ctt tcc att aag cag tct ttg ctt gag tct gga cag aag gat     1632
Lys Thr Leu Ser Ile Lys Gln Ser Leu Leu Glu Ser Gly Gln Lys Asp
    530                 535                 540

aag gtt gag cca aac gct act act ctt gag ctt caa cct tgg caa tct     1680
Lys Val Glu Pro Asn Ala Thr Thr Leu Glu Leu Gln Pro Trp Gln Ser
545                 550                 555                 560

gga atc tac cag ctc aac tga                                         1701
Gly Ile Tyr Gln Leu Asn
                565


<210> SEQ ID NO 17
<211> LENGTH: 566
<212> TYPE: PRT
<213> ORGANISM: unknown
<220> FEATURE:
<223> OTHER INFORMATION: Synthetic Construct
```

<400> SEQUENCE: 17

Met Val Ala Val Asn Asp Gly Val Ser Ala His Pro Val Trp Trp Lys
1               5                   10                  15

Glu Ala Val Phe Tyr Gln Val Tyr Pro Arg Ser Phe Lys Asp Ser Asp
            20                  25                  30

Gly Asp Gly Ile Gly Asp Leu Lys Gly Leu Thr Glu Lys Leu Asp Tyr
        35                  40                  45

Leu Lys Ala Leu Gly Ile Asn Ala Ile Trp Ile Asn Pro His Tyr Asp
    50                  55                  60

Ser Pro Asn Thr Asp Asn Gly Tyr Asp Ile Arg Asp Tyr Arg Lys Ile
65                  70                  75                  80

Met Lys Glu Tyr Gly Thr Met Asp Asp Phe Asp Arg Leu Ile Ala Glu
                85                  90                  95

Met Lys Lys Arg Asp Met Arg Leu Met Ile Asp Val Val Val Asn His
            100                 105                 110

Thr Ser Asp Glu His Glu Trp Phe Val Glu Ser Lys Lys Ser Lys Asp
        115                 120                 125

Asn Pro Tyr Arg Asp Tyr Tyr Ile Trp Arg Asp Gly Lys Asp Gly Thr
    130                 135                 140

Gln Pro Asn Asn Tyr Pro Ser Phe Phe Gly Gly Ser Ala Trp Gln Lys
145                 150                 155                 160

Asp Asn Ala Thr Gln Gln Tyr Tyr Leu His Tyr Phe Gly Val Gln Gln
                165                 170                 175

Pro Asp Leu Asn Trp Asp Asn Pro Lys Val Arg Glu Glu Val Tyr Asp
            180                 185                 190

Met Leu Arg Phe Trp Ile Asp Lys Gly Val Ser Gly Leu Arg Met Asp
        195                 200                 205

Thr Val Ala Thr Phe Ser Lys Asn Pro Ala Phe Pro Asp Leu Thr Pro
    210                 215                 220

Lys Gln Leu Gln Asn Phe Ala Tyr Thr Tyr Thr Gln Gly Pro Asn Leu
225                 230                 235                 240

His Arg Tyr Ile Gln Glu Met His Gln Lys Val Leu Ala Lys Tyr Asp
                245                 250                 255

Val Val Ser Ala Gly Glu Ile Phe Gly Val Pro Leu Glu Glu Ala Ala
            260                 265                 270

Pro Phe Ile Asp Gln Arg Arg Lys Glu Leu Asp Met Ala Phe Ser Phe
        275                 280                 285

Asp Leu Ile Arg Leu Asp Arg Ala Val Glu Glu Arg Trp Arg Arg Asn
    290                 295                 300

Asp Trp Thr Leu Ser Gln Phe Arg Gln Ile Asn Asn Arg Leu Val Asp
305                 310                 315                 320

Met Ala Gly Gln His Gly Trp Asn Thr Phe Phe Leu Ser Asn His Asp
                325                 330                 335

Asn Pro Arg Ala Val Ser His Phe Gly Asp Asp Arg Pro Glu Trp Arg
            340                 345                 350

Thr Arg Ser Ala Lys Ala Leu Ala Thr Leu Ala Leu Thr Gln Arg Ala
        355                 360                 365

Thr Pro Phe Ile Tyr Gln Gly Asp Glu Leu Gly Met Thr Asn Tyr Pro
    370                 375                 380

Phe Thr Ser Leu Ser Glu Phe Asp Asp Ile Glu Val Lys Gly Phe Trp
385                 390                 395                 400

Gln Asp Phe Val Glu Thr Gly Lys Val Lys Pro Asp Val Phe Leu Glu
                405                 410                 415

```
Asn Val Lys Gln Thr Ser Arg Asp Asn Ser Arg Thr Pro Phe Gln Trp
            420                 425                 430

Ser Asn Thr Ala Gln Ala Gly Phe Thr Thr Gly Thr Pro Trp Phe Arg
        435                 440                 445

Ile Asn Pro Asn Tyr Lys Asn Ile Asn Ala Glu Glu Gln Thr Gln Asn
    450                 455                 460

Pro Asp Ser Ile Phe His Phe Tyr Arg Gln Leu Ile Glu Leu Arg His
465                 470                 475                 480

Ala Thr Pro Ala Phe Thr Tyr Gly Thr Tyr Gln Asp Leu Asp Pro Asn
                485                 490                 495

Asn Asn Glu Val Leu Ala Tyr Thr Arg Glu Leu Asn Gln Gln Arg Tyr
            500                 505                 510

Leu Val Val Val Asn Phe Lys Glu Lys Pro Val His Tyr Val Leu Pro
        515                 520                 525

Lys Thr Leu Ser Ile Lys Gln Ser Leu Leu Glu Ser Gly Gln Lys Asp
    530                 535                 540

Lys Val Glu Pro Asn Ala Thr Thr Leu Glu Leu Gln Pro Trp Gln Ser
545                 550                 555                 560

Gly Ile Tyr Gln Leu Asn
                565
```

<210> SEQ ID NO 18
<211> LENGTH: 1993
<212> TYPE: DNA
<213> ORGANISM: Zea maize
<220> FEATURE:
<221> NAME/KEY: promoter
<222> LOCATION: (1)..(1993)
<223> OTHER INFORMATION: maize UBQ promoter

<400> SEQUENCE: 18

```
ctgcagtgca gcgtgacccg gtcgtgcccc tctctagaga taatgagcat tgcatgtcta      60

agttataaaa aattaccaca tattttttt gtcacacttg tttgaagtgc agtttatcta     120

tctttataca tatatttaaa ctttactcta cgaataatat aatctatagt actacaataa     180

tatcagtgtt ttagagaatc atataaatga acagttagac atggtctaaa ggacaattga     240

gtattttgac aacaggactc tacagtttta tctttttagt gtgcatgtgt tctccttttt     300

ttttgcaaat agcttcacct atataatact tcatccattt tattagtaca tccatttagg     360

gtttagggtt aatggttttt atagactaat ttttttagta catctatttt attctatttt     420

agcctctaaa ttaagaaaac taaaactcta ttttagtttt tttatttaat aatttagata     480

taaaatagaa taaaataaag tgactaaaaa ttaaacaaat accctttaag aaattaaaaa     540

aactaaggaa acatttttct tgtttcgagt agataatgcc agcctgttaa acgccgccga     600

cgagtctaac ggacaccaac cagcgaacca gcagcgtcgc gtcgggccaa gcgaagcaga     660

cggcacggca tctctgtcgc tgcctctgga cccctctcga gagttccgct ccaccgttgg     720

acttgctccg ctgtcggcat ccagaaattg cgtggcggag cggcagacgt gagccggcac     780

ggcaggcggc ctcctcctcc tctcacggca ccggcagcta cgggggattc ctttcccacc     840

gctccttcgc tttcccttcc tcgcccgccg taataaatag acacccctc cacaccctct     900

ttccccaacc tcgtgttgtt cggagcgcac acacacacaa ccagatctcc cccaaatcca     960

cccgtcggca cctccgcttc aaggtacgcc gctcgtcctc cccccccccc cctctctacc    1020

ttctctagat cggcgttccg gtccatagtt agggcccggt agttctactt ctgttcatgt    1080
```

```
ttgtgttaga tccgtgtttg tgttagatcc gtgctgttag cgttcgtaca cggatgcgac   1140

ctgtacgtca gacacgttct gattgctaac ttgccagtgt ttctctttgg ggaatcctgg   1200

gatggctcta gccgttccgc agacgggatc gatttcatga ttttttttgt ttcgttgcat   1260

agggtttggt ttgccctttt cctttatttc aatatatgcc gtgcacttgt ttgtcgggtc   1320

atcttttcat gctttttttt gtcttggttg tgatgatgtg gtctggttgg gcggtcgttc   1380

tagatcggag tagaattctg tttcaaacta cctggtggat ttattaattt tggatctgta   1440

tgtgtgtgcc atacatattc atagttacga attgaagatg atggatggaa atatcgatct   1500

aggataggta tacatgttga tgcgggtttt actgatgcat atacagagat gctttttgtt   1560

cgcttggttg tgatgatgtg gtgtggttgg gcggtcgttc attcgttcta gatcggagta   1620

gaatactgtt tcaaactacc tggtgtattt attaattttg gaactgtatg tgtgtgtcat   1680

acatcttcat agttacgagt ttaagatgga tggaaatatc gatctaggat aggtatacat   1740

gttgatgtgg gttttactga tgcatataca tgatggcata tgcagcatct attcatatgc   1800

tctaaccttg agtacctatc tattataata aacaagtatg ttttataatt attttgatct   1860

tgatatactt ggatgatggc atatgcagca gctatatgtg gatttttta gccctgcctt    1920

catacgctat ttatttgctt ggtactgttt cttttgtcga tgctcaccct gttgtttggt   1980

gttacttctg cag                                                      1993
```

```
<210> SEQ ID NO 19
<211> LENGTH: 20
<212> TYPE: PRT
<213> ORGANISM: Zea maize
<220> FEATURE:
<221> NAME/KEY: signal
<222> LOCATION: (1)..(20)
<223> OTHER INFORMATION: ER targeting sequence monocot

<400> SEQUENCE: 19

Met Arg Val Leu Leu Val Ala Leu Ala Leu Leu Ala Leu Ala Ala Ala
1               5                   10                  15

Ser Ala Thr Ser
            20


<210> SEQ ID NO 20
<211> LENGTH: 1698
<212> TYPE: DNA
<213> ORGANISM: unknown
<220> FEATURE:
<223> OTHER INFORMATION: artificial sequence
<220> FEATURE:
<221> NAME/KEY: CDS
<222> LOCATION: (1)..(1698)
<223> OTHER INFORMATION: monocot optimized sucrose isomerase

<400> SEQUENCE: 20

gtg gcc gtg aac gac ggc gtg tcc gcc cac cca gtg tgg tgg aag gag       48
Val Ala Val Asn Asp Gly Val Ser Ala His Pro Val Trp Trp Lys Glu
1               5                   10                  15

gcc gtt ttc tac cag gtg tac ccg cgc agc ttc aag gac agc gac ggc       96
Ala Val Phe Tyr Gln Val Tyr Pro Arg Ser Phe Lys Asp Ser Asp Gly
            20                  25                  30

gac ggc atc ggc gac ctg aag ggc ctg acc gag aag ctg gac tac ctg      144
Asp Gly Ile Gly Asp Leu Lys Gly Leu Thr Glu Lys Leu Asp Tyr Leu
        35                  40                  45

aag gcc ctg ggc atc aac gcc atc tgg atc aac ccg cac tac gac agc      192
Lys Ala Leu Gly Ile Asn Ala Ile Trp Ile Asn Pro His Tyr Asp Ser
    50                  55                  60
```

```
ccg aac acc gac aac ggc tac gat atc cgc gac tac cgc aag atc atg      240
Pro Asn Thr Asp Asn Gly Tyr Asp Ile Arg Asp Tyr Arg Lys Ile Met
65                  70                  75                  80

aag gaa tac ggc acg atg gac gac ttc gac cgc ctg atc gcc gag atg      288
Lys Glu Tyr Gly Thr Met Asp Asp Phe Asp Arg Leu Ile Ala Glu Met
                85                  90                  95

aag aag cgc gac atg cgc ctg atg atc gac gtg gtg gtg aac cac acc      336
Lys Lys Arg Asp Met Arg Leu Met Ile Asp Val Val Val Asn His Thr
            100                 105                 110

agc gac gag cac gag tgg ttc gtg gag agc aag aag tcc aag gac aac      384
Ser Asp Glu His Glu Trp Phe Val Glu Ser Lys Lys Ser Lys Asp Asn
        115                 120                 125

ccg tac cgc gac tac tac atc tgg cgc gac ggc aag gac ggc acc cag      432
Pro Tyr Arg Asp Tyr Tyr Ile Trp Arg Asp Gly Lys Asp Gly Thr Gln
    130                 135                 140

ccg aac aac tac ccg agc ttc ttc ggc ggc agc gcc tgg cag aag gac      480
Pro Asn Asn Tyr Pro Ser Phe Phe Gly Gly Ser Ala Trp Gln Lys Asp
145                 150                 155                 160

aac gcc acc cag cag tac tac ctg cac tac ttc ggc gtc cag cag ccg      528
Asn Ala Thr Gln Gln Tyr Tyr Leu His Tyr Phe Gly Val Gln Gln Pro
                165                 170                 175

gac ctg aac tgg gac aac ccg aaa gtg agg gag gag gtg tac gac atg      576
Asp Leu Asn Trp Asp Asn Pro Lys Val Arg Glu Glu Val Tyr Asp Met
            180                 185                 190

ctg agg ttc tgg atc gac aag ggc gtg tcc ggc ctg agg atg gac acc      624
Leu Arg Phe Trp Ile Asp Lys Gly Val Ser Gly Leu Arg Met Asp Thr
        195                 200                 205

gtg gcc acc ttc agc aag aac ccg gcc ttc ccg gac ctg acc ccg aag      672
Val Ala Thr Phe Ser Lys Asn Pro Ala Phe Pro Asp Leu Thr Pro Lys
    210                 215                 220

cag ctc cag aac ttc gcc tac acc tac acc cag ggc ccg aac ctg cac      720
Gln Leu Gln Asn Phe Ala Tyr Thr Tyr Thr Gln Gly Pro Asn Leu His
225                 230                 235                 240

cgc tac atc cag gag atg cac cag aag gtc ctg gcc aag tac gac gtg      768
Arg Tyr Ile Gln Glu Met His Gln Lys Val Leu Ala Lys Tyr Asp Val
                245                 250                 255

gtg tct gcc ggc gag atc ttc ggc gtg ccg ctc gag gag gcc gct ccg      816
Val Ser Ala Gly Glu Ile Phe Gly Val Pro Leu Glu Glu Ala Ala Pro
            260                 265                 270

ttc atc gac cag cgc cgg aag gaa ctg gac atg gcc ttc agc ttc gac      864
Phe Ile Asp Gln Arg Arg Lys Glu Leu Asp Met Ala Phe Ser Phe Asp
        275                 280                 285

ctg atc cgc ctc gac agg gcc gtg gag gag agg tgg cgc cgc aac gac      912
Leu Ile Arg Leu Asp Arg Ala Val Glu Glu Arg Trp Arg Arg Asn Asp
    290                 295                 300

tgg acc ctg agc cag ttc cgc cag atc aac aac cgc ctg gtg gac atg      960
Trp Thr Leu Ser Gln Phe Arg Gln Ile Asn Asn Arg Leu Val Asp Met
305                 310                 315                 320

gcc ggc cag cac ggc tgg aac acg ttc ttc ctc agc aac cac gac aac     1008
Ala Gly Gln His Gly Trp Asn Thr Phe Phe Leu Ser Asn His Asp Asn
                325                 330                 335

ccg agg gcc gtg tcc cac ttc ggc gac gac agg cca gag tgg agg acc     1056
Pro Arg Ala Val Ser His Phe Gly Asp Asp Arg Pro Glu Trp Arg Thr
            340                 345                 350

cgc agc gcc aag gcc ctg gcc acc ctg gcc ctg acc cag agg gct acc     1104
Arg Ser Ala Lys Ala Leu Ala Thr Leu Ala Leu Thr Gln Arg Ala Thr
        355                 360                 365

cca ttc atc tac cag ggc gac gag ctg ggc atg acc aac tac ccg ttc     1152
Pro Phe Ile Tyr Gln Gly Asp Glu Leu Gly Met Thr Asn Tyr Pro Phe
```

```
    370                 375                 380

acc agc ctg agc gag ttc gac gat atc gag gtg aag ggc ttc tgg cag     1200
Thr Ser Leu Ser Glu Phe Asp Asp Ile Glu Val Lys Gly Phe Trp Gln
385                 390                 395                 400

gac ttc gtg gag act ggc aag gtg aag cca gac gtg ttc ctc gag aac     1248
Asp Phe Val Glu Thr Gly Lys Val Lys Pro Asp Val Phe Leu Glu Asn
                405                 410                 415

gtg aag cag acc agc cgc gac aac agc cgc acc ccg ttc cag tgg agc     1296
Val Lys Gln Thr Ser Arg Asp Asn Ser Arg Thr Pro Phe Gln Trp Ser
            420                 425                 430

aac acc gcc cag gcc ggc ttc acc acc ggc acc ccg tgg ttc cgc atc     1344
Asn Thr Ala Gln Ala Gly Phe Thr Thr Gly Thr Pro Trp Phe Arg Ile
        435                 440                 445

aac ccg aac tac aag aac atc aac gcc gag gag cag acc cag aac ccg     1392
Asn Pro Asn Tyr Lys Asn Ile Asn Ala Glu Glu Gln Thr Gln Asn Pro
    450                 455                 460

gac agc atc ttc cac ttc tac cgc cag ctg atc gag ctg agg cac gcc     1440
Asp Ser Ile Phe His Phe Tyr Arg Gln Leu Ile Glu Leu Arg His Ala
465                 470                 475                 480

acc ccg gcc ttc acc tac ggc acc tac cag gac ctg gac ccg aac aac     1488
Thr Pro Ala Phe Thr Tyr Gly Thr Tyr Gln Asp Leu Asp Pro Asn Asn
                485                 490                 495

aac gag gtg ctg gcc tac acc cgc gag ctg aac cag cag cgc tac ctg     1536
Asn Glu Val Leu Ala Tyr Thr Arg Glu Leu Asn Gln Gln Arg Tyr Leu
            500                 505                 510

gtg gtg gtc aac ttc aag gag aag ccg gtc cac tac gtg ctg ccc aag     1584
Val Val Val Asn Phe Lys Glu Lys Pro Val His Tyr Val Leu Pro Lys
        515                 520                 525

acc ctg agc atc aag cag agc ctg ctc gag agc ggc cag aag gac aag     1632
Thr Leu Ser Ile Lys Gln Ser Leu Leu Glu Ser Gly Gln Lys Asp Lys
    530                 535                 540

gtc gag ccg aac gcc acc acc ctc gag ctt cag ccc tgg cag agc ggc     1680
Val Glu Pro Asn Ala Thr Thr Leu Glu Leu Gln Pro Trp Gln Ser Gly
545                 550                 555                 560

atc tat cag ctg aac tga                                             1698
Ile Tyr Gln Leu Asn
                565


<210> SEQ ID NO 21
<211> LENGTH: 565
<212> TYPE: PRT
<213> ORGANISM: unknown
<220> FEATURE:
<223> OTHER INFORMATION: Synthetic Construct

<400> SEQUENCE: 21

Val Ala Val Asn Asp Gly Val Ser Ala His Pro Val Trp Trp Lys Glu
1               5                   10                  15

Ala Val Phe Tyr Gln Val Tyr Pro Arg Ser Phe Lys Asp Ser Asp Gly
            20                  25                  30

Asp Gly Ile Gly Asp Leu Lys Gly Leu Thr Glu Lys Leu Asp Tyr Leu
        35                  40                  45

Lys Ala Leu Gly Ile Asn Ala Ile Trp Ile Asn Pro His Tyr Asp Ser
    50                  55                  60

Pro Asn Thr Asp Asn Gly Tyr Asp Ile Arg Asp Tyr Arg Lys Ile Met
65                  70                  75                  80

Lys Glu Tyr Gly Thr Met Asp Asp Phe Asp Arg Leu Ile Ala Glu Met
                85                  90                  95

Lys Lys Arg Asp Met Arg Leu Met Ile Asp Val Val Val Asn His Thr
```

-continued

```
            100                 105                 110

Ser Asp Glu His Glu Trp Phe Val Glu Ser Lys Lys Ser Lys Asp Asn
        115                 120                 125

Pro Tyr Arg Asp Tyr Tyr Ile Trp Arg Asp Gly Lys Asp Gly Thr Gln
    130                 135                 140

Pro Asn Asn Tyr Pro Ser Phe Phe Gly Gly Ser Ala Trp Gln Lys Asp
145                 150                 155                 160

Asn Ala Thr Gln Gln Tyr Tyr Leu His Tyr Phe Gly Val Gln Gln Pro
                165                 170                 175

Asp Leu Asn Trp Asp Asn Pro Lys Val Arg Glu Glu Val Tyr Asp Met
            180                 185                 190

Leu Arg Phe Trp Ile Asp Lys Gly Val Ser Gly Leu Arg Met Asp Thr
        195                 200                 205

Val Ala Thr Phe Ser Lys Asn Pro Ala Phe Pro Asp Leu Thr Pro Lys
    210                 215                 220

Gln Leu Gln Asn Phe Ala Tyr Thr Tyr Thr Gln Gly Pro Asn Leu His
225                 230                 235                 240

Arg Tyr Ile Gln Glu Met His Gln Lys Val Leu Ala Lys Tyr Asp Val
                245                 250                 255

Val Ser Ala Gly Glu Ile Phe Gly Val Pro Leu Glu Glu Ala Ala Pro
            260                 265                 270

Phe Ile Asp Gln Arg Arg Lys Glu Leu Asp Met Ala Phe Ser Phe Asp
        275                 280                 285

Leu Ile Arg Leu Asp Arg Ala Val Glu Glu Arg Trp Arg Arg Asn Asp
    290                 295                 300

Trp Thr Leu Ser Gln Phe Arg Gln Ile Asn Asn Arg Leu Val Asp Met
305                 310                 315                 320

Ala Gly Gln His Gly Trp Asn Thr Phe Phe Leu Ser Asn His Asp Asn
                325                 330                 335

Pro Arg Ala Val Ser His Phe Gly Asp Asp Arg Pro Glu Trp Arg Thr
            340                 345                 350

Arg Ser Ala Lys Ala Leu Ala Thr Leu Ala Leu Thr Gln Arg Ala Thr
        355                 360                 365

Pro Phe Ile Tyr Gln Gly Asp Glu Leu Gly Met Thr Asn Tyr Pro Phe
    370                 375                 380

Thr Ser Leu Ser Glu Phe Asp Asp Ile Glu Val Lys Gly Phe Trp Gln
385                 390                 395                 400

Asp Phe Val Glu Thr Gly Lys Val Lys Pro Asp Val Phe Leu Glu Asn
                405                 410                 415

Val Lys Gln Thr Ser Arg Asp Asn Ser Arg Thr Pro Phe Gln Trp Ser
            420                 425                 430

Asn Thr Ala Gln Ala Gly Phe Thr Thr Gly Thr Pro Trp Phe Arg Ile
        435                 440                 445

Asn Pro Asn Tyr Lys Asn Ile Asn Ala Glu Glu Gln Thr Gln Asn Pro
    450                 455                 460

Asp Ser Ile Phe His Phe Tyr Arg Gln Leu Ile Glu Leu Arg His Ala
465                 470                 475                 480

Thr Pro Ala Phe Thr Tyr Gly Thr Tyr Gln Asp Leu Asp Pro Asn Asn
                485                 490                 495

Asn Glu Val Leu Ala Tyr Thr Arg Glu Leu Asn Gln Gln Arg Tyr Leu
            500                 505                 510

Val Val Val Asn Phe Lys Glu Lys Pro Val His Tyr Val Leu Pro Lys
        515                 520                 525
```

```
Thr Leu Ser Ile Lys Gln Ser Leu Leu Glu Ser Gly Gln Lys Asp Lys
    530                 535                 540

Val Glu Pro Asn Ala Thr Thr Leu Glu Leu Gln Pro Trp Gln Ser Gly
545                 550                 555                 560

Ile Tyr Gln Leu Asn
                565


<210> SEQ ID NO 22
<211> LENGTH: 194
<212> TYPE: DNA
<213> ORGANISM: Fig wort mosaic virus
<220> FEATURE:
<221> NAME/KEY: enhancer
<222> LOCATION: (1)..(194)

<400> SEQUENCE: 22

agctgcttgt ggggaccaga caaaaaagga atggtgcaga attgttaggc gcacctacca      60

aaagcatctt tgcctttatt gcaaagataa agcagattcc tctagtacaa gtggggaaca     120

aaataacgtg gaaaagagct gtcctgacag cccactcact aatgcgtatg acgaacgcag     180

tgacgaccac aaaa                                                       194


<210> SEQ ID NO 23
<211> LENGTH: 293
<212> TYPE: DNA
<213> ORGANISM: 35S virus
<220> FEATURE:
<221> NAME/KEY: enhancer
<222> LOCATION: (1)..(293)

<400> SEQUENCE: 23

acttttcaac aaagggtaat atccggaaac ctcctcggat tccattgccc agctatctgt      60

cactttattg tgaagatagt ggaaaaggaa ggtggctcct acaaatgcca tcattgcgat     120

aaaggaaagg ctatcgttga agatgcctct gccgacagtg gtcccaaaga tggaccccca     180

cccacgagga gcatcgtgga aaaagaagac gttccaacca cgtcttcaaa gcaagtggat     240

tgatgtgata tctccactga cgtaagggat gacgaacaat cccactatcc ttc            293


<210> SEQ ID NO 24
<211> LENGTH: 1701
<212> TYPE: DNA
<213> ORGANISM: unknown
<220> FEATURE:
<223> OTHER INFORMATION: artificial sequence
<220> FEATURE:
<221> NAME/KEY: CDS
<222> LOCATION: (1)..(1701)
<223> OTHER INFORMATION: monocot optimized sucrose isomerase

<400> SEQUENCE: 24

atg gtg gcc gtg aac gac ggc gtg tcc gcc cac cca gtg tgg tgg aag       48
Met Val Ala Val Asn Asp Gly Val Ser Ala His Pro Val Trp Trp Lys
1               5                   10                  15

gag gcc gtt ttc tac cag gtg tac ccg cgc agc ttc aag gac agc gac       96
Glu Ala Val Phe Tyr Gln Val Tyr Pro Arg Ser Phe Lys Asp Ser Asp
            20                  25                  30

ggc gac ggc atc ggc gac ctg aag ggc ctg acc gag aag ctg gac tac      144
Gly Asp Gly Ile Gly Asp Leu Lys Gly Leu Thr Glu Lys Leu Asp Tyr
        35                  40                  45

ctg aag gcc ctg ggc atc aac gcc atc tgg atc aac ccg cac tac gac      192
Leu Lys Ala Leu Gly Ile Asn Ala Ile Trp Ile Asn Pro His Tyr Asp
    50                  55                  60
```

-continued

```
agc ccg aac acc gac aac ggc tac gat atc cgc gac tac cgc aag atc      240
Ser Pro Asn Thr Asp Asn Gly Tyr Asp Ile Arg Asp Tyr Arg Lys Ile
65                  70                  75                  80

atg aag gaa tac ggc acg atg gac gac ttc gac cgc ctg atc gcc gag      288
Met Lys Glu Tyr Gly Thr Met Asp Asp Phe Asp Arg Leu Ile Ala Glu
                85                  90                  95

atg aag aag cgc gac atg cgc ctg atg atc gac gtg gtg gtg aac cac      336
Met Lys Lys Arg Asp Met Arg Leu Met Ile Asp Val Val Val Asn His
            100                 105                 110

acc agc gac gag cac gag tgg ttc gtg gag agc aag aag tcc aag gac      384
Thr Ser Asp Glu His Glu Trp Phe Val Glu Ser Lys Lys Ser Lys Asp
        115                 120                 125

aac ccg tac cgc gac tac tac atc tgg cgc gac ggc aag gac ggc acc      432
Asn Pro Tyr Arg Asp Tyr Tyr Ile Trp Arg Asp Gly Lys Asp Gly Thr
    130                 135                 140

cag ccg aac aac tac ccg agc ttc ttc ggc ggc agc gcc tgg cag aag      480
Gln Pro Asn Asn Tyr Pro Ser Phe Phe Gly Gly Ser Ala Trp Gln Lys
145                 150                 155                 160

gac aac gcc acc cag cag tac tac ctg cac tac ttc ggc gtc cag cag      528
Asp Asn Ala Thr Gln Gln Tyr Tyr Leu His Tyr Phe Gly Val Gln Gln
                165                 170                 175

ccg gac ctg aac tgg gac aac ccg aaa gtg agg gag gag gtg tac gac      576
Pro Asp Leu Asn Trp Asp Asn Pro Lys Val Arg Glu Glu Val Tyr Asp
            180                 185                 190

atg ctg agg ttc tgg atc gac aag ggc gtg tcc ggc ctg agg atg gac      624
Met Leu Arg Phe Trp Ile Asp Lys Gly Val Ser Gly Leu Arg Met Asp
        195                 200                 205

acc gtg gcc acc ttc agc aag aac ccg gcc ttc ccg gac ctg acc ccg      672
Thr Val Ala Thr Phe Ser Lys Asn Pro Ala Phe Pro Asp Leu Thr Pro
    210                 215                 220

aag cag ctc cag aac ttc gcc tac acc tac acc cag ggc ccg aac ctg      720
Lys Gln Leu Gln Asn Phe Ala Tyr Thr Tyr Thr Gln Gly Pro Asn Leu
225                 230                 235                 240

cac cgc tac atc cag gag atg cac cag aag gtc ctg gcc aag tac gac      768
His Arg Tyr Ile Gln Glu Met His Gln Lys Val Leu Ala Lys Tyr Asp
                245                 250                 255

gtg gtg tct gcc ggc gag atc ttc ggc gtg ccg ctc gag gag gcc gct      816
Val Val Ser Ala Gly Glu Ile Phe Gly Val Pro Leu Glu Glu Ala Ala
            260                 265                 270

ccg ttc atc gac cag cgc cgg aag gaa ctg gac atg gcc ttc agc ttc      864
Pro Phe Ile Asp Gln Arg Arg Lys Glu Leu Asp Met Ala Phe Ser Phe
        275                 280                 285

gac ctg atc cgc ctc gac agg gcc gtg gag gag agg tgg cgc cgc aac      912
Asp Leu Ile Arg Leu Asp Arg Ala Val Glu Glu Arg Trp Arg Arg Asn
    290                 295                 300

gac tgg acc ctg agc cag ttc cgc cag atc aac aac cgc ctg gtg gac      960
Asp Trp Thr Leu Ser Gln Phe Arg Gln Ile Asn Asn Arg Leu Val Asp
305                 310                 315                 320

atg gcc ggc cag cac ggc tgg aac acg ttc ttc ctc agc aac cac gac     1008
Met Ala Gly Gln His Gly Trp Asn Thr Phe Phe Leu Ser Asn His Asp
                325                 330                 335

aac ccg agg gcc gtg tcc cac ttc ggc gac gac agg cca gag tgg agg     1056
Asn Pro Arg Ala Val Ser His Phe Gly Asp Asp Arg Pro Glu Trp Arg
            340                 345                 350

acc cgc agc gcc aag gcc ctg gcc acc ctg gcc ctg acc cag agg gct     1104
Thr Arg Ser Ala Lys Ala Leu Ala Thr Leu Ala Leu Thr Gln Arg Ala
        355                 360                 365

acc cca ttc atc tac cag ggc gac gag ctg ggc atg acc aac tac ccg     1152
Thr Pro Phe Ile Tyr Gln Gly Asp Glu Leu Gly Met Thr Asn Tyr Pro
```

```
    370                 375                 380

ttc acc agc ctg agc gag ttc gac gat atc gag gtg aag ggc ttc tgg      1200
Phe Thr Ser Leu Ser Glu Phe Asp Asp Ile Glu Val Lys Gly Phe Trp
385                 390                 395                 400

cag gac ttc gtg gag act ggc aag gtg aag cca gac gtg ttc ctc gag      1248
Gln Asp Phe Val Glu Thr Gly Lys Val Lys Pro Asp Val Phe Leu Glu
                405                 410                 415

aac gtg aag cag acc agc cgc gac aac agc cgc acc ccg ttc cag tgg      1296
Asn Val Lys Gln Thr Ser Arg Asp Asn Ser Arg Thr Pro Phe Gln Trp
            420                 425                 430

agc aac acc gcc cag gcc ggc ttc acc acc ggc acc ccg tgg ttc cgc      1344
Ser Asn Thr Ala Gln Ala Gly Phe Thr Thr Gly Thr Pro Trp Phe Arg
        435                 440                 445

atc aac ccg aac tac aag aac atc aac gcc gag gag cag acc cag aac      1392
Ile Asn Pro Asn Tyr Lys Asn Ile Asn Ala Glu Glu Gln Thr Gln Asn
    450                 455                 460

ccg gac agc atc ttc cac ttc tac cgc cag ctg atc gag ctg agg cac      1440
Pro Asp Ser Ile Phe His Phe Tyr Arg Gln Leu Ile Glu Leu Arg His
465                 470                 475                 480

gcc acc ccg gcc ttc acc tac ggc acc tac cag gac ctg gac ccg aac      1488
Ala Thr Pro Ala Phe Thr Tyr Gly Thr Tyr Gln Asp Leu Asp Pro Asn
                485                 490                 495

aac aac gag gtg ctg gcc tac acc cgc gag ctg aac cag cag cgc tac      1536
Asn Asn Glu Val Leu Ala Tyr Thr Arg Glu Leu Asn Gln Gln Arg Tyr
            500                 505                 510

ctg gtg gtg gtc aac ttc aag gag aag ccg gtc cac tac gtg ctg ccc      1584
Leu Val Val Val Asn Phe Lys Glu Lys Pro Val His Tyr Val Leu Pro
        515                 520                 525

aag acc ctg agc atc aag cag agc ctg ctc gag agc ggc cag aag gac      1632
Lys Thr Leu Ser Ile Lys Gln Ser Leu Leu Glu Ser Gly Gln Lys Asp
    530                 535                 540

aag gtc gag ccg aac gcc acc acc ctc gag ctt cag ccc tgg cag agc      1680
Lys Val Glu Pro Asn Ala Thr Thr Leu Glu Leu Gln Pro Trp Gln Ser
545                 550                 555                 560

ggc atc tat cag ctg aac tga                                          1701
Gly Ile Tyr Gln Leu Asn
                565


<210> SEQ ID NO 25
<211> LENGTH: 566
<212> TYPE: PRT
<213> ORGANISM: unknown
<220> FEATURE:
<223> OTHER INFORMATION: Synthetic Construct

<400> SEQUENCE: 25

Met Val Ala Val Asn Asp Gly Val Ser Ala His Pro Val Trp Trp Lys
1               5                   10                  15

Glu Ala Val Phe Tyr Gln Val Tyr Pro Arg Ser Phe Lys Asp Ser Asp
            20                  25                  30

Gly Asp Gly Ile Gly Asp Leu Lys Gly Leu Thr Glu Lys Leu Asp Tyr
        35                  40                  45

Leu Lys Ala Leu Gly Ile Asn Ala Ile Trp Ile Asn Pro His Tyr Asp
    50                  55                  60

Ser Pro Asn Thr Asp Asn Gly Tyr Asp Ile Arg Asp Tyr Arg Lys Ile
65                  70                  75                  80

Met Lys Glu Tyr Gly Thr Met Asp Asp Phe Asp Arg Leu Ile Ala Glu
                85                  90                  95

Met Lys Lys Arg Asp Met Arg Leu Met Ile Asp Val Val Val Asn His
```

```
            100                 105                 110

Thr Ser Asp Glu His Glu Trp Phe Val Glu Ser Lys Lys Ser Lys Asp
        115                 120                 125

Asn Pro Tyr Arg Asp Tyr Tyr Ile Trp Arg Asp Gly Lys Asp Gly Thr
    130                 135                 140

Gln Pro Asn Asn Tyr Pro Ser Phe Phe Gly Gly Ser Ala Trp Gln Lys
145                 150                 155                 160

Asp Asn Ala Thr Gln Gln Tyr Tyr Leu His Tyr Phe Gly Val Gln Gln
                165                 170                 175

Pro Asp Leu Asn Trp Asp Asn Pro Lys Val Arg Glu Glu Val Tyr Asp
            180                 185                 190

Met Leu Arg Phe Trp Ile Asp Lys Gly Val Ser Gly Leu Arg Met Asp
        195                 200                 205

Thr Val Ala Thr Phe Ser Lys Asn Pro Ala Phe Pro Asp Leu Thr Pro
    210                 215                 220

Lys Gln Leu Gln Asn Phe Ala Tyr Thr Tyr Thr Gln Gly Pro Asn Leu
225                 230                 235                 240

His Arg Tyr Ile Gln Glu Met His Gln Lys Val Leu Ala Lys Tyr Asp
                245                 250                 255

Val Val Ser Ala Gly Glu Ile Phe Gly Val Pro Leu Glu Glu Ala Ala
            260                 265                 270

Pro Phe Ile Asp Gln Arg Arg Lys Glu Leu Asp Met Ala Phe Ser Phe
        275                 280                 285

Asp Leu Ile Arg Leu Asp Arg Ala Val Glu Glu Arg Trp Arg Arg Asn
    290                 295                 300

Asp Trp Thr Leu Ser Gln Phe Arg Gln Ile Asn Asn Arg Leu Val Asp
305                 310                 315                 320

Met Ala Gly Gln His Gly Trp Asn Thr Phe Phe Leu Ser Asn His Asp
                325                 330                 335

Asn Pro Arg Ala Val Ser His Phe Gly Asp Asp Arg Pro Glu Trp Arg
            340                 345                 350

Thr Arg Ser Ala Lys Ala Leu Ala Thr Leu Ala Leu Thr Gln Arg Ala
        355                 360                 365

Thr Pro Phe Ile Tyr Gln Gly Asp Glu Leu Gly Met Thr Asn Tyr Pro
    370                 375                 380

Phe Thr Ser Leu Ser Glu Phe Asp Asp Ile Glu Val Lys Gly Phe Trp
385                 390                 395                 400

Gln Asp Phe Val Glu Thr Gly Lys Val Lys Pro Asp Val Phe Leu Glu
                405                 410                 415

Asn Val Lys Gln Thr Ser Arg Asp Asn Ser Arg Thr Pro Phe Gln Trp
            420                 425                 430

Ser Asn Thr Ala Gln Ala Gly Phe Thr Thr Gly Thr Pro Trp Phe Arg
        435                 440                 445

Ile Asn Pro Asn Tyr Lys Asn Ile Asn Ala Glu Glu Gln Thr Gln Asn
    450                 455                 460

Pro Asp Ser Ile Phe His Phe Tyr Arg Gln Leu Ile Glu Leu Arg His
465                 470                 475                 480

Ala Thr Pro Ala Phe Thr Tyr Gly Thr Tyr Gln Asp Leu Asp Pro Asn
                485                 490                 495

Asn Asn Glu Val Leu Ala Tyr Thr Arg Glu Leu Asn Gln Gln Arg Tyr
            500                 505                 510

Leu Val Val Val Asn Phe Lys Glu Lys Pro Val His Tyr Val Leu Pro
        515                 520                 525
```

```
Lys Thr Leu Ser Ile Lys Gln Ser Leu Leu Glu Ser Gly Gln Lys Asp
    530                 535                 540

Lys Val Glu Pro Asn Ala Thr Thr Leu Glu Leu Gln Pro Trp Gln Ser
545                 550                 555                 560

Gly Ile Tyr Gln Leu Asn
                565


<210> SEQ ID NO 26
<211> LENGTH: 65
<212> TYPE: PRT
<213> ORGANISM: Cyanophora paradoxa
<220> FEATURE:
<221> NAME/KEY: signal
<222> LOCATION: (1)..(65)
<223> OTHER INFORMATION: FNR plastid targeting sequence

<400> SEQUENCE: 26

Met Ala Phe Val Ala Ser Val Pro Val Phe Ala Asn Ala Ser Gly Leu
1               5                   10                  15

Lys Thr Glu Ala Lys Val Cys Gln Lys Pro Ala Leu Lys Asn Ser Phe
            20                  25                  30

Phe Arg Gly Glu Glu Val Thr Ser Arg Ser Phe Phe Ala Ser Gln Ala
        35                  40                  45

Val Ser Ala Lys Pro Ala Thr Thr Gly Glu Val Asp Thr Thr Ile Arg
    50                  55                  60

Ala
65


<210> SEQ ID NO 27
<211> LENGTH: 1764
<212> TYPE: DNA
<213> ORGANISM: Bacillus
<220> FEATURE:
<221> NAME/KEY: CDS
<222> LOCATION: (1)..(1764)
<223> OTHER INFORMATION: dicot optimized alpha-1,1-glucosidase

<400> SEQUENCE: 27

atg tcc act gct ctt act cag act tct act aac tct cag cag tct cca       48
Met Ser Thr Ala Leu Thr Gln Thr Ser Thr Asn Ser Gln Gln Ser Pro
1               5                   10                  15

att aga agg gct tgg tgg aaa gag gct gtt gtt tac caa atc tac cca       96
Ile Arg Arg Ala Trp Trp Lys Glu Ala Val Val Tyr Gln Ile Tyr Pro
            20                  25                  30

cgt tct ttc atg gat tcc aac ggt gat gga att gga gat ctt agg gga      144
Arg Ser Phe Met Asp Ser Asn Gly Asp Gly Ile Gly Asp Leu Arg Gly
        35                  40                  45

att ctc tcc aag ttg gat tac ctt aag ttg ctc gga gtt gat gtt ctt      192
Ile Leu Ser Lys Leu Asp Tyr Leu Lys Leu Leu Gly Val Asp Val Leu
    50                  55                  60

tgg ctc aac cca atc tac gat tcc cca aac gat gat atg gga tac gat      240
Trp Leu Asn Pro Ile Tyr Asp Ser Pro Asn Asp Asp Met Gly Tyr Asp
65                  70                  75                  80

atc agg gat tac tac aag atc atg gaa gag ttc gga act atg gaa gat      288
Ile Arg Asp Tyr Tyr Lys Ile Met Glu Glu Phe Gly Thr Met Glu Asp
                85                  90                  95

ttc gag gaa ctt ctt aga gaa gtt cac gct cgt gga atg aag ttg gtg      336
Phe Glu Glu Leu Leu Arg Glu Val His Ala Arg Gly Met Lys Leu Val
            100                 105                 110

atg gat ctt gtt gct aac cac act tct gat gag cac cct tgg ttt att      384
Met Asp Leu Val Ala Asn His Thr Ser Asp Glu His Pro Trp Phe Ile
```

-continued

```
        115                 120                 125

gag tct agg tcc tct agg gat aat cca tac cgt gat tgg tac att tgg      432
Glu Ser Arg Ser Ser Arg Asp Asn Pro Tyr Arg Asp Trp Tyr Ile Trp
    130                 135                 140

cgt gat cca aag gat gga aga gag cca aat aac tgg ctt tct tac ttc      480
Arg Asp Pro Lys Asp Gly Arg Glu Pro Asn Asn Trp Leu Ser Tyr Phe
145                 150                 155                 160

tct gga tct gct tgg gaa tat gat gag agg act gga cag tac tac ctt      528
Ser Gly Ser Ala Trp Glu Tyr Asp Glu Arg Thr Gly Gln Tyr Tyr Leu
                165                 170                 175

cac ttg ttc tct aga agg cag cca gat ctt aat tgg gag aac cca aaa      576
His Leu Phe Ser Arg Arg Gln Pro Asp Leu Asn Trp Glu Asn Pro Lys
            180                 185                 190

gtg cgt gaa gct atc ttt gag atg atg agg ttc tgg ctc gat aag gga      624
Val Arg Glu Ala Ile Phe Glu Met Met Arg Phe Trp Leu Asp Lys Gly
        195                 200                 205

att gat gga ttc agg atg gat gtg atc aac gct att gct aag gct gaa      672
Ile Asp Gly Phe Arg Met Asp Val Ile Asn Ala Ile Ala Lys Ala Glu
    210                 215                 220

gga ctt cca gat gct cca gct aga cca ggt gaa aga tat gct tgg gga      720
Gly Leu Pro Asp Ala Pro Ala Arg Pro Gly Glu Arg Tyr Ala Trp Gly
225                 230                 235                 240

gga cag tat ttc ctt aac cag cca aag gtt cac gaa tac ctc aga gag      768
Gly Gln Tyr Phe Leu Asn Gln Pro Lys Val His Glu Tyr Leu Arg Glu
                245                 250                 255

atg tac gat aag gtt ctc tcc cac tac gat att atg act gtg gga gag      816
Met Tyr Asp Lys Val Leu Ser His Tyr Asp Ile Met Thr Val Gly Glu
            260                 265                 270

act ggt gga gtt act act aag gat gca ctc ttg ttc gct ggt gaa gat      864
Thr Gly Gly Val Thr Thr Lys Asp Ala Leu Leu Phe Ala Gly Glu Asp
        275                 280                 285

aga agg gaa ctc aac atg gtt ttc cag ttc gag cac atg gat atc gat      912
Arg Arg Glu Leu Asn Met Val Phe Gln Phe Glu His Met Asp Ile Asp
    290                 295                 300

gct act gat ggt gat aag tgg agg cca aga cct tgg aga ctt act gag      960
Ala Thr Asp Gly Asp Lys Trp Arg Pro Arg Pro Trp Arg Leu Thr Glu
305                 310                 315                 320

ctt aag act atc atg act agg tgg cag aat gat ctt tat gga aag gct     1008
Leu Lys Thr Ile Met Thr Arg Trp Gln Asn Asp Leu Tyr Gly Lys Ala
                325                 330                 335

tgg aac tct ctc tac tgg act aat cat gat cag cca agg gct gtt tct     1056
Trp Asn Ser Leu Tyr Trp Thr Asn His Asp Gln Pro Arg Ala Val Ser
            340                 345                 350

aga ttc gga aac gat gga cca tat cgt gtt gag tct gct aag atg ctt     1104
Arg Phe Gly Asn Asp Gly Pro Tyr Arg Val Glu Ser Ala Lys Met Leu
        355                 360                 365

gct act gtg ctt cat atg atg caa ggt aca cct tac atc tac cag ggt     1152
Ala Thr Val Leu His Met Met Gln Gly Thr Pro Tyr Ile Tyr Gln Gly
    370                 375                 380

gaa gag att gga atg act aac tgc cca ttc gat tcc att gat gag tac     1200
Glu Glu Ile Gly Met Thr Asn Cys Pro Phe Asp Ser Ile Asp Glu Tyr
385                 390                 395                 400

cgt gat gtg gag att cat aac ctt tgg agg cac aga gtt atg gaa ggt     1248
Arg Asp Val Glu Ile His Asn Leu Trp Arg His Arg Val Met Glu Gly
                405                 410                 415

gga caa gat cca gct gaa gtt ctt agg gtg atc caa ctt aag gga agg     1296
Gly Gln Asp Pro Ala Glu Val Leu Arg Val Ile Gln Leu Lys Gly Arg
            420                 425                 430

gat aat gct aga act cca atg caa tgg gat gat tct cca aac gct gga     1344
```

-continued

```
Asp Asn Ala Arg Thr Pro Met Gln Trp Asp Asp Ser Pro Asn Ala Gly
        435                 440                 445

ttc act act gga aca cct tgg att aag gtg aac cca aac tac cga gag      1392
Phe Thr Thr Gly Thr Pro Trp Ile Lys Val Asn Pro Asn Tyr Arg Glu
    450                 455                 460

atc aac gtt aag cag gct ctt gct gat cca aac tcc atc ttc cat tac      1440
Ile Asn Val Lys Gln Ala Leu Ala Asp Pro Asn Ser Ile Phe His Tyr
465                 470                 475                 480

tac cgt aga ctt atc caa ctt agg aag cag cat cca atc gtt gtt tac      1488
Tyr Arg Arg Leu Ile Gln Leu Arg Lys Gln His Pro Ile Val Val Tyr
                485                 490                 495

gga aag tac gat ctc att ctc cca gat cac gaa gag att tgg gct tac      1536
Gly Lys Tyr Asp Leu Ile Leu Pro Asp His Glu Glu Ile Trp Ala Tyr
            500                 505                 510

act agg act ctt gga gat gag aga tgg ctt atc gtg gct aat ttc ttc      1584
Thr Arg Thr Leu Gly Asp Glu Arg Trp Leu Ile Val Ala Asn Phe Phe
        515                 520                 525

gga gga act cca gaa ttt gaa ctt cca cct gaa gtt aga tgt gag ggt      1632
Gly Gly Thr Pro Glu Phe Glu Leu Pro Pro Glu Val Arg Cys Glu Gly
    530                 535                 540

gct gag ttg gtt att gct aac tac cca gtg gat gat tct gaa gca ggt      1680
Ala Glu Leu Val Ile Ala Asn Tyr Pro Val Asp Asp Ser Glu Ala Gly
545                 550                 555                 560

gga cca gct gct gcc ggt gct cct cat agg ttt agg ctt agg cca tat      1728
Gly Pro Ala Ala Ala Gly Ala Pro His Arg Phe Arg Leu Arg Pro Tyr
                565                 570                 575

gag tgt cgt gtt tac cgt ctt ttg gga tgg cac taa                      1764
Glu Cys Arg Val Tyr Arg Leu Leu Gly Trp His
            580                 585


<210> SEQ ID NO 28
<211> LENGTH: 587
<212> TYPE: PRT
<213> ORGANISM: Bacillus

<400> SEQUENCE: 28

Met Ser Thr Ala Leu Thr Gln Thr Ser Thr Asn Ser Gln Gln Ser Pro
1               5                   10                  15

Ile Arg Arg Ala Trp Trp Lys Glu Ala Val Val Tyr Gln Ile Tyr Pro
            20                  25                  30

Arg Ser Phe Met Asp Ser Asn Gly Asp Gly Ile Gly Asp Leu Arg Gly
        35                  40                  45

Ile Leu Ser Lys Leu Asp Tyr Leu Lys Leu Leu Gly Val Asp Val Leu
    50                  55                  60

Trp Leu Asn Pro Ile Tyr Asp Ser Pro Asn Asp Asp Met Gly Tyr Asp
65                  70                  75                  80

Ile Arg Asp Tyr Tyr Lys Ile Met Glu Glu Phe Gly Thr Met Glu Asp
                85                  90                  95

Phe Glu Glu Leu Leu Arg Glu Val His Ala Arg Gly Met Lys Leu Val
            100                 105                 110

Met Asp Leu Val Ala Asn His Thr Ser Asp Glu His Pro Trp Phe Ile
        115                 120                 125

Glu Ser Arg Ser Ser Arg Asp Asn Pro Tyr Arg Asp Trp Tyr Ile Trp
    130                 135                 140

Arg Asp Pro Lys Asp Gly Arg Glu Pro Asn Asn Trp Leu Ser Tyr Phe
145                 150                 155                 160

Ser Gly Ser Ala Trp Glu Tyr Asp Glu Arg Thr Gly Gln Tyr Tyr Leu
                165                 170                 175
```

-continued

```
His Leu Phe Ser Arg Arg Gln Pro Asp Leu Asn Trp Glu Asn Pro Lys
            180                 185                 190

Val Arg Glu Ala Ile Phe Glu Met Met Arg Phe Trp Leu Asp Lys Gly
        195                 200                 205

Ile Asp Gly Phe Arg Met Asp Val Ile Asn Ala Ile Ala Lys Ala Glu
    210                 215                 220

Gly Leu Pro Asp Ala Pro Ala Arg Pro Gly Glu Arg Tyr Ala Trp Gly
225                 230                 235                 240

Gly Gln Tyr Phe Leu Asn Gln Pro Lys Val His Glu Tyr Leu Arg Glu
                245                 250                 255

Met Tyr Asp Lys Val Leu Ser His Tyr Asp Ile Met Thr Val Gly Glu
            260                 265                 270

Thr Gly Gly Val Thr Thr Lys Asp Ala Leu Leu Phe Ala Gly Glu Asp
        275                 280                 285

Arg Arg Glu Leu Asn Met Val Phe Gln Phe Glu His Met Asp Ile Asp
    290                 295                 300

Ala Thr Asp Gly Asp Lys Trp Arg Pro Arg Pro Trp Arg Leu Thr Glu
305                 310                 315                 320

Leu Lys Thr Ile Met Thr Arg Trp Gln Asn Asp Leu Tyr Gly Lys Ala
                325                 330                 335

Trp Asn Ser Leu Tyr Trp Thr Asn His Asp Gln Pro Arg Ala Val Ser
            340                 345                 350

Arg Phe Gly Asn Asp Gly Pro Tyr Arg Val Glu Ser Ala Lys Met Leu
        355                 360                 365

Ala Thr Val Leu His Met Met Gln Gly Thr Pro Tyr Ile Tyr Gln Gly
    370                 375                 380

Glu Glu Ile Gly Met Thr Asn Cys Pro Phe Asp Ser Ile Asp Glu Tyr
385                 390                 395                 400

Arg Asp Val Glu Ile His Asn Leu Trp Arg His Arg Val Met Glu Gly
                405                 410                 415

Gly Gln Asp Pro Ala Glu Val Leu Arg Val Ile Gln Leu Lys Gly Arg
            420                 425                 430

Asp Asn Ala Arg Thr Pro Met Gln Trp Asp Asp Ser Pro Asn Ala Gly
        435                 440                 445

Phe Thr Thr Gly Thr Pro Trp Ile Lys Val Asn Pro Asn Tyr Arg Glu
    450                 455                 460

Ile Asn Val Lys Gln Ala Leu Ala Asp Pro Asn Ser Ile Phe His Tyr
465                 470                 475                 480

Tyr Arg Arg Leu Ile Gln Leu Arg Lys Gln His Pro Ile Val Val Tyr
                485                 490                 495

Gly Lys Tyr Asp Leu Ile Leu Pro Asp His Glu Glu Ile Trp Ala Tyr
            500                 505                 510

Thr Arg Thr Leu Gly Asp Glu Arg Trp Leu Ile Val Ala Asn Phe Phe
        515                 520                 525

Gly Gly Thr Pro Glu Phe Glu Leu Pro Pro Glu Val Arg Cys Glu Gly
    530                 535                 540

Ala Glu Leu Val Ile Ala Asn Tyr Pro Val Asp Asp Ser Glu Ala Gly
545                 550                 555                 560

Gly Pro Ala Ala Ala Gly Ala Pro His Arg Phe Arg Leu Arg Pro Tyr
                565                 570                 575

Glu Cys Arg Val Tyr Arg Leu Leu Gly Trp His
            580                 585
```

<210> SEQ ID NO 29
<211> LENGTH: 1541
<212> TYPE: PRT
<213> ORGANISM: artificial sequence
<220> FEATURE:
<223> OTHER INFORMATION: synthetic gene
<220> FEATURE:
<221> NAME/KEY: enzyme
<222> LOCATION: (1)..(1541)
<223> OTHER INFORMATION: dextransucrase with leucrose synthase activity

<400> SEQUENCE: 29

```
Met Leu Glu Ser Gly Val Val His Ala Asp Asp Val Lys Gln Val Val
1               5                   10                  15

Val Gln Glu Pro Ala Thr Ala Gln Thr Ser Gly Pro Gly Gln Gln Thr
            20                  25                  30

Pro Ala Gln Ala Lys Ile Ala Ser Glu Gln Glu Ala Glu Lys Val Thr
        35                  40                  45

Pro Ala Asp Lys Val Thr Asp Asp Val Ala Ala Ser Glu Lys Pro Ala
    50                  55                  60

Lys Pro Ala Glu Asn Thr Glu Ala Thr Val Gln Thr Asn Ala Gln Glu
65                  70                  75                  80

Pro Ala Lys Pro Ala Asp Thr Lys Glu Ala Ser Thr Glu Lys Ala Ala
                85                  90                  95

Val Ala Glu Glu Val Lys Ala Ala Asn Ala Ile Thr Glu Ile Pro Lys
            100                 105                 110

Thr Glu Val Ala Asp Gln Asn Lys Gln Ala Arg Pro Thr Thr Ala Gln
        115                 120                 125

Asp Gln Glu Gly Asp Lys Arg Glu Lys Thr Ala Val Glu Asp Lys Ile
    130                 135                 140

Val Ala Asn Pro Lys Val Ala Lys Lys Asp Arg Leu Pro Glu Pro Gly
145                 150                 155                 160

Ser Lys Gln Gly Ala Ile Ala Glu Arg Met Val Ala Asp Gln Ala Gln
                165                 170                 175

Pro Ala Pro Val Asn Ala Asp His Asp Asp Asp Val Leu Ser His Ile
            180                 185                 190

Lys Thr Ile Asp Gly Lys Asn Tyr Tyr Val Gln Asp Asp Gly Thr Val
        195                 200                 205

Lys Lys Asn Phe Ala Val Glu Leu Asn Gly Arg Ile Leu Tyr Phe Asp
    210                 215                 220

Ala Glu Thr Gly Ala Leu Val Asp Ser Asn Glu Tyr Gln Phe Gln Gln
225                 230                 235                 240

Gly Thr Ser Ser Leu Asn Asn Glu Phe Ser Gln Lys Asn Ala Phe Tyr
                245                 250                 255

Gly Thr Thr Asp Lys Asp Ile Glu Thr Val Asp Gly Tyr Leu Thr Ala
            260                 265                 270

Asp Ser Trp Tyr Arg Pro Lys Phe Ile Leu Lys Asp Gly Lys Thr Trp
        275                 280                 285

Thr Ala Ser Thr Glu Thr Asp Leu Arg Pro Leu Leu Met Ala Trp Trp
    290                 295                 300

Pro Asp Lys Arg Thr Gln Ile Asn Tyr Leu Asn Tyr Met Asn Gln Gln
305                 310                 315                 320

Gly Leu Gly Ala Gly Ala Phe Glu Asn Lys Val Glu Gln Ala Leu Leu
                325                 330                 335

Thr Gly Ala Ser Gln Gln Val Gln Arg Lys Ile Glu Glu Lys Ile Gly
            340                 345                 350
```

```
Lys Glu Gly Asp Thr Lys Trp Leu Arg Thr Leu Met Gly Ala Phe Val
        355                 360                 365

Lys Thr Gln Pro Asn Trp Asn Ile Lys Thr Glu Ser Glu Thr Thr Gly
    370                 375                 380

Thr Lys Lys Asp His Leu Gln Gly Gly Ala Leu Leu Tyr Thr Asn Asn
385                 390                 395                 400

Glu Lys Ser Pro His Ala Asp Ser Lys Phe Arg Leu Leu Asn Arg Thr
                405                 410                 415

Pro Thr Ser Gln Thr Gly Thr Pro Lys Tyr Phe Ile Asp Lys Ser Asn
            420                 425                 430

Gly Gly Tyr Glu Phe Leu Leu Ala Asn Asp Phe Asp Asn Ser Asn Pro
        435                 440                 445

Ala Val Gln Ala Glu Gln Leu Asn Trp Leu His Tyr Met Met Asn Phe
    450                 455                 460

Gly Ser Ile Val Ala Asn Asp Pro Thr Ala Asn Phe Asp Gly Val Arg
465                 470                 475                 480

Val Asp Ala Val Asp Asn Val Asn Ala Asp Leu Leu Gln Ile Ala Ser
                485                 490                 495

Asp Tyr Phe Lys Ser Arg Tyr Lys Val Gly Glu Ser Glu Glu Glu Ala
            500                 505                 510

Ile Lys His Leu Ser Ile Leu Glu Ala Trp Ser Asp Asn Asp Pro Asp
        515                 520                 525

Tyr Asn Lys Asp Thr Lys Gly Ala Gln Leu Ala Ile Asp Asn Lys Leu
    530                 535                 540

Arg Leu Ser Leu Leu Tyr Ser Phe Met Arg Asn Leu Ser Ile Arg Ser
545                 550                 555                 560

Gly Val Glu Pro Thr Ile Thr Asn Ser Leu Asn Asp Arg Ser Ser Glu
                565                 570                 575

Lys Lys Asn Gly Glu Arg Met Ala Asn Tyr Ile Phe Val Arg Ala His
            580                 585                 590

Asp Asp Glu Val Gln Thr Val Ile Ala Asp Ile Ile Arg Glu Asn Ile
        595                 600                 605

Asn Pro Asn Thr Asp Gly Leu Thr Phe Thr Met Asp Glu Leu Lys Gln
    610                 615                 620

Ala Phe Lys Ile Tyr Asn Glu Asp Met Arg Lys Ala Asp Lys Lys Tyr
625                 630                 635                 640

Thr Gln Phe Asn Ile Pro Thr Ala His Ala Leu Met Leu Ser Asn Lys
                645                 650                 655

Asp Ser Ile Thr Arg Val Tyr Tyr Gly Asp Leu Tyr Thr Asp Asp Gly
            660                 665                 670

Gln Tyr Met Glu Lys Lys Ser Pro Tyr His Asp Ala Ile Asp Ala Leu
        675                 680                 685

Leu Arg Ala Arg Ile Lys Tyr Val Ala Gly Gly Gln Asp Met Lys Val
    690                 695                 700

Thr Tyr Met Gly Val Pro Arg Glu Ala Asp Lys Trp Ser Tyr Asn Gly
705                 710                 715                 720

Ile Leu Thr Ser Val Arg Tyr Gly Thr Gly Ala Asn Glu Ala Thr Asp
                725                 730                 735

Glu Gly Thr Ala Glu Thr Arg Thr Gln Gly Met Ala Val Ile Ala Ser
            740                 745                 750

Asn Asn Pro Asn Leu Lys Leu Asn Glu Trp Asp Lys Leu Gln Val Asn
        755                 760                 765
```

```
Met Gly Ala Ala His Lys Asn Gln Tyr Tyr Arg Pro Val Leu Leu Thr
    770                 775                 780

Thr Lys Asp Gly Ile Ser Arg Tyr Leu Thr Asp Glu Glu Val Pro Gln
785                 790                 795                 800

Ser Leu Trp Lys Lys Thr Asp Ala Asn Gly Ile Leu Thr Phe Asp Met
                805                 810                 815

Asn Asp Ile Ala Gly Tyr Ser Asn Val Gln Val Ser Gly Tyr Leu Ala
            820                 825                 830

Val Trp Val Pro Val Gly Ala Lys Ala Asp Gln Asp Ala Arg Thr Thr
        835                 840                 845

Ala Ser Lys Lys Lys Asn Ala Ser Gly Gln Val Tyr Glu Ser Ser Ala
    850                 855                 860

Ala Leu Asp Ser Gln Leu Ile Tyr Glu Gly Phe Ser Asn Phe Gln Asp
865                 870                 875                 880

Phe Ala Thr Arg Asp Asp Gln Tyr Thr Asn Lys Val Ile Ala Lys Asn
                885                 890                 895

Val Asn Leu Phe Lys Glu Trp Gly Val Thr Ser Phe Glu Leu Pro Pro
            900                 905                 910

Gln Tyr Val Ser Ser Gln Asp Gly Thr Phe Leu Asp Ser Ile Ile Gln
        915                 920                 925

Asn Gly Tyr Ala Phe Glu Asp Arg Tyr Asp Met Ala Met Ser Lys Asn
    930                 935                 940

Asn Lys Tyr Gly Ser Leu Lys Asp Leu Leu Asn Ala Leu Arg Ala Leu
945                 950                 955                 960

His Ser Val Asn Ile Gln Ala Ile Ala Asp Trp Val Pro Asp Gln Ile
                965                 970                 975

Tyr Asn Leu Pro Gly Lys Glu Val Val Thr Ala Thr Arg Val Asn Asn
            980                 985                 990

Tyr Gly Thr Tyr Arg Glu Gly Ala  Glu Ile Lys Glu Lys  Leu Tyr Val
        995                 1000                1005

Ala Asn  Ser Lys Thr Asn Glu  Thr Asp Phe Gln Gly  Lys Tyr Gly
    1010                1015                1020

Gly Ala  Phe Leu Asp Glu Leu  Lys Ala Lys Tyr Pro  Glu Ile Phe
    1025                1030                1035

Glu Arg  Val Gln Ile Ser Asn  Gly Gln Lys Met Thr  Thr Asp Glu
    1040                1045                1050

Lys Ile  Thr Lys Trp Ser Ala  Lys Tyr Phe Asn Gly  Thr Asn Ile
    1055                1060                1065

Leu Gly  Arg Gly Ala Tyr Tyr  Val Leu Lys Asp Trp  Ala Ser Asn
    1070                1075                1080

Asp Tyr  Leu Thr Asn Arg Asn  Gly Glu Ile Val Leu  Pro Lys Gln
    1085                1090                1095

Leu Val  Asn Lys Asn Ser Tyr  Thr Gly Phe Val Ser  Asp Ala Asn
    1100                1105                1110

Gly Thr  Lys Phe Tyr Ser Thr  Ser Gly Tyr Gln Ala  Lys Asn Ser
    1115                1120                1125

Phe Ile  Gln Asp Glu Asn Gly  Asn Trp Tyr Tyr Phe  Asp Lys Arg
    1130                1135                1140

Gly Tyr  Leu Val Thr Gly Ala  His Glu Ile Asp Gly  Lys His Val
    1145                1150                1155

Tyr Phe  Leu Lys Asn Gly Ile  Gln Leu Arg Asp Ser  Ile Arg Glu
    1160                1165                1170

Asp Glu  Asn Gly Asn Gln Tyr  Tyr Tyr Asp Gln Thr  Gly Ala Gln
```

-continued

```
    1175                1180                1185

Val Leu  Asn Arg Tyr Tyr Thr  Thr Asp Gly Gln Asn  Trp Arg Tyr
    1190                1195                1200

Phe Asp  Ala Lys Gly Val Met  Ala Arg Gly Leu Val  Lys Ile Gly
    1205                1210                1215

Asp Gly  Gln Gln Phe Phe Asp  Glu Asn Gly Tyr Gln  Val Lys Gly
    1220                1225                1230

Lys Ile  Val Ser Ala Lys Asp  Gly Lys Leu Arg Tyr  Phe Asp Lys
    1235                1240                1245

Asp Ser  Gly Asn Ala Val Ile  Asn Arg Phe Ala Gln  Gly Asp Asn
    1250                1255                1260

Pro Ser  Asp Trp Tyr Tyr Phe  Gly Val Glu Phe Ala  Lys Leu Thr
    1265                1270                1275

Gly Leu  Gln Lys Ile Gly Gln  Gln Thr Leu Tyr Phe  Asp Gln Asp
    1280                1285                1290

Gly Lys  Gln Val Lys Gly Lys  Ile Val Thr Leu Ser  Asp Lys Ser
    1295                1300                1305

Ile Arg  Tyr Phe Asp Ala Asn  Ser Gly Glu Met Ala  Val Gly Lys
    1310                1315                1320

Phe Ala  Glu Gly Ala Lys Asn  Glu Trp Tyr Tyr Phe  Asp Lys Thr
    1325                1330                1335

Gly Lys  Ala Val Thr Gly Leu  Gln Lys Ile Gly Lys  Gln Thr Leu
    1340                1345                1350

Tyr Phe  Asp Gln Asp Gly Lys  Gln Val Lys Gly Lys  Val Val Thr
    1355                1360                1365

Leu Ala  Asp Lys Ser Ile Arg  Tyr Phe Asp Ala Asp  Ser Gly Glu
    1370                1375                1380

Met Ala  Val Gly Lys Phe Ala  Glu Gly Ala Lys Asn  Glu Trp Tyr
    1385                1390                1395

Tyr Phe  Asp Gln Thr Gly Lys  Ala Val Thr Gly Leu  Gln Lys Ile
    1400                1405                1410

Asp Lys  Gln Thr Leu Tyr Phe  Asp Gln Asp Gly Lys  Gln Val Lys
    1415                1420                1425

Gly Lys  Ile Val Thr Leu Ser  Asp Lys Ser Ile Arg  Tyr Phe Asp
    1430                1435                1440

Ala Asn  Ser Gly Glu Met Ala  Thr Asn Lys Phe Val  Glu Gly Ser
    1445                1450                1455

Gln Asn  Glu Trp Tyr Tyr Phe  Asp Gln Ala Gly Lys  Ala Val Thr
    1460                1465                1470

Gly Leu  Gln Gln Val Gly Gln  Gln Thr Leu Tyr Phe  Thr Gln Asp
    1475                1480                1485

Gly Lys  Gln Val Lys Gly Lys  Val Val Asp Val Asn  Gly Val Ser
    1490                1495                1500

Arg Tyr  Phe Asp Ala Asn Ser  Gly Asp Met Ala Arg  Ser Lys Trp
    1505                1510                1515

Ile Gln  Leu Glu Asp Gly Ser  Trp Met Tyr Phe Asp  Arg Asp Gly
    1520                1525                1530

Arg Gly  Gln Asn Phe Gly Arg  Asn
    1535                1540
```

<210> SEQ ID NO 30
<211> LENGTH: 529
<212> TYPE: PRT
<213> ORGANISM: Thermus thermophilus
<220> FEATURE:
<221> NAME/KEY: enzyme
<222> LOCATION: (1)..(508)
<223> OTHER INFORMATION: deletion of signal sequence GK24, alpha-1,5,
-glucosidase

<400> SEQUENCE: 30

```
Met Ser Trp Trp Gln Arg Ala Val Ile Tyr Gln Val Tyr Pro Arg Ser
1               5                   10                  15

Phe Gln Asp Thr Asn Gly Asp Gly Val Gly Asp Leu Glu Gly Ile Arg
            20                  25                  30

Arg Arg Leu Pro Tyr Phe Lys Ser Leu Gly Val Asp Ala Phe Trp Leu
        35                  40                  45

Ser Pro Phe Tyr Lys Ser Pro Met Lys Asp Phe Gly Tyr Asp Val Ala
    50                  55                  60

Asp Tyr Cys Asp Val Asp Pro Val Phe Gly Thr Leu Gln Asp Phe Asp
65                  70                  75                  80

Arg Leu Leu Glu Glu Ala His Ala Leu Gly Leu Lys Val Leu Val Asp
                85                  90                  95

Leu Val Pro Asn His Thr Ser Ser Glu His Pro Trp Phe Leu Glu Ser
            100                 105                 110

Arg Ala Ser Arg Asn Ser Pro Lys Arg Asp Trp Tyr Val Trp Lys Asp
        115                 120                 125

Pro Ala Pro Asp Gly Gly Pro Pro Asn Asn Trp Gln Ser Phe Phe Gly
    130                 135                 140

Gly Pro Ala Trp Thr Leu Asp Glu Ala Thr Gly Gln Tyr Tyr Leu His
145                 150                 155                 160

Leu Phe Leu Pro Glu Gln Pro Asp Leu Asn Trp Asp Asn Pro Glu Val
                165                 170                 175

Arg Glu Ala Ile Lys Glu Val Met Arg Phe Trp Leu Arg Arg Gly Val
            180                 185                 190

Asp Gly Phe Arg Val Asp Val Leu Trp Leu Leu Gly Lys Asp Pro Leu
        195                 200                 205

Phe Arg Asp Glu Pro Gly Ser Pro Leu Trp Arg Pro Gly Leu Pro Asp
    210                 215                 220

Arg Ala Arg His Glu His Leu Tyr Thr Glu Asp Gln Pro Glu Thr Tyr
225                 230                 235                 240

Ala Tyr Val Arg Glu Met Arg Gln Val Leu Asp Glu Phe Ser Glu Pro
                245                 250                 255

Gly Arg Glu Arg Val Met Val Gly Glu Ile Tyr Leu Pro Leu Pro Arg
            260                 265                 270

Leu Val Arg Tyr Tyr Ala Ala Gly Cys His Leu Pro Phe Asn Phe Ser
        275                 280                 285

Leu Val Thr Glu Gly Leu Ser Asp Trp Arg Pro Glu Asn Leu Ala Arg
    290                 295                 300

Ile Val Glu Thr Tyr Glu Gly Leu Leu Thr Arg Trp Asp Trp Pro Asn
305                 310                 315                 320

Trp Val Leu Gly Asn His Asp Gln Pro Arg Leu Ala Ser Arg Leu Gly
                325                 330                 335

Glu Pro Gln Ala Arg Val Ala Ala Met Leu Leu Phe Thr Leu Arg Gly
            340                 345                 350

Thr Pro Thr Trp Tyr Tyr Gly Asp Glu Leu Ala Leu Pro Asn Gly Leu
        355                 360                 365

Ile Pro Pro Glu Lys Val Gln Asp Pro Ala Ala Leu Arg Gln Arg Asp
    370                 375                 380
```

Arg Glu Pro Thr Ala Tyr His Thr Leu Gly Arg Asp Pro Glu Arg Thr
385 390 395 400

Pro Met Pro Trp Asp Ala Ser Pro Tyr Gly Gly Phe Ser Thr Val Glu
405 410 415

Pro Trp Leu Pro Leu Asn Pro Asp Tyr Lys Thr Arg Asn Val Ala Ala
420 425 430

Gln Glu Lys Asp Pro Arg Ser Met Leu His Leu Val Lys Arg Leu Ile
435 440 445

Ala Leu Arg Lys Asp Pro Gly Leu Leu Tyr Gly Ala Tyr Arg Thr Tyr
450 455 460

Arg Ala Arg Glu Gly Val Tyr Ala Tyr Leu Arg Gly Glu Gly Trp Leu
465 470 475 480

Val Ala Leu Asn Leu Thr Glu Lys Glu Lys Ala Leu Glu Leu Pro Arg
485 490 495

Gly Gly Arg Val Val Leu Ser Thr His Leu Asp Arg Glu Glu Arg Val
500 505 510

Gly Glu Arg Leu Phe Leu Arg Pro Asp Glu Gly Val Ala Val Arg Leu
515 520 525

Asp

<210> SEQ ID NO 31
<211> LENGTH: 575
<212> TYPE: PRT
<213> ORGANISM: Thermus thermophilus
<220> FEATURE:
<221> NAME/KEY: enzyme
<222> LOCATION: (1)..(554)
<223> OTHER INFORMATION: alpha-1,5-glucosidase

<400> SEQUENCE: 31

Met Val Asp Gly Glu Gly Arg Leu Leu Gly Ile Val Thr Arg Gly Arg
1 5 10 15

Leu Leu Ala Ala Leu Ala Gly Arg Tyr Thr Pro Glu Val Pro Gln Ser
20 25 30

Gly Val Asp Ser Gly Pro Gln Ser Gly Val Asp Ser Gly Ser Met Ser
35 40 45

Trp Trp Gln Arg Ala Val Ile Tyr Gln Val Tyr Pro Arg Ser Phe Gln
50 55 60

Asp Thr Asn Gly Asp Gly Val Gly Asp Leu Glu Gly Ile Arg Arg Arg
65 70 75 80

Leu Pro Tyr Phe Lys Ser Leu Gly Val Asp Ala Phe Trp Leu Ser Pro
85 90 95

Phe Tyr Lys Ser Pro Met Lys Asp Phe Gly Tyr Asp Val Ala Asp Tyr
100 105 110

Cys Asp Val Asp Pro Val Phe Gly Thr Leu Gln Asp Phe Asp Arg Leu
115 120 125

Leu Glu Glu Ala His Ala Leu Gly Leu Lys Val Leu Val Asp Leu Val
130 135 140

Pro Asn His Thr Ser Ser Glu His Pro Trp Phe Leu Glu Ser Arg Ala
145 150 155 160

Ser Arg Asn Ser Pro Lys Arg Asp Trp Tyr Val Trp Lys Asp Pro Ala
165 170 175

Pro Asp Gly Gly Pro Pro Asn Asn Trp Gln Ser Phe Phe Gly Gly Pro
180 185 190

Ala Trp Thr Leu Asp Glu Ala Thr Gly Gln Tyr Tyr Leu His Leu Phe

```
        195                 200                 205

Leu Pro Glu Gln Pro Asp Leu Asn Trp Asp Asn Pro Glu Val Arg Glu
    210                 215                 220

Ala Ile Lys Glu Val Met Arg Phe Trp Leu Arg Arg Gly Val Asp Gly
225                 230                 235                 240

Phe Arg Val Asp Val Leu Trp Leu Leu Gly Lys Asp Pro Leu Phe Arg
                245                 250                 255

Asp Glu Pro Gly Ser Pro Leu Trp Arg Pro Gly Leu Pro Asp Arg Ala
            260                 265                 270

Arg His Glu His Leu Tyr Thr Glu Asp Gln Pro Glu Thr Tyr Ala Tyr
        275                 280                 285

Val Arg Glu Met Arg Gln Val Leu Asp Glu Phe Ser Glu Pro Gly Arg
    290                 295                 300

Glu Arg Val Met Val Gly Glu Ile Tyr Leu Pro Leu Pro Arg Leu Val
305                 310                 315                 320

Arg Tyr Tyr Ala Ala Gly Cys His Leu Pro Phe Asn Phe Ser Leu Val
                325                 330                 335

Thr Glu Gly Leu Ser Asp Trp Arg Pro Glu Asn Leu Ala Arg Ile Val
            340                 345                 350

Glu Thr Tyr Glu Gly Leu Leu Thr Arg Trp Asp Trp Pro Asn Trp Val
        355                 360                 365

Leu Gly Asn His Asp Gln Pro Arg Leu Ala Ser Arg Leu Gly Glu Pro
    370                 375                 380

Gln Ala Arg Val Ala Ala Met Leu Leu Phe Thr Leu Arg Gly Thr Pro
385                 390                 395                 400

Thr Trp Tyr Tyr Gly Asp Glu Leu Ala Leu Pro Asn Gly Leu Ile Pro
                405                 410                 415

Pro Glu Lys Val Gln Asp Pro Ala Ala Leu Arg Gln Arg Asp Arg Glu
            420                 425                 430

Pro Thr Ala Tyr His Thr Leu Gly Arg Asp Pro Glu Arg Thr Pro Met
        435                 440                 445

Pro Trp Asp Ala Ser Pro Tyr Gly Gly Phe Ser Thr Val Glu Pro Trp
    450                 455                 460

Leu Pro Leu Asn Pro Asp Tyr Lys Thr Arg Asn Val Ala Ala Gln Glu
465                 470                 475                 480

Lys Asp Pro Arg Ser Met Leu His Leu Val Lys Arg Leu Ile Ala Leu
                485                 490                 495

Arg Lys Asp Pro Gly Leu Leu Tyr Gly Ala Tyr Arg Thr Tyr Arg Ala
            500                 505                 510

Arg Glu Gly Val Tyr Ala Tyr Leu Arg Gly Glu Gly Trp Leu Val Ala
        515                 520                 525

Leu Asn Leu Thr Glu Lys Glu Lys Ala Leu Glu Leu Pro Arg Gly Gly
    530                 535                 540

Arg Val Val Leu Ser Thr His Leu Asp Arg Glu Glu Arg Val Gly Glu
545                 550                 555                 560

Arg Leu Phe Leu Arg Pro Asp Glu Gly Val Ala Val Arg Leu Asp
                565                 570                 575
```

<210> SEQ ID NO 32
<211> LENGTH: 528
<212> TYPE: PRT
<213> ORGANISM: Thermus thermophilus
<220> FEATURE:
<221> NAME/KEY: enzyme
<222> LOCATION: (1)..(507)

<223> OTHER INFORMATION: alpha-1,5-glucosidase

<400> SEQUENCE: 32

```
Met Trp Trp Lys Glu Ala Val Ile Tyr Gln Val Tyr Pro Arg Ser Phe
1               5                   10                  15

Gln Asp Thr Asn Gly Asp Gly Val Gly Asp Leu Glu Gly Val Arg Arg
            20                  25                  30

Arg Leu Pro Tyr Leu Lys Ser Leu Gly Val Asp Ala Leu Trp Leu Ser
        35                  40                  45

Pro Phe Tyr Lys Ser Pro Met Lys Asp Phe Gly Tyr Asp Val Ala Asp
    50                  55                  60

Tyr Cys Asp Val Asp Pro Val Phe Gly Thr Leu Gln Asp Phe Asp Arg
65                  70                  75                  80

Leu Leu Glu Glu Ala His Ala Leu Gly Leu Lys Val Leu Val Asp Leu
                85                  90                  95

Val Pro Asn His Thr Ser Ser Glu His Pro Trp Phe Leu Glu Ser Arg
            100                 105                 110

Ala Ser Arg Asn Ser Pro Lys Arg Asp Trp Tyr Ile Trp Lys Asp Pro
        115                 120                 125

Ala Pro Asp Gly Gly Pro Pro Asn Asn Trp Gln Ser Phe Phe Gly Gly
    130                 135                 140

Pro Ala Trp Thr Leu Asp Glu Ala Thr Gly Gln Tyr Tyr Leu His Gln
145                 150                 155                 160

Phe Leu Pro Glu Gln Pro Asp Leu Asn Trp Arg Asn Pro Glu Val Arg
                165                 170                 175

Glu Ala Ile Tyr Glu Val Met Arg Phe Trp Leu Arg Arg Gly Val Asp
            180                 185                 190

Gly Phe Arg Val Asp Val Leu Trp Leu Leu Ala Glu Asp Leu Leu Phe
        195                 200                 205

Arg Asp Glu Pro Gly Asn Pro Asp Trp Arg Pro Gly Met Trp Asp Arg
    210                 215                 220

Gly Arg His Leu His Ile Phe Thr Glu Asp Gln Pro Glu Thr Tyr Ala
225                 230                 235                 240

Tyr Val Arg Glu Met Arg Gln Val Leu Asp Glu Phe Ser Glu Pro Gly
                245                 250                 255

Arg Glu Arg Val Met Val Gly Glu Ile Tyr Leu Pro Tyr Pro Gln Leu
            260                 265                 270

Val Arg Tyr Tyr Gln Ala Gly Cys His Leu Pro Phe Asn Phe His Leu
        275                 280                 285

Ile Phe Arg Gly Leu Pro Asp Trp Arg Pro Glu Asn Leu Ala Arg Ile
    290                 295                 300

Val Glu Glu Tyr Glu Ser Leu Leu Thr Arg Trp Asp Trp Pro Asn Trp
305                 310                 315                 320

Val Leu Gly Asn His Asp Gln Pro Arg Leu Ala Ser Arg Leu Gly Glu
                325                 330                 335

Ala Gln Ala Arg Val Ala Ala Met Leu Leu Phe Thr Leu Arg Gly Thr
            340                 345                 350

Pro Thr Trp Tyr Tyr Gly Asp Glu Ile Gly Met Lys Asn Gly Glu Ile
        355                 360                 365

Pro Pro Glu Lys Val Gln Asp Pro Ala Ala Leu Arg Gln Lys Asp Arg
    370                 375                 380

Leu Gly Glu His Asn Leu Pro Pro Gly Arg Asp Pro Glu Arg Thr Pro
385                 390                 395                 400
```

```
Met Gln Trp Asp Asp Thr Pro Phe Ala Gly Phe Ser Thr Val Glu Pro
                405                 410                 415

Trp Leu Pro Val Asn Pro Asp Tyr Lys Thr Arg Asn Val Ala Ala Gln
            420                 425                 430

Glu Gln Asp Pro Arg Ser Met Leu His Leu Val Arg Arg Leu Ile Ala
        435                 440                 445

Leu Arg Lys Asp Pro Asp Leu Leu Tyr Gly Ala Tyr Arg Thr Tyr Arg
    450                 455                 460

Ala Arg Glu Gly Val Tyr Ala Tyr Leu Arg Gly Glu Gly Trp Leu Val
465                 470                 475                 480

Ala Leu Asn Leu Thr Glu Lys Glu Lys Ala Leu Glu Leu Pro Arg Gly
                485                 490                 495

Gly Arg Val Val Leu Ser Thr His Leu Asp Arg Glu Glu Arg Val Gly
            500                 505                 510

Glu Arg Leu Phe Leu Arg Pro Asp Glu Gly Val Ala Val Arg Leu Asp
        515                 520                 525


<210> SEQ ID NO 33
<211> LENGTH: 529
<212> TYPE: PRT
<213> ORGANISM: Thermus thermophilus
<220> FEATURE:
<221> NAME/KEY: enzyme
<222> LOCATION: (1)..(508)
<223> OTHER INFORMATION: alpha-1,5-glucosidase

<400> SEQUENCE: 33

Met Ser Trp Trp Gln Arg Ala Val Ile Tyr Gln Val Tyr Pro Arg Ser
1               5                   10                  15

Phe Gln Asp Thr Asn Gly Asp Gly Val Gly Asp Leu Glu Gly Ile Arg
            20                  25                  30

Arg Arg Leu Pro Tyr Leu Lys Ser Leu Gly Val Asp Ala Leu Trp Leu
        35                  40                  45

Ser Pro Phe Tyr Lys Ser Pro Met Lys Asp Phe Gly Tyr Asp Val Ala
    50                  55                  60

Asp Tyr Cys Asp Val Asp Pro Val Phe Gly Thr Leu Gln Asp Phe Asp
65                  70                  75                  80

Arg Leu Leu Glu Glu Ala His Ala Leu Gly Leu Lys Val Leu Val Asp
                85                  90                  95

Leu Val Pro Asn His Thr Ser Ser Glu His Pro Trp Phe Leu Glu Ser
            100                 105                 110

Arg Ala Ser Arg Asn Ser Pro Lys Arg Asp Trp Tyr Ile Trp Lys Asp
        115                 120                 125

Pro Ala Pro Asp Gly Gly Pro Pro Asn Asn Trp Gln Ser Phe Phe Gly
    130                 135                 140

Gly Pro Ala Trp Thr Leu Asp Glu Ala Thr Gly Gln Tyr Tyr Leu His
145                 150                 155                 160

Leu Phe Leu Pro Glu Gln Pro Asp Leu Asn Trp Arg Asn Pro Glu Val
                165                 170                 175

Arg Glu Ala Ile Lys Glu Val Met Arg Phe Trp Leu Arg Arg Gly Val
            180                 185                 190

Asp Gly Phe Arg Val Asp Val Leu Trp Leu Leu Gly Lys Asp Pro Leu
        195                 200                 205

Phe Arg Asp Glu Pro Gly Ser Pro Leu Trp Arg Pro Gly Leu Pro Asp
    210                 215                 220

Arg Ala Arg His Glu His Leu Tyr Thr Glu Asp Gln Pro Glu Thr Tyr
```

```
225                 230                 235                 240

Ala Tyr Val Arg Glu Met Arg Gln Val Leu Asp Glu Phe Ser Glu Pro
                245                 250                 255

Gly Arg Glu Arg Val Met Val Gly Glu Ile Tyr Leu Pro Leu Pro Arg
            260                 265                 270

Leu Val Arg Tyr Tyr Ala Ala Gly Cys His Leu Pro Phe Asn Phe Ser
        275                 280                 285

Leu Val Thr Glu Gly Leu Ser Asp Trp Arg Pro Glu Asn Leu Ala Arg
    290                 295                 300

Ile Val Glu Thr Tyr Glu Gly Leu Leu Ser Arg Trp Asp Trp Pro Asn
305                 310                 315                 320

Trp Val Leu Gly Asn His Asp Gln Pro Arg Leu Ala Ser Arg Leu Gly
                325                 330                 335

Glu Pro Gln Ala Arg Val Ala Ala Met Leu Leu Phe Thr Leu Arg Gly
            340                 345                 350

Thr Pro Thr Trp Tyr Tyr Gly Asp Glu Leu Ala Leu Pro Asn Gly Leu
        355                 360                 365

Ile Pro Pro Glu Lys Val Gln Asp Pro Ala Ala Leu Arg Gln Arg Asp
    370                 375                 380

Arg Glu Pro Thr Ala Tyr His Thr Leu Gly Arg Asp Pro Glu Arg Thr
385                 390                 395                 400

Pro Met Pro Trp Asp Ala Ser Pro Tyr Gly Gly Phe Ser Thr Val Glu
                405                 410                 415

Pro Trp Leu Pro Leu Asn Pro Asp Tyr Arg Thr Arg Asn Val Ala Ala
            420                 425                 430

Gln Glu Lys Asp Pro Arg Ser Met Leu His Leu Val Lys Arg Leu Ile
        435                 440                 445

Ala Leu Arg Lys Asp Pro Asp Leu Leu Tyr Gly Ala Tyr Arg Thr Tyr
    450                 455                 460

Arg Ala Arg Glu Gly Val Tyr Ala Tyr Leu Arg Gly Glu Gly Trp Leu
465                 470                 475                 480

Val Ala Leu Asn Leu Thr Glu Lys Glu Lys Ala Leu Glu Leu Pro Arg
                485                 490                 495

Gly Gly Arg Val Val Leu Ser Thr His Leu Asp Arg Glu Glu Arg Val
            500                 505                 510

Gly Glu Arg Leu Phe Leu Arg Pro Asp Glu Gly Val Ala Val Arg Leu
        515                 520                 525

Asp
```

<210> SEQ ID NO 34
<211> LENGTH: 587
<212> TYPE: PRT
<213> ORGANISM: Bacillus
<220> FEATURE:
<221> NAME/KEY: enzyme
<222> LOCATION: (1)..(587)
<223> OTHER INFORMATION: alpha-1,1-glucosidase

<400> SEQUENCE: 34

```
Met Ser Thr Ala Leu Thr Gln Thr Ser Thr Asn Ser Gln Gln Ser Pro
1               5                   10                  15

Ile Arg Arg Ala Trp Trp Lys Glu Ala Val Val Tyr Gln Ile Tyr Pro
            20                  25                  30

Arg Ser Phe Met Asp Ser Asn Gly Asp Gly Ile Gly Asp Leu Arg Gly
        35                  40                  45
```

-continued

```
Ile Leu Ser Lys Leu Asp Tyr Leu Lys Leu Leu Gly Val Asp Val Leu
    50                  55                  60

Trp Leu Asn Pro Ile Tyr Asp Ser Pro Asn Asp Asp Met Gly Tyr Asp
65                  70                  75                  80

Ile Arg Asp Tyr Tyr Lys Ile Met Glu Glu Phe Gly Thr Met Glu Asp
                85                  90                  95

Phe Glu Glu Leu Leu Arg Glu Val His Ala Arg Gly Met Lys Leu Val
            100                 105                 110

Met Asp Leu Val Ala Asn His Thr Ser Asp Glu His Pro Trp Phe Ile
        115                 120                 125

Glu Ser Arg Ser Ser Arg Asp Asn Pro Tyr Arg Asp Trp Tyr Ile Trp
    130                 135                 140

Arg Asp Pro Lys Asp Gly Arg Glu Pro Asn Asn Trp Leu Ser Tyr Phe
145                 150                 155                 160

Ser Gly Ser Ala Trp Glu Tyr Asp Glu Arg Thr Gly Gln Tyr Tyr Leu
                165                 170                 175

His Leu Phe Ser Arg Arg Gln Pro Asp Leu Asn Trp Glu Asn Pro Lys
            180                 185                 190

Val Arg Glu Ala Ile Phe Glu Met Met Arg Phe Trp Leu Asp Lys Gly
        195                 200                 205

Ile Asp Gly Phe Arg Met Asp Val Ile Asn Ala Ile Ala Lys Ala Glu
    210                 215                 220

Gly Leu Pro Asp Ala Pro Ala Arg Pro Gly Glu Arg Tyr Ala Trp Gly
225                 230                 235                 240

Gly Gln Tyr Phe Leu Asn Gln Pro Lys Val His Glu Tyr Leu Arg Glu
                245                 250                 255

Met Tyr Asp Lys Val Leu Ser His Tyr Asp Ile Met Thr Val Gly Glu
            260                 265                 270

Thr Gly Gly Val Thr Thr Lys Asp Ala Leu Leu Phe Ala Gly Glu Asp
        275                 280                 285

Arg Arg Glu Leu Asn Met Val Phe Gln Phe Glu His Met Asp Ile Asp
    290                 295                 300

Ala Thr Asp Gly Asp Lys Trp Arg Pro Arg Pro Trp Arg Leu Thr Glu
305                 310                 315                 320

Leu Lys Thr Ile Met Thr Arg Trp Gln Asn Asp Leu Tyr Gly Lys Ala
                325                 330                 335

Trp Asn Ser Leu Tyr Trp Thr Asn His Asp Gln Pro Arg Ala Val Ser
            340                 345                 350

Arg Phe Gly Asn Asp Gly Pro Tyr Arg Val Glu Ser Ala Lys Met Leu
        355                 360                 365

Ala Thr Val Leu His Met Met Gln Gly Thr Pro Tyr Ile Tyr Gln Gly
    370                 375                 380

Glu Glu Ile Gly Met Thr Asn Cys Pro Phe Asp Ser Ile Asp Glu Tyr
385                 390                 395                 400

Arg Asp Val Glu Ile His Asn Leu Trp Arg His Arg Val Met Glu Gly
                405                 410                 415

Gly Gln Asp Pro Ala Glu Val Leu Arg Val Ile Gln Leu Lys Gly Arg
            420                 425                 430

Asp Asn Ala Arg Thr Pro Met Gln Trp Asp Asp Ser Pro Asn Ala Gly
        435                 440                 445

Phe Thr Thr Gly Thr Pro Trp Ile Lys Val Asn Pro Asn Tyr Arg Glu
    450                 455                 460

Ile Asn Val Lys Gln Ala Leu Ala Asp Pro Asn Ser Ile Phe His Tyr
```

```
465                 470                 475                 480

Tyr Arg Arg Leu Ile Gln Leu Arg Lys Gln His Pro Ile Val Val Tyr
                485                 490                 495

Gly Lys Tyr Asp Leu Ile Leu Pro Asp His Glu Glu Ile Trp Ala Tyr
            500                 505                 510

Thr Arg Thr Leu Gly Asp Glu Arg Trp Leu Ile Val Ala Asn Phe Phe
        515                 520                 525

Gly Gly Thr Pro Glu Phe Glu Leu Pro Pro Glu Val Arg Cys Glu Gly
    530                 535                 540

Ala Glu Leu Val Ile Ala Asn Tyr Pro Val Asp Asp Ser Glu Ala Gly
545                 550                 555                 560

Gly Pro Ala Ala Ala Gly Ala Pro His Arg Phe Arg Leu Arg Pro Tyr
                565                 570                 575

Glu Cys Arg Val Tyr Arg Leu Leu Gly Trp His
            580                 585


<210> SEQ ID NO 35
<211> LENGTH: 4626
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(4626)
<223> OTHER INFORMATION: dicot optimized dextransucrase with leucrose
      synthase activity

<400> SEQUENCE: 35

atg ctt gag tct ggt gtt gtt cac gct gat gat gtt aag caa gtg gtt       48
Met Leu Glu Ser Gly Val Val His Ala Asp Asp Val Lys Gln Val Val
1               5                   10                  15

gtt caa gaa cca gct act gct caa act tct gga cca gga caa caa act       96
Val Gln Glu Pro Ala Thr Ala Gln Thr Ser Gly Pro Gly Gln Gln Thr
            20                  25                  30

cca gct cag gct aag att gct tct gaa caa gag gct gag aaa gtt act      144
Pro Ala Gln Ala Lys Ile Ala Ser Glu Gln Glu Ala Glu Lys Val Thr
        35                  40                  45

cca gct gat aag gtg aca gat gat gtt gct gct tct gaa aag cca gct      192
Pro Ala Asp Lys Val Thr Asp Asp Val Ala Ala Ser Glu Lys Pro Ala
    50                  55                  60

aaa cca gct gag aat act gag gct act gtt cag act aat gct caa gag      240
Lys Pro Ala Glu Asn Thr Glu Ala Thr Val Gln Thr Asn Ala Gln Glu
65                  70                  75                  80

cca gca aag cct gct gat aca aaa gaa gct tcc act gag aag gct gct      288
Pro Ala Lys Pro Ala Asp Thr Lys Glu Ala Ser Thr Glu Lys Ala Ala
                85                  90                  95

gtt gct gaa gaa gtt aag gct gct aac gct att act gag atc cca aag      336
Val Ala Glu Glu Val Lys Ala Ala Asn Ala Ile Thr Glu Ile Pro Lys
            100                 105                 110

act gaa gtt gct gat cag aat aag caa gct agg cca act act gct caa      384
Thr Glu Val Ala Asp Gln Asn Lys Gln Ala Arg Pro Thr Thr Ala Gln
        115                 120                 125

gat caa gag ggt gat aag agg gaa aag act gct gtg gag gat aag att      432
Asp Gln Glu Gly Asp Lys Arg Glu Lys Thr Ala Val Glu Asp Lys Ile
    130                 135                 140

gtg gct aac cca aag gtt gca aag aag gat aga ctt cca gaa cca gga      480
Val Ala Asn Pro Lys Val Ala Lys Lys Asp Arg Leu Pro Glu Pro Gly
145                 150                 155                 160

tct aag caa ggt gct att gct gaa agg atg gtg gct gat caa gct caa      528
```

-continued

```
Ser Lys Gln Gly Ala Ile Ala Glu Arg Met Val Ala Asp Gln Ala Gln
                165                 170                 175

cca gct cca gtt aat gct gat cac gat gat gat gtg ctt tcc cac atc      576
Pro Ala Pro Val Asn Ala Asp His Asp Asp Asp Val Leu Ser His Ile
            180                 185                 190

aag act atc gat gga aag aac tac tac gtt cag gat gat gga act gtg      624
Lys Thr Ile Asp Gly Lys Asn Tyr Tyr Val Gln Asp Asp Gly Thr Val
        195                 200                 205

aag aag aac ttc gct gtt gag ctt aac gga cgt atc ctt tac ttt gat      672
Lys Lys Asn Phe Ala Val Glu Leu Asn Gly Arg Ile Leu Tyr Phe Asp
    210                 215                 220

gct gag act ggt gct ctt gtt gat tct aac gag tac caa ttc cag cag      720
Ala Glu Thr Gly Ala Leu Val Asp Ser Asn Glu Tyr Gln Phe Gln Gln
225                 230                 235                 240

gga act tct tca ctt aac aac gag ttc tcc cag aag aat gct ttc tac      768
Gly Thr Ser Ser Leu Asn Asn Glu Phe Ser Gln Lys Asn Ala Phe Tyr
                245                 250                 255

gga act act gat aag gat atc gag act gtg gat gga tat ctt act gct      816
Gly Thr Thr Asp Lys Asp Ile Glu Thr Val Asp Gly Tyr Leu Thr Ala
            260                 265                 270

gat tcc tgg tat cgt cca aag ttc atc ctc aag gat gga aag act tgg      864
Asp Ser Trp Tyr Arg Pro Lys Phe Ile Leu Lys Asp Gly Lys Thr Trp
        275                 280                 285

act gct tcc act gaa act gat ctt agg cca ctt ctt atg gct tgg tgg      912
Thr Ala Ser Thr Glu Thr Asp Leu Arg Pro Leu Leu Met Ala Trp Trp
    290                 295                 300

cca gat aag agg act cag atc aac tac ctc aac tac atg aat cag caa      960
Pro Asp Lys Arg Thr Gln Ile Asn Tyr Leu Asn Tyr Met Asn Gln Gln
305                 310                 315                 320

gga ctt gga gct ggt gct ttc gag aat aag gtt gag cag gct ctt ttg     1008
Gly Leu Gly Ala Gly Ala Phe Glu Asn Lys Val Glu Gln Ala Leu Leu
                325                 330                 335

act ggt gct tct caa caa gtt cag agg aag atc gaa gag aag atc gga     1056
Thr Gly Ala Ser Gln Gln Val Gln Arg Lys Ile Glu Glu Lys Ile Gly
            340                 345                 350

aaa gaa ggt gat aca aag tgg ctt agg act ctt atg gga gct ttc gtt     1104
Lys Glu Gly Asp Thr Lys Trp Leu Arg Thr Leu Met Gly Ala Phe Val
        355                 360                 365

aag act cag cca aac tgg aac att aag act gag tcc gag act act gga     1152
Lys Thr Gln Pro Asn Trp Asn Ile Lys Thr Glu Ser Glu Thr Thr Gly
    370                 375                 380

act aag aag gat cat ctt cag gga ggt gca ctt ctt tac act aac aac     1200
Thr Lys Lys Asp His Leu Gln Gly Gly Ala Leu Leu Tyr Thr Asn Asn
385                 390                 395                 400

gag aag tct cca cat gct gat tct aag ttc agg ctc ctt aac aga act     1248
Glu Lys Ser Pro His Ala Asp Ser Lys Phe Arg Leu Leu Asn Arg Thr
                405                 410                 415

cca act tcc caa act ggt act cca aag tac ttc atc gat aag tcc aat     1296
Pro Thr Ser Gln Thr Gly Thr Pro Lys Tyr Phe Ile Asp Lys Ser Asn
            420                 425                 430

ggt gga tac gag ttc ctt ctc gct aac gat ttc gat aac tcc aat cct     1344
Gly Gly Tyr Glu Phe Leu Leu Ala Asn Asp Phe Asp Asn Ser Asn Pro
        435                 440                 445

gcc gta caa gct gaa cag ctt aac tgg ctc cac tac atg atg aac ttc     1392
Ala Val Gln Ala Glu Gln Leu Asn Trp Leu His Tyr Met Met Asn Phe
    450                 455                 460

gga tct atc gtt gct aat gat cca act gct aac ttc gat ggt gtt aga     1440
Gly Ser Ile Val Ala Asn Asp Pro Thr Ala Asn Phe Asp Gly Val Arg
465                 470                 475                 480
```

-continued

```
gtt gat gct gtg gat aac gtg aac gct gat ctt ctt cag att gct tcc      1488
Val Asp Ala Val Asp Asn Val Asn Ala Asp Leu Leu Gln Ile Ala Ser
                485                 490                 495

gat tac ttc aag tcc agg tac aaa gtt gga gaa tct gag gaa gag gct      1536
Asp Tyr Phe Lys Ser Arg Tyr Lys Val Gly Glu Ser Glu Glu Glu Ala
            500                 505                 510

att aag cac ctt tct atc ctt gaa gct tgg agt gat aac gat cca gat      1584
Ile Lys His Leu Ser Ile Leu Glu Ala Trp Ser Asp Asn Asp Pro Asp
        515                 520                 525

tac aac aag gat aca aag ggt gct cag ttg gct att gat aac aag ctt      1632
Tyr Asn Lys Asp Thr Lys Gly Ala Gln Leu Ala Ile Asp Asn Lys Leu
    530                 535                 540

agg ctt tct ctt ctc tac tcc ttc atg agg aac ctt tct att aga tcc      1680
Arg Leu Ser Leu Leu Tyr Ser Phe Met Arg Asn Leu Ser Ile Arg Ser
545                 550                 555                 560

ggt gtt gag cca act att act aac tcc ctc aac gat agg tca tct gag      1728
Gly Val Glu Pro Thr Ile Thr Asn Ser Leu Asn Asp Arg Ser Ser Glu
                565                 570                 575

aag aaa aac ggt gaa agg atg gct aac tac atc ttt gtt agg gca cac      1776
Lys Lys Asn Gly Glu Arg Met Ala Asn Tyr Ile Phe Val Arg Ala His
            580                 585                 590

gat gat gag gtt cag act gtg atc gct gat atc atc aga gag aac atc      1824
Asp Asp Glu Val Gln Thr Val Ile Ala Asp Ile Ile Arg Glu Asn Ile
        595                 600                 605

aac cca aac act gat gga ctc act ttc act atg gat gag ctt aag cag      1872
Asn Pro Asn Thr Asp Gly Leu Thr Phe Thr Met Asp Glu Leu Lys Gln
    610                 615                 620

gct ttc aag atc tac aac gag gat atg agg aag gct gat aag aag tac      1920
Ala Phe Lys Ile Tyr Asn Glu Asp Met Arg Lys Ala Asp Lys Lys Tyr
625                 630                 635                 640

act cag ttc aac att cca act gct cac gct ctt atg ctt tcc aac aag      1968
Thr Gln Phe Asn Ile Pro Thr Ala His Ala Leu Met Leu Ser Asn Lys
                645                 650                 655

gat tcc atc act agg gtt tac tac ggt gat ctc tac act gat gat gga      2016
Asp Ser Ile Thr Arg Val Tyr Tyr Gly Asp Leu Tyr Thr Asp Asp Gly
            660                 665                 670

cag tac atg gaa aag aag tcc cca tac cac gac gct att gat gct ttg      2064
Gln Tyr Met Glu Lys Lys Ser Pro Tyr His Asp Ala Ile Asp Ala Leu
        675                 680                 685

ctc agg gct agg att aag tat gtt gct gga gga cag gat atg aag gtg      2112
Leu Arg Ala Arg Ile Lys Tyr Val Ala Gly Gly Gln Asp Met Lys Val
    690                 695                 700

aca tat atg gga gtt cca aga gaa gct gat aag tgg tcc tac aac gga      2160
Thr Tyr Met Gly Val Pro Arg Glu Ala Asp Lys Trp Ser Tyr Asn Gly
705                 710                 715                 720

att ctt act tct gtg cgt tat gga act ggt gct aac gaa gct act gat      2208
Ile Leu Thr Ser Val Arg Tyr Gly Thr Gly Ala Asn Glu Ala Thr Asp
                725                 730                 735

gaa ggt act gct gag act aga act cag gga atg gct gtg att gct tcc      2256
Glu Gly Thr Ala Glu Thr Arg Thr Gln Gly Met Ala Val Ile Ala Ser
            740                 745                 750

aat aac cca aac ctc aag ctt aat gag tgg gat aag ctc caa gtt aat      2304
Asn Asn Pro Asn Leu Lys Leu Asn Glu Trp Asp Lys Leu Gln Val Asn
        755                 760                 765

atg gga gct gct cac aag aat cag tac tac cgt cca gtg ctt ctt act      2352
Met Gly Ala Ala His Lys Asn Gln Tyr Tyr Arg Pro Val Leu Leu Thr
    770                 775                 780

act aag gat gga atc tcc cgt tat ctc act gat gaa gag gtt cca cag      2400
Thr Lys Asp Gly Ile Ser Arg Tyr Leu Thr Asp Glu Glu Val Pro Gln
785                 790                 795                 800
```

```
tct ttg tgg aag aaa act gat gct aac gga atc ctc act ttc gat atg     2448
Ser Leu Trp Lys Lys Thr Asp Ala Asn Gly Ile Leu Thr Phe Asp Met
                805                 810                 815

aac gat atc gct gga tac tct aac gtt cag gtg tca gga tat ctt gct     2496
Asn Asp Ile Ala Gly Tyr Ser Asn Val Gln Val Ser Gly Tyr Leu Ala
            820                 825                 830

gtt tgg gtt cca gtt gga gct aag gct gat caa gat gct aga act act     2544
Val Trp Val Pro Val Gly Ala Lys Ala Asp Gln Asp Ala Arg Thr Thr
        835                 840                 845

gct tcc aag aag aag aac gct tct gga caa gtt tac gag tca tct gct     2592
Ala Ser Lys Lys Lys Asn Ala Ser Gly Gln Val Tyr Glu Ser Ser Ala
    850                 855                 860

gct ctt gat tct cag ctt atc tac gag gga ttc tcc aat ttt cag gat     2640
Ala Leu Asp Ser Gln Leu Ile Tyr Glu Gly Phe Ser Asn Phe Gln Asp
865                 870                 875                 880

ttc gct act agg gat gat cag tac act aac aag gtg atc gct aag aac     2688
Phe Ala Thr Arg Asp Asp Gln Tyr Thr Asn Lys Val Ile Ala Lys Asn
                885                 890                 895

gtg aac ctt ttc aaa gag tgg gga gtt act tct ttt gag ctt cca cca     2736
Val Asn Leu Phe Lys Glu Trp Gly Val Thr Ser Phe Glu Leu Pro Pro
            900                 905                 910

cag tac gtt tct tct cag gat gga act ttc ctc gat tcc atc atc caa     2784
Gln Tyr Val Ser Ser Gln Asp Gly Thr Phe Leu Asp Ser Ile Ile Gln
        915                 920                 925

aac gga tac gct ttt gag gat cgt tac gat atg gct atg tcc aag aac     2832
Asn Gly Tyr Ala Phe Glu Asp Arg Tyr Asp Met Ala Met Ser Lys Asn
    930                 935                 940

aac aag tac ggt tct ctt aag gat ctt ctc aac gct ctt agg gca ctt     2880
Asn Lys Tyr Gly Ser Leu Lys Asp Leu Leu Asn Ala Leu Arg Ala Leu
945                 950                 955                 960

cac tct gtc aac atc cag gct att gct gat tgg gtg ccc gat cag atc     2928
His Ser Val Asn Ile Gln Ala Ile Ala Asp Trp Val Pro Asp Gln Ile
                965                 970                 975

tat aac ctc cct gga aaa gaa gtt gtt act gct act agg gtg aac aac     2976
Tyr Asn Leu Pro Gly Lys Glu Val Val Thr Ala Thr Arg Val Asn Asn
            980                 985                 990

tac gga act tat cgt gaa ggt gct  gag atc aaa gag aag  ctc tac gtt   3024
Tyr Gly Thr Tyr Arg Glu Gly Ala  Glu Ile Lys Glu Lys  Leu Tyr Val
        995                 1000                1005

gct aac  tct aag act aac gag  act gat ttc cag gga  aag tat ggt      3069
Ala Asn  Ser Lys Thr Asn Glu  Thr Asp Phe Gln Gly  Lys Tyr Gly
    1010                1015                1020

gga gct  ttc ctt gat gag ttg  aag gct aag tac cca  gag att ttc      3114
Gly Ala  Phe Leu Asp Glu Leu  Lys Ala Lys Tyr Pro  Glu Ile Phe
    1025                1030                1035

gag agg  gtt cag att tct aac  gga cag aag atg act  act gac gag      3159
Glu Arg  Val Gln Ile Ser Asn  Gly Gln Lys Met Thr  Thr Asp Glu
    1040                1045                1050

aag atc  act aag tgg agt gct  aag tac ttc aac gga  act aac att      3204
Lys Ile  Thr Lys Trp Ser Ala  Lys Tyr Phe Asn Gly  Thr Asn Ile
    1055                1060                1065

ctt gga  agg gga gct tac tac  gtt ctt aag gat tgg  gct tcc aac      3249
Leu Gly  Arg Gly Ala Tyr Tyr  Val Leu Lys Asp Trp  Ala Ser Asn
    1070                1075                1080

gat tac  ctt act aac agg aac  ggt gaa atc gtt ctt  cca aag cag      3294
Asp Tyr  Leu Thr Asn Arg Asn  Gly Glu Ile Val Leu  Pro Lys Gln
    1085                1090                1095

ctt gtg  aac aag aac tcc tac  act gga ttc gtt tca  gat gct aac      3339
Leu Val  Asn Lys Asn Ser Tyr  Thr Gly Phe Val Ser  Asp Ala Asn
```

```
    1100                1105                1110

ggt act  aag ttc tac tct act  tcc gga tac cag gct  aag aac tcc      3384
Gly Thr  Lys Phe Tyr Ser Thr  Ser Gly Tyr Gln Ala  Lys Asn Ser
    1115                1120                1125

ttc att  cag gat gag aac gga  aac tgg tac tac ttt  gat aag agg      3429
Phe Ile  Gln Asp Glu Asn Gly  Asn Trp Tyr Tyr Phe  Asp Lys Arg
    1130                1135                1140

ggt tac  ctt gtt act ggt gct  cat gag att gat gga  aag cac gtg      3474
Gly Tyr  Leu Val Thr Gly Ala  His Glu Ile Asp Gly  Lys His Val
    1145                1150                1155

tac ttt  ctc aag aac gga att  cag ctt agg gat tcc  att aga gaa      3519
Tyr Phe  Leu Lys Asn Gly Ile  Gln Leu Arg Asp Ser  Ile Arg Glu
    1160                1165                1170

gat gag  aac ggt aac cag tat  tac tac gat caa act  ggt gct caa      3564
Asp Glu  Asn Gly Asn Gln Tyr  Tyr Tyr Asp Gln Thr  Gly Ala Gln
    1175                1180                1185

gtg ctt  aac agg tac tac act  act gat gga caa aac  tgg cgt tac      3609
Val Leu  Asn Arg Tyr Tyr Thr  Thr Asp Gly Gln Asn  Trp Arg Tyr
    1190                1195                1200

ttc gat  gct aag ggt gtt atg  gct agg gga ctc gtt  aag att gga      3654
Phe Asp  Ala Lys Gly Val Met  Ala Arg Gly Leu Val  Lys Ile Gly
    1205                1210                1215

gat gga  cag caa ttc ttc gat  gag aat gga tac cag  gtg aag gga      3699
Asp Gly  Gln Gln Phe Phe Asp  Glu Asn Gly Tyr Gln  Val Lys Gly
    1220                1225                1230

aag att  gtg tct gct aaa gat  gga aag ctc aga tac  ttc gat aag      3744
Lys Ile  Val Ser Ala Lys Asp  Gly Lys Leu Arg Tyr  Phe Asp Lys
    1235                1240                1245

gat tcc  gga aac gct gtt att  aac cgt ttc gct cag  ggt gat aat      3789
Asp Ser  Gly Asn Ala Val Ile  Asn Arg Phe Ala Gln  Gly Asp Asn
    1250                1255                1260

cca tcc  gat tgg tac tat ttc  gga gtg gag ttc gct  aag ttg act      3834
Pro Ser  Asp Trp Tyr Tyr Phe  Gly Val Glu Phe Ala  Lys Leu Thr
    1265                1270                1275

gga ctt  cag aag att gga cag  cag act ctc tac ttc  gat cag gat      3879
Gly Leu  Gln Lys Ile Gly Gln  Gln Thr Leu Tyr Phe  Asp Gln Asp
    1280                1285                1290

gga aag  caa gtt aag ggc aag  att gtg act ctt tcc  gac aag tct      3924
Gly Lys  Gln Val Lys Gly Lys  Ile Val Thr Leu Ser  Asp Lys Ser
    1295                1300                1305

atc cgt  tac ttc gac gca aat  tct ggt gaa atg gct  gtt gga aag      3969
Ile Arg  Tyr Phe Asp Ala Asn  Ser Gly Glu Met Ala  Val Gly Lys
    1310                1315                1320

ttt gct  gag ggt gct aag aat  gag tgg tac tac ttc  gac aag act      4014
Phe Ala  Glu Gly Ala Lys Asn  Glu Trp Tyr Tyr Phe  Asp Lys Thr
    1325                1330                1335

gga aag  gct gtt act gga ctc  caa aag atc ggc aag  caa acc ctt      4059
Gly Lys  Ala Val Thr Gly Leu  Gln Lys Ile Gly Lys  Gln Thr Leu
    1340                1345                1350

tat ttc  gat cag gac ggt aaa  cag gtc aag gga aag  gtg gtg act      4104
Tyr Phe  Asp Gln Asp Gly Lys  Gln Val Lys Gly Lys  Val Val Thr
    1355                1360                1365

ctt gct  gat aag agc att aga  tac ttc gac gct gat  agt gga gag      4149
Leu Ala  Asp Lys Ser Ile Arg  Tyr Phe Asp Ala Asp  Ser Gly Glu
    1370                1375                1380

atg gca  gtg gga aaa ttc gct  gaa ggc gca aag aac  gaa tgg tat      4194
Met Ala  Val Gly Lys Phe Ala  Glu Gly Ala Lys Asn  Glu Trp Tyr
    1385                1390                1395

tac ttt  gat cag acc gga aaa  gct gtg act ggc ctc  cag aaa atc      4239
```

```
Tyr Phe  Asp Gln Thr Gly Lys  Ala Val Thr Gly Leu  Gln Lys Ile
    1400                 1405                 1410

gac aag  cag acc ttg tac ttc  gac caa gac ggc aag  caa gtg aaa      4284
Asp Lys  Gln Thr Leu Tyr Phe  Asp Gln Asp Gly Lys  Gln Val Lys
    1415                 1420                 1425

ggg aag  atc gtg acc ctc tct  gat aag tcc att cgt  tat ttc gac      4329
Gly Lys  Ile Val Thr Leu Ser  Asp Lys Ser Ile Arg  Tyr Phe Asp
    1430                 1435                 1440

gct aac  tca ggc gag atg gct  act aat aag ttc gtg  gag gga tct      4374
Ala Asn  Ser Gly Glu Met Ala  Thr Asn Lys Phe Val  Glu Gly Ser
    1445                 1450                 1455

caa aac  gag tgg tat tat ttc  gat caa gca ggc aaa  gcc gtt act      4419
Gln Asn  Glu Trp Tyr Tyr Phe  Asp Gln Ala Gly Lys  Ala Val Thr
    1460                 1465                 1470

gga ttg  caa caa gtg gga cag  caa aca ctt tac ttc  aca cag gac      4464
Gly Leu  Gln Gln Val Gly Gln  Gln Thr Leu Tyr Phe  Thr Gln Asp
    1475                 1480                 1485

ggg aaa  caa gta aaa ggc aag  gtt gtg gat gtt aac  ggt gtg tcc      4509
Gly Lys  Gln Val Lys Gly Lys  Val Val Asp Val Asn  Gly Val Ser
    1490                 1495                 1500

cgt tat  ttt gac gct aac agc  gga gat atg gct cgt  tct aag tgg      4554
Arg Tyr  Phe Asp Ala Asn Ser  Gly Asp Met Ala Arg  Ser Lys Trp
    1505                 1510                 1515

att cag  ctt gag gat ggt tcc  tgg atg tat ttc gat  agg gat gga      4599
Ile Gln  Leu Glu Asp Gly Ser  Trp Met Tyr Phe Asp  Arg Asp Gly
    1520                 1525                 1530

agg gga  caa aat ttc ggc agg  aac taa                               4626
Arg Gly  Gln Asn Phe Gly Arg  Asn
    1535                 1540


<210> SEQ ID NO 36
<211> LENGTH: 1541
<212> TYPE: PRT
<213> ORGANISM: unknown
<220> FEATURE:
<223> OTHER INFORMATION: Synthetic Construct

<400> SEQUENCE: 36

Met Leu Glu Ser Gly Val Val His Ala Asp Asp Val Lys Gln Val Val
1               5                   10                  15

Val Gln Glu Pro Ala Thr Ala Gln Thr Ser Gly Pro Gly Gln Gln Thr
            20                  25                  30

Pro Ala Gln Ala Lys Ile Ala Ser Glu Gln Glu Ala Glu Lys Val Thr
        35                  40                  45

Pro Ala Asp Lys Val Thr Asp Asp Val Ala Ala Ser Glu Lys Pro Ala
    50                  55                  60

Lys Pro Ala Glu Asn Thr Glu Ala Thr Val Gln Thr Asn Ala Gln Glu
65                  70                  75                  80

Pro Ala Lys Pro Ala Asp Thr Lys Glu Ala Ser Thr Glu Lys Ala Ala
                85                  90                  95

Val Ala Glu Glu Val Lys Ala Ala Asn Ala Ile Thr Glu Ile Pro Lys
            100                 105                 110

Thr Glu Val Ala Asp Gln Asn Lys Gln Ala Arg Pro Thr Thr Ala Gln
        115                 120                 125

Asp Gln Glu Gly Asp Lys Arg Glu Lys Thr Ala Val Glu Asp Lys Ile
    130                 135                 140

Val Ala Asn Pro Lys Val Ala Lys Lys Asp Arg Leu Pro Glu Pro Gly
145                 150                 155                 160
```

-continued

```
Ser Lys Gln Gly Ala Ile Ala Glu Arg Met Val Ala Asp Gln Ala Gln
                165                 170                 175

Pro Ala Pro Val Asn Ala Asp His Asp Asp Asp Val Leu Ser His Ile
            180                 185                 190

Lys Thr Ile Asp Gly Lys Asn Tyr Tyr Val Gln Asp Asp Gly Thr Val
        195                 200                 205

Lys Lys Asn Phe Ala Val Glu Leu Asn Gly Arg Ile Leu Tyr Phe Asp
    210                 215                 220

Ala Glu Thr Gly Ala Leu Val Asp Ser Asn Glu Tyr Gln Phe Gln Gln
225                 230                 235                 240

Gly Thr Ser Ser Leu Asn Asn Glu Phe Ser Gln Lys Asn Ala Phe Tyr
                245                 250                 255

Gly Thr Thr Asp Lys Asp Ile Glu Thr Val Asp Gly Tyr Leu Thr Ala
            260                 265                 270

Asp Ser Trp Tyr Arg Pro Lys Phe Ile Leu Lys Asp Gly Lys Thr Trp
        275                 280                 285

Thr Ala Ser Thr Glu Thr Asp Leu Arg Pro Leu Leu Met Ala Trp Trp
    290                 295                 300

Pro Asp Lys Arg Thr Gln Ile Asn Tyr Leu Asn Tyr Met Asn Gln Gln
305                 310                 315                 320

Gly Leu Gly Ala Gly Ala Phe Glu Asn Lys Val Glu Gln Ala Leu Leu
                325                 330                 335

Thr Gly Ala Ser Gln Gln Val Gln Arg Lys Ile Glu Glu Lys Ile Gly
            340                 345                 350

Lys Glu Gly Asp Thr Lys Trp Leu Arg Thr Leu Met Gly Ala Phe Val
        355                 360                 365

Lys Thr Gln Pro Asn Trp Asn Ile Lys Thr Glu Ser Glu Thr Thr Gly
    370                 375                 380

Thr Lys Lys Asp His Leu Gln Gly Gly Ala Leu Leu Tyr Thr Asn Asn
385                 390                 395                 400

Glu Lys Ser Pro His Ala Asp Ser Lys Phe Arg Leu Leu Asn Arg Thr
                405                 410                 415

Pro Thr Ser Gln Thr Gly Thr Pro Lys Tyr Phe Ile Asp Lys Ser Asn
            420                 425                 430

Gly Gly Tyr Glu Phe Leu Leu Ala Asn Asp Phe Asp Asn Ser Asn Pro
        435                 440                 445

Ala Val Gln Ala Glu Gln Leu Asn Trp Leu His Tyr Met Met Asn Phe
    450                 455                 460

Gly Ser Ile Val Ala Asn Asp Pro Thr Ala Asn Phe Asp Gly Val Arg
465                 470                 475                 480

Val Asp Ala Val Asp Asn Val Asn Ala Asp Leu Leu Gln Ile Ala Ser
                485                 490                 495

Asp Tyr Phe Lys Ser Arg Tyr Lys Val Gly Glu Ser Glu Glu Glu Ala
            500                 505                 510

Ile Lys His Leu Ser Ile Leu Glu Ala Trp Ser Asp Asn Asp Pro Asp
        515                 520                 525

Tyr Asn Lys Asp Thr Lys Gly Ala Gln Leu Ala Ile Asp Asn Lys Leu
    530                 535                 540

Arg Leu Ser Leu Leu Tyr Ser Phe Met Arg Asn Leu Ser Ile Arg Ser
545                 550                 555                 560

Gly Val Glu Pro Thr Ile Thr Asn Ser Leu Asn Asp Arg Ser Ser Glu
                565                 570                 575

Lys Lys Asn Gly Glu Arg Met Ala Asn Tyr Ile Phe Val Arg Ala His
```

-continued

```
            580                 585                 590

Asp Asp Glu Val Gln Thr Val Ile Ala Asp Ile Ile Arg Glu Asn Ile
        595                 600                 605

Asn Pro Asn Thr Asp Gly Leu Thr Phe Thr Met Asp Glu Leu Lys Gln
    610                 615                 620

Ala Phe Lys Ile Tyr Asn Glu Asp Met Arg Lys Ala Asp Lys Lys Tyr
625                 630                 635                 640

Thr Gln Phe Asn Ile Pro Thr Ala His Ala Leu Met Leu Ser Asn Lys
                645                 650                 655

Asp Ser Ile Thr Arg Val Tyr Tyr Gly Asp Leu Tyr Thr Asp Asp Gly
            660                 665                 670

Gln Tyr Met Glu Lys Lys Ser Pro Tyr His Asp Ala Ile Asp Ala Leu
        675                 680                 685

Leu Arg Ala Arg Ile Lys Tyr Val Ala Gly Gly Gln Asp Met Lys Val
    690                 695                 700

Thr Tyr Met Gly Val Pro Arg Glu Ala Asp Lys Trp Ser Tyr Asn Gly
705                 710                 715                 720

Ile Leu Thr Ser Val Arg Tyr Gly Thr Gly Ala Asn Glu Ala Thr Asp
                725                 730                 735

Glu Gly Thr Ala Glu Thr Arg Thr Gln Gly Met Ala Val Ile Ala Ser
            740                 745                 750

Asn Asn Pro Asn Leu Lys Leu Asn Glu Trp Asp Lys Leu Gln Val Asn
        755                 760                 765

Met Gly Ala Ala His Lys Asn Gln Tyr Tyr Arg Pro Val Leu Leu Thr
    770                 775                 780

Thr Lys Asp Gly Ile Ser Arg Tyr Leu Thr Asp Glu Glu Val Pro Gln
785                 790                 795                 800

Ser Leu Trp Lys Lys Thr Asp Ala Asn Gly Ile Leu Thr Phe Asp Met
                805                 810                 815

Asn Asp Ile Ala Gly Tyr Ser Asn Val Gln Val Ser Gly Tyr Leu Ala
            820                 825                 830

Val Trp Val Pro Val Gly Ala Lys Ala Asp Gln Asp Ala Arg Thr Thr
        835                 840                 845

Ala Ser Lys Lys Lys Asn Ala Ser Gly Gln Val Tyr Glu Ser Ser Ala
    850                 855                 860

Ala Leu Asp Ser Gln Leu Ile Tyr Glu Gly Phe Ser Asn Phe Gln Asp
865                 870                 875                 880

Phe Ala Thr Arg Asp Asp Gln Tyr Thr Asn Lys Val Ile Ala Lys Asn
                885                 890                 895

Val Asn Leu Phe Lys Glu Trp Gly Val Thr Ser Phe Glu Leu Pro Pro
            900                 905                 910

Gln Tyr Val Ser Ser Gln Asp Gly Thr Phe Leu Asp Ser Ile Ile Gln
        915                 920                 925

Asn Gly Tyr Ala Phe Glu Asp Arg Tyr Asp Met Ala Met Ser Lys Asn
    930                 935                 940

Asn Lys Tyr Gly Ser Leu Lys Asp Leu Leu Asn Ala Leu Arg Ala Leu
945                 950                 955                 960

His Ser Val Asn Ile Gln Ala Ile Ala Asp Trp Val Pro Asp Gln Ile
                965                 970                 975

Tyr Asn Leu Pro Gly Lys Glu Val Val Thr Ala Thr Arg Val Asn Asn
            980                 985                 990

Tyr Gly Thr Tyr Arg Glu Gly Ala  Glu Ile Lys Glu Lys  Leu Tyr Val
        995                 1000                1005
```

```
Ala Asn Ser Lys Thr Asn Glu Thr Asp Phe Gln Gly Lys Tyr Gly
    1010                1015                1020

Gly Ala Phe Leu Asp Glu Leu Lys Ala Lys Tyr Pro Glu Ile Phe
    1025                1030                1035

Glu Arg Val Gln Ile Ser Asn Gly Gln Lys Met Thr Thr Asp Glu
    1040                1045                1050

Lys Ile Thr Lys Trp Ser Ala Lys Tyr Phe Asn Gly Thr Asn Ile
    1055                1060                1065

Leu Gly Arg Gly Ala Tyr Tyr Val Leu Lys Asp Trp Ala Ser Asn
    1070                1075                1080

Asp Tyr Leu Thr Asn Arg Asn Gly Glu Ile Val Leu Pro Lys Gln
    1085                1090                1095

Leu Val Asn Lys Asn Ser Tyr Thr Gly Phe Val Ser Asp Ala Asn
    1100                1105                1110

Gly Thr Lys Phe Tyr Ser Thr Ser Gly Tyr Gln Ala Lys Asn Ser
    1115                1120                1125

Phe Ile Gln Asp Glu Asn Gly Asn Trp Tyr Tyr Phe Asp Lys Arg
    1130                1135                1140

Gly Tyr Leu Val Thr Gly Ala His Glu Ile Asp Gly Lys His Val
    1145                1150                1155

Tyr Phe Leu Lys Asn Gly Ile Gln Leu Arg Asp Ser Ile Arg Glu
    1160                1165                1170

Asp Glu Asn Gly Asn Gln Tyr Tyr Tyr Asp Gln Thr Gly Ala Gln
    1175                1180                1185

Val Leu Asn Arg Tyr Tyr Thr Thr Asp Gly Gln Asn Trp Arg Tyr
    1190                1195                1200

Phe Asp Ala Lys Gly Val Met Ala Arg Gly Leu Val Lys Ile Gly
    1205                1210                1215

Asp Gly Gln Gln Phe Phe Asp Glu Asn Gly Tyr Gln Val Lys Gly
    1220                1225                1230

Lys Ile Val Ser Ala Lys Asp Gly Lys Leu Arg Tyr Phe Asp Lys
    1235                1240                1245

Asp Ser Gly Asn Ala Val Ile Asn Arg Phe Ala Gln Gly Asp Asn
    1250                1255                1260

Pro Ser Asp Trp Tyr Tyr Phe Gly Val Glu Phe Ala Lys Leu Thr
    1265                1270                1275

Gly Leu Gln Lys Ile Gly Gln Gln Thr Leu Tyr Phe Asp Gln Asp
    1280                1285                1290

Gly Lys Gln Val Lys Gly Lys Ile Val Thr Leu Ser Asp Lys Ser
    1295                1300                1305

Ile Arg Tyr Phe Asp Ala Asn Ser Gly Glu Met Ala Val Gly Lys
    1310                1315                1320

Phe Ala Glu Gly Ala Lys Asn Glu Trp Tyr Tyr Phe Asp Lys Thr
    1325                1330                1335

Gly Lys Ala Val Thr Gly Leu Gln Lys Ile Gly Lys Gln Thr Leu
    1340                1345                1350

Tyr Phe Asp Gln Asp Gly Lys Gln Val Lys Gly Lys Val Val Thr
    1355                1360                1365

Leu Ala Asp Lys Ser Ile Arg Tyr Phe Asp Ala Asp Ser Gly Glu
    1370                1375                1380

Met Ala Val Gly Lys Phe Ala Glu Gly Ala Lys Asn Glu Trp Tyr
    1385                1390                1395
```

```
Tyr Phe  Asp Gln Thr Gly Lys  Ala Val Thr Gly Leu  Gln Lys Ile
    1400                 1405                 1410

Asp Lys  Gln Thr Leu Tyr Phe  Asp Gln Asp Gly Lys  Gln Val Lys
    1415                 1420                 1425

Gly Lys  Ile Val Thr Leu Ser  Asp Lys Ser Ile Arg  Tyr Phe Asp
    1430                 1435                 1440

Ala Asn  Ser Gly Glu Met Ala  Thr Asn Lys Phe Val  Glu Gly Ser
    1445                 1450                 1455

Gln Asn  Glu Trp Tyr Tyr Phe  Asp Gln Ala Gly Lys  Ala Val Thr
    1460                 1465                 1470

Gly Leu  Gln Gln Val Gly Gln  Gln Thr Leu Tyr Phe  Thr Gln Asp
    1475                 1480                 1485

Gly Lys  Gln Val Lys Gly Lys  Val Val Asp Val Asn  Gly Val Ser
    1490                 1495                 1500

Arg Tyr  Phe Asp Ala Asn Ser  Gly Asp Met Ala Arg  Ser Lys Trp
    1505                 1510                 1515

Ile Gln  Leu Glu Asp Gly Ser  Trp Met Tyr Phe Asp  Arg Asp Gly
    1520                 1525                 1530

Arg Gly  Gln Asn Phe Gly Arg  Asn
    1535                 1540


<210> SEQ ID NO 37
<211> LENGTH: 4626
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(4626)
<223> OTHER INFORMATION: monocot optimized dextransucrase with leucrose
      synthase activity

<400> SEQUENCE: 37

atg ctc gag tct ggc gtg gtg cac gcc gat gac gtg aag cag gtg gtg       48
Met Leu Glu Ser Gly Val Val His Ala Asp Asp Val Lys Gln Val Val
1               5                   10                  15

gtg caa gag cca gct acc gcc cag acc tct ggc cca ggg cag cag acc       96
Val Gln Glu Pro Ala Thr Ala Gln Thr Ser Gly Pro Gly Gln Gln Thr
            20                  25                  30

cct gcc caa gcc aag atc gcg agc gag caa gag gcc gag aag gtg acc      144
Pro Ala Gln Ala Lys Ile Ala Ser Glu Gln Glu Ala Glu Lys Val Thr
        35                  40                  45

cca gcc gac aag gtg acc gac gac gtg gcc gcc agc gag aag cca gcc      192
Pro Ala Asp Lys Val Thr Asp Asp Val Ala Ala Ser Glu Lys Pro Ala
    50                  55                  60

aag ccg gcc gag aac acc gag gcc acc gtc cag acc aac gcc caa gag      240
Lys Pro Ala Glu Asn Thr Glu Ala Thr Val Gln Thr Asn Ala Gln Glu
65                  70                  75                  80

ccg gcc aag ccc gcc gac acc aag gaa gcc agc acc gag aag gcc gcc      288
Pro Ala Lys Pro Ala Asp Thr Lys Glu Ala Ser Thr Glu Lys Ala Ala
                85                  90                  95

gtg gcc gag gaa gtg aag gcc gcc aac gcc atc acc gag atc ccc aag      336
Val Ala Glu Glu Val Lys Ala Ala Asn Ala Ile Thr Glu Ile Pro Lys
            100                 105                 110

acc gag gtg gcc gac cag aac aag cag gcc agg ccg acc acc gct cag      384
Thr Glu Val Ala Asp Gln Asn Lys Gln Ala Arg Pro Thr Thr Ala Gln
        115                 120                 125

gac caa gag ggc gac aag cgc gaa aag acc gcc gtg gag gac aag atc      432
Asp Gln Glu Gly Asp Lys Arg Glu Lys Thr Ala Val Glu Asp Lys Ile
```

```
    130                 135                 140

gtg gcc aac ccg aag gtg gcc aag aag gac agg ctg ccc gag cca ggc      480
Val Ala Asn Pro Lys Val Ala Lys Lys Asp Arg Leu Pro Glu Pro Gly
145                 150                 155                 160

agc aag cag ggc gcg atc gcc gag agg atg gtc gcc gac cag gcc cag      528
Ser Lys Gln Gly Ala Ile Ala Glu Arg Met Val Ala Asp Gln Ala Gln
                165                 170                 175

cca gcc cca gtg aac gcc gac cac gac gat gat gtg ctg tcc cac atc      576
Pro Ala Pro Val Asn Ala Asp His Asp Asp Asp Val Leu Ser His Ile
            180                 185                 190

aag acc atc gac ggc aag aac tac tac gtc cag gac gac ggc acc gtg      624
Lys Thr Ile Asp Gly Lys Asn Tyr Tyr Val Gln Asp Asp Gly Thr Val
        195                 200                 205

aag aag aac ttc gcc gtc gag ctg aac ggc cgc atc ctg tac ttc gac      672
Lys Lys Asn Phe Ala Val Glu Leu Asn Gly Arg Ile Leu Tyr Phe Asp
    210                 215                 220

gcc gag act ggc gcc ctg gtg gac agc aac gag tac cag ttc cag cag      720
Ala Glu Thr Gly Ala Leu Val Asp Ser Asn Glu Tyr Gln Phe Gln Gln
225                 230                 235                 240

ggc acc agc agc ctg aac aac gag ttc agc cag aag aac gcc ttc tac      768
Gly Thr Ser Ser Leu Asn Asn Glu Phe Ser Gln Lys Asn Ala Phe Tyr
                245                 250                 255

ggc acc acc gac aag gac atc gag act gtg gac ggc tac ctg acc gcc      816
Gly Thr Thr Asp Lys Asp Ile Glu Thr Val Asp Gly Tyr Leu Thr Ala
            260                 265                 270

gac agc tgg tat cgc ccg aag ttc atc ctg aag gac ggc aag acc tgg      864
Asp Ser Trp Tyr Arg Pro Lys Phe Ile Leu Lys Asp Gly Lys Thr Trp
        275                 280                 285

acc gcc tcc acc gag act gac ctg cgc ccg ctg ctg atg gcc tgg tgg      912
Thr Ala Ser Thr Glu Thr Asp Leu Arg Pro Leu Leu Met Ala Trp Trp
    290                 295                 300

ccg gac aag cgc acc cag atc aac tac ctg aac tac atg aac cag caa      960
Pro Asp Lys Arg Thr Gln Ile Asn Tyr Leu Asn Tyr Met Asn Gln Gln
305                 310                 315                 320

ggc ctg ggc gct ggc gct ttc gag aac aag gtg gag cag gcc ctc ctg     1008
Gly Leu Gly Ala Gly Ala Phe Glu Asn Lys Val Glu Gln Ala Leu Leu
                325                 330                 335

acc ggc gct agc cag cag gtc cag cgc aag atc gag gaa aag atc ggc     1056
Thr Gly Ala Ser Gln Gln Val Gln Arg Lys Ile Glu Glu Lys Ile Gly
            340                 345                 350

aag gaa ggc gac acc aag tgg ctg cgc acc ctg atg ggc gcc ttc gtc     1104
Lys Glu Gly Asp Thr Lys Trp Leu Arg Thr Leu Met Gly Ala Phe Val
        355                 360                 365

aag acc cag ccg aac tgg aac atc aag acc gag agc gag act acc ggc     1152
Lys Thr Gln Pro Asn Trp Asn Ile Lys Thr Glu Ser Glu Thr Thr Gly
    370                 375                 380

acc aag aag gac cac ctc cag ggc ggt gcc ctg ctg tac acc aac aac     1200
Thr Lys Lys Asp His Leu Gln Gly Gly Ala Leu Leu Tyr Thr Asn Asn
385                 390                 395                 400

gag aag tct ccg cac gcc gac agc aag ttc cgc ctg ctg aac cgc acc     1248
Glu Lys Ser Pro His Ala Asp Ser Lys Phe Arg Leu Leu Asn Arg Thr
                405                 410                 415

cca acc agc cag acc ggc acc ccg aag tac ttc atc gac aag agc aac     1296
Pro Thr Ser Gln Thr Gly Thr Pro Lys Tyr Phe Ile Asp Lys Ser Asn
            420                 425                 430

ggc ggc tac gag ttc ctg ctg gcc aac gac ttc gac aac agc aac ccg     1344
Gly Gly Tyr Glu Phe Leu Leu Ala Asn Asp Phe Asp Asn Ser Asn Pro
        435                 440                 445

gcc gtc cag gcc gag cag ctg aac tgg ctg cac tac atg atg aac ttc     1392
```

-continued

```
Ala Val Gln Ala Glu Gln Leu Asn Trp Leu His Tyr Met Met Asn Phe
    450                 455                 460

ggc agc atc gtc gcc aac gac ccg acc gcc aac ttc gac ggt gtc cgc     1440
Gly Ser Ile Val Ala Asn Asp Pro Thr Ala Asn Phe Asp Gly Val Arg
465                 470                 475                 480

gtg gac gcc gtg gac aac gtc aac gcc gac ctg ctc cag atc gcc tcc     1488
Val Asp Ala Val Asp Asn Val Asn Ala Asp Leu Leu Gln Ile Ala Ser
                485                 490                 495

gac tac ttc aag agc cgc tac aaa gtg ggc gag agc gag gaa gag gcc     1536
Asp Tyr Phe Lys Ser Arg Tyr Lys Val Gly Glu Ser Glu Glu Glu Ala
            500                 505                 510

atc aag cac ctg agc atc ctc gag gcg tgg agc gac aac gac ccg gac     1584
Ile Lys His Leu Ser Ile Leu Glu Ala Trp Ser Asp Asn Asp Pro Asp
        515                 520                 525

tac aac aag gac acc aag ggc gcc cag ctg gcc atc gac aac aag ctg     1632
Tyr Asn Lys Asp Thr Lys Gly Ala Gln Leu Ala Ile Asp Asn Lys Leu
    530                 535                 540

cgc ctg agc ctg ctg tac tcc ttc atg cgc aac ctg tcc atc cgc agc     1680
Arg Leu Ser Leu Leu Tyr Ser Phe Met Arg Asn Leu Ser Ile Arg Ser
545                 550                 555                 560

ggc gtc gag ccg acc atc acc aac agc ctc aac gac cgc agc agc gag     1728
Gly Val Glu Pro Thr Ile Thr Asn Ser Leu Asn Asp Arg Ser Ser Glu
                565                 570                 575

aag aaa aac ggc gag cgc atg gcc aac tac atc ttt gtc cgc gct cac     1776
Lys Lys Asn Gly Glu Arg Met Ala Asn Tyr Ile Phe Val Arg Ala His
            580                 585                 590

gac gac gag gtc cag acc gtg atc gcc gac atc atc cgc gag aac atc     1824
Asp Asp Glu Val Gln Thr Val Ile Ala Asp Ile Ile Arg Glu Asn Ile
        595                 600                 605

aac ccg aac acc gac ggc ctg acc ttc acc atg gac gag ctg aag cag     1872
Asn Pro Asn Thr Asp Gly Leu Thr Phe Thr Met Asp Glu Leu Lys Gln
    610                 615                 620

gcc ttc aag atc tac aac gag gac atg cgc aag gcc gac aag aag tac     1920
Ala Phe Lys Ile Tyr Asn Glu Asp Met Arg Lys Ala Asp Lys Lys Tyr
625                 630                 635                 640

acc cag ttc aac atc ccg acc gcc cac gcc ctg atg ctg tcc aac aag     1968
Thr Gln Phe Asn Ile Pro Thr Ala His Ala Leu Met Leu Ser Asn Lys
                645                 650                 655

gac agc atc acc cgc gtg tac tac ggc gac ctg tac acc gac gac ggc     2016
Asp Ser Ile Thr Arg Val Tyr Tyr Gly Asp Leu Tyr Thr Asp Asp Gly
            660                 665                 670

cag tac atg gaa aag aag tcc ccg tac cac gac gcc atc gac gcc ctg     2064
Gln Tyr Met Glu Lys Lys Ser Pro Tyr His Asp Ala Ile Asp Ala Leu
        675                 680                 685

ctg agg gcc cgc atc aag tac gtg gct ggc ggc cag gac atg aag gtg     2112
Leu Arg Ala Arg Ile Lys Tyr Val Ala Gly Gly Gln Asp Met Lys Val
    690                 695                 700

acc tac atg ggc gtg ccc cgc gag gcc gac aag tgg agc tac aac ggc     2160
Thr Tyr Met Gly Val Pro Arg Glu Ala Asp Lys Trp Ser Tyr Asn Gly
705                 710                 715                 720

atc ctg acc tct gtg cgc tac ggc acc ggc gcc aac gag gct acc gac     2208
Ile Leu Thr Ser Val Arg Tyr Gly Thr Gly Ala Asn Glu Ala Thr Asp
                725                 730                 735

gag ggc acc gcc gag act agg acc cag ggc atg gcc gtg atc gcc agc     2256
Glu Gly Thr Ala Glu Thr Arg Thr Gln Gly Met Ala Val Ile Ala Ser
            740                 745                 750

aac aac ccg aac ctg aag ctg aac gag tgg gac aag ctc cag gtg aac     2304
Asn Asn Pro Asn Leu Lys Leu Asn Glu Trp Asp Lys Leu Gln Val Asn
        755                 760                 765
```

-continued

```
atg ggc gct gcc cac aag aac cag tac tac cgc ccg gtg ctg ctg acc      2352
Met Gly Ala Ala His Lys Asn Gln Tyr Tyr Arg Pro Val Leu Leu Thr
    770                 775                 780

acc aag gac ggc atc tcg cgc tac ctc acc gac gag gaa gtg ccg cag      2400
Thr Lys Asp Gly Ile Ser Arg Tyr Leu Thr Asp Glu Glu Val Pro Gln
785                 790                 795                 800

agc ctc tgg aag aaa acc gac gcg aac ggc atc ctc act ttc gac atg      2448
Ser Leu Trp Lys Lys Thr Asp Ala Asn Gly Ile Leu Thr Phe Asp Met
                805                 810                 815

aac gat atc gcc ggc tac tcc aac gtc cag gtg tcc ggc tac ctg gct      2496
Asn Asp Ile Ala Gly Tyr Ser Asn Val Gln Val Ser Gly Tyr Leu Ala
            820                 825                 830

gtg tgg gtg cca gtg ggc gcc aag gcc gac cag gac gcc agg acc acc      2544
Val Trp Val Pro Val Gly Ala Lys Ala Asp Gln Asp Ala Arg Thr Thr
        835                 840                 845

gcc tcc aag aag aag aac gcc agc ggc cag gtg tac gag agc agc gcc      2592
Ala Ser Lys Lys Lys Asn Ala Ser Gly Gln Val Tyr Glu Ser Ser Ala
    850                 855                 860

gct ctg gac agc cag ctg atc tac gag ggc ttc agc aac ttc cag gac      2640
Ala Leu Asp Ser Gln Leu Ile Tyr Glu Gly Phe Ser Asn Phe Gln Asp
865                 870                 875                 880

ttc gcg acc cgc gac gac cag tac acg aac aag gtg atc gcc aag aac      2688
Phe Ala Thr Arg Asp Asp Gln Tyr Thr Asn Lys Val Ile Ala Lys Asn
                885                 890                 895

gtg aac ctg ttc aag gaa tgg ggc gtg acc agc ttc gag ctg ccg ccg      2736
Val Asn Leu Phe Lys Glu Trp Gly Val Thr Ser Phe Glu Leu Pro Pro
            900                 905                 910

cag tac gtg tct agc cag gac ggc acc ttc ctg gac agc atc atc cag      2784
Gln Tyr Val Ser Ser Gln Asp Gly Thr Phe Leu Asp Ser Ile Ile Gln
        915                 920                 925

aac ggc tac gcc ttc gag gac cgc tac gac atg gcc atg agc aag aac      2832
Asn Gly Tyr Ala Phe Glu Asp Arg Tyr Asp Met Ala Met Ser Lys Asn
    930                 935                 940

aac aag tac ggc agc ctg aag gac ctg ctg aac gcc ctg cgc gcc ctg      2880
Asn Lys Tyr Gly Ser Leu Lys Asp Leu Leu Asn Ala Leu Arg Ala Leu
945                 950                 955                 960

cac agc gtg aac atc cag gcg atc gct gac tgg gtg ccg gac cag atc      2928
His Ser Val Asn Ile Gln Ala Ile Ala Asp Trp Val Pro Asp Gln Ile
                965                 970                 975

tac aac ctg ccg ggc aag gaa gtg gtg acc gcc acc cgc gtg aac aac      2976
Tyr Asn Leu Pro Gly Lys Glu Val Val Thr Ala Thr Arg Val Asn Asn
            980                 985                 990

tac ggc acc tac cgc gag ggc gcc  gag atc aag gaa aag  ctg tac gtc    3024
Tyr Gly Thr Tyr Arg Glu Gly Ala  Glu Ile Lys Glu Lys  Leu Tyr Val
        995                 1000                 1005

gcc aac  agc aag acc aac gag  act gac ttc cag ggc  aag tac ggc      3069
Ala Asn  Ser Lys Thr Asn Glu  Thr Asp Phe Gln Gly  Lys Tyr Gly
    1010                 1015                 1020

ggt gcc  ttc ctg gat gag ctg  aag gcc aag tac ccc  gag atc ttc      3114
Gly Ala  Phe Leu Asp Glu Leu  Lys Ala Lys Tyr Pro  Glu Ile Phe
    1025                 1030                 1035

gag cgc  gtc cag atc agc aac  ggc cag aag atg acc  acc gac gag      3159
Glu Arg  Val Gln Ile Ser Asn  Gly Gln Lys Met Thr  Thr Asp Glu
    1040                 1045                 1050

aag atc  acc aag tgg agc gcc  aag tac ttc aac ggc  acc aac atc      3204
Lys Ile  Thr Lys Trp Ser Ala  Lys Tyr Phe Asn Gly  Thr Asn Ile
    1055                 1060                 1065

ctg ggc  agg ggc gcc tac tac  gtg ctg aag gac tgg  gcc agc aac      3249
Leu Gly  Arg Gly Ala Tyr Tyr  Val Leu Lys Asp Trp  Ala Ser Asn
    1070                 1075                 1080
```

```
gac tac  ctg acc aac cgc aac  ggc gag atc gtg ctg  ccg aag cag      3294
Asp Tyr  Leu Thr Asn Arg Asn  Gly Glu Ile Val Leu  Pro Lys Gln
    1085                 1090                 1095

ctg gtg  aac aag aac agc tac  acc ggc ttc gtg tcc  gac gcc aac      3339
Leu Val  Asn Lys Asn Ser Tyr  Thr Gly Phe Val Ser  Asp Ala Asn
    1100                 1105                 1110

ggc acg  aag ttc tac tcc acc  tcc ggg tat caa gcc  aag aac agc      3384
Gly Thr  Lys Phe Tyr Ser Thr  Ser Gly Tyr Gln Ala  Lys Asn Ser
    1115                 1120                 1125

ttc atc  caa gac gag aat ggc  aac tgg tac tac ttc  gac aag cgc      3429
Phe Ile  Gln Asp Glu Asn Gly  Asn Trp Tyr Tyr Phe  Asp Lys Arg
    1130                 1135                 1140

ggc tac  ctg gtg acc ggc gct  cac gag atc gac ggg  aag cac gtg      3474
Gly Tyr  Leu Val Thr Gly Ala  His Glu Ile Asp Gly  Lys His Val
    1145                 1150                 1155

tac ttt  ctg aag aac ggc atc  cag ctg cgc gac tcc  atc cgc gag      3519
Tyr Phe  Leu Lys Asn Gly Ile  Gln Leu Arg Asp Ser  Ile Arg Glu
    1160                 1165                 1170

gat gag  aac ggg aat cag tac  tac tac gac cag aca  ggc gcc cag      3564
Asp Glu  Asn Gly Asn Gln Tyr  Tyr Tyr Asp Gln Thr  Gly Ala Gln
    1175                 1180                 1185

gtg ctg  aac cgc tac tac acc  acc gac ggc cag aac  tgg cgc tac      3609
Val Leu  Asn Arg Tyr Tyr Thr  Thr Asp Gly Gln Asn  Trp Arg Tyr
    1190                 1195                 1200

ttc gac  gcg aag ggc gtg atg  gcc agg ggc ctg gtg  aag atc ggc      3654
Phe Asp  Ala Lys Gly Val Met  Ala Arg Gly Leu Val  Lys Ile Gly
    1205                 1210                 1215

gac ggc  cag cag ttc ttc gat  gag aac ggc tac caa  gtg aag ggc      3699
Asp Gly  Gln Gln Phe Phe Asp  Glu Asn Gly Tyr Gln  Val Lys Gly
    1220                 1225                 1230

aag atc  gtg tcc gcc aag gac  ggg aag ctc cgc tac  ttc gat aag      3744
Lys Ile  Val Ser Ala Lys Asp  Gly Lys Leu Arg Tyr  Phe Asp Lys
    1235                 1240                 1245

gac agc  ggc aac gcc gtg atc  aac cgc ttc gct cag  ggc gac aac      3789
Asp Ser  Gly Asn Ala Val Ile  Asn Arg Phe Ala Gln  Gly Asp Asn
    1250                 1255                 1260

ccg agc  gat tgg tac tac ttt  ggc gtg gag ttc gcc  aag ctg acc      3834
Pro Ser  Asp Trp Tyr Tyr Phe  Gly Val Glu Phe Ala  Lys Leu Thr
    1265                 1270                 1275

ggc ctc  cag aag att ggc cag  cag acg ctc tac ttc  gac cag gac      3879
Gly Leu  Gln Lys Ile Gly Gln  Gln Thr Leu Tyr Phe  Asp Gln Asp
    1280                 1285                 1290

ggc aag  cag gtc aag ggg aag  att gtc acc ctg agc  gac aag tcg      3924
Gly Lys  Gln Val Lys Gly Lys  Ile Val Thr Leu Ser  Asp Lys Ser
    1295                 1300                 1305

atc cgc  tac ttt gat gcc aac  agc ggc gag atg gct  gtg ggc aag      3969
Ile Arg  Tyr Phe Asp Ala Asn  Ser Gly Glu Met Ala  Val Gly Lys
    1310                 1315                 1320

ttc gcc  gag ggc gcc aag aac  gag tgg tac tac ttt  gat aag acc      4014
Phe Ala  Glu Gly Ala Lys Asn  Glu Trp Tyr Tyr Phe  Asp Lys Thr
    1325                 1330                 1335

ggc aag  gcc gtc acc ggg ctg  caa aag atc ggg aag  cag acc ctg      4059
Gly Lys  Ala Val Thr Gly Leu  Gln Lys Ile Gly Lys  Gln Thr Leu
    1340                 1345                 1350

tac ttt  gat cag gat ggg aag  caa gtt aag ggc aag  gtg gtg acc      4104
Tyr Phe  Asp Gln Asp Gly Lys  Gln Val Lys Gly Lys  Val Val Thr
    1355                 1360                 1365

ctg gcc  gac aag agc atc aga  tac ttc gac gct gac  tcg ggt gaa      4149
Leu Ala  Asp Lys Ser Ile Arg  Tyr Phe Asp Ala Asp  Ser Gly Glu
```

1370 1375 1380 atg gct gtc ggt aag ttt gcg gaa ggg gcg aag aat gaa tgg tat 4194
Met Ala Val Gly Lys Phe Ala Glu Gly Ala Lys Asn Glu Trp Tyr
1385 1390 1395 tat ttc gat caa act ggg aag gcg gtg acg ggg ctt cag aag atc 4239
Tyr Phe Asp Gln Thr Gly Lys Ala Val Thr Gly Leu Gln Lys Ile
1400 1405 1410 gac aag caa acg ttg tac ttc gac caa gac ggg aag caa gtg aag 4284
Asp Lys Gln Thr Leu Tyr Phe Asp Gln Asp Gly Lys Gln Val Lys
1415 1420 1425 ggc aag att gtg acc ctc tcc gac aag tcc att cgg tac ttc gat 4329
Gly Lys Ile Val Thr Leu Ser Asp Lys Ser Ile Arg Tyr Phe Asp
1430 1435 1440 gcc aac tcc ggg gag atg gcc acc aac aag ttc gtg gag ggc tcg 4374
Ala Asn Ser Gly Glu Met Ala Thr Asn Lys Phe Val Glu Gly Ser
1445 1450 1455 cag aat gag tgg tac tac ttc gac cag gct ggc aag gct gtg acc 4419
Gln Asn Glu Trp Tyr Tyr Phe Asp Gln Ala Gly Lys Ala Val Thr
1460 1465 1470 ggc ctt cag caa gtg ggg cag caa act ctg tac ttc acc caa gat 4464
Gly Leu Gln Gln Val Gly Gln Gln Thr Leu Tyr Phe Thr Gln Asp
1475 1480 1485 ggc aag caa gtc aag ggc aag gtc gtg gac gtg aac ggc gtg tcc 4509
Gly Lys Gln Val Lys Gly Lys Val Val Asp Val Asn Gly Val Ser
1490 1495 1500 cgg tac ttt gac gcg aac tct ggc gac atg gcc cgc agc aag tgg 4554
Arg Tyr Phe Asp Ala Asn Ser Gly Asp Met Ala Arg Ser Lys Trp
1505 1510 1515 att cag ctc gag gac ggc agc tgg atg tac ttc gat cgc gac ggc 4599
Ile Gln Leu Glu Asp Gly Ser Trp Met Tyr Phe Asp Arg Asp Gly
1520 1525 1530 agg ggc cag aac ttc ggc cgc aac tga 4626
Arg Gly Gln Asn Phe Gly Arg Asn
1535 1540

<210> SEQ ID NO 38
<211> LENGTH: 1541
<212> TYPE: PRT
<213> ORGANISM: unknown
<220> FEATURE:
<223> OTHER INFORMATION: Synthetic Construct

<400> SEQUENCE: 38

Met Leu Glu Ser Gly Val Val His Ala Asp Asp Val Lys Gln Val Val
1 5 10 15

Val Gln Glu Pro Ala Thr Ala Gln Thr Ser Gly Pro Gly Gln Gln Thr
20 25 30

Pro Ala Gln Ala Lys Ile Ala Ser Glu Gln Glu Ala Glu Lys Val Thr
35 40 45

Pro Ala Asp Lys Val Thr Asp Asp Val Ala Ala Ser Glu Lys Pro Ala
50 55 60

Lys Pro Ala Glu Asn Thr Glu Ala Thr Val Gln Thr Asn Ala Gln Glu
65 70 75 80

Pro Ala Lys Pro Ala Asp Thr Lys Glu Ala Ser Thr Glu Lys Ala Ala
85 90 95

Val Ala Glu Glu Val Lys Ala Ala Asn Ala Ile Thr Glu Ile Pro Lys
100 105 110

Thr Glu Val Ala Asp Gln Asn Lys Gln Ala Arg Pro Thr Thr Ala Gln
115 120 125

```
Asp Gln Glu Gly Asp Lys Arg Glu Lys Thr Ala Val Glu Asp Lys Ile
    130                 135                 140

Val Ala Asn Pro Lys Val Ala Lys Lys Asp Arg Leu Pro Glu Pro Gly
145                 150                 155                 160

Ser Lys Gln Gly Ala Ile Ala Glu Arg Met Val Ala Asp Gln Ala Gln
                165                 170                 175

Pro Ala Pro Val Asn Ala Asp His Asp Asp Asp Val Leu Ser His Ile
            180                 185                 190

Lys Thr Ile Asp Gly Lys Asn Tyr Tyr Val Gln Asp Asp Gly Thr Val
        195                 200                 205

Lys Lys Asn Phe Ala Val Glu Leu Asn Gly Arg Ile Leu Tyr Phe Asp
    210                 215                 220

Ala Glu Thr Gly Ala Leu Val Asp Ser Asn Glu Tyr Gln Phe Gln Gln
225                 230                 235                 240

Gly Thr Ser Ser Leu Asn Asn Glu Phe Ser Gln Lys Asn Ala Phe Tyr
                245                 250                 255

Gly Thr Thr Asp Lys Asp Ile Glu Thr Val Asp Gly Tyr Leu Thr Ala
            260                 265                 270

Asp Ser Trp Tyr Arg Pro Lys Phe Ile Leu Lys Asp Gly Lys Thr Trp
        275                 280                 285

Thr Ala Ser Thr Glu Thr Asp Leu Arg Pro Leu Leu Met Ala Trp Trp
    290                 295                 300

Pro Asp Lys Arg Thr Gln Ile Asn Tyr Leu Asn Tyr Met Asn Gln Gln
305                 310                 315                 320

Gly Leu Gly Ala Gly Ala Phe Glu Asn Lys Val Glu Gln Ala Leu Leu
                325                 330                 335

Thr Gly Ala Ser Gln Gln Val Gln Arg Lys Ile Glu Glu Lys Ile Gly
            340                 345                 350

Lys Glu Gly Asp Thr Lys Trp Leu Arg Thr Leu Met Gly Ala Phe Val
        355                 360                 365

Lys Thr Gln Pro Asn Trp Asn Ile Lys Thr Glu Ser Glu Thr Thr Gly
    370                 375                 380

Thr Lys Lys Asp His Leu Gln Gly Gly Ala Leu Leu Tyr Thr Asn Asn
385                 390                 395                 400

Glu Lys Ser Pro His Ala Asp Ser Lys Phe Arg Leu Leu Asn Arg Thr
                405                 410                 415

Pro Thr Ser Gln Thr Gly Thr Pro Lys Tyr Phe Ile Asp Lys Ser Asn
            420                 425                 430

Gly Gly Tyr Glu Phe Leu Leu Ala Asn Asp Phe Asp Asn Ser Asn Pro
        435                 440                 445

Ala Val Gln Ala Glu Gln Leu Asn Trp Leu His Tyr Met Met Asn Phe
    450                 455                 460

Gly Ser Ile Val Ala Asn Asp Pro Thr Ala Asn Phe Asp Gly Val Arg
465                 470                 475                 480

Val Asp Ala Val Asp Asn Val Asn Ala Asp Leu Leu Gln Ile Ala Ser
                485                 490                 495

Asp Tyr Phe Lys Ser Arg Tyr Lys Val Gly Glu Ser Glu Glu Glu Ala
            500                 505                 510

Ile Lys His Leu Ser Ile Leu Glu Ala Trp Ser Asp Asn Asp Pro Asp
        515                 520                 525

Tyr Asn Lys Asp Thr Lys Gly Ala Gln Leu Ala Ile Asp Asn Lys Leu
    530                 535                 540
```

```
Arg Leu Ser Leu Leu Tyr Ser Phe Met Arg Asn Leu Ser Ile Arg Ser
545                 550                 555                 560

Gly Val Glu Pro Thr Ile Thr Asn Ser Leu Asn Asp Arg Ser Ser Glu
                565                 570                 575

Lys Lys Asn Gly Glu Arg Met Ala Asn Tyr Ile Phe Val Arg Ala His
            580                 585                 590

Asp Asp Glu Val Gln Thr Val Ile Ala Asp Ile Ile Arg Glu Asn Ile
        595                 600                 605

Asn Pro Asn Thr Asp Gly Leu Thr Phe Thr Met Asp Glu Leu Lys Gln
    610                 615                 620

Ala Phe Lys Ile Tyr Asn Glu Asp Met Arg Lys Ala Asp Lys Lys Tyr
625                 630                 635                 640

Thr Gln Phe Asn Ile Pro Thr Ala His Ala Leu Met Leu Ser Asn Lys
                645                 650                 655

Asp Ser Ile Thr Arg Val Tyr Tyr Gly Asp Leu Tyr Thr Asp Asp Gly
            660                 665                 670

Gln Tyr Met Glu Lys Lys Ser Pro Tyr His Asp Ala Ile Asp Ala Leu
        675                 680                 685

Leu Arg Ala Arg Ile Lys Tyr Val Ala Gly Gly Gln Asp Met Lys Val
    690                 695                 700

Thr Tyr Met Gly Val Pro Arg Glu Ala Asp Lys Trp Ser Tyr Asn Gly
705                 710                 715                 720

Ile Leu Thr Ser Val Arg Tyr Gly Thr Gly Ala Asn Glu Ala Thr Asp
                725                 730                 735

Glu Gly Thr Ala Glu Thr Arg Thr Gln Gly Met Ala Val Ile Ala Ser
            740                 745                 750

Asn Asn Pro Asn Leu Lys Leu Asn Glu Trp Asp Lys Leu Gln Val Asn
        755                 760                 765

Met Gly Ala Ala His Lys Asn Gln Tyr Tyr Arg Pro Val Leu Leu Thr
    770                 775                 780

Thr Lys Asp Gly Ile Ser Arg Tyr Leu Thr Asp Glu Glu Val Pro Gln
785                 790                 795                 800

Ser Leu Trp Lys Lys Thr Asp Ala Asn Gly Ile Leu Thr Phe Asp Met
                805                 810                 815

Asn Asp Ile Ala Gly Tyr Ser Asn Val Gln Val Ser Gly Tyr Leu Ala
            820                 825                 830

Val Trp Val Pro Val Gly Ala Lys Ala Asp Gln Asp Ala Arg Thr Thr
        835                 840                 845

Ala Ser Lys Lys Lys Asn Ala Ser Gly Gln Val Tyr Glu Ser Ser Ala
    850                 855                 860

Ala Leu Asp Ser Gln Leu Ile Tyr Glu Gly Phe Ser Asn Phe Gln Asp
865                 870                 875                 880

Phe Ala Thr Arg Asp Asp Gln Tyr Thr Asn Lys Val Ile Ala Lys Asn
                885                 890                 895

Val Asn Leu Phe Lys Glu Trp Gly Val Thr Ser Phe Glu Leu Pro Pro
            900                 905                 910

Gln Tyr Val Ser Ser Gln Asp Gly Thr Phe Leu Asp Ser Ile Ile Gln
        915                 920                 925

Asn Gly Tyr Ala Phe Glu Asp Arg Tyr Asp Met Ala Met Ser Lys Asn
    930                 935                 940

Asn Lys Tyr Gly Ser Leu Lys Asp Leu Leu Asn Ala Leu Arg Ala Leu
945                 950                 955                 960

His Ser Val Asn Ile Gln Ala Ile Ala Asp Trp Val Pro Asp Gln Ile
```

```
                965                 970                 975

Tyr Asn Leu Pro Gly Lys Glu Val Val Thr Ala Thr Arg Val Asn Asn
            980                 985                 990

Tyr Gly Thr Tyr Arg Glu Gly Ala  Glu Ile Lys Glu Lys  Leu Tyr Val
        995                 1000                1005

Ala Asn  Ser Lys Thr Asn Glu  Thr Asp Phe Gln Gly  Lys Tyr Gly
    1010                 1015                 1020

Gly Ala  Phe Leu Asp Glu Leu  Lys Ala Lys Tyr Pro  Glu Ile Phe
    1025                 1030                 1035

Glu Arg  Val Gln Ile Ser Asn  Gly Gln Lys Met Thr  Thr Asp Glu
    1040                 1045                 1050

Lys Ile  Thr Lys Trp Ser Ala  Lys Tyr Phe Asn Gly  Thr Asn Ile
    1055                 1060                 1065

Leu Gly  Arg Gly Ala Tyr Tyr  Val Leu Lys Asp Trp  Ala Ser Asn
    1070                 1075                 1080

Asp Tyr  Leu Thr Asn Arg Asn  Gly Glu Ile Val Leu  Pro Lys Gln
    1085                 1090                 1095

Leu Val  Asn Lys Asn Ser Tyr  Thr Gly Phe Val Ser  Asp Ala Asn
    1100                 1105                 1110

Gly Thr  Lys Phe Tyr Ser Thr  Ser Gly Tyr Gln Ala  Lys Asn Ser
    1115                 1120                 1125

Phe Ile  Gln Asp Glu Asn Gly  Asn Trp Tyr Tyr Phe  Asp Lys Arg
    1130                 1135                 1140

Gly Tyr  Leu Val Thr Gly Ala  His Glu Ile Asp Gly  Lys His Val
    1145                 1150                 1155

Tyr Phe  Leu Lys Asn Gly Ile  Gln Leu Arg Asp Ser  Ile Arg Glu
    1160                 1165                 1170

Asp Glu  Asn Gly Asn Gln Tyr  Tyr Tyr Asp Gln Thr  Gly Ala Gln
    1175                 1180                 1185

Val Leu  Asn Arg Tyr Tyr Thr  Thr Asp Gly Gln Asn  Trp Arg Tyr
    1190                 1195                 1200

Phe Asp  Ala Lys Gly Val Met  Ala Arg Gly Leu Val  Lys Ile Gly
    1205                 1210                 1215

Asp Gly  Gln Gln Phe Phe Asp  Glu Asn Gly Tyr Gln  Val Lys Gly
    1220                 1225                 1230

Lys Ile  Val Ser Ala Lys Asp  Gly Lys Leu Arg Tyr  Phe Asp Lys
    1235                 1240                 1245

Asp Ser  Gly Asn Ala Val Ile  Asn Arg Phe Ala Gln  Gly Asp Asn
    1250                 1255                 1260

Pro Ser  Asp Trp Tyr Tyr Phe  Gly Val Glu Phe Ala  Lys Leu Thr
    1265                 1270                 1275

Gly Leu  Gln Lys Ile Gly Gln  Gln Thr Leu Tyr Phe  Asp Gln Asp
    1280                 1285                 1290

Gly Lys  Gln Val Lys Gly Lys  Ile Val Thr Leu Ser  Asp Lys Ser
    1295                 1300                 1305

Ile Arg  Tyr Phe Asp Ala Asn  Ser Gly Glu Met Ala  Val Gly Lys
    1310                 1315                 1320

Phe Ala  Glu Gly Ala Lys Asn  Glu Trp Tyr Tyr Phe  Asp Lys Thr
    1325                 1330                 1335

Gly Lys  Ala Val Thr Gly Leu  Gln Lys Ile Gly Lys  Gln Thr Leu
    1340                 1345                 1350

Tyr Phe  Asp Gln Asp Gly Lys  Gln Val Lys Gly Lys  Val Val Thr
    1355                 1360                 1365
```

Leu Ala Asp Lys Ser Ile Arg Tyr Phe Asp Ala Asp Ser Gly Glu
1370 1375 1380

Met Ala Val Gly Lys Phe Ala Glu Gly Ala Lys Asn Glu Trp Tyr
1385 1390 1395

Tyr Phe Asp Gln Thr Gly Lys Ala Val Thr Gly Leu Gln Lys Ile
1400 1405 1410

Asp Lys Gln Thr Leu Tyr Phe Asp Gln Asp Gly Lys Gln Val Lys
1415 1420 1425

Gly Lys Ile Val Thr Leu Ser Asp Lys Ser Ile Arg Tyr Phe Asp
1430 1435 1440

Ala Asn Ser Gly Glu Met Ala Thr Asn Lys Phe Val Glu Gly Ser
1445 1450 1455

Gln Asn Glu Trp Tyr Tyr Phe Asp Gln Ala Gly Lys Ala Val Thr
1460 1465 1470

Gly Leu Gln Gln Val Gly Gln Gln Thr Leu Tyr Phe Thr Gln Asp
1475 1480 1485

Gly Lys Gln Val Lys Gly Lys Val Val Asp Val Asn Gly Val Ser
1490 1495 1500

Arg Tyr Phe Asp Ala Asn Ser Gly Asp Met Ala Arg Ser Lys Trp
1505 1510 1515

Ile Gln Leu Glu Asp Gly Ser Trp Met Tyr Phe Asp Arg Asp Gly
1520 1525 1530

Arg Gly Gln Asn Phe Gly Arg Asn
1535 1540

<210> SEQ ID NO 39
<211> LENGTH: 3014
<212> TYPE: DNA
<213> ORGANISM: Zea maize
<220> FEATURE:
<221> NAME/KEY: promoter
<222> LOCATION: (1)..(3014)
<223> OTHER INFORMATION: maize ubiquitin promoter

<400> SEQUENCE: 39
gacaaacctc tatatgtaga gtacaggagc ttttacagga ccctgctgga gccagcctta 60
gggggaaaac ttccaggcgg taggtcacat acatcagtga ggtaggagaa atgtgccaac 120
cacgtggtgt cgaccaatct acattctaat ctatatcatt atataattta tcagtttaaa 180
ctttacaaaa tctatctaaa caaatcacat ctacacccat aacattcgtt aaatctaaca 240
cagtatcaaa actagcggtt caaatcgatg gataacatgt tctcccatat ccattcaaat 300
ctgatagata atattattta gatcatgtat tctctctccc ctctccctcg acgcctcctc 360
ctgccccgtg tccctgacct gtctccctca cttatgatgt tgtctctatc atcaatcgct 420
ccttttatat tgtgatcact gtccacccct attcctactc gggattaggg atggcaatgg 480
aaaatttctc atcgaggaat agctcttcat acccatccca cgacgcagaa atttcctcgc 540
gggaataccc acgaacgttt acagaagaca tttcttcccc atccatattc cccacgggca 600
taaatttccg acggagatca acgtccctat ttacattata attaggaaat gcatcctttg 660
ttattaataa aaacactttc acttatatat attgttagat gtaagaaatc attatgggta 720
tattaaaata aacatatttg tacaatgatt gatctcttac ccaaataatt atttgttttt 780
attattagct agtatacgaa aacatcacca cgtacaggtt tgacggattc ccacagaaac 840
agggatgaaa aatacttcta catccctgtc ccgtttaccc atctgagaaa gcgggaaatc 900

```
gggcatagga tccattgcca aagatcgtag ggctataacc taagcgttgc aacgaagcga    960
agcagacggt ggagacgttg acgcaaagca atgaacttga acggcatctc tctcgctggc   1020
cctggccttc tcgaaggctc tgcgtgggtc cttgcgcagt tgcgccgcag cgggctggca   1080
gcatccggaa attgcgtctt gcgtggcgga gcagacacta aggtactatt ttacgttcta   1140
tttagttgga ctgtggcggt aaactatgaa aaaaactatt gcagactatg agctattaaa   1200
aagctaaaaa ttatttagtg taaaccacta aaaaccatta aaaattcttt gatatatatt   1260
ttcacagttt tataaaaaat ccactaaaaa caggtcaaat aagctttcaa ttttacacta   1320
cgaaaaagtc agcttttaaa aaaaactgct taaatccagt cctttagttt aatttttatc   1380
ttttaggaaa caaaagccaa aactaaaacc aaaccaaacc tacctttaaa accgatctaa   1440
taggaacgcg gtgtttggaa caactagata ttaattttag aggttagacc gccacgaaag   1500
cgtcactgca cacggcattc ccctccccta gcgttatcgt cgcaccataa ataaccatcc   1560
tctcctcgcc tttccccaca tctcatcttc gtctgtgttc ttgggcgtac gcggacacag   1620
ccccgatccg aatcgtcgtc cttgcgagcc tcgccgatcc cccactcccc tcccctcgct   1680
tcaaggtaac tgcgatcatc catcctcccg cttccactct cccttcacct cctctgcttg   1740
ctaggtatac gaacatacga tttattacgg gttatatggg ggcttcgatt cccagatctg   1800
gcgatctatt atcgtagctc cgagtcctcg atctagtaat tgtgggatat gcttgtaaga   1860
ggctctgaga tgggttgggt tgggttgggt cgctgtgacg attccaacag cctcgtttct   1920
tagggttgga tcttctcgtg gtttcctttt taattaaata agtacctgat gcagaatggt   1980
gcgtcctatt agatggaacc ttgatcttga tgcatctaac cttgatcttg ttcgctgtga   2040
tgattccaac aggctcgttt cttaggcctg ttcgtctggt tcgtcagatc agtttcgttg   2100
cttttggcct cgttgtaagg tccatccaga tcggagtaga atcgaatgat ttattatacg   2160
gtagctgctg gtctcattag atttggatct gcatgggttg aacatatgta ttcataatta   2220
atatggtgta tacgtactag tttgctggtc ttattttttt agcctgattg cttctgcctt   2280
tctggcaacg cctgatccac gcgttagcta gagtggattt tagttccttg tttacgcggc   2340
cacacctgcc gcctagaaaa gctgcagcga gaactctaat taaatttgga tctacatgtg   2400
ctagcatata tgtttgtaat taatatgatg gatgaatatg tgcttcagag ttgagttcct   2460
gttgatgctg tagttctgcc tgaattgttg aggctgtagc ttctgcctga ttaaaatgca   2520
ccgtgcctat ctgttaaact ctagggtgtg tgatttagcc ggtgacggtg gtttaatatg   2580
tgtaatttca ctgcttatag taatgcaatt cacctttgct tgaacatgca ttgtcttgtt   2640
gctttgttct atacacatgc ttagctatta tctgatgagc atgcactgtt ttgttctgtt   2700
tgatatgcat gctcagaaat atgtagatgt gtggctcctg ctcggttgtt ctttatcatc   2760
cacctgttga acatgcatgt tcttgtcgct tatctttatt atatattacc ttcgttctcg   2820
aatatttgtc gcccgctagt tcatttttga actaaaccgt gacaaataaa atagaacgta   2880
gggagtggca tcatgctgct actgtacctt acggtggcaa ctacatcttg agcacgcata   2940
tatcttatag tgttcctttt cttttcctcc ttggtctact gttatatgct taccttttt    3000
tggtttcctt gcag                                                     3014
```

<210> SEQ ID NO 40
<211> LENGTH: 68
<212> TYPE: DNA
<213> ORGANISM: tobacco mosaic virus
<220> FEATURE:
<221> NAME/KEY: enhancer
<222> LOCATION: (1)..(68)
<223> OTHER INFORMATION: TMV enhancer

<400> SEQUENCE: 40
gtatttttac aacaattacc aacaacaaca aacaacaaac aacattacaa ttactattta 60
cataaacc 68

<210> SEQ ID NO 41
<211> LENGTH: 195
<212> TYPE: DNA
<213> ORGANISM: Cyanophora paradoxa
<220> FEATURE:
<221> NAME/KEY: CDS
<222> LOCATION: (1)..(195)
<223> OTHER INFORMATION: chloroplast targeting sequence FNR

<400> SEQUENCE: 41

```
atg gct ttc gtt gcc agc gtg cca gtt ttc gct aac gct tcc ggc ctt       48
Met Ala Phe Val Ala Ser Val Pro Val Phe Ala Asn Ala Ser Gly Leu
1               5                   10                  15

aaa act gaa gcc aag gtg tgc cag aag cct gcc ttg aag aat tca ttt       96
Lys Thr Glu Ala Lys Val Cys Gln Lys Pro Ala Leu Lys Asn Ser Phe
            20                  25                  30

ttc agg ggc gag gaa gtc aca tct aga tct ttt ttt gcc tcc caa gca      144
Phe Arg Gly Glu Glu Val Thr Ser Arg Ser Phe Phe Ala Ser Gln Ala
        35                  40                  45

gtg tcc gct aaa cca gca aca acc ggc gag gtt gat act acc att agg      192
Val Ser Ala Lys Pro Ala Thr Thr Gly Glu Val Asp Thr Thr Ile Arg
    50                  55                  60

gca                                                                  195
Ala
65
```

<210> SEQ ID NO 42
<211> LENGTH: 65
<212> TYPE: PRT
<213> ORGANISM: Cyanophora paradoxa

<400> SEQUENCE: 42

```
Met Ala Phe Val Ala Ser Val Pro Val Phe Ala Asn Ala Ser Gly Leu
1               5                   10                  15

Lys Thr Glu Ala Lys Val Cys Gln Lys Pro Ala Leu Lys Asn Ser Phe
            20                  25                  30

Phe Arg Gly Glu Glu Val Thr Ser Arg Ser Phe Phe Ala Ser Gln Ala
        35                  40                  45

Val Ser Ala Lys Pro Ala Thr Thr Gly Glu Val Asp Thr Thr Ile Arg
    50                  55                  60

Ala
65
```

<210> SEQ ID NO 43
<211> LENGTH: 1590
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1590)
<223> OTHER INFORMATION: maize codon optimized alpha-1,5-glucosidase from Thermus thermophilus

<400> SEQUENCE: 43

-continued

```
atg tcc tgg tgg cag cgc gcc gtg atc tac cag gtg tac ccg cgc agc       48
Met Ser Trp Trp Gln Arg Ala Val Ile Tyr Gln Val Tyr Pro Arg Ser
1               5                   10                  15

ttc cag gac acc aac ggc gac gga gtg ggc gac ctc gag ggc atc agg       96
Phe Gln Asp Thr Asn Gly Asp Gly Val Gly Asp Leu Glu Gly Ile Arg
            20                  25                  30

cgc agg ctg ccg tac ctg aag tcc ctg gga gtg gat gcc ctg tgg ctg      144
Arg Arg Leu Pro Tyr Leu Lys Ser Leu Gly Val Asp Ala Leu Trp Leu
        35                  40                  45

tcc ccg ttc tac aag agc ccg atg aag gac ttt gga tac gat gtg gct      192
Ser Pro Phe Tyr Lys Ser Pro Met Lys Asp Phe Gly Tyr Asp Val Ala
    50                  55                  60

gac tac tgc gac gtg gac ccg gtg ttc ggc acc ctc cag gac ttc gac      240
Asp Tyr Cys Asp Val Asp Pro Val Phe Gly Thr Leu Gln Asp Phe Asp
65                  70                  75                  80

cgc ctg ctc gag gaa gct cac gct ctt gga ctg aag gtt ctc gtc gat      288
Arg Leu Leu Glu Glu Ala His Ala Leu Gly Leu Lys Val Leu Val Asp
                85                  90                  95

ctc gtg ccg aac cac acc agc agc gag cac ccg tgg ttc ctc gag agc      336
Leu Val Pro Asn His Thr Ser Ser Glu His Pro Trp Phe Leu Glu Ser
            100                 105                 110

cgc gcc agc agg aac agc ccg aag cgc gac tgg tac atc tgg aag gac      384
Arg Ala Ser Arg Asn Ser Pro Lys Arg Asp Trp Tyr Ile Trp Lys Asp
        115                 120                 125

cca gcc cca gat ggc ggc cca ccg aac aac tgg cag agc ttc ttc gga      432
Pro Ala Pro Asp Gly Gly Pro Pro Asn Asn Trp Gln Ser Phe Phe Gly
    130                 135                 140

ggg cca gct tgg act ctg gac gag gct aca ggc caa tat tac ctc cac      480
Gly Pro Ala Trp Thr Leu Asp Glu Ala Thr Gly Gln Tyr Tyr Leu His
145                 150                 155                 160

ctg ttc ctc cca gag cag ccg gac ctg aac tgg cgc aac ccc gaa gtg      528
Leu Phe Leu Pro Glu Gln Pro Asp Leu Asn Trp Arg Asn Pro Glu Val
                165                 170                 175

cgc gag gcc atc aag gaa gtg atg cgc ttc tgg ctc aga cgc ggt gtc      576
Arg Glu Ala Ile Lys Glu Val Met Arg Phe Trp Leu Arg Arg Gly Val
            180                 185                 190

gat ggc ttc agg gtg gac gtg ctg tgg ctg ctg ggc aag gac ccg ctg      624
Asp Gly Phe Arg Val Asp Val Leu Trp Leu Leu Gly Lys Asp Pro Leu
        195                 200                 205

ttc agg gac gag ccg ggc agc cca ctg tgg agg cca ggc ctg cca gac      672
Phe Arg Asp Glu Pro Gly Ser Pro Leu Trp Arg Pro Gly Leu Pro Asp
    210                 215                 220

agg gcc agg cac gag cac ctg tac acc gag gac cag ccc gag act tac      720
Arg Ala Arg His Glu His Leu Tyr Thr Glu Asp Gln Pro Glu Thr Tyr
225                 230                 235                 240

gcc tat gtg cgc gag atg cgc cag gtg ctg gac gag ttc agc gag cca      768
Ala Tyr Val Arg Glu Met Arg Gln Val Leu Asp Glu Phe Ser Glu Pro
                245                 250                 255

ggc cgc gag agg gtg atg gtg ggc gag atc tac ctc cca ctc cca cgg      816
Gly Arg Glu Arg Val Met Val Gly Glu Ile Tyr Leu Pro Leu Pro Arg
            260                 265                 270

ctt gtg agg tac tac gcc gct ggc tgc cac ctc ccg ttc aac ttc agc      864
Leu Val Arg Tyr Tyr Ala Ala Gly Cys His Leu Pro Phe Asn Phe Ser
        275                 280                 285

ctg gtg acg gaa ggt ctc agc gac tgg cgc cca gag aac ctg gcc cgc      912
Leu Val Thr Glu Gly Leu Ser Asp Trp Arg Pro Glu Asn Leu Ala Arg
    290                 295                 300

atc gtg gag act tac gag ggg ctc ctg tct aga tgg gat tgg cca aac      960
Ile Val Glu Thr Tyr Glu Gly Leu Leu Ser Arg Trp Asp Trp Pro Asn
305                 310                 315                 320
```

```
tgg gtg ctg ggc aac cac gat caa cct cgc ctc gct tcc cgc ctc ggc      1008
Trp Val Leu Gly Asn His Asp Gln Pro Arg Leu Ala Ser Arg Leu Gly
                325                 330                 335

gag cca cag gcc agg gtg gcc gcc atg ctg ctg ttc acc ctg agg ggc      1056
Glu Pro Gln Ala Arg Val Ala Ala Met Leu Leu Phe Thr Leu Arg Gly
            340                 345                 350

acc ccg acc tgg tac tac ggg gat gaa ctc gct ctc ccg aac ggg ctc      1104
Thr Pro Thr Trp Tyr Tyr Gly Asp Glu Leu Ala Leu Pro Asn Gly Leu
        355                 360                 365

att cca cca gag aag gtc caa gac cca gca gca ctg agg cag agg gac      1152
Ile Pro Pro Glu Lys Val Gln Asp Pro Ala Ala Leu Arg Gln Arg Asp
    370                 375                 380

cgc gag cca acc gcc tac cac acc ctg ggc cgc gat cca gag cgg act      1200
Arg Glu Pro Thr Ala Tyr His Thr Leu Gly Arg Asp Pro Glu Arg Thr
385                 390                 395                 400

cca atg cct tgg gac gcc agc cca tac ggc ggc ttc agc acc gtg gag      1248
Pro Met Pro Trp Asp Ala Ser Pro Tyr Gly Gly Phe Ser Thr Val Glu
                405                 410                 415

cct tgg ctc cca ctg aac ccg gac tac cgc acc agg aac gtg gct gct      1296
Pro Trp Leu Pro Leu Asn Pro Asp Tyr Arg Thr Arg Asn Val Ala Ala
            420                 425                 430

caa gag aag gac cca cgg tcc atg ctc cac ctg gtg aag cgc ctg att      1344
Gln Glu Lys Asp Pro Arg Ser Met Leu His Leu Val Lys Arg Leu Ile
        435                 440                 445

gct ctc cgc aag gac ccg gac ctc ctg tac ggc gcc tac cgc acc tac      1392
Ala Leu Arg Lys Asp Pro Asp Leu Leu Tyr Gly Ala Tyr Arg Thr Tyr
    450                 455                 460

cgc gct cgg gag gga gtc tac gcc tac ctc cgc ggg gag ggc tgg ctc      1440
Arg Ala Arg Glu Gly Val Tyr Ala Tyr Leu Arg Gly Glu Gly Trp Leu
465                 470                 475                 480

gtg gcc ctg aac ctg acc gag aag gaa aag gcc ctc gag ctg cca agg      1488
Val Ala Leu Asn Leu Thr Glu Lys Glu Lys Ala Leu Glu Leu Pro Arg
                485                 490                 495

ggc ggc agg gtg gtg ctg tcc acc cac ctg gac aga gag gaa aga gtc      1536
Gly Gly Arg Val Val Leu Ser Thr His Leu Asp Arg Glu Glu Arg Val
            500                 505                 510

ggg gaa agg ctg ttc ctc aga cct gat gaa ggc gtc gct gtc aga ctg      1584
Gly Glu Arg Leu Phe Leu Arg Pro Asp Glu Gly Val Ala Val Arg Leu
        515                 520                 525

gac tga                                                              1590
Asp


<210> SEQ ID NO 44
<211> LENGTH: 529
<212> TYPE: PRT
<213> ORGANISM: unknown
<220> FEATURE:
<223> OTHER INFORMATION: Synthetic Construct

<400> SEQUENCE: 44

Met Ser Trp Trp Gln Arg Ala Val Ile Tyr Gln Val Tyr Pro Arg Ser
1               5                   10                  15

Phe Gln Asp Thr Asn Gly Asp Gly Val Gly Asp Leu Glu Gly Ile Arg
            20                  25                  30

Arg Arg Leu Pro Tyr Leu Lys Ser Leu Gly Val Asp Ala Leu Trp Leu
        35                  40                  45

Ser Pro Phe Tyr Lys Ser Pro Met Lys Asp Phe Gly Tyr Asp Val Ala
    50                  55                  60

Asp Tyr Cys Asp Val Asp Pro Val Phe Gly Thr Leu Gln Asp Phe Asp
```

-continued

```
65                  70                  75                  80

Arg Leu Leu Glu Glu Ala His Ala Leu Gly Leu Lys Val Leu Val Asp
                85                  90                  95

Leu Val Pro Asn His Thr Ser Ser Glu His Pro Trp Phe Leu Glu Ser
            100                 105                 110

Arg Ala Ser Arg Asn Ser Pro Lys Arg Asp Trp Tyr Ile Trp Lys Asp
        115                 120                 125

Pro Ala Pro Asp Gly Gly Pro Pro Asn Asn Trp Gln Ser Phe Phe Gly
    130                 135                 140

Gly Pro Ala Trp Thr Leu Asp Glu Ala Thr Gly Gln Tyr Tyr Leu His
145                 150                 155                 160

Leu Phe Leu Pro Glu Gln Pro Asp Leu Asn Trp Arg Asn Pro Glu Val
                165                 170                 175

Arg Glu Ala Ile Lys Glu Val Met Arg Phe Trp Leu Arg Arg Gly Val
            180                 185                 190

Asp Gly Phe Arg Val Asp Val Leu Trp Leu Leu Gly Lys Asp Pro Leu
        195                 200                 205

Phe Arg Asp Glu Pro Gly Ser Pro Leu Trp Arg Pro Gly Leu Pro Asp
    210                 215                 220

Arg Ala Arg His Glu His Leu Tyr Thr Glu Asp Gln Pro Glu Thr Tyr
225                 230                 235                 240

Ala Tyr Val Arg Glu Met Arg Gln Val Leu Asp Glu Phe Ser Glu Pro
                245                 250                 255

Gly Arg Glu Arg Val Met Val Gly Glu Ile Tyr Leu Pro Leu Pro Arg
            260                 265                 270

Leu Val Arg Tyr Tyr Ala Ala Gly Cys His Leu Pro Phe Asn Phe Ser
        275                 280                 285

Leu Val Thr Glu Gly Leu Ser Asp Trp Arg Pro Glu Asn Leu Ala Arg
    290                 295                 300

Ile Val Glu Thr Tyr Glu Gly Leu Leu Ser Arg Trp Asp Trp Pro Asn
305                 310                 315                 320

Trp Val Leu Gly Asn His Asp Gln Pro Arg Leu Ala Ser Arg Leu Gly
                325                 330                 335

Glu Pro Gln Ala Arg Val Ala Ala Met Leu Leu Phe Thr Leu Arg Gly
            340                 345                 350

Thr Pro Thr Trp Tyr Tyr Gly Asp Glu Leu Ala Leu Pro Asn Gly Leu
        355                 360                 365

Ile Pro Pro Glu Lys Val Gln Asp Pro Ala Ala Leu Arg Gln Arg Asp
    370                 375                 380

Arg Glu Pro Thr Ala Tyr His Thr Leu Gly Arg Asp Pro Glu Arg Thr
385                 390                 395                 400

Pro Met Pro Trp Asp Ala Ser Pro Tyr Gly Gly Phe Ser Thr Val Glu
                405                 410                 415

Pro Trp Leu Pro Leu Asn Pro Asp Tyr Arg Thr Arg Asn Val Ala Ala
            420                 425                 430

Gln Glu Lys Asp Pro Arg Ser Met Leu His Leu Val Lys Arg Leu Ile
        435                 440                 445

Ala Leu Arg Lys Asp Pro Asp Leu Leu Tyr Gly Ala Tyr Arg Thr Tyr
    450                 455                 460

Arg Ala Arg Glu Gly Val Tyr Ala Tyr Leu Arg Gly Glu Gly Trp Leu
465                 470                 475                 480

Val Ala Leu Asn Leu Thr Glu Lys Glu Lys Ala Leu Glu Leu Pro Arg
                485                 490                 495
```

```
Gly Gly Arg Val Val Leu Ser Thr His Leu Asp Arg Glu Glu Arg Val
            500                 505                 510

Gly Glu Arg Leu Phe Leu Arg Pro Asp Glu Gly Val Ala Val Arg Leu
        515                 520                 525

Asp


<210> SEQ ID NO 45
<211> LENGTH: 1001
<212> TYPE: DNA
<213> ORGANISM: Zea maize
<220> FEATURE:
<221> NAME/KEY: terminator
<222> LOCATION: (1)..(1001)
<223> OTHER INFORMATION: maize ubi terminator

<400> SEQUENCE: 45

gccatcagtc gttgaagctg ctgctgtatc tgggttatct agtgtctctg ccattgccca     60

aggatggtgc tgtctttcaa agtatttgta tggtttgtgt cgtgagtcgt gactgagctg    120

gtttcatgga ccagttgtgt tctcgttacc caaaactatc gtgcgaccgc atatggctta    180

atcatgaata aatgttgttt gaatttaaac tattcgctga atattgttgt tttttgtcat    240

gtcagttaat gttactaaat tggttgcctt ctaatttttg tttactggtg tttgtcgcac    300

cttatctttt tactgtatgt ttacttcagg ttctggcagt ctcatttttt gtgactagtt    360

aaaacttaca gctaaaaaaa tgcagttttt cattttcatt tgaagtttga ttagagctat    420

tgatacccgg accatcaggt taggttagtt gtgcatagaa tcataaatat taatcatgtt    480

ttctatgaat taagtcaaac ttgaaagtct ggctgaatat agtttctatg aatcatattg    540

atatacatgt ttgattattt gttttgctat tagctattta ctttggtgaa tctatatagg    600

cttatgcaga accttttttt ttgttctata tatccatatc ctagtactca gtagctctat    660

gttttctgga gactagtggc ttgctttttc gtatgtctaa ttttttgctt gaccattgca    720

aaacaaaaat tacctagtgt aatctctttt tataataatc ttgtaatgcg tctacctata    780

ggtcaaagta ggttttgttt ggaaccctta gagctaactg ttagctagtt gataaattat    840

tagctgagtt aagctagcta atgaactagt tttgatatta gctgaggatg tttgaaacct    900

aataattatt ttttattagc taactatact aaattttagt agagagattc caaacaggag    960

ttaacatggg atcagattgg ctatgcgttt gcaatcccat a                       1001


<210> SEQ ID NO 46
<211> LENGTH: 1590
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1590)
<223> OTHER INFORMATION: dicot optimized alpha-1,5-glucosidase HB8

<400> SEQUENCE: 46

atg tct tgg tgg caa agg gct gtt atc tac caa gtt tac cca aga tcc       48
Met Ser Trp Trp Gln Arg Ala Val Ile Tyr Gln Val Tyr Pro Arg Ser
1               5                   10                  15

ttc cag gat aca aac ggt gat ggt gtt gga gat ctt gag gga att aga       96
Phe Gln Asp Thr Asn Gly Asp Gly Val Gly Asp Leu Glu Gly Ile Arg
            20                  25                  30

aga agg ctt cca tac ctt aag tct ctt gga gtt gat gct ctt tgg ctt      144
Arg Arg Leu Pro Tyr Leu Lys Ser Leu Gly Val Asp Ala Leu Trp Leu
```

```
        35                  40                  45

tcc cca ttc tac aag tcc cca atg aag gat ttc gga tac gat gtt gct      192
Ser Pro Phe Tyr Lys Ser Pro Met Lys Asp Phe Gly Tyr Asp Val Ala
    50                  55                  60

gat tac tgt gat gtt gat cca gtg ttc gga act ctt cag gat ttc gat      240
Asp Tyr Cys Asp Val Asp Pro Val Phe Gly Thr Leu Gln Asp Phe Asp
65                  70                  75                  80

agg ctt ctt gaa gag gct cat gct ctt gga ctt aag gtg ttg gtt gat      288
Arg Leu Leu Glu Glu Ala His Ala Leu Gly Leu Lys Val Leu Val Asp
                85                  90                  95

ctt gtt cca aac cac act tct tca gag cat cct tgg ttt ctt gaa tct      336
Leu Val Pro Asn His Thr Ser Ser Glu His Pro Trp Phe Leu Glu Ser
            100                 105                 110

agg gct tct agg aat tct cca aag agg gat tgg tac atc tgg aaa gat      384
Arg Ala Ser Arg Asn Ser Pro Lys Arg Asp Trp Tyr Ile Trp Lys Asp
        115                 120                 125

cca gct cca gat ggt gga cca cca aat aac tgg cag tct ttc ttt ggt      432
Pro Ala Pro Asp Gly Gly Pro Pro Asn Asn Trp Gln Ser Phe Phe Gly
    130                 135                 140

ggt cct gct tgg act ctt gat gaa gct act gga cag tac tac ctt cac      480
Gly Pro Ala Trp Thr Leu Asp Glu Ala Thr Gly Gln Tyr Tyr Leu His
145                 150                 155                 160

ttg ttc ctt cca gag cag cca gat ctt aat tgg agg aac cca gaa gtt      528
Leu Phe Leu Pro Glu Gln Pro Asp Leu Asn Trp Arg Asn Pro Glu Val
                165                 170                 175

aga gag gct atc aaa gaa gtt atg agg ttc tgg ctt aga aga ggt gtt      576
Arg Glu Ala Ile Lys Glu Val Met Arg Phe Trp Leu Arg Arg Gly Val
            180                 185                 190

gat gga ttc aga gtg gat gtg ctt tgg ctt ctt gga aaa gat cca ctc      624
Asp Gly Phe Arg Val Asp Val Leu Trp Leu Leu Gly Lys Asp Pro Leu
        195                 200                 205

ttt agg gat gaa cca gga tct cca ctt tgg agg cca gga ctt cca gat      672
Phe Arg Asp Glu Pro Gly Ser Pro Leu Trp Arg Pro Gly Leu Pro Asp
    210                 215                 220

aga gct agg cat gag cat ctt tac act gag gat cag cca gag act tat      720
Arg Ala Arg His Glu His Leu Tyr Thr Glu Asp Gln Pro Glu Thr Tyr
225                 230                 235                 240

gct tat gtg aga gag atg agg caa gtt ctt gat gag ttt tct gag cca      768
Ala Tyr Val Arg Glu Met Arg Gln Val Leu Asp Glu Phe Ser Glu Pro
                245                 250                 255

gga cgt gaa aga gtt atg gtt gga gag atc tac ctt cca ctt cca agg      816
Gly Arg Glu Arg Val Met Val Gly Glu Ile Tyr Leu Pro Leu Pro Arg
            260                 265                 270

ctt gtt agg tat tat gct gct gga tgc cat ctt cca ttc aac ttc tca      864
Leu Val Arg Tyr Tyr Ala Ala Gly Cys His Leu Pro Phe Asn Phe Ser
        275                 280                 285

ctt gtg act gag gga ctt tct gat tgg agg cca gaa aac ctt gct aga      912
Leu Val Thr Glu Gly Leu Ser Asp Trp Arg Pro Glu Asn Leu Ala Arg
    290                 295                 300

atc gtg gaa act tac gag gga ctt ctt tct aga tgg gat tgg cca aat      960
Ile Val Glu Thr Tyr Glu Gly Leu Leu Ser Arg Trp Asp Trp Pro Asn
305                 310                 315                 320

tgg gtt ttg gga aac cat gat cag cct aga ctt gct tct aga ctt gga     1008
Trp Val Leu Gly Asn His Asp Gln Pro Arg Leu Ala Ser Arg Leu Gly
                325                 330                 335

gaa cca caa gct aga gtt gct gct atg ctt ttg ttc act ctc aga gga     1056
Glu Pro Gln Ala Arg Val Ala Ala Met Leu Leu Phe Thr Leu Arg Gly
            340                 345                 350

act cca act tgg tat tac ggt gat gag ctt gct ttg cca aac gga ctt     1104
```

```
Thr Pro Thr Trp Tyr Tyr Gly Asp Glu Leu Ala Leu Pro Asn Gly Leu
        355                 360                 365

att cca cca gag aag gtt caa gat cca gct gct ctt aga caa aga gat      1152
Ile Pro Pro Glu Lys Val Gln Asp Pro Ala Ala Leu Arg Gln Arg Asp
    370                 375                 380

aga gag cca act gct tac cat act ctt ggt aga gat cca gaa aga act      1200
Arg Glu Pro Thr Ala Tyr His Thr Leu Gly Arg Asp Pro Glu Arg Thr
385                 390                 395                 400

cca atg cct tgg gat gct tct cca tat ggt gga ttc tct act gtt gaa      1248
Pro Met Pro Trp Asp Ala Ser Pro Tyr Gly Gly Phe Ser Thr Val Glu
                405                 410                 415

cct tgg ctt cca ctt aat cca gat tac cgt act agg aat gtt gct gct      1296
Pro Trp Leu Pro Leu Asn Pro Asp Tyr Arg Thr Arg Asn Val Ala Ala
            420                 425                 430

caa gag aaa gat cca aga tct atg ctt cac ctt gtg aag agg ctt att      1344
Gln Glu Lys Asp Pro Arg Ser Met Leu His Leu Val Lys Arg Leu Ile
        435                 440                 445

gct ctc agg aaa gat cct gat ctt ctc tat ggt gct tac cgt act tat      1392
Ala Leu Arg Lys Asp Pro Asp Leu Leu Tyr Gly Ala Tyr Arg Thr Tyr
    450                 455                 460

cgt gct aga gag ggc gtt tac gct tat ctt agg ggt gaa gga tgg ctt      1440
Arg Ala Arg Glu Gly Val Tyr Ala Tyr Leu Arg Gly Glu Gly Trp Leu
465                 470                 475                 480

gtt gct ctt aac ctc act gag aaa gag aag gct ctt gaa ctt cca aga      1488
Val Ala Leu Asn Leu Thr Glu Lys Glu Lys Ala Leu Glu Leu Pro Arg
                485                 490                 495

ggt gga aga gtt gtg ctt tct act cac ctt gat agg gaa gaa aga gtt      1536
Gly Gly Arg Val Val Leu Ser Thr His Leu Asp Arg Glu Glu Arg Val
            500                 505                 510

gga gag agg ctt ttt ctt agg cct gat gaa ggt gtt gct gtt aga ctt      1584
Gly Glu Arg Leu Phe Leu Arg Pro Asp Glu Gly Val Ala Val Arg Leu
        515                 520                 525

gat taa                                                              1590
Asp


<210> SEQ ID NO 47
<211> LENGTH: 529
<212> TYPE: PRT
<213> ORGANISM: unknown
<220> FEATURE:
<223> OTHER INFORMATION: Synthetic Construct

<400> SEQUENCE: 47

Met Ser Trp Trp Gln Arg Ala Val Ile Tyr Gln Val Tyr Pro Arg Ser
1               5                   10                  15

Phe Gln Asp Thr Asn Gly Asp Gly Val Gly Asp Leu Glu Gly Ile Arg
            20                  25                  30

Arg Arg Leu Pro Tyr Leu Lys Ser Leu Gly Val Asp Ala Leu Trp Leu
        35                  40                  45

Ser Pro Phe Tyr Lys Ser Pro Met Lys Asp Phe Gly Tyr Asp Val Ala
    50                  55                  60

Asp Tyr Cys Asp Val Asp Pro Val Phe Gly Thr Leu Gln Asp Phe Asp
65                  70                  75                  80

Arg Leu Leu Glu Glu Ala His Ala Leu Gly Leu Lys Val Leu Val Asp
                85                  90                  95

Leu Val Pro Asn His Thr Ser Ser Glu His Pro Trp Phe Leu Glu Ser
            100                 105                 110

Arg Ala Ser Arg Asn Ser Pro Lys Arg Asp Trp Tyr Ile Trp Lys Asp
        115                 120                 125
```

```
Pro Ala Pro Asp Gly Gly Pro Pro Asn Asn Trp Gln Ser Phe Phe Gly
    130                 135                 140

Gly Pro Ala Trp Thr Leu Asp Glu Ala Thr Gly Gln Tyr Tyr Leu His
145                 150                 155                 160

Leu Phe Leu Pro Glu Gln Pro Asp Leu Asn Trp Arg Asn Pro Glu Val
                165                 170                 175

Arg Glu Ala Ile Lys Glu Val Met Arg Phe Trp Leu Arg Arg Gly Val
            180                 185                 190

Asp Gly Phe Arg Val Asp Val Leu Trp Leu Leu Gly Lys Asp Pro Leu
        195                 200                 205

Phe Arg Asp Glu Pro Gly Ser Pro Leu Trp Arg Pro Gly Leu Pro Asp
    210                 215                 220

Arg Ala Arg His Glu His Leu Tyr Thr Glu Asp Gln Pro Glu Thr Tyr
225                 230                 235                 240

Ala Tyr Val Arg Glu Met Arg Gln Val Leu Asp Glu Phe Ser Glu Pro
                245                 250                 255

Gly Arg Glu Arg Val Met Val Gly Glu Ile Tyr Leu Pro Leu Pro Arg
            260                 265                 270

Leu Val Arg Tyr Tyr Ala Ala Gly Cys His Leu Pro Phe Asn Phe Ser
        275                 280                 285

Leu Val Thr Glu Gly Leu Ser Asp Trp Arg Pro Glu Asn Leu Ala Arg
    290                 295                 300

Ile Val Glu Thr Tyr Glu Gly Leu Leu Ser Arg Trp Asp Trp Pro Asn
305                 310                 315                 320

Trp Val Leu Gly Asn His Asp Gln Pro Arg Leu Ala Ser Arg Leu Gly
                325                 330                 335

Glu Pro Gln Ala Arg Val Ala Ala Met Leu Leu Phe Thr Leu Arg Gly
            340                 345                 350

Thr Pro Thr Trp Tyr Tyr Gly Asp Glu Leu Ala Leu Pro Asn Gly Leu
        355                 360                 365

Ile Pro Pro Glu Lys Val Gln Asp Pro Ala Ala Leu Arg Gln Arg Asp
    370                 375                 380

Arg Glu Pro Thr Ala Tyr His Thr Leu Gly Arg Asp Pro Glu Arg Thr
385                 390                 395                 400

Pro Met Pro Trp Asp Ala Ser Pro Tyr Gly Gly Phe Ser Thr Val Glu
                405                 410                 415

Pro Trp Leu Pro Leu Asn Pro Asp Tyr Arg Thr Arg Asn Val Ala Ala
            420                 425                 430

Gln Glu Lys Asp Pro Arg Ser Met Leu His Leu Val Lys Arg Leu Ile
        435                 440                 445

Ala Leu Arg Lys Asp Pro Asp Leu Leu Tyr Gly Ala Tyr Arg Thr Tyr
    450                 455                 460

Arg Ala Arg Glu Gly Val Tyr Ala Tyr Leu Arg Gly Glu Gly Trp Leu
465                 470                 475                 480

Val Ala Leu Asn Leu Thr Glu Lys Glu Lys Ala Leu Glu Leu Pro Arg
                485                 490                 495

Gly Gly Arg Val Val Leu Ser Thr His Leu Asp Arg Glu Glu Arg Val
            500                 505                 510

Gly Glu Arg Leu Phe Leu Arg Pro Asp Glu Gly Val Ala Val Arg Leu
        515                 520                 525

Asp
```

```
<210> SEQ ID NO 48
<211> LENGTH: 60
<212> TYPE: DNA
<213> ORGANISM: unknown
<220> FEATURE:
<223> OTHER INFORMATION: synthetic sequence
<220> FEATURE:
<221> NAME/KEY: CDS
<222> LOCATION: (1)..(60)
<223> OTHER INFORMATION: gamma zein signal sequence like

<400> SEQUENCE: 48

atg ggc cgc gtg ctg ctc gtg gcc ctg gcc ctg ctc gct ctc gcc gcc       48
Met Gly Arg Val Leu Leu Val Ala Leu Ala Leu Leu Ala Leu Ala Ala
1               5                   10                  15

agc gct acc tct                                                       60
Ser Ala Thr Ser
            20


<210> SEQ ID NO 49
<211> LENGTH: 20
<212> TYPE: PRT
<213> ORGANISM: unknown
<220> FEATURE:
<223> OTHER INFORMATION: Synthetic Construct

<400> SEQUENCE: 49

Met Gly Arg Val Leu Leu Val Ala Leu Ala Leu Leu Ala Leu Ala Ala
1               5                   10                  15

Ser Ala Thr Ser
            20


<210> SEQ ID NO 50
<211> LENGTH: 1761
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1761)
<223> OTHER INFORMATION: maize optimized alpha-1,1-glucosidase B.
      SAM1606

<400> SEQUENCE: 50

atg agc acc gcc ctg acc cag acc agc acc aac agc cag cag agc ccg       48
Met Ser Thr Ala Leu Thr Gln Thr Ser Thr Asn Ser Gln Gln Ser Pro
1               5                   10                  15

atc agg cgc gcg tgg tgg aag gaa gct gtt gtc tac cag atc tac ccg       96
Ile Arg Arg Ala Trp Trp Lys Glu Ala Val Val Tyr Gln Ile Tyr Pro
            20                  25                  30

cgc agc ttc atg gac agc aac ggc gac ggc atc ggc gac ctg agg ggc      144
Arg Ser Phe Met Asp Ser Asn Gly Asp Gly Ile Gly Asp Leu Arg Gly
        35                  40                  45

atc ctg agc aag ctg gac tac ctg aag ctg ctg ggc gtg gac gtg ctg      192
Ile Leu Ser Lys Leu Asp Tyr Leu Lys Leu Leu Gly Val Asp Val Leu
    50                  55                  60

tgg ctg aac ccg atc tac gac agc ccg aac gac gac atg ggc tac gac      240
Trp Leu Asn Pro Ile Tyr Asp Ser Pro Asn Asp Asp Met Gly Tyr Asp
65                  70                  75                  80

atc cgc gac tac tac aag atc atg gaa gaa ttc ggc act atg gaa gat      288
Ile Arg Asp Tyr Tyr Lys Ile Met Glu Glu Phe Gly Thr Met Glu Asp
                85                  90                  95

ttc gag gaa ctg ctg cgc gag gtg cac gcc agg ggc atg aag ctg gtg      336
Phe Glu Glu Leu Leu Arg Glu Val His Ala Arg Gly Met Lys Leu Val
            100                 105                 110
```

```
atg gac ctg gtg gcc aac cac acc agc gac gag cac ccg tgg ttc atc      384
Met Asp Leu Val Ala Asn His Thr Ser Asp Glu His Pro Trp Phe Ile
        115                 120                 125

gag agc cgc agc agc cgc gac aac ccg tac cgc gac tgg tac atc tgg      432
Glu Ser Arg Ser Ser Arg Asp Asn Pro Tyr Arg Asp Trp Tyr Ile Trp
    130                 135                 140

cgc gac ccg aag gac ggc cgc gag ccg aac aac tgg ctg tcc tac ttc      480
Arg Asp Pro Lys Asp Gly Arg Glu Pro Asn Asn Trp Leu Ser Tyr Phe
145                 150                 155                 160

agc ggc agc gcc tgg gag tac gac gag cgc acc ggc cag tac tac ctc      528
Ser Gly Ser Ala Trp Glu Tyr Asp Glu Arg Thr Gly Gln Tyr Tyr Leu
                165                 170                 175

cac ctg ttc agc agg cgc cag ccg gac ctg aac tgg gag aac cct aaa      576
His Leu Phe Ser Arg Arg Gln Pro Asp Leu Asn Trp Glu Asn Pro Lys
            180                 185                 190

gtt cgc gag gcc atc ttc gag atg atg cgc ttc tgg ctg gac aag ggc      624
Val Arg Glu Ala Ile Phe Glu Met Met Arg Phe Trp Leu Asp Lys Gly
        195                 200                 205

atc gac ggc ttc cgc atg gac gtg atc aac gcg atc gcc aag gcc gag      672
Ile Asp Gly Phe Arg Met Asp Val Ile Asn Ala Ile Ala Lys Ala Glu
    210                 215                 220

ggc ctg cca gac gcc cca gct agg cct ggg gag aga tac gct tgg ggt      720
Gly Leu Pro Asp Ala Pro Ala Arg Pro Gly Glu Arg Tyr Ala Trp Gly
225                 230                 235                 240

ggc cag tac ttc ctg aac cag ccg aag gtg cac gag tac ctc cgc gag      768
Gly Gln Tyr Phe Leu Asn Gln Pro Lys Val His Glu Tyr Leu Arg Glu
                245                 250                 255

atg tac gac aag gtg ctg tcc cac tac gac atc atg act gtg ggg gag      816
Met Tyr Asp Lys Val Leu Ser His Tyr Asp Ile Met Thr Val Gly Glu
            260                 265                 270

act ggg ggt gtc acc acc aag gac gcc ctg ctg ttc gct ggg gag gac      864
Thr Gly Gly Val Thr Thr Lys Asp Ala Leu Leu Phe Ala Gly Glu Asp
        275                 280                 285

agg cgc gag ctg aac atg gtg ttc cag ttc gag cac atg gac atc gac      912
Arg Arg Glu Leu Asn Met Val Phe Gln Phe Glu His Met Asp Ile Asp
    290                 295                 300

gcc acc gac ggc gac aag tgg agg cca agg ccg tgg agg ctg acc gag      960
Ala Thr Asp Gly Asp Lys Trp Arg Pro Arg Pro Trp Arg Leu Thr Glu
305                 310                 315                 320

ctt aag acc atc atg acc cgc tgg cag aac gac ctg tac ggc aag gcc     1008
Leu Lys Thr Ile Met Thr Arg Trp Gln Asn Asp Leu Tyr Gly Lys Ala
                325                 330                 335

tgg aac agc ctg tac tgg acc aac cac gac cag ccg agg gcc gtg tcc     1056
Trp Asn Ser Leu Tyr Trp Thr Asn His Asp Gln Pro Arg Ala Val Ser
            340                 345                 350

cgc ttc ggc aac gac ggc ccg tac cgc gtg gag agc gcc aag atg ctg     1104
Arg Phe Gly Asn Asp Gly Pro Tyr Arg Val Glu Ser Ala Lys Met Leu
        355                 360                 365

gcc acc gtg ctg cac atg atg cag ggc acc ccg tac atc tac cag ggc     1152
Ala Thr Val Leu His Met Met Gln Gly Thr Pro Tyr Ile Tyr Gln Gly
    370                 375                 380

gaa gaa atc ggc atg acc aat tgc cct ttc gac agc atc gac gag tac     1200
Glu Glu Ile Gly Met Thr Asn Cys Pro Phe Asp Ser Ile Asp Glu Tyr
385                 390                 395                 400

cgc gac gtg gag atc cac aac ctt tgg aga cat cgc gtg atg gaa ggc     1248
Arg Asp Val Glu Ile His Asn Leu Trp Arg His Arg Val Met Glu Gly
                405                 410                 415

ggc cag gac cct gct gag gtg ctg cgc gtg atc cag ctg aag ggc cgc     1296
Gly Gln Asp Pro Ala Glu Val Leu Arg Val Ile Gln Leu Lys Gly Arg
```

```
            420                 425                 430

gac aac gcc agg acc ccg atg cag tgg gac gac tcc ccg aac gcc ggc     1344
Asp Asn Ala Arg Thr Pro Met Gln Trp Asp Asp Ser Pro Asn Ala Gly
        435                 440                 445

ttt acg acc ggg act cct tgg atc aag gtg aac ccg aac tac cgc gag     1392
Phe Thr Thr Gly Thr Pro Trp Ile Lys Val Asn Pro Asn Tyr Arg Glu
    450                 455                 460

atc aac gtg aag cag gct ctg gct gat ccg aac agc atc ttc cac tac     1440
Ile Asn Val Lys Gln Ala Leu Ala Asp Pro Asn Ser Ile Phe His Tyr
465                 470                 475                 480

tac cgc cgc ctc att cag ctc cgc aag cag cac ccg atc gtg gtg tac     1488
Tyr Arg Arg Leu Ile Gln Leu Arg Lys Gln His Pro Ile Val Val Tyr
                485                 490                 495

ggc aag tac gac ctg atc ctg ccg gac cac gag gaa atc tgg gcc tac     1536
Gly Lys Tyr Asp Leu Ile Leu Pro Asp His Glu Glu Ile Trp Ala Tyr
            500                 505                 510

acc cgc acc ctg ggc gac gag cgc tgg ctg atc gtg gcc aac ttc ttc     1584
Thr Arg Thr Leu Gly Asp Glu Arg Trp Leu Ile Val Ala Asn Phe Phe
        515                 520                 525

ggc ggc acc ccc gag ttc gag ctg ccg cca gaa gtg cgc tgc gag ggg     1632
Gly Gly Thr Pro Glu Phe Glu Leu Pro Pro Glu Val Arg Cys Glu Gly
    530                 535                 540

gca gaa ctt gtc att gcc aat tac ccg gtg gac gac agc gag gct ggc     1680
Ala Glu Leu Val Ile Ala Asn Tyr Pro Val Asp Asp Ser Glu Ala Gly
545                 550                 555                 560

ggc cca gct gct gct ggc gct ccg cac agg ttc agg ctg cgc ccc tac     1728
Gly Pro Ala Ala Ala Gly Ala Pro His Arg Phe Arg Leu Arg Pro Tyr
                565                 570                 575

gag tgc cgc gtg tac cgc ctg ctg ggc tgg cac                         1761
Glu Cys Arg Val Tyr Arg Leu Leu Gly Trp His
            580                 585


<210> SEQ ID NO 51
<211> LENGTH: 587
<212> TYPE: PRT
<213> ORGANISM: unknown
<220> FEATURE:
<223> OTHER INFORMATION: Synthetic Construct

<400> SEQUENCE: 51

Met Ser Thr Ala Leu Thr Gln Thr Ser Thr Asn Ser Gln Gln Ser Pro
1               5                   10                  15

Ile Arg Arg Ala Trp Trp Lys Glu Ala Val Val Tyr Gln Ile Tyr Pro
            20                  25                  30

Arg Ser Phe Met Asp Ser Asn Gly Asp Gly Ile Gly Asp Leu Arg Gly
        35                  40                  45

Ile Leu Ser Lys Leu Asp Tyr Leu Lys Leu Leu Gly Val Asp Val Leu
    50                  55                  60

Trp Leu Asn Pro Ile Tyr Asp Ser Pro Asn Asp Asp Met Gly Tyr Asp
65                  70                  75                  80

Ile Arg Asp Tyr Tyr Lys Ile Met Glu Glu Phe Gly Thr Met Glu Asp
                85                  90                  95

Phe Glu Glu Leu Leu Arg Glu Val His Ala Arg Gly Met Lys Leu Val
            100                 105                 110

Met Asp Leu Val Ala Asn His Thr Ser Asp Glu His Pro Trp Phe Ile
        115                 120                 125

Glu Ser Arg Ser Ser Arg Asp Asn Pro Tyr Arg Asp Trp Tyr Ile Trp
    130                 135                 140
```

```
Arg Asp Pro Lys Asp Gly Arg Glu Pro Asn Asn Trp Leu Ser Tyr Phe
145                 150                 155                 160

Ser Gly Ser Ala Trp Glu Tyr Asp Glu Arg Thr Gly Gln Tyr Tyr Leu
                165                 170                 175

His Leu Phe Ser Arg Arg Gln Pro Asp Leu Asn Trp Glu Asn Pro Lys
            180                 185                 190

Val Arg Glu Ala Ile Phe Glu Met Met Arg Phe Trp Leu Asp Lys Gly
        195                 200                 205

Ile Asp Gly Phe Arg Met Asp Val Ile Asn Ala Ile Ala Lys Ala Glu
    210                 215                 220

Gly Leu Pro Asp Ala Pro Ala Arg Pro Gly Glu Arg Tyr Ala Trp Gly
225                 230                 235                 240

Gly Gln Tyr Phe Leu Asn Gln Pro Lys Val His Glu Tyr Leu Arg Glu
                245                 250                 255

Met Tyr Asp Lys Val Leu Ser His Tyr Asp Ile Met Thr Val Gly Glu
            260                 265                 270

Thr Gly Gly Val Thr Thr Lys Asp Ala Leu Leu Phe Ala Gly Glu Asp
        275                 280                 285

Arg Arg Glu Leu Asn Met Val Phe Gln Phe Glu His Met Asp Ile Asp
    290                 295                 300

Ala Thr Asp Gly Asp Lys Trp Arg Pro Arg Pro Trp Arg Leu Thr Glu
305                 310                 315                 320

Leu Lys Thr Ile Met Thr Arg Trp Gln Asn Asp Leu Tyr Gly Lys Ala
                325                 330                 335

Trp Asn Ser Leu Tyr Trp Thr Asn His Asp Gln Pro Arg Ala Val Ser
            340                 345                 350

Arg Phe Gly Asn Asp Gly Pro Tyr Arg Val Glu Ser Ala Lys Met Leu
        355                 360                 365

Ala Thr Val Leu His Met Met Gln Gly Thr Pro Tyr Ile Tyr Gln Gly
    370                 375                 380

Glu Glu Ile Gly Met Thr Asn Cys Pro Phe Asp Ser Ile Asp Glu Tyr
385                 390                 395                 400

Arg Asp Val Glu Ile His Asn Leu Trp Arg His Arg Val Met Glu Gly
                405                 410                 415

Gly Gln Asp Pro Ala Glu Val Leu Arg Val Ile Gln Leu Lys Gly Arg
            420                 425                 430

Asp Asn Ala Arg Thr Pro Met Gln Trp Asp Asp Ser Pro Asn Ala Gly
        435                 440                 445

Phe Thr Thr Gly Thr Pro Trp Ile Lys Val Asn Pro Asn Tyr Arg Glu
    450                 455                 460

Ile Asn Val Lys Gln Ala Leu Ala Asp Pro Asn Ser Ile Phe His Tyr
465                 470                 475                 480

Tyr Arg Arg Leu Ile Gln Leu Arg Lys Gln His Pro Ile Val Val Tyr
                485                 490                 495

Gly Lys Tyr Asp Leu Ile Leu Pro Asp His Glu Glu Ile Trp Ala Tyr
            500                 505                 510

Thr Arg Thr Leu Gly Asp Glu Arg Trp Leu Ile Val Ala Asn Phe Phe
        515                 520                 525

Gly Gly Thr Pro Glu Phe Glu Leu Pro Pro Glu Val Arg Cys Glu Gly
    530                 535                 540

Ala Glu Leu Val Ile Ala Asn Tyr Pro Val Asp Asp Ser Glu Ala Gly
545                 550                 555                 560

Gly Pro Ala Ala Ala Gly Ala Pro His Arg Phe Arg Leu Arg Pro Tyr
```

```
                565                 570                 575

Glu Cys Arg Val Tyr Arg Leu Leu Gly Trp His
            580                 585


<210> SEQ ID NO 52
<211> LENGTH: 6
<212> TYPE: PRT
<213> ORGANISM: unknown
<220> FEATURE:
<223> OTHER INFORMATION: synthetic sequence
<220> FEATURE:
<221> NAME/KEY: signal
<222> LOCATION: (1)..(6)
<223> OTHER INFORMATION: ER retention sequence

<400> SEQUENCE: 52

Ser Glu Lys Asp Glu Leu
1               5


<210> SEQ ID NO 53
<211> LENGTH: 1764
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1764)
<223> OTHER INFORMATION: dicot optimized alpha-1,1-glucosidase BSAM1606

<400> SEQUENCE: 53

atg tct act gct ctt act cag act tct act aac tct cag cag tct cca       48
Met Ser Thr Ala Leu Thr Gln Thr Ser Thr Asn Ser Gln Gln Ser Pro
1               5                   10                  15

att aga agg gct tgg tgg aaa gag gct gtt gtt tac caa atc tac cca       96
Ile Arg Arg Ala Trp Trp Lys Glu Ala Val Val Tyr Gln Ile Tyr Pro
            20                  25                  30

cgt tct ttc atg gat tcc aac ggt gat gga att gga gat ctt agg gga      144
Arg Ser Phe Met Asp Ser Asn Gly Asp Gly Ile Gly Asp Leu Arg Gly
        35                  40                  45

att ctc tcc aag ttg gat tac ctt aag ttg ctc gga gtt gat gtt ctt      192
Ile Leu Ser Lys Leu Asp Tyr Leu Lys Leu Leu Gly Val Asp Val Leu
    50                  55                  60

tgg ctc aac cca atc tac gat tcc cca aac gat gat atg gga tac gat      240
Trp Leu Asn Pro Ile Tyr Asp Ser Pro Asn Asp Asp Met Gly Tyr Asp
65                  70                  75                  80

atc agg gat tac tac aag atc atg gaa gag ttc gga act atg gaa gat      288
Ile Arg Asp Tyr Tyr Lys Ile Met Glu Glu Phe Gly Thr Met Glu Asp
                85                  90                  95

ttc gag gaa ctt ctt aga gaa gtt cac gct cgt gga atg aag ttg gtg      336
Phe Glu Glu Leu Leu Arg Glu Val His Ala Arg Gly Met Lys Leu Val
            100                 105                 110

atg gat ctt gtt gct aac cac act tct gat gag cac cct tgg ttt att      384
Met Asp Leu Val Ala Asn His Thr Ser Asp Glu His Pro Trp Phe Ile
        115                 120                 125

gag tct agg tcc tct agg gat aat cca tac cgt gat tgg tac att tgg      432
Glu Ser Arg Ser Ser Arg Asp Asn Pro Tyr Arg Asp Trp Tyr Ile Trp
    130                 135                 140

cgt gat cca aag gat gga aga gag cca aat aac tgg ctt tct tac ttc      480
Arg Asp Pro Lys Asp Gly Arg Glu Pro Asn Asn Trp Leu Ser Tyr Phe
145                 150                 155                 160

tct gga tct gct tgg gaa tat gat gag agg act gga cag tac tac ctt      528
Ser Gly Ser Ala Trp Glu Tyr Asp Glu Arg Thr Gly Gln Tyr Tyr Leu
                165                 170                 175
```

-continued

```
cac ttg ttc tct aga agg cag cca gat ctt aat tgg gag aac cca aaa      576
His Leu Phe Ser Arg Arg Gln Pro Asp Leu Asn Trp Glu Asn Pro Lys
            180                 185                 190

gtg cgt gaa gct atc ttt gag atg atg agg ttc tgg ctc gat aag gga      624
Val Arg Glu Ala Ile Phe Glu Met Met Arg Phe Trp Leu Asp Lys Gly
        195                 200                 205

att gat gga ttc agg atg gat gtg atc aac gct att gct aag gct gaa      672
Ile Asp Gly Phe Arg Met Asp Val Ile Asn Ala Ile Ala Lys Ala Glu
    210                 215                 220

gga ctt cca gat gct cca gct aga cca ggt gaa aga tat gct tgg gga      720
Gly Leu Pro Asp Ala Pro Ala Arg Pro Gly Glu Arg Tyr Ala Trp Gly
225                 230                 235                 240

gga cag tat ttc ctt aac cag cca aag gtt cac gaa tac ctc aga gag      768
Gly Gln Tyr Phe Leu Asn Gln Pro Lys Val His Glu Tyr Leu Arg Glu
                245                 250                 255

atg tac gat aag gtt ctc tcc cac tac gat att atg act gtg gga gag      816
Met Tyr Asp Lys Val Leu Ser His Tyr Asp Ile Met Thr Val Gly Glu
            260                 265                 270

act ggt gga gtt act act aag gat gct ctc ttg ttc gca ggc gaa gat      864
Thr Gly Gly Val Thr Thr Lys Asp Ala Leu Leu Phe Ala Gly Glu Asp
        275                 280                 285

aga agg gaa ctc aac atg gtt ttc cag ttc gag cac atg gat atc gat      912
Arg Arg Glu Leu Asn Met Val Phe Gln Phe Glu His Met Asp Ile Asp
    290                 295                 300

gct act gat ggt gat aag tgg agg cca aga cct tgg aga ctt act gag      960
Ala Thr Asp Gly Asp Lys Trp Arg Pro Arg Pro Trp Arg Leu Thr Glu
305                 310                 315                 320

ctt aag act atc atg act agg tgg cag aat gat ctt tat gga aag gct     1008
Leu Lys Thr Ile Met Thr Arg Trp Gln Asn Asp Leu Tyr Gly Lys Ala
                325                 330                 335

tgg aac tct ctc tac tgg act aat cat gat cag cca agg gct gtt tct     1056
Trp Asn Ser Leu Tyr Trp Thr Asn His Asp Gln Pro Arg Ala Val Ser
            340                 345                 350

aga ttc gga aac gat gga cca tat cgt gtt gag tct gct aag atg ctt     1104
Arg Phe Gly Asn Asp Gly Pro Tyr Arg Val Glu Ser Ala Lys Met Leu
        355                 360                 365

gct act gtg ctt cat atg atg caa ggt aca cct tac atc tac cag ggt     1152
Ala Thr Val Leu His Met Met Gln Gly Thr Pro Tyr Ile Tyr Gln Gly
    370                 375                 380

gaa gag att gga atg act aac tgc cca ttc gat tcc att gat gag tac     1200
Glu Glu Ile Gly Met Thr Asn Cys Pro Phe Asp Ser Ile Asp Glu Tyr
385                 390                 395                 400

cgt gat gtg gag att cat aac ctt tgg agg cac aga gtt atg gaa ggt     1248
Arg Asp Val Glu Ile His Asn Leu Trp Arg His Arg Val Met Glu Gly
                405                 410                 415

gga caa gat cca gct gaa gtt ctt agg gtg atc caa ctt aag gga agg     1296
Gly Gln Asp Pro Ala Glu Val Leu Arg Val Ile Gln Leu Lys Gly Arg
            420                 425                 430

gat aat gct aga act cca atg caa tgg gat gat tct cca aac gct gga     1344
Asp Asn Ala Arg Thr Pro Met Gln Trp Asp Asp Ser Pro Asn Ala Gly
        435                 440                 445

ttc act act gga aca cct tgg att aag gtg aac cca aac tac aga gag     1392
Phe Thr Thr Gly Thr Pro Trp Ile Lys Val Asn Pro Asn Tyr Arg Glu
    450                 455                 460

atc aac gtt aag cag gct ctt gct gat cca aac tcc atc ttc cat tac     1440
Ile Asn Val Lys Gln Ala Leu Ala Asp Pro Asn Ser Ile Phe His Tyr
465                 470                 475                 480

tac cgt aga ctt atc caa ctt agg aag cag cat cca atc gtt gtt tac     1488
Tyr Arg Arg Leu Ile Gln Leu Arg Lys Gln His Pro Ile Val Val Tyr
```

```
                485                 490                 495

gga aag tac gat ctc att ctc cca gat cac gaa gag att tgg gct tac      1536
Gly Lys Tyr Asp Leu Ile Leu Pro Asp His Glu Glu Ile Trp Ala Tyr
            500                 505                 510

act agg act ctt gga gat gag aga tgg ctt atc gtg gct aat ttc ttc      1584
Thr Arg Thr Leu Gly Asp Glu Arg Trp Leu Ile Val Ala Asn Phe Phe
        515                 520                 525

gga gga act cca gaa ttt gaa ctt cca cct gaa gtt aga tgt gag ggt      1632
Gly Gly Thr Pro Glu Phe Glu Leu Pro Pro Glu Val Arg Cys Glu Gly
    530                 535                 540

gct gag ttg gtt att gct aac tac cca gtg gat gat tct gaa gct ggc      1680
Ala Glu Leu Val Ile Ala Asn Tyr Pro Val Asp Asp Ser Glu Ala Gly
545                 550                 555                 560

ggt cct gct gct gct ggt gct cca cat agg ttt agg ctt agg cca tat      1728
Gly Pro Ala Ala Ala Gly Ala Pro His Arg Phe Arg Leu Arg Pro Tyr
                565                 570                 575

gag tgt cgt gtt tac cgt ctt ttg gga tgg cat taa                      1764
Glu Cys Arg Val Tyr Arg Leu Leu Gly Trp His
            580                 585


<210> SEQ ID NO 54
<211> LENGTH: 587
<212> TYPE: PRT
<213> ORGANISM: unknown
<220> FEATURE:
<223> OTHER INFORMATION: Synthetic Construct

<400> SEQUENCE: 54

Met Ser Thr Ala Leu Thr Gln Thr Ser Thr Asn Ser Gln Gln Ser Pro
1               5                   10                  15

Ile Arg Arg Ala Trp Trp Lys Glu Ala Val Val Tyr Gln Ile Tyr Pro
            20                  25                  30

Arg Ser Phe Met Asp Ser Asn Gly Asp Gly Ile Gly Asp Leu Arg Gly
        35                  40                  45

Ile Leu Ser Lys Leu Asp Tyr Leu Lys Leu Leu Gly Val Asp Val Leu
    50                  55                  60

Trp Leu Asn Pro Ile Tyr Asp Ser Pro Asn Asp Asp Met Gly Tyr Asp
65                  70                  75                  80

Ile Arg Asp Tyr Tyr Lys Ile Met Glu Glu Phe Gly Thr Met Glu Asp
                85                  90                  95

Phe Glu Glu Leu Leu Arg Glu Val His Ala Arg Gly Met Lys Leu Val
            100                 105                 110

Met Asp Leu Val Ala Asn His Thr Ser Asp Glu His Pro Trp Phe Ile
        115                 120                 125

Glu Ser Arg Ser Ser Arg Asp Asn Pro Tyr Arg Asp Trp Tyr Ile Trp
    130                 135                 140

Arg Asp Pro Lys Asp Gly Arg Glu Pro Asn Asn Trp Leu Ser Tyr Phe
145                 150                 155                 160

Ser Gly Ser Ala Trp Glu Tyr Asp Glu Arg Thr Gly Gln Tyr Tyr Leu
                165                 170                 175

His Leu Phe Ser Arg Arg Gln Pro Asp Leu Asn Trp Glu Asn Pro Lys
            180                 185                 190

Val Arg Glu Ala Ile Phe Glu Met Met Arg Phe Trp Leu Asp Lys Gly
        195                 200                 205

Ile Asp Gly Phe Arg Met Asp Val Ile Asn Ala Ile Ala Lys Ala Glu
    210                 215                 220

Gly Leu Pro Asp Ala Pro Ala Arg Pro Gly Glu Arg Tyr Ala Trp Gly
```

-continued

```
225                 230                 235                 240

Gly Gln Tyr Phe Leu Asn Gln Pro Lys Val His Glu Tyr Leu Arg Glu
                245                 250                 255

Met Tyr Asp Lys Val Leu Ser His Tyr Asp Ile Met Thr Val Gly Glu
            260                 265                 270

Thr Gly Gly Val Thr Thr Lys Asp Ala Leu Leu Phe Ala Gly Glu Asp
        275                 280                 285

Arg Arg Glu Leu Asn Met Val Phe Gln Phe Glu His Met Asp Ile Asp
    290                 295                 300

Ala Thr Asp Gly Asp Lys Trp Arg Pro Arg Pro Trp Arg Leu Thr Glu
305                 310                 315                 320

Leu Lys Thr Ile Met Thr Arg Trp Gln Asn Asp Leu Tyr Gly Lys Ala
                325                 330                 335

Trp Asn Ser Leu Tyr Trp Thr Asn His Asp Gln Pro Arg Ala Val Ser
            340                 345                 350

Arg Phe Gly Asn Asp Gly Pro Tyr Arg Val Glu Ser Ala Lys Met Leu
        355                 360                 365

Ala Thr Val Leu His Met Met Gln Gly Thr Pro Tyr Ile Tyr Gln Gly
    370                 375                 380

Glu Glu Ile Gly Met Thr Asn Cys Pro Phe Asp Ser Ile Asp Glu Tyr
385                 390                 395                 400

Arg Asp Val Glu Ile His Asn Leu Trp Arg His Arg Val Met Glu Gly
                405                 410                 415

Gly Gln Asp Pro Ala Glu Val Leu Arg Val Ile Gln Leu Lys Gly Arg
            420                 425                 430

Asp Asn Ala Arg Thr Pro Met Gln Trp Asp Asp Ser Pro Asn Ala Gly
        435                 440                 445

Phe Thr Thr Gly Thr Pro Trp Ile Lys Val Asn Pro Asn Tyr Arg Glu
    450                 455                 460

Ile Asn Val Lys Gln Ala Leu Ala Asp Pro Asn Ser Ile Phe His Tyr
465                 470                 475                 480

Tyr Arg Arg Leu Ile Gln Leu Arg Lys Gln His Pro Ile Val Val Tyr
                485                 490                 495

Gly Lys Tyr Asp Leu Ile Leu Pro Asp His Glu Glu Ile Trp Ala Tyr
            500                 505                 510

Thr Arg Thr Leu Gly Asp Glu Arg Trp Leu Ile Val Ala Asn Phe Phe
        515                 520                 525

Gly Gly Thr Pro Glu Phe Glu Leu Pro Pro Glu Val Arg Cys Glu Gly
    530                 535                 540

Ala Glu Leu Val Ile Ala Asn Tyr Pro Val Asp Asp Ser Glu Ala Gly
545                 550                 555                 560

Gly Pro Ala Ala Ala Gly Ala Pro His Arg Phe Arg Leu Arg Pro Tyr
                565                 570                 575

Glu Cys Arg Val Tyr Arg Leu Leu Gly Trp His
            580                 585
```

<210> SEQ ID NO 55
<211> LENGTH: 1764
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1764)
<223> OTHER INFORMATION: monocot optimized alpha-1,6-glucosidase

<400> SEQUENCE: 55

```
atg ggc cgc gtg ctg ctc gtg gcc ctg gcc ctg ctc gct ctc gcc gcc       48
Met Gly Arg Val Leu Leu Val Ala Leu Ala Leu Leu Ala Leu Ala Ala
1               5                   10                  15

agc gct acc tct gaa aga gtg tgg tgg aag gaa gcc gtc gtc tac cag       96
Ser Ala Thr Ser Glu Arg Val Trp Trp Lys Glu Ala Val Val Tyr Gln
            20                  25                  30

atc tac ccg cgc agc ttc tac gac agc aac ggc gac ggc atc ggc gac      144
Ile Tyr Pro Arg Ser Phe Tyr Asp Ser Asn Gly Asp Gly Ile Gly Asp
        35                  40                  45

atc cgc ggc atc att gcc aag ctg gac tac ctg aag gaa ctg ggc gtc      192
Ile Arg Gly Ile Ile Ala Lys Leu Asp Tyr Leu Lys Glu Leu Gly Val
    50                  55                  60

gac gtt gtg tgg ctg tcc ccg gtg tac aag agc ccg aac gat gac aat      240
Asp Val Val Trp Leu Ser Pro Val Tyr Lys Ser Pro Asn Asp Asp Asn
65                  70                  75                  80

ggc tac gat atc tcc gac tac cgc gac atc atg gac gag ttc ggc acg      288
Gly Tyr Asp Ile Ser Asp Tyr Arg Asp Ile Met Asp Glu Phe Gly Thr
                85                  90                  95

atg gcc gac tgg aag acc atg ctc gag gaa atg cac aag cgc ggc atc      336
Met Ala Asp Trp Lys Thr Met Leu Glu Glu Met His Lys Arg Gly Ile
            100                 105                 110

aag ctg gtg atg gac ctg gtg gtg aac cac acc agc gac gag cac ccg      384
Lys Leu Val Met Asp Leu Val Val Asn His Thr Ser Asp Glu His Pro
        115                 120                 125

tgg ttc atc gag agc cgc aag agc aag gac aac ccg tac cgc gac tac      432
Trp Phe Ile Glu Ser Arg Lys Ser Lys Asp Asn Pro Tyr Arg Asp Tyr
    130                 135                 140

tac atc tgg cgc cca ggc aag aac ggc aag gaa ccg aac aac tgg gag      480
Tyr Ile Trp Arg Pro Gly Lys Asn Gly Lys Glu Pro Asn Asn Trp Glu
145                 150                 155                 160

agc gtg ttc agc ggc agc gcc tgg gag tac gac gag atg acc ggc gag      528
Ser Val Phe Ser Gly Ser Ala Trp Glu Tyr Asp Glu Met Thr Gly Glu
                165                 170                 175

tac tac ctc cac ctg ttc agc aag aag cag ccg gac ctg aac tgg gag      576
Tyr Tyr Leu His Leu Phe Ser Lys Lys Gln Pro Asp Leu Asn Trp Glu
            180                 185                 190

aac ccg aag gtg cgc cgc gag gtg tac gag atg atg aag ttc tgg ctg      624
Asn Pro Lys Val Arg Arg Glu Val Tyr Glu Met Met Lys Phe Trp Leu
        195                 200                 205

gac aag ggc gtg gac ggc ttc cgc atg gac gtg atc aac atg atc agc      672
Asp Lys Gly Val Asp Gly Phe Arg Met Asp Val Ile Asn Met Ile Ser
    210                 215                 220

aag gtg ccc gag ctg cca gat ggc gag ccg cag agc ggc aag aag tac      720
Lys Val Pro Glu Leu Pro Asp Gly Glu Pro Gln Ser Gly Lys Lys Tyr
225                 230                 235                 240

gcc tct ggc tcc cgc tac tac atg aac ggc ccg agg gtg cac gag ttc      768
Ala Ser Gly Ser Arg Tyr Tyr Met Asn Gly Pro Arg Val His Glu Phe
                245                 250                 255

ctc caa gaa atg aat cgc gaa gtg ctc tcc aag tac gac atc atg act      816
Leu Gln Glu Met Asn Arg Glu Val Leu Ser Lys Tyr Asp Ile Met Thr
            260                 265                 270

gtg ggc gag act ccg ggc gtg acc ccg aag gaa ggc atc ctg tac acc      864
Val Gly Glu Thr Pro Gly Val Thr Pro Lys Glu Gly Ile Leu Tyr Thr
        275                 280                 285

gac ccg agc agg cgc gag ctg aac atg gtg ttc cag ttc gag cac atg      912
Asp Pro Ser Arg Arg Glu Leu Asn Met Val Phe Gln Phe Glu His Met
    290                 295                 300
```

```
gac ctc gac tct ggt cca ggc ggc aag tgg gac atc agg ccg tgg agc      960
Asp Leu Asp Ser Gly Pro Gly Gly Lys Trp Asp Ile Arg Pro Trp Ser
305                 310                 315                 320

ctg gcc gac ctg aag aag acc atg acc aag tgg cag aag gaa ctt gag     1008
Leu Ala Asp Leu Lys Lys Thr Met Thr Lys Trp Gln Lys Glu Leu Glu
                325                 330                 335

ggc aag ggc tgg aac agc ctg tac ctg aac aac cac gac cag ccg agg     1056
Gly Lys Gly Trp Asn Ser Leu Tyr Leu Asn Asn His Asp Gln Pro Arg
            340                 345                 350

gcc gtg tcc aga ttc ggc gac gac ggc aag tac cgc gtg gag agc gcc     1104
Ala Val Ser Arg Phe Gly Asp Asp Gly Lys Tyr Arg Val Glu Ser Ala
        355                 360                 365

aag atg ctg gcc acc ttc ctg cac atg atg caa ggc acc ccg tac atc     1152
Lys Met Leu Ala Thr Phe Leu His Met Met Gln Gly Thr Pro Tyr Ile
    370                 375                 380

tac cag ggc gaa gaa atc ggc atg acc aat gtg cgc ttc ccg agc atc     1200
Tyr Gln Gly Glu Glu Ile Gly Met Thr Asn Val Arg Phe Pro Ser Ile
385                 390                 395                 400

gag gac tac cgg gac atc gag act ctg aac atg tac aag gaa cgc gtc     1248
Glu Asp Tyr Arg Asp Ile Glu Thr Leu Asn Met Tyr Lys Glu Arg Val
                405                 410                 415

gag gaa tac ggc gag gac ccg caa gag gtg atg gaa aag atc tac tac     1296
Glu Glu Tyr Gly Glu Asp Pro Gln Glu Val Met Glu Lys Ile Tyr Tyr
            420                 425                 430

aag ggc cgc gac aac gcc agg acc ccg atg caa tgg gac gac agc gag     1344
Lys Gly Arg Asp Asn Ala Arg Thr Pro Met Gln Trp Asp Asp Ser Glu
        435                 440                 445

aac gcc ggc ttc acc gcc ggc acc ccg tgg att ccg gtg aac ccg aac     1392
Asn Ala Gly Phe Thr Ala Gly Thr Pro Trp Ile Pro Val Asn Pro Asn
    450                 455                 460

tac aag gaa atc aac gtc aag gcc gcc ctc gaa gat cca aac agc gtg     1440
Tyr Lys Glu Ile Asn Val Lys Ala Ala Leu Glu Asp Pro Asn Ser Val
465                 470                 475                 480

ttc cac tac tac aag aag ctg atc cag ctg cgc aag cag cac gac atc     1488
Phe His Tyr Tyr Lys Lys Leu Ile Gln Leu Arg Lys Gln His Asp Ile
                485                 490                 495

atc gtg tac ggc acc tac gac ctg atc ctc gag gac gac cct tac atc     1536
Ile Val Tyr Gly Thr Tyr Asp Leu Ile Leu Glu Asp Asp Pro Tyr Ile
            500                 505                 510

tac cgc tac acc cgc acc ctg ggc aac gag cag ctg atc gtg atc acc     1584
Tyr Arg Tyr Thr Arg Thr Leu Gly Asn Glu Gln Leu Ile Val Ile Thr
        515                 520                 525

aac ttc agc gaa aag acc ccg gtg ttc cgc ctg ccg gac cac atc atc     1632
Asn Phe Ser Glu Lys Thr Pro Val Phe Arg Leu Pro Asp His Ile Ile
    530                 535                 540

tac aag acc aag gaa ctc ctc atc tct aac tac gac gtg gac gag gcc     1680
Tyr Lys Thr Lys Glu Leu Leu Ile Ser Asn Tyr Asp Val Asp Glu Ala
545                 550                 555                 560

gag gaa ctg aag gaa atc agg ctg agg ccc tgg gag gcc cgc gtg tac     1728
Glu Glu Leu Lys Glu Ile Arg Leu Arg Pro Trp Glu Ala Arg Val Tyr
                565                 570                 575

aag atc agg ctg cca agc gag aag gac gag ctg tga                     1764
Lys Ile Arg Leu Pro Ser Glu Lys Asp Glu Leu
            580                 585
```

<210> SEQ ID NO 56
<211> LENGTH: 587
<212> TYPE: PRT
<213> ORGANISM: unknown
<220> FEATURE:
<223> OTHER INFORMATION: Synthetic Construct

<400> SEQUENCE: 56

Met Gly Arg Val Leu Leu Val Ala Leu Ala Leu Leu Ala Leu Ala Ala
1               5                   10                  15

Ser Ala Thr Ser Glu Arg Val Trp Trp Lys Glu Ala Val Val Tyr Gln
            20                  25                  30

Ile Tyr Pro Arg Ser Phe Tyr Asp Ser Asn Gly Asp Gly Ile Gly Asp
        35                  40                  45

Ile Arg Gly Ile Ile Ala Lys Leu Asp Tyr Leu Lys Glu Leu Gly Val
    50                  55                  60

Asp Val Val Trp Leu Ser Pro Val Tyr Lys Ser Pro Asn Asp Asp Asn
65                  70                  75                  80

Gly Tyr Asp Ile Ser Asp Tyr Arg Asp Ile Met Asp Glu Phe Gly Thr
                85                  90                  95

Met Ala Asp Trp Lys Thr Met Leu Glu Glu Met His Lys Arg Gly Ile
            100                 105                 110

Lys Leu Val Met Asp Leu Val Val Asn His Thr Ser Asp Glu His Pro
        115                 120                 125

Trp Phe Ile Glu Ser Arg Lys Ser Lys Asp Asn Pro Tyr Arg Asp Tyr
    130                 135                 140

Tyr Ile Trp Arg Pro Gly Lys Asn Gly Lys Glu Pro Asn Asn Trp Glu
145                 150                 155                 160

Ser Val Phe Ser Gly Ser Ala Trp Glu Tyr Asp Glu Met Thr Gly Glu
                165                 170                 175

Tyr Tyr Leu His Leu Phe Ser Lys Lys Gln Pro Asp Leu Asn Trp Glu
            180                 185                 190

Asn Pro Lys Val Arg Arg Glu Val Tyr Glu Met Met Lys Phe Trp Leu
        195                 200                 205

Asp Lys Gly Val Asp Gly Phe Arg Met Asp Val Ile Asn Met Ile Ser
    210                 215                 220

Lys Val Pro Glu Leu Pro Asp Gly Glu Pro Gln Ser Gly Lys Lys Tyr
225                 230                 235                 240

Ala Ser Gly Ser Arg Tyr Tyr Met Asn Gly Pro Arg Val His Glu Phe
                245                 250                 255

Leu Gln Glu Met Asn Arg Glu Val Leu Ser Lys Tyr Asp Ile Met Thr
            260                 265                 270

Val Gly Glu Thr Pro Gly Val Thr Pro Lys Glu Gly Ile Leu Tyr Thr
        275                 280                 285

Asp Pro Ser Arg Arg Glu Leu Asn Met Val Phe Gln Phe Glu His Met
    290                 295                 300

Asp Leu Asp Ser Gly Pro Gly Gly Lys Trp Asp Ile Arg Pro Trp Ser
305                 310                 315                 320

Leu Ala Asp Leu Lys Lys Thr Met Thr Lys Trp Gln Lys Glu Leu Glu
                325                 330                 335

Gly Lys Gly Trp Asn Ser Leu Tyr Leu Asn Asn His Asp Gln Pro Arg
            340                 345                 350

Ala Val Ser Arg Phe Gly Asp Asp Gly Lys Tyr Arg Val Glu Ser Ala
        355                 360                 365

Lys Met Leu Ala Thr Phe Leu His Met Met Gln Gly Thr Pro Tyr Ile
    370                 375                 380

Tyr Gln Gly Glu Glu Ile Gly Met Thr Asn Val Arg Phe Pro Ser Ile
385                 390                 395                 400

Glu Asp Tyr Arg Asp Ile Glu Thr Leu Asn Met Tyr Lys Glu Arg Val

-continued

```
                405                 410                 415

Glu Glu Tyr Gly Glu Asp Pro Gln Glu Val Met Glu Lys Ile Tyr Tyr
            420                 425                 430

Lys Gly Arg Asp Asn Ala Arg Thr Pro Met Gln Trp Asp Asp Ser Glu
        435                 440                 445

Asn Ala Gly Phe Thr Ala Gly Thr Pro Trp Ile Pro Val Asn Pro Asn
    450                 455                 460

Tyr Lys Glu Ile Asn Val Lys Ala Ala Leu Glu Asp Pro Asn Ser Val
465                 470                 475                 480

Phe His Tyr Tyr Lys Lys Leu Ile Gln Leu Arg Lys Gln His Asp Ile
                485                 490                 495

Ile Val Tyr Gly Thr Tyr Asp Leu Ile Leu Glu Asp Asp Pro Tyr Ile
            500                 505                 510

Tyr Arg Tyr Thr Arg Thr Leu Gly Asn Glu Gln Leu Ile Val Ile Thr
        515                 520                 525

Asn Phe Ser Glu Lys Thr Pro Val Phe Arg Leu Pro Asp His Ile Ile
    530                 535                 540

Tyr Lys Thr Lys Glu Leu Leu Ile Ser Asn Tyr Asp Val Asp Glu Ala
545                 550                 555                 560

Glu Glu Leu Lys Glu Ile Arg Leu Arg Pro Trp Glu Ala Arg Val Tyr
                565                 570                 575

Lys Ile Arg Leu Pro Ser Glu Lys Asp Glu Leu
            580                 585
```

<210> SEQ ID NO 57
<211> LENGTH: 1689
<212> TYPE: DNA
<213> ORGANISM: unknown
<220> FEATURE:
<223> OTHER INFORMATION: synthetic gene
<220> FEATURE:
<221> NAME/KEY: CDS
<222> LOCATION: (1)..(1689)
<223> OTHER INFORMATION: monocot optimized alpha-1,6-glucosidase Geo

<400> SEQUENCE: 57

```
atg gaa aga gtg tgg tgg aag gaa gcc gtc gtc tac cag atc tac ccg       48
Met Glu Arg Val Trp Trp Lys Glu Ala Val Val Tyr Gln Ile Tyr Pro
1               5                   10                  15

cgc agc ttc tac gac agc aac ggc gac ggc atc ggc gac atc cgc ggc       96
Arg Ser Phe Tyr Asp Ser Asn Gly Asp Gly Ile Gly Asp Ile Arg Gly
            20                  25                  30

atc att gcc aag ctg gac tac ctg aag gaa ctg ggc gtc gac gtt gtg      144
Ile Ile Ala Lys Leu Asp Tyr Leu Lys Glu Leu Gly Val Asp Val Val
        35                  40                  45

tgg ctg tcc ccg gtg tac aag agc ccg aac gat gac aat ggc tac gat      192
Trp Leu Ser Pro Val Tyr Lys Ser Pro Asn Asp Asp Asn Gly Tyr Asp
    50                  55                  60

atc tcc gac tac cgc gac atc atg gac gag ttc ggc acg atg gcc gac      240
Ile Ser Asp Tyr Arg Asp Ile Met Asp Glu Phe Gly Thr Met Ala Asp
65                  70                  75                  80

tgg aag acc atg ctc gag gaa atg cac aag cgc ggc atc aag ctg gtg      288
Trp Lys Thr Met Leu Glu Glu Met His Lys Arg Gly Ile Lys Leu Val
                85                  90                  95

atg gac ctg gtg gtg aac cac acc agc gac gag cac ccg tgg ttc atc      336
Met Asp Leu Val Val Asn His Thr Ser Asp Glu His Pro Trp Phe Ile
            100                 105                 110

gag agc cgc aag agc aag gac aac ccg tac cgc gac tac tac atc tgg      384
Glu Ser Arg Lys Ser Lys Asp Asn Pro Tyr Arg Asp Tyr Tyr Ile Trp
```

-continued

```
        115                 120                 125

cgc cca ggc aag aac ggc aag gaa ccg aac aac tgg gag agc gtg ttc      432
Arg Pro Gly Lys Asn Gly Lys Glu Pro Asn Asn Trp Glu Ser Val Phe
    130                 135                 140

agc ggc agc gcc tgg gag tac gac gag atg acc ggc gag tac tac ctc      480
Ser Gly Ser Ala Trp Glu Tyr Asp Glu Met Thr Gly Glu Tyr Tyr Leu
145                 150                 155                 160

cac ctg ttc agc aag aag cag ccg gac ctg aac tgg gag aac ccg aag      528
His Leu Phe Ser Lys Lys Gln Pro Asp Leu Asn Trp Glu Asn Pro Lys
                165                 170                 175

gtg cgc cgc gag gtg tac gag atg atg aag ttc tgg ctg gac aag ggc      576
Val Arg Arg Glu Val Tyr Glu Met Met Lys Phe Trp Leu Asp Lys Gly
            180                 185                 190

gtg gac ggc ttc cgc atg gac gtg atc aac atg atc agc aag gtg ccc      624
Val Asp Gly Phe Arg Met Asp Val Ile Asn Met Ile Ser Lys Val Pro
        195                 200                 205

gag ctg cca gat ggc gag ccg cag agc ggc aag aag tac gcc tct ggc      672
Glu Leu Pro Asp Gly Glu Pro Gln Ser Gly Lys Lys Tyr Ala Ser Gly
    210                 215                 220

tcc cgc tac tac atg aac ggc ccg agg gtg cac gag ttc ctc caa gaa      720
Ser Arg Tyr Tyr Met Asn Gly Pro Arg Val His Glu Phe Leu Gln Glu
225                 230                 235                 240

atg aat cgc gaa gtg ctc tcc aag tac gac atc atg act gtg ggc gag      768
Met Asn Arg Glu Val Leu Ser Lys Tyr Asp Ile Met Thr Val Gly Glu
                245                 250                 255

act ccg ggc gtg acc ccg aag gaa ggc atc ctg tac acc gac ccg agc      816
Thr Pro Gly Val Thr Pro Lys Glu Gly Ile Leu Tyr Thr Asp Pro Ser
            260                 265                 270

agg cgc gag ctg aac atg gtg ttc cag ttc gag cac atg gac ctc gac      864
Arg Arg Glu Leu Asn Met Val Phe Gln Phe Glu His Met Asp Leu Asp
        275                 280                 285

tct ggt cca ggc ggc aag tgg gac atc agg ccg tgg agc ctg gcc gac      912
Ser Gly Pro Gly Gly Lys Trp Asp Ile Arg Pro Trp Ser Leu Ala Asp
    290                 295                 300

ctg aag aag acc atg acc aag tgg cag aag gaa ctt gag ggc aag ggc      960
Leu Lys Lys Thr Met Thr Lys Trp Gln Lys Glu Leu Glu Gly Lys Gly
305                 310                 315                 320

tgg aac agc ctg tac ctg aac aac cac gac cag ccg agg gcc gtg tcc     1008
Trp Asn Ser Leu Tyr Leu Asn Asn His Asp Gln Pro Arg Ala Val Ser
                325                 330                 335

aga ttc ggc gac gac ggc aag tac cgc gtg gag agc gcc aag atg ctg     1056
Arg Phe Gly Asp Asp Gly Lys Tyr Arg Val Glu Ser Ala Lys Met Leu
            340                 345                 350

gcc acc ttc ctg cac atg atg caa ggc acc ccg tac atc tac cag ggc     1104
Ala Thr Phe Leu His Met Met Gln Gly Thr Pro Tyr Ile Tyr Gln Gly
        355                 360                 365

gaa gaa atc ggc atg acc aat gtg cgc ttc ccg agc atc gag gac tac     1152
Glu Glu Ile Gly Met Thr Asn Val Arg Phe Pro Ser Ile Glu Asp Tyr
    370                 375                 380

cgg gac atc gag act ctg aac atg tac aag gaa cgc gtc gag gaa tac     1200
Arg Asp Ile Glu Thr Leu Asn Met Tyr Lys Glu Arg Val Glu Glu Tyr
385                 390                 395                 400

ggc gag gac ccg caa gag gtg atg gaa aag atc tac tac aag ggc cgc     1248
Gly Glu Asp Pro Gln Glu Val Met Glu Lys Ile Tyr Tyr Lys Gly Arg
                405                 410                 415

gac aac gcc agg acc ccg atg caa tgg gac gac agc gag aac gcc ggc     1296
Asp Asn Ala Arg Thr Pro Met Gln Trp Asp Asp Ser Glu Asn Ala Gly
            420                 425                 430

ttc acc gcc ggc acc ccg tgg att ccg gtg aac ccg aac tac aag gaa     1344
```

```
Phe Thr Ala Gly Thr Pro Trp Ile Pro Val Asn Pro Asn Tyr Lys Glu
        435                 440                 445

atc aac gtc aag gcc gcc ctc gaa gat cca aac agc gtg ttc cac tac      1392
Ile Asn Val Lys Ala Ala Leu Glu Asp Pro Asn Ser Val Phe His Tyr
    450                 455                 460

tac aag aag ctg atc cag ctg cgc aag cag cac gac atc atc gtg tac      1440
Tyr Lys Lys Leu Ile Gln Leu Arg Lys Gln His Asp Ile Ile Val Tyr
465                 470                 475                 480

ggc acc tac gac ctg atc ctc gag gac gac cct tac atc tac cgc tac      1488
Gly Thr Tyr Asp Leu Ile Leu Glu Asp Asp Pro Tyr Ile Tyr Arg Tyr
                485                 490                 495

acc cgc acc ctg ggc aac gag cag ctg atc gtg atc acc aac ttc agc      1536
Thr Arg Thr Leu Gly Asn Glu Gln Leu Ile Val Ile Thr Asn Phe Ser
            500                 505                 510

gaa aag acc ccg gtg ttc cgc ctg ccg gac cac atc atc tac aag acc      1584
Glu Lys Thr Pro Val Phe Arg Leu Pro Asp His Ile Ile Tyr Lys Thr
        515                 520                 525

aag gaa ctc ctc atc tct aac tac gac gtg gac gag gcc gag gaa ctg      1632
Lys Glu Leu Leu Ile Ser Asn Tyr Asp Val Asp Glu Ala Glu Glu Leu
    530                 535                 540

aag gaa atc agg ctg agg ccc tgg gag gcc cgc gtg tac aag atc agg      1680
Lys Glu Ile Arg Leu Arg Pro Trp Glu Ala Arg Val Tyr Lys Ile Arg
545                 550                 555                 560

ctg cca tga                                                          1689
Leu Pro


<210> SEQ ID NO 58
<211> LENGTH: 562
<212> TYPE: PRT
<213> ORGANISM: unknown
<220> FEATURE:
<223> OTHER INFORMATION: Synthetic Construct

<400> SEQUENCE: 58

Met Glu Arg Val Trp Trp Lys Glu Ala Val Val Tyr Gln Ile Tyr Pro
1               5                   10                  15

Arg Ser Phe Tyr Asp Ser Asn Gly Asp Gly Ile Gly Asp Ile Arg Gly
            20                  25                  30

Ile Ile Ala Lys Leu Asp Tyr Leu Lys Glu Leu Gly Val Asp Val Val
        35                  40                  45

Trp Leu Ser Pro Val Tyr Lys Ser Pro Asn Asp Asp Asn Gly Tyr Asp
    50                  55                  60

Ile Ser Asp Tyr Arg Asp Ile Met Asp Glu Phe Gly Thr Met Ala Asp
65                  70                  75                  80

Trp Lys Thr Met Leu Glu Glu Met His Lys Arg Gly Ile Lys Leu Val
                85                  90                  95

Met Asp Leu Val Val Asn His Thr Ser Asp Glu His Pro Trp Phe Ile
            100                 105                 110

Glu Ser Arg Lys Ser Lys Asp Asn Pro Tyr Arg Asp Tyr Tyr Ile Trp
        115                 120                 125

Arg Pro Gly Lys Asn Gly Lys Glu Pro Asn Asn Trp Glu Ser Val Phe
    130                 135                 140

Ser Gly Ser Ala Trp Glu Tyr Asp Glu Met Thr Gly Glu Tyr Tyr Leu
145                 150                 155                 160

His Leu Phe Ser Lys Lys Gln Pro Asp Leu Asn Trp Glu Asn Pro Lys
                165                 170                 175

Val Arg Arg Glu Val Tyr Glu Met Met Lys Phe Trp Leu Asp Lys Gly
            180                 185                 190
```

-continued

```
Val Asp Gly Phe Arg Met Asp Val Ile Asn Met Ile Ser Lys Val Pro
        195                 200                 205

Glu Leu Pro Asp Gly Glu Pro Gln Ser Gly Lys Lys Tyr Ala Ser Gly
    210                 215                 220

Ser Arg Tyr Tyr Met Asn Gly Pro Arg Val His Glu Phe Leu Gln Glu
225                 230                 235                 240

Met Asn Arg Glu Val Leu Ser Lys Tyr Asp Ile Met Thr Val Gly Glu
                245                 250                 255

Thr Pro Gly Val Thr Pro Lys Glu Gly Ile Leu Tyr Thr Asp Pro Ser
            260                 265                 270

Arg Arg Glu Leu Asn Met Val Phe Gln Phe Glu His Met Asp Leu Asp
        275                 280                 285

Ser Gly Pro Gly Gly Lys Trp Asp Ile Arg Pro Trp Ser Leu Ala Asp
    290                 295                 300

Leu Lys Lys Thr Met Thr Lys Trp Gln Lys Glu Leu Glu Gly Lys Gly
305                 310                 315                 320

Trp Asn Ser Leu Tyr Leu Asn Asn His Asp Gln Pro Arg Ala Val Ser
                325                 330                 335

Arg Phe Gly Asp Asp Gly Lys Tyr Arg Val Glu Ser Ala Lys Met Leu
            340                 345                 350

Ala Thr Phe Leu His Met Met Gln Gly Thr Pro Tyr Ile Tyr Gln Gly
        355                 360                 365

Glu Glu Ile Gly Met Thr Asn Val Arg Phe Pro Ser Ile Glu Asp Tyr
    370                 375                 380

Arg Asp Ile Glu Thr Leu Asn Met Tyr Lys Glu Arg Val Glu Glu Tyr
385                 390                 395                 400

Gly Glu Asp Pro Gln Glu Val Met Glu Lys Ile Tyr Tyr Lys Gly Arg
                405                 410                 415

Asp Asn Ala Arg Thr Pro Met Gln Trp Asp Asp Ser Glu Asn Ala Gly
            420                 425                 430

Phe Thr Ala Gly Thr Pro Trp Ile Pro Val Asn Pro Asn Tyr Lys Glu
        435                 440                 445

Ile Asn Val Lys Ala Ala Leu Glu Asp Pro Asn Ser Val Phe His Tyr
    450                 455                 460

Tyr Lys Lys Leu Ile Gln Leu Arg Lys Gln His Asp Ile Ile Val Tyr
465                 470                 475                 480

Gly Thr Tyr Asp Leu Ile Leu Glu Asp Asp Pro Tyr Ile Tyr Arg Tyr
                485                 490                 495

Thr Arg Thr Leu Gly Asn Glu Gln Leu Ile Val Ile Thr Asn Phe Ser
            500                 505                 510

Glu Lys Thr Pro Val Phe Arg Leu Pro Asp His Ile Ile Tyr Lys Thr
        515                 520                 525

Lys Glu Leu Leu Ile Ser Asn Tyr Asp Val Asp Glu Ala Glu Glu Leu
    530                 535                 540

Lys Glu Ile Arg Leu Arg Pro Trp Glu Ala Arg Val Tyr Lys Ile Arg
545                 550                 555                 560

Leu Pro
```

COMPOSITIONS AND METHODS FOR PRODUCING FERMENTABLE CARBOHYDRATES

RELATED APPLICATIONS

This application is a national phase application claiming the benefit of priority under 35 U.S.C. §371 to Patent Convention Treaty (PCT) International Application Serial No. PCT/US2009/04698 having an international filing date of Jun. 11, 2009 (published as WO 2009/152285, on Dec. 17, 2009), which claims the benefit of priority under 35 U.S.C. §119(e) to U.S. Provisional Application Ser. No. 61/060,789 filed Jun. 11, 2006. The aforementioned applications are explicitly incorporated herein by reference in their entirety and for all purposes.

REFERENCE TO SEQUENCE LISTING SUBMITTED ELECTRONICALLY

The official copy of the sequence listing is submitted concurrently with the specification as a text file via EFS-Web, in compliance with the American Standard Code for Information Interchange (ASCII), with a file name of "71825USPSP2 sequence listing.txt, created Jun. 10, 2009, and a size of 313 KB. The sequence listing filed via EFS-Web is part of the specification and is hereby incorporated in its entirety by reference herein.

FIELD OF THE INVENTION

This invention relates to plant molecular biology, particularly to methods and compositions for improving plants for obtaining commercially desirable harvested plant material, particularly for ethanol production.

BACKGROUND OF THE INVENTION

Plant biomass is comprised of sugars and represents the greatest source of renewable hydrocarbon on earth. Unlike other renewable energy sources, biomass can be converted directly into liquid fuels. The two most common types of biofuels are ethanol (ethyl alcohol) and biodiesel. Ethanol is an alcohol, which can be produced by fermenting any biomass high in carbohydrates (starches, sugars, or celluloses) once fermentable sugars have been obtained from the biomass material. Sugars generated from degradation of plant biomass could provide plentiful, economically competitive feedstocks for fermentation to produce chemicals, plastics, and fuels or any other product of interest.

Fuel ethanol could be made from crops which contain starch such as feed grains, food grains, and tubers, such as potatoes and sweet potatoes. Crops containing sugar, such as sugar beets, sugarcane, and sweet sorghum also could be used for the production of ethanol. Sugar, in the form of raw or refined sugar, or as sugar in molasses requires no pre-hydrolysis (unlike corn starch) prior to fermentation. Consequently, the process of producing ethanol from sugar is simpler than converting corn starch into ethanol.

The yield and concentration of desired carbohydrates in plants are key determinants of the technical and economic feasibility of downstream industrial processes. However, the metabolic networks of plants for biosynthesis of sugars show substantial internal buffering and redundancy, with the consequence that alteration to a key gene in metabolism of a sugar commonly results in no useful change to the harvestable yield of the sugar (Moore, Australian Journal of Plant Physiology 22: 661-679 (1995); Nguyen-Quoc and Foyer, J of Experimental Botany 52: 881-889 (2001); Fernie et al., Trends in Plant Science 7: 35-41 (2002)).

SUMMARY OF THE INVENTION

Provided herein are methods for producing locked carbohydrates in a plant tissue by providing one or more carbohydrate-metabolizing enzymed that catalyze the conversion of an endogenous carbohydrate to a non-native carbohydrate. The invention encompasses plants and plant parts that produce one or more carbohydrate-metabolizing enzymes to yield a locked carbohydrate, with the consequence of increasing the total locked carbohydrate content in the plant. Further provided are hydrolytic enzymes (key enzymes) for converting the locked carbohydrate into a fermentable sugar. Fermentable sugars are used for a variety of industrial purposes including the production of ethanol.

DETAILED DESCRIPTION OF THE INVENTION

Overview

Plants accumulating large amounts of sugar are valuable as fermentation feedstocks for the downstream production of commercially-useful products. However, plants have various mechanisms to regulate the flow of sugars, therefore, sugar accumulation is limited in many plants. Plants contain both internal receptors and membrane-bound external receptors for monitoring sugar biosynthesis, transport, and uptake (reviewed in Lalonde et al. (1999) Plant Cell 11:707-726). Intracellular receptors modulate metabolic processes such as photosynthesis. Extracellular receptors sense external sugar concentrations in order to control sugar influx from the surrounding environment. Thus, the plant cells are capable of maintaining sufficient levels of sucrose by regulating metabolic processes and sugar uptake.

Provided herein is a method for producing locked storage carbohydrates in plants so that they cannot be metabolized by the plant. The methods comprise introducing into the plant or plant part one or more enzymes capable of converting an endogenous sugar into a locked carbohydrate. By "endogenous sugar" or "native sugar" is intended a sugar that is normally produced by a particular variety of plant. In contrast, a "locked carbohydrate" or a "locked sugar" is one that is not produced under normal conditions of growth or development of that variety of plant or in a particular plant part or plant organelle. Expression of an enzyme capable of converting the endogenous sugar into a locked carbohydrate (which is herein referred to as a "lock enzyme") in a plant will allow accumulation of the locked carbohydrates in the plant. Because these locked carbohydrates are not metabolized in plants, they are unlikely to be subject to "futile cycles" of degradation and synthesis in the mature storage tissues, which have the potential to decrease storage efficiency and harvestable yield. Many of these oligosaccharides, polysaccharides, or monosaccharides will also evade the plant's carbohydrate detecting mechanisms, such as sucrose sensing, such that native and non-native carbohydrate synthesis may occur to compensate for decreases in endogenous carbohydrates which have been diverted into the locked carbohydrate storage pathway.

Recently, Wu and Birch, infra, have demonstrated that converting sucrose to the non-metabolized sucrose isomer isomaltulose allows accumulation of isomaltulose and sucrose providing combined sugar production in sugarcane. Isomaltulose is currently used to manufacture sugar alcohols consumed as low-calorie sweeteners (Schiweck et al. (1991) In F. W. Lichtenthaler (ed.), Carbohydrates as organic raw materials. Wiley-VCH, Weinheim, Germany), and it is an attractive renewable starting material for the manufacture of biosurfactants and biocompatible polymers (Lichtenthaler (2002) Accounts Chem. Res. 35:728-737).

The invention also comprises expressing hydrolytic enzymes capable of hydrolyzing the locked carbohydrates into fermentable sugars. These enzymes are herein referred to as "key enzymes." These enzymes may be of plant, bacterial, fungal, archeal, or other origin; may be provided exogenously in an enzyme preparation, may be expressed in a separate line of plants or the same line of plants, or in yeast or other microbes, or may be provided in microbes that are used in a fermentative process converting fermentable sugars, carbohydrates or di, tri, oligo or polymeric saccharides to useful fermentation products. Fermentable sugars are carbohydrates which can be metabolized by conventional organisms such as yeast. Fermentation is the process of energy production in a cell and is not limited to the production of alcohols. Fermentation refers to the breakdown and re-assembly of biochemicals for industry in either aerobic or anaerobic growth conditions. It generally is the process of energy production in a cell and is not limited to the production of alcohols. Commonly known fermentable sugars include but are not limited to sucrose, glucose and fructose.

Commercial applications of the invention include the production of sugarcane, sugar beet, or other plants capable of producing locked carbohydrates. In some embodiments, accumulation of the normal storage carbohydrates (e.g., sucrose) is not affected in these plants. These plants or their extracts are then treated with enzyme preparations or with microbes or plant materials expressing key enzymes capable of hydrolyzing locked carbohydrates into fermentable sugar. These sugars could then be used in fermentation for many purposes including ethanol production or any other product of interest.

Thus, the methods of the invention find particular use in the integration of current practices for the cultivation of crop plants for the purpose of obtaining a commercially desired plant material with increased accumulation of carbohydrates (locked or native) in a plant, and the use of the crop plant or plant part as a source of biomass for the production of fermentable sugars, or for agricultural and/or human consumption.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, oats, tobacco, strawberry, *Miscanthus* grass, Switch grass, trees, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the chromosome and cell in which it naturally occurs. A sequence is also isolated if separated from the chromosome and cell in which it naturally occurs in but inserted into a genetic context, chromosome, or cell in which it does not naturally occur.

Locked Carbohydrates

Sucrose is the major intermediary in carbon flux between source (photosynthetic) tissues and sink (growth and storage) tissues within plants, and it is the primary storage product in certain plants such as sugarcane and sugar beet. Plants have highly adapted sensors and transporters for sucrose, but it is generally considered that these sucrose sensors and transporters are not able to respond in the same way to locked carbohydrates (Loreti et al., Plant Physiol 123: 939-948 (2000); Sinha et al., Plant Physiol 128: 1480-1489 (2002)). In stark contrast with sucrose, plants are unable to metabolize these locked carbohydrates as a source of carbon and energy (Sinha et al., 2002).

While not bound by any particular theory or mechanism, specific alterations to metabolism, involving the conversion of a carbohydrate normally sensed by the plant into a locked carbohydrate that is not perceived in an equivalent manner, can shift metabolism and result in the accumulation of higher concentrations of locked carbohydrates or, in some cases, accumulation of higher concentrations of total carbohydrates.

Thus, provided herein are methods for the expression in a plant of an enzyme capable of converting an endogenous sugar into a locked sugar. The endogenous sugars produced by different plants may differ and as such an endogenous sugar of one plant may be non-native to another. Where the sugar is non-native to a particular plant, that plant is a candidate for production of a locked carbohydrate using the methods of the invention. Also, a non-native carbohydrate may also refer to a carbohydrate that is not normally produced in a particular subcellular compartment, or in a particular plant part of the native plant. In this embodiment, the subcellular compartment or the plant part would normally not be capable of metabolizing or transporting out of the compartment or plant part any non-native carbohydrate produced therein. Thus, it is essential to determine which carbohydrates are endogenously produced by a chosen plant or plant part to thereby deduce which carbohydrates are non-native to the plant and the type of carbohydrate-metabolizing enzyme(s) that could be useful for producing a locked carbohydrate in the plant.

For example, amylose (i.e., a type of starch) is a polysaccharide consisting of glucosyl residues linked by alpha-(1-4) bonds and is the primary carbohydrate storage compound found in most plants. Producing starch in plants that use sucrose as their primary carbohydrate storage compound, such as sugarcane, may permit the accumulation of starch which would behave as a "locked" sugar (i.e., sugar that cannot be metabolized by the plant).

The types of carbohydrates endogenously produced by plants can be determined using methods well known to persons of skill in the art. These methods include separation of sugars or sugar derivatives by electrophoresis or chromatography (including paper chromatography, thin layer chromatography, gas chromatography, gas-liquid chromatography and high-performance liquid chromatography) techniques. The separated components are typically identified by comparison of separation profiles with standards of known identity, or by analytical techniques such as mass spectrometry and nuclear magnetic resonance spectroscopy. See, for example, reference may be made to Robinson 1980, The Organic Constituents of Higher Plants, Cordus Press, North Amherst, USA; Adams et al. 1999, Anal. Biochem. 266:77-84; Veronese and Perlot 1999, Enz. Microbial Tech. 24:263-269; Hendrix and Salvucci 2001, J. Insect Physiol. 47:423-432; Thompson et al. 2001, Carbohydrate Res. 331:149-161; each of which is incorporated by reference herein for their teachings regarding analysis of sugar content.

The endogenous or the non-native carbohydrates may include monosaccharides, oligosaccharides, sugar alcohols, sugar acids, amino sugars or other variants such as deoxy sugars, methyl sugars and the like. Examples of monosaccharides include compounds with formula (CH.sub.2O).sub.n where n=3 or more but suitably less than 10; including compounds comprising tetroses (e.g., erythrose, threose, erythrulose), pentoses (e.g., ribose, arabinose, xylose, lyxose, ribulose, xylulose), hexoses (e.g., allose, altrose, glucose, mannose, gulose, idose, galactose, talose, psicose, fructose, sorbose, tagatose), and longer molecules such as sedoheptulose or mannoheptulose. Oligosaccharides, which are formed by linking together two or more monosaccharide units through glycosidic bonds, may be selected from disaccharides (e.g., maltose, lactose, gentibiose, melibiose, trehalose, sophorose, primeverose, rutinose, sucrose, isomaltulose, trehalulose, turanose, maltulose, leucrose, 2-keto-sucrose) and longer oligomers such as raffinose, melezitose, isobemisiose or stachyose. Examples of sugar alcohols include, but are not limited to, erythritol, ribitol, mannitol, sorbitol. Non-limiting examples of sugar acids include gluconic acid, glucaric acid, glucuronic acid. Non-limiting examples of amino sugars include glucosamine, galactosamine. Endogenous or non-native sugars may also be selected from other variants such as deoxy sugars and methyl sugars. Further encompassed are isobemisiose, tagatose, isomaltotriose, dextrin, cyclodextrins, lactose, verbascose, amylose, and rhamnose.

Isomaltulose and Trehalulose

In certain embodiments, the locked carbohydrate is an isomer of the endogenous carbohydrate. In one example of this embodiment, the endogenous sugar is sucrose and the sugar-metabolizing enzyme is a sucrose isomerase, which converts the sucrose by isomerization to a locked sugar selected from isomaltulose and trehalulose. Isomaltulose .alpha.-D-glucopyranosyl-1,6-D-fructofuranose (also called palatinose) is a nutritive disaccharide, with sweetness and bulk similar to sucrose. Several characteristics make isomaltulose advantageous over sucrose for some applications in the food industry: 1) noncariogenic (not causing dental decay); 2) low glycemic index (useful for diabetics); 3) selective promotion of growth of beneficial bifidobacteria among human intestinal microflora; 4) greater stability of isomaltulose-containing foods and beverages; 5) less hygroscopic; 6) simple conversion into sugar alcohols with other useful properties as foods.

Sucrose isomerases (E.C. 5.4.99.11) are enzymes produced by organisms including various microbes, with the capability to convert the disaccharide sucrose into isomers such as isomaltulose (palatinose) or trehalulose. Sucrose isomerases vary in their properties including the disaccharide reaction products, the proportion of monosaccharides such as glucose and fructose in the reaction products, the kinetic properties of the enzymes, the optimal reaction conditions, and the sensitivity of the enzyme to variations from the optimal conditions (Veronese and Perlot, Enzyme. Microb. Technol 24: 263-269 (1999)). An isolate of *Pantoea dispersa* designated UQ68J is exceptionally efficient in sucrose isomerase activity (Wu and Birch (2004) J. Appl. Microbiol. 97:93-103). Another exemplary sucrose isomerase has been isolated from *Erwinia carotovora* (GENBANK Accession No. YP049947).

Dextrans and Fructans

This invention also comprises transforming plants with one or more genes involved in the synthesis of fructans or dextrans. These genes may come from plant, bacterial, or fungal sources and should catalyze the formation of fructose and glucose polysaccharides or polysaccharides comprised of mixed sugars that are found in cane or sugar beet, sweet sorghum, mangel-wurzel or other sugar crops. The oligo—or polysaccharides produced may also comprise mixed sugar monomers, for example glucose, fructose, mannose and galactose.

By producing these fructan, dextran and mixed fructan and dextran carbohydrates in plants whose primary storage carbohydrate is sucrose, such as sugarcane and sugarbeet, a method for sequestering carbohydrates is provided in a form that is non-metabolizable for the plant. Such compounds may evade the sucrose sensing mechanisms of the plant so that they can be accumulated for later enzymatic hydrolysis to fermentable sugars.

Dextran is a collective name for high-molecular-weight polymers composed of D-glucose units connected with alpha-1,6 linkages and various amounts of side branches linked with alpha-1,2, alpha-1,3, or alpha-1,4 to the main chains. The enzymes that synthesize these glucans from sucrose are known by the generic term dextransucrase (1,6-alpha-D-glucan-6-alpha-glucosyltransferase, EC2.4.1.5.). The biosynthesis of dextran has been demonstrated in numerous bacteria, especially in *Streptococcus mutans, Leuconostoc mesenteroides* ssp. *mesenteroides* and *Leuconostoc mesenteroides* ssp. *dextranicum. Leuconostoc* produce the enzyme dextran sucrase and secrete it into the culture medium in the presence of sucrose. This enzyme, dextran sucrase, then synthesizes dextran from the sucrose substrate. Dextran has applications in several fields. It is used especially in biochemistry as a support for filtration chromatography on a gel of the Sephadex type. Additionally, in the field of therapeutics, it is used as a substitute for blood plasma (Biochimie generale (General Biochemistry)—J. H. WEIL—Masson, 6th edition—1990—p. 171).

Exemplary dextransucrase enzymes include (but are not limited to): the dextransucrase from *Streptococcus downei*, gtfS gene (Gilmore et al. (1990) Infect. Immun. 58 (8), 2452-2458; GENBANK Accession No. P29336); the dextransucrase from *Streptococcus mutans*, gtfI gene, produces a 1,3 glucose soluble dextrans (Shiroza et al. (1987) J. Bacteriol. 169 (9), 4263-4270; GENBANK Accession No. P08987);

and the dextransucrase from *Streptococcus mutans* gtfD gene, gtfS protein (Terao et al. (1998) FEMS Microbiol. Lett. 161 (2), 331-336; GENBANK Accession No. P49331)

There is no common class of enzymes identified as "Leucrose synthases." Instead leucrose [O-alpha-D-glucopyranosyl-(1→5)-D-fructopyranoside] is generally a byproduct of dextransucrase enzyme (EC 2.4.1.5) activity. These enzymes act as glucosyltransferases, and normally transfer a glucose unit hydrolyzed from a sucrose molecule to a growing dextran chain, or in the case of leucrose to a pyranosyl-fructose molecule yielding leucrose. Glucose can also serve as an acceptor for the transglycosylase reaction resulting in isomaltose (O-α-D-glucopyranosyl-α[1-6]-α-D-glucopyranoside) production. Since the 1950's leucrose has been made enzymatically typically using the *Leuconostoc mesenteroides* dextransucrase (The Preparation, Properties and Structure of the Disaccharide Leucrose Journal of the American Chemical Society, Stodola et. al; (1956) 78: 2415) followed by chemical purification.

Dextransucrases can be mutated to produce more leucrose and or turanose. This has been shown for the dextransucrase of *Streptococcus oralis* (Engineering the Glucansucrase GTFR Enzyme Reaction and Glycosidic Bond Specificity: Toward Tailor-Made Polymer and Oligosaccharide Products, Biochemistry 2008, 47, 6678-6684, Hendrik Hellmuth et. al). Since dextransucrases can be mutated to produce leucrose it is reasonable to assume that other related enzymes (e.g. amylosucrases EC 2.4.1.4) or unrelated enzymes that also produce sucrose isomers could be mutated to produce leucrose. Leucrose synthase activity is attributed to any enzyme that produces leucrose by any mechanism, i.e. isomerization, transglycosylation, hydrolysis, dehydrogenation, reduction, etc.

The production of leucrose can be assayed using HPAE chromatography with pulsed amperometric detection (PAD). This technique is widely accepted as a preferred method for separating carbohydrates and is effective in separating sucrose isomers. Comparison of peak elution times with known standards is one method for determining the presence of leucrose. Full verification of the bond arrangements in the carbohydrate molecules can be determined either by methylation and acetylation of leucrose followed by GC MS, or directly by NMR spectroscopy if the samples are of sufficient quantity and purity.

Sucrose:sucrose fructosyltransferase (SST) (EC 2.4.1.99), 1,2-β-fructan 1-fructosyltransferase (FFT) (EC 2.4.1.100), 2-β-fructan 1-fructosyltransferase (FFT) (EC 2.4.1.100), glucan sucrase, and levan sucrase (EC 2.4.1.10) are enzymes within the larger class of fructosyl transferases. The fructosyl transferase enzymes catalyze the formation of fructans composed of fructose linked by β(2→1) and/or β(2→6) glucoside bonds. Fructosyl transferases may be identified and isolated from plant, bacterial, or fungal sources. These enzymes may be expressed in plants to accumulate fructans as storage carbohydrates. Accumulation of this polysaccharide (fructan) in sugarcane or other plants may allow the accumulation of excess carbohydrates.

Inulin is a fructan type carbohydrate polymer which occurs as a polydisperse composition in many plants and can also be produced by certain bacteria and fungi. Inulin from plant origin consists of a polydisperse composition of mainly linear chains composed of fructose units, mostly terminating in one glucose unit, which are linked to each other through .beta.(2-1) fructosyl-fructose linkages.

Inulin molecules are synthesised by the concerted action of two enzymes: sucrose:sucrose 1-fructosyltransferase (in short 1-SST enzyme or 1-SST, used interchangeably) and fructan:fructan 1-fructosyltransferase (in short 1-FFT enzyme or 1-FFT, used interchangeably) (Koops and Jonker, J of Experimental Botany 45: 1623-1631 (1994); and Koopos and Jonker, Plant Physiol 110: 1167-1175 (1996)). Both 1-SST and 1-FFT are active during the period of inulin synthesis and accumulation: 1-SST catalyses the initial reaction of inulin biosynthesis, the conversion of sucrose into the smallest inulin molecule, the trisaccharide kestose (GFF). 1-FFT catalyzes the redistribution of terminal fructosyl units (-F) between inulin molecules, which results in a stepwise increase in chain length.

Amylose

This invention further comprises transforming plants with one or more genes involved in the synthesis of novel carbohydrates such as amylosucrase (E.C. 2.4.1.4) to produce amylose in order to accumulate carbohydrates for later fermentation into ethanol. Examples of enzymes that may catalyze the desired conversions include isomerases, epimerases, mutases, kinases, aldolases, transferases, transketolases, phosphatases, synthases, carboxylases, dehydrogenases and hydrolases. An exemplary amylosucrase includes the enzyme produced by *Neisseria polysacharea* (GENBANK Accession number Q9ZEU2), which catalyzes the conversion of sucrose to a linear alpha-1,4-linked glucan.

Alternan

Alternan is a polysaccharide consisting of glucosyl residues linked by alternate alpha-(1-3)/alpha-(1-6) bonds. This polymer is highly soluble and has very low viscosity. Accumulation of this polysaccharide in sugarcane or other plants may allow the accumulation of excess carbohydrates.

Alternansucrase is an enzyme which catalyzes the conversion of sucrose to alternan. Alternansucrase is encoded by the Asr gene of *Leuconostoc mesenteroides* described in Jeannes et al. (1954) Am Chem Soc 76:5041-5052.

Key Enzymes

The invention also comprises expressing hydrolytic enzymes capable of hydrolyzing the locked carbohydrates into fermentable sugars. These enzymes are herein referred to as "key enzymes." These enzymes may be of plant, bacterial, fungal, archeal, or other origin; may be provided exogenously in an enzyme preparation, may be expressed in a separate line of plants or the same line of plants, or in yeast or other microbes, or may be provided in microbes that are used in a fermentative process to convert the locked carbohydrates into fermentable sugars. Yeast or microbes used in the fermentative process may also be identified or engineered to convert locked carbohydrates to energy. Furthermore, the locked carbohydrates may be converted to a fermentable sugar by chemical methods, e.g., by one or more chemicals capable of converting a locked carbohydrate into a fermentable sugar. The chemical(s) can be added prior to fermentation, or during the fermentation process.

Key enzymes can be isolated from, produced by, provided by a wide range of sources. Recombinant organisms such as plants, microbes or yeast, can be engineered to express a key enzyme. The recombinant organism can be used directly in a method of converting locked carbohydrates to fermentable sugars without further purification of the enzyme. Alternatively, key enzymes may be isolated from recombinant organisms for further use in the processing of locked carbohydrates. Native sources for key enzymes may also be used either directly (such as yeast or microbes which express a key enzyme normally) or by further isolation of the key enzyme. A key enzyme may be provided by a source selected from the group consisting of transgenic plant expressing one or more key enzymes, recombinant microbe expressing one or more key enzymes, transgenic yeast expressing one or more key enzymes, microbe expressing one or more key enzymes, and yeast expressing one or more key enzymes.

Isomaltulose and trehalulose can be hydrolyzed by alpha-1,6-glucosidase enzymes. Exemplary glucosidase enzymes are set forth in SEQ ID NO:1-6 herein. Additional sequences are described in U.S. Pat. No. 5,786,140, and in Börnke et al. (2001) Journal of Bacteriology 183(8):2425-2430, each of which is herein incorporated by reference in its entirety.

Dextran-degrading enzymes form a diverse group of different carbohydrases and transferases. These enzymes have often been classified as endo- and exodextranases based on the mode of action and commonly called dextranases and include enzymes such as dextranases (EC3.2.1.11), glucan-1,6-alpha-D-glucosidases (EC3.2.1.70), glucan-1,6-alpha-isomaltosidases (EC3.2.1.94), dextran 1,6-alpha-isomaltotriosidases (EC3.2.1.95), and branched-dextran exo-1,2-alpha-glucosidases (EC3.2.1.115)

Exodextranases, such as glucodextranase (EC3.2.1.70; glucan 1,6-alpha-glucosidase), catalyze stepwise hydrolysis of the reducing terminus of dextran and derived oligosaccharides to yield solely alpha-D-glucose; i.e., hydrolysis is accompanied by inversion at carbon-1 in such a way that new reducing ends are released only in the alpha-configuration. Some bacteria and yeasts are known to produce glucodextranases. Dextran-inducible extracellular glucodextranase occurs in *Arthrobacter globiformis* strains I42 and T-3044 (Oguma and Kobayashi (1996) J. Appl. Glycosci. 43:73-78; Oguma et al. (1999) Biosci. Biotechnol. Biochem. 63:2174-2182).

Intracellular dextran glucosidases (EC3.2.1.) producing alpha-D-glucose from dextran exist in several strains of *Streptococcus mitis* (Linder and Sund (1981) Caries Res. 15:436-444; Walker and Pulkownik (1973) Carbohydr. Res. 29:1-14; Walker and Pulkownik (1974) Carbohydr. Res. 36:53-66).

The soil bacterium *A. globiformis* T6 isomaltodextranase (EC3.2.1.94; 1,6-alpha-D-glucan isomaltohydrolase) is an extracellular exoenzyme capable of hydrolyzing dextran by removing successive isomaltose units from the nonreducing ends of the dextran chains (Sawai and Yano (1974) J. Biochem. 75:105-112; Sawai and Nawa (1976) Agric. Biol. Chem. 40:1246-1250).

Branched dextran exo-1,2-alpha-glucosidase (EC3.2.1.115) was found in the culture supernatant of the soil bacterium *Flavobacterium* sp. strain M-73 by Mitsubishi et al. (1979) Agric. Biol. Chem. 43:2283-2290. The enzyme had a strict specificity for 1,2-alpha-D-glucosidic linkage at the branch points of dextrans (containing 12 to 34% of 1,2-alpha linkages) and related polysaccharides producing free D-glucose as the only reducing sugar.

A list of additional exemplary microbial dextran-hydrolyzing enzymes and their substrate specificities and hydrolysis products is provided in Khalikova et al. (2005) Microbiology and Molecular Biology Reviews 2005:306-325, which is herein incorporated by reference as it describes and lists various dextran-hydrolyzing enzymes.

Fructanases are fructosydases which catalyze the hydrolysis of fructosidic linkages in fructans to break the fructan down into simpler sugar molecules. Fructans can be hydrolyzed to fermentable sugars through the catalytic activity of fructanases. For example, the fructanase 2,1-β-D-fructan fructanohydrolase [EC 3.2.1.7] can hydrolyze fructan polymers into fructose monosaccharides which can be fermented to form ethanol.

Inulin can be converted to a fermentable carbohydrate using one or more inulase enzymes. Microbial inulinases (2,1-β-D-fructan fructanohydrolase [EC 3.2.1.7]) are usually inducible and exo-acting enzymes, which catalyze the hydrolysis of inulin by splitting off terminal fructosyl units (D-fructose).

Alternans can be hydrolyzed to form fermentable sugars by the activity of a alpha-1,6-glucosidase or alpha-1,3-glucosidase.

Methods

Provided herein are methods for improving the yield of carbohydrate in plants by expressing an enzyme capable of converting endogenous carbohydrate into locked carbohydrate. The locked carbohydrates accumulated in the plants described herein can be converted to fermentable carbohydrates using one or more of the key enzymes disclosed herein, which can then be used as fermentation feedstocks for ethanol, propanol, butanol or other fuel alcohol, ethanol-containing beverages (such as malted beverages and distilled spirits), and other fermentation products such as foods, nutraceuticals, enzymes and industrial materials. The methods for fermentation using plant-derived carbohydrate feedstocks are well known to those skilled in the art, with established processes for various fermentation products (see for example Vogel et al. 1996, Fermentation and Biochemical Engineering Handbook: Principles, Process Design, and Equipment, Noyes Publications, Park Ridge, N.J., USA and references cited therein). Key enzyme proteins could also be incorporated into the ethanol production process downstream of the feedstock step. It is envisioned that locked carbohydrates could be harvested and, in the process of making ethanol, the key enzyme is added during the production process. Key enzyme proteins could also be incorporated into the fermentable sugar production process downstream of the feedstock step. It is envisioned that locked carbohydrates could be harvested and, in the process of making fermentable sugar, the key enzyme is added during the production process.

In one embodiment, the use of the methods disclosed herein results in a substrate that leads to higher ethanol yields compared to the ethanol yield from plant material not accumulating locked carbohydrates. The increase in ethanol yield can be at least about 1%, at least about 2%, at least about 3%, at least about 4%, at least about 5%, at least about 6%, at least about 7%, at least about 8%, at least about 9%, at least about 10%, at least about 20%, at least about 20%, at least about 30%, at least about 40%, at least about 50%, at least about 60%, at least about 70%, at least about 80%, at least about 90%, at least about 100%, at least about 2-fold, at least about 3-fold, at least about 4-fold, at least about 5-fold, or greater. Even small increases in ethanol yield will translate to large volumes of ethanol produced over time in a commercial-scale fermentation process. Such improvements in ethanol production could result in a significant increase in profit to the ethanol producer.

In one embodiment, the use of the methods disclosed herein results in a substrate that leads to higher carbohydrate yields compared to the carbohydrate yield from plant material not accumulating locked carbohydrates. The increase in carbohydrate yield can be at least about 1%, at least about 2%, at least about 3%, at least about 4%, at least about 5%, at least about 6%, at least about 7%, at least about 8%, at least about 9%, at least about 10%, at least about 20%, at least about 20%, at least about 30%, at least about 40%, at least about 50%, at least about 60%, at least about 70%, at least about 80%, at least about 90%, at least about 100%, at least about 2-fold, at least about 3-fold, at least about 4-fold, at least about 5-fold, or greater. Even small increases in carbohydrate yield will translate to large volumes of carbohydrate produced over time in a commercial-scale fermentation process. The carbohydrate may be sucrose or a combination of sucrose and a locked sugar.

In another embodiment, the plants accumulating locked carbohydrates can be used in various other downstream products other than ethanol production. Locked carbohydrates can be converted into fermentable sugars which are used in many commercial fermentation processes including growing recombinant yeast which produce important chemicals such as insulin, antibodies, or enzymes. Isomaltulose is currently used to manufacture sugar alcohols consumed as low-calorie, non-cariogenic sweeteners. Fructose also has value as a sweetener in high fructose syrups such as high fructose corn syrup. Plants engineered to produce fructans as a locked sugar may be used as a source of fructans which, after hydrolysis by a fructanase enzyme, produce a solution with a high fructose concentration. In such plants the yield of fructan may be increased by expressing an additional enzyme (e.g., glucose isomerase) to catalyze the conversion of glucose to fructose. The glucose isomerase (invertase) could be expressed in maize endosperm, or expressed in microbes. The purified enzyme could be used to produce fructans, glucans and alternans.

Sweeter plant products can be generated by expressing in plants a combination of enzymes that first allow for the accumulation of fructans in the plant and then convert the fructans directly or indirectly to fructose. Expressing invertase (glucose isomerase) in plants accumulating fructans will lead to a higher sweetness index in the plant.

In another embodiment, plants accumulating locked carbohydrates as described herein are useful for providing protection of the plant against disease. While not being bound by any particular theory or mechanism, plants accumulating locked sugars may be more tolerant or resistant to microbial infection due to the presence of carbohydrates other than sucrose, since infection by some microbes depends upon the content of sucrose in the plant.

Enzyme Extracts for Key Enzyme

In various embodiments of the present invention, the enzyme capable of converting the locked carbohydrate to a fermentable carbohydrate (referred to herein as the "key" enzyme) is provided as a purified or partially-purified preparation of the enzyme. The exogenously-added key enzyme may be de novo synthesized, or may be isolated from an organism expressing the enzyme prior to addition of the enzyme to the locked carbohydrate-containing plant material.

A purified or semi-purified preparation of enzyme will contain at least one class of key enzyme, but may also contain one or more additional enzymes of the same or different class. The preparation may further comprise one or more additional enzymes useful in the starch conversion method, such as amylase or glucoamylase. A "semi-purified" enzyme preparation will contain one or more key enzymes, one or more additional enzymes useful in the starch conversion process, or may contain other buffers or stabilizing agents (e.g., glycerol). Furthermore, the semi-purified enzyme preparation may also be culture supernatant or crude extract collected from a cell population expressing and/or secreting the enzyme. The preparation may also be a lyophilized formulation of enzyme that is reconstituted upon addition to the locked carbohydrate-containing plant material.

The various key enzymes discussed herein can be expressed in and isolated from any number of eukaryotic and prokaryotic organisms. Appropriate expression cassettes, vectors, transformation, and transfection techniques for a particular organism of interest will be evident to one of skill in the art.

In one embodiment, bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Microbacterium*, and *Staphylococcus* can be used as a host to express one or more classes of key enzymes encompassed herein. Methods for transformation of bacterial hosts are described in, for example, U.S. Patent Publication No. 2003/0135885.

In another embodiment, fungal hosts, such as fungal host cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces*, etc. may be used. Transformation of fungus may be accomplished according to Gonni et al. Agric. Biol. Chem., 51:2549 (1987).

Another suitable host includes any number of eukaryotic cells, for example, insect cells such as *Drosophila* S2 and *Spodoptera* Sf9; animal cells such as CHO, COS or Bowes melanoma, C127, 3T3, CHO, HeLa and BHK cell lines. Any host can be used insofar as it can express the gene of interest. The American Type Culture Collection maintains cell lines from a wide variety of sources and many of these cultures can be used to generate a transgenic cell line capable of expressing a heterologous enzyme. Transformation vectors appropriate for eukaryotic cells are available commercially such as pXT1, pSG5 (Stratagene) pSVK3, pBPV, pMSG, and pSVLSV40 (Pharmacia). Techniques for transformation and selection of transgenic eukaryotic cells are well known in the art. Exemplary methods are also described elsewhere herein.

In another embodiment, the key enzymes can be isolated from an organism that endogenously expresses the enzyme, or the organism expressing the enzyme can be used in one or more fermentation steps without the need for purification or isolation of the enzyme from the organism.

Additional methods for generating an enzyme extract are described in, for example, Conrad et al. (1995) *Eur. J. Biochem.* 230, 481-490; Chiang et al. (1979) Starch 31 Nr.3, S.86-92; Schwardt, E. (1990) Food Biotechnology, 4(1), 337-351; Morgan and Priest (1981) Journal of Applied Bacteriology 50, 107-114; Laderman et al. (1993) Journal of Biological Chemistry Vol. 268, No. 32, pp. 24394-24401, each of which is herein incorporated by reference in its entirety.

Transgenic Plants

In one embodiment of the present invention, the locked carbohydrate-containing plant material comprises plant parts derived from at least one variety of a transgenic plant expressing at least one polynucleotide encoding a lock enzyme. In another embodiment, the transgenic plant material expresses more than one lock enzyme, resulting in the accumulation of more than one type of locked carbohydrate. In yet another embodiment, both the lock and the key enzymes are expressed in plant material. Where both the lock and the key enzymes are provided as transgenic plant material, each class of enzyme may be expressed in the same plant variety, or may be expressed in different plant varieties.

As used herein the term "transgenic" refers to plants that include an exogenous polynucleotide (e.g., gene) that is stably maintained in the transformed plant and is stably inherited by progeny in successive generations. The term "transgenic plant" can refer either to the initially transformed plant or to the progeny of the initially transformed plant. Techniques for transforming plants, plant cells or plant tissues can include, but are not limited to, transformation with DNA employing *A. tumefaciens* or *A. rhizogenes* as the transforming agent, electroporation, DNA injection, microprojectile bombardment, and particle acceleration. See, for example, EP 295959 and EP 138341. As used herein, the terms "plant material" or "plant part" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

Where both the lock and the key enzymes are provided by transgenic plant material, it is not necessary for the plant material expressing the key enzyme to be 100% transgenic for the key enzyme. Rather, it is only necessary for the plant material to contain an amount of key enzyme that is sufficient for the downstream use (e.g., for conversion of locked carbohydrates to fermentable sugars). For example, for fermentation purposes, a sufficient amount of the key enzyme may be provided in the fermentation process by less than 100% key enzyme-expressing plant material. For example, a sufficient amount of key enzyme may be provided to the fermentation process when only about 0.1% of the locked carbohydrate-containing plant material expresses the key enzyme, or only about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%, of the plant material. However, it is contemplated that the percentage of plant material expressing the key enzyme could be as much as 100%, including, for example, about 25%, about 30%, about 35%, about 40%, about 50%, about 60%, about 65%, about 70%, about 80%, about 90%, about 95%, or about 99% of the plant material.

The methods of the invention are particularly useful in plants producing high amounts of sugar, such as (for example), sugarcane, sugar beet, and sorghum. However, the plant material can be derived from any plant, including but not limited to plants producing edible flowers such as cauliflower (*Brassica oleracea*), artichoke (*Cynara scolvmus*), and safflower (*Carthamus*, e.g. *tinctorius*); fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (Citrus limon), melon (*Cucumis melo*), nuts (such as the walnut, Juglans, e.g. regia; peanut, *Arachis* hypoaeae), orange (Citrus, e.g. maxima), peach (*Prunus*, e.g. *persica*), pear (*Pyra*, e.g. *communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leafs, such as alfalfa (*Medicago*, e.g. *sativa*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. oleraceae), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (Glycine, e.g. max), wheat (*Triticum*, e.g. *aestivum*), barley (*Hordeum*, e.g. *vulgare*), corn (*Zea*, e.g. *mays*), rice (*Oryza*, e.g. *sativa*); grasses, such as *Miscanthus* grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. oleraceae), potato (*Solanum*, e.g. *tuberosum*), and the like.

The locked carbohydrate-containing plant material may also comprise one or more varieties of plants having naturally-occurring genetic variability resulting in altered starch metabolism. Many such plants carry mutations in genes encoding isoforms of starch synthesis or starch degradation enzymes. For example, plants have been identified which are heterozygous or homozygous for one or more of the waxy (wx), amylose extender (ae), dull (du), horny (h), shrunken (sh), brittle (bt), floury (fl), opaque (O), or sugary (su) mutant alleles. See, for example, U.S. Pat. Nos. 4,428,972; 4,767,849; 4,774,328; 4,789,738; 4,789,557; 4,790,997; 4,792,458; 4,798,735; and 4,801,470, herein incorporated by reference.

Dual Expression of Lock Enzymes

The invention also comprises the simultaneous expression of two lock enzymes such as two sucrose isomerases, one that produces predominantly isomaltulose, and one that produces predominantly trehalulose, so that both isomers of sucrose may be accumulated in the same plant. Sugarcane possesses an excess capacity for carbohydrate synthesis, however, there is a continuous "futile cycle" of sucrose synthesis and breakdown in sugarcane. By diverting carbohydrates into a form that is not metabolized by the plant, these carbohydrates may be removed from that futile cycle, and the plant may make up for the loss by producing more sucrose. The fact that Wu and Birch have seen isomaltulose accumulate to the same level as sucrose, without decreasing the amount of sucrose, suggests that this excess capacity of sugarcane for sugar synthesis has not been exhausted. By genetically modifying sugarcane with two or more lock enzymes that produce more than one isomers of sucrose (isomaltulose, trehalulose, leucrose, etc.) at equivalent levels it may be possible to significantly increase the total sugar content in sugarcane, or to increase the level of locked sugar in the sugarcane.

In one embodiment, the total carbohydrate content, or the total locked carbohydrate content, or both, is increased at least about 10%, at least about 20%, at least about 50%, at least about 100%, at least about 125%, at least about 150%, at least about 2-fold, at least about 3-fold, at least about 4-fold or greater when compared to the same variety of plant that does not accumulate locked carbohydrate according to the methods of the invention.

Sucrose isomerase enzymes producing predominantly isomaltulose include, for example, the *P. dispersa* UQ68J enzyme described in U.S. Pat. No. 7,250,282, which is herein incorporated by reference in its entirety. Other enzymes producing predominantly trehalulose include, for example, the whitefly enzyme characterized by Salvucci (2003) Comp. Biochem. Physiol. B 135:385-395. While not to be limited by theory, the whitefly enzyme may be a representative of the lock enzyme trehalulose synthase.

Subcellular Targeting

For the purpose of producing starch in a transgenic plant, it may be advantageous to target the lock enzyme in the plant to subcellular compartments that have high concentrations of sucrose, such as the vacuole of sugarcane. Another target may be the vacuole of the maize endosperm. Targeting an enzyme capable of synthesizing starch from sucrose to the vacuole of maize endosperm cells may permit the accumulation of more starch in the maize endosperm as naturally occurring enzymes do not produce starch in the vacuoles of maize endosperm cells. Alternatively targeting to the apoplast is another way to achieve conversion of sucrose into locked sugars such as starch or isomaltulose. In plants such as maize, sucrose accumulates in the leaf and is transported to the ear during grain filling which provides a carbon sink.

In one embodiment, the lock enzyme is targeted to the amyloplast, where locked carbohydrate can accumulate, and the key enzyme (when expressed in the same plant) is targeted to the apoplast. The key enzyme can be targeted to the apoplast using, for example, the maize Gamma zein N-terminal signal sequence, which confers apoplast-specific targeting of proteins. The lock enzyme may be targeted to the amyloplast by, for example, fusion to the waxy amyloplast targeting peptide (Klosgen et al., 1986) or to a starch granule. For example, the polynucleotide encoding the lock enzyme may be operably linked to a chloroplast (amyloplast) transit peptide (CTP) and a starch binding domain, e.g., from the waxy gene.

Directing the key enzyme to the apoplast will allow the enzyme to be localized in a manner that it will not come into contact with the locked carbohydrate substrate. In this manner the enzymatic action of the enzyme will not occur until the enzyme contacts its substrate. The enzyme can be contacted with its substrate by the process of milling (physical disruption of the cell integrity), or heating the cells or plant tissues to disrupt the physical integrity of the plant cells or organs that contain the enzyme. For example the key enzyme can be targeted to the apoplast or to the endoplasmic reticulum so as not to come into contact with the locked carbohydrate in the amyloplast. Milling of the grain will disrupt the integrity of the grain and the key enzyme will then contact the starch granules. In this manner the potential negative effects of co-localization of an enzyme and the locked carbohydrate can be circumvented.

Locked Carbohydrates as Selectable Markers

Plant transformation requires the use of positive selectable marker genes for identification and propagation of transformed tissue and the elimination of non-transformed tissue. One advantage of this system would be the ability to select and/or screen for expression and/or accumulation of the key enzyme involved in the breakdown of the locked carbohydrates, from the very earliest stages of the plant transformation process. A transformation system using the desired enzyme end product as a means of initial selection would permit early screening for position effects or genomic insertion sites that lead to high level or constitutive expression of the transgene. Also, the use of the desired end product as the selectable marker can reduce the number of genes that must be transferred into the plant. This will reduce the size of the T-DNA needed for transformation and be useful in the production of "molecular stacks" in which multiple transgenes are desired in a single transgenic plant, i.e., eliminate the need for an extraneous selectable marker gene such as PMI, or antibiotic resistance genes that are necessary for production of transgenic plants, but are no longer useful to the plant after transformation/selection. However, it is contemplated that multiple selectable markers can be used in the methods of the invention, including those used solely for selection.

In one embodiment, an alpha-1,6-glucosidase enzyme may be used to cleave the alpha-1,6-glucoside linkage between glucose and fructose in the disaccharide isomaltulose. This enzyme is desirable for converting isomaltulose produced by transgenic sugarcane plants into fermentable sugar or ethanol and may be useful as a novel selectable marker for sugarcane transformation.

Expression Cassettes

A plant or plant part expressing a lock and/or key enzyme can be obtained by introducing into the plant or plant part a heterologous nucleic acid sequence encoding the enzyme. The heterologous nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the heterologous nucleotide sequence of interest (i.e., lock and/or key enzyme) which is operatively linked to termination signals. It also typically comprises sequences required for proper translation of the nucleotide sequence. The expression cassette comprising the lock and/or key enzyme may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the lock and/or key enzyme. See, Guo et al. (2003) Plant J. 34:383-92 and Chen et al. (2003) Plant 3.36:731-40 for examples of sequences allowing for inducible expression.

The regulatory sequences of the expression construct are operably linked to the nucleic acid sequence encoding the lock and/or key enzyme. By "operably linked" is intended a functional linkage between a first sequence and a second sequence for instance, the first sequence may be a promoter sequence which is operably linked to a second sequence wherein the promoter sequence initiates and mediates transcription of the DNA sequence corresponding to the second sequence. Generally, operably linked means that the nucleotide sequences being linked are contiguous; however, the sequences may have linking sequences that join them together, thus the operably linked sequences may not be directly linked.

Promoter

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

The choice of promoters to be included depends upon several factors, including, but not limited to, efficiency, selectability, inducibility, desired expression level, and cell- or tissue-preferential expression. For example, where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. It is a routine matter for one of skill in the art to modulate the expression of a sequence by appropriately selecting and positioning promoters and other regulatory regions relative to that sequence.

A number of plant promoters have been described with various expression characteristics. Examples of some constitutive promoters which have been described include the rice actin 1 (Wang et al., Mol. Cell. Biol., 12:3399 (1992); U.S. Pat. No. 5,641,876), CaMV 35S (Odell et al., Nature, 313:810 (1985)), CaMV 19S (Lawton et al., 1987), nos (Ebert et al., 1987), Adh (Walker et al., 1987), sucrose synthase (Yang & Russell, 1990), and the ubiquitin promoters.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and smas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm.

Tissue specific expression may be functionally accomplished by introducing a constitutively expressed gene (all tissues) in combination with an antisense gene that is expressed only in those tissues where the gene product is not desired.

Moreover, several tissue-specific regulated genes and/or promoters have been reported in plants. Some reported tissue-specific genes include the genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al., Seed Science Research, 1:209 (1991)). Examples of tissue-specific promoters, which have been described include the lectin (Vodkin, Prog. Clin. Biol. Res., 138; 87 (1983); Lindstrom et al., Der. Genet., 11:160 (1990)), corn alcohol dehydrogenase 1 (Vogel et al., EMBO J., 11:157 (1989); Dennis et al., Nucleic Acids Res., 12:3983 (1984)), corn light harvesting complex (Simpson, 1986; Bansal et al., Proc. Natl. Acad. Sci. USA, 89:3654 (1992)), corn heat shock protein (Odell et al., Nature, 313: 810 (1985)); pea small subunit RuBP carboxylase ((Poulsen et al., Mol. Gen. Genet. 205:193 (1986)); Ti plasmid mannopine synthase ((Langridge et al., Cell 34:1015 (1989)), Ti plasmid nopaline synthase ((Langridge et al., Cell 34:1015 (1989)), petunia chalcone isomerase (vanTunen et al., EMBO J., 7; 1257 (1988)), bean glycine rich protein 1 (Keller et al., Genes Dev., 3:1639 (1989)), truncated CaMV 35S (Odell et al., Nature, 313:810 (1985)), potato patatin (Wenzler et al., Plant Mol. Biol., 13:347 (1989)), root cell (Yamamoto et al., Nucleic Acids Res., 18:7449 (1990)), maize zein (Reina et al., Nucleic Acids Res., 18:6425 (1990); Kriz et al., Mol. Gen. Genet., 207:90 (1987); Wandelt et al., Nucleic Acids Res., 17:2354 (1989); Langridge et al., Cell, 34:1015 (1983); Reina et al., Nucleic Acids Res., 18:7449 (1990)), globulin-1 (Belanger et al., Genetics, 129:863 (1991)), α-tubulin, cab (Sullivan et al., Mol. Gen. Genet., 215:431 (1989)), PEPCase ((Hudspeth et al., Plant Mo. Bio., 12:579 (1989)), R gene complex-associated promoters (Chandler et al., Plant Cell, 1:1175 (1989)), and chalcone synthase promoters (Franken et al., EMBO J., 10:2605 (1991)). Particularly useful for seed-specific expression is the pea vicilin promoter (Czako et al., Mol. Gen. Genet., 235:33 (1992). (See also U.S. Pat. No. 5,625,136, herein incorporated by reference.) Other useful promoters for expression in mature leaves are those that are switched on at the onset of senescence, such as the SAG promoter from *Arabidopsis* (Gan et al., Science, 270:1986 (1995).

In various embodiments, the lock and/or key enzyme is active in the fruit of the plant. A class of fruit-specific promoters expressed at or during antithesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., Proc. Natl. Acad. Sci. USA, 89:5769 (1992). cDNA clones from tomato displaying differential expression during fruit development have been isolated and characterized (Mansson et al., Gen. Genet., 200:356 (1985), Slater et al., Plant Mol. Biol., 5:137 (1985)). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065, which disclosures are incorporated herein by reference. The fruit specific E8 promoter is described in Deikman et al. (1988, EMBO J. 2: 3315-3320) and DellaPenna et al. (1989, Plant Cell 1: 53-63). In another embodiment, promoters that selectively express coding sequences in sucrose storage tissues (such as the mature stems of sugarcane and the tubers of sugar beet) may be used. For example, promoters specific for the mature stems of sugarcane are described in International Publication WO 01/18211.

In another embodiment, the expression of the lock enzyme is under the control of a sink tissue-specific promoter. By "sink tissue-specific promoter" is meant a promoter that preferentially directs expression of an operably linked transcribable sequence in the sink tissue of a plant as compared to expression in other tissues of the plant, including source tissues (e.g., leaf). "Sink cell" and "sink tissue" as used herein, refer to cells, tissues or organs which at the time of harvest comprise organic carbon that has entered the cells by net inflow in a form other than carbon dioxide. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., Proc. Natl. Acad. Sci. USA, 89:5769 (1992). The E6 gene is most active in fiber, although low levels of transcripts are found in leaf, ovule and flower. Other tissue-specific promoters can be isolated by one skilled in the art (see U.S. Pat. No. 5,589,379).

Several inducible promoters have been reported. Many are described in a review by Gatz, in Current Opinion in Biotechnology, 7:168 (1996) and Gatz, C., Annu. Rev. Plant Physiol. Plant Mol. Biol., 48:89 (1997), Examples include tetracycline repressor system, Lac repressor system, copper-inducible systems, salicylate-inducible systems (such as the PR1a system), glucocorticoid-inducible (Aoyama T. et al., N—H Plant Journal, 11:605 (1997)) and ecdysone-inducible systems. Other inducible promoters include ABA- and turgor-inducible promoters, the promoter of the auxin-binding protein gene (Schwob et al., Plant J., 4:423 (1993)), the UDP glucose flavonoid glycosyl-transferase gene promoter (Ralston et al., Genetics, 119:185 (1988)), the MPI proteinase inhibitor promoter (Cordero et al., Plant J., 6:141 (1994)), and the glyceraldehyde-3-phosphate dehydrogenase gene promoter (Kohler et al., Plant Mal. Biol., 29; 1293 (1995); Quigley et al., J. Mol. Evol., 29:412 (1989); Martinez et al., J. Mol. Biol., 208:551 (1989)). Also included are the benzene sulphonamide-inducible (U.S. Pat. No. 5,364,780) and alcohol-inducible (WO 97/06269 and WO 97/06268) systems and glutathione S-transferase promoters.

Other studies have focused on genes inducibly regulated in response to environmental stress or stimuli such as increased salinity, drought, pathogen and wounding. (Graham et al., J. Biol. Chem., 260:6555 (1985); Graham et al., J. Biol. Chem., 260:6561 (1985), Smith et al., Planta, 168:94 (1986)). Accumulation of metallocarboxypeptidase-inhibitor protein has been reported in leaves of wounded potato plants (Graham et al., Biochem. Biophys. Res. Comm., 101:1164 (1981)). Other plant genes have been reported to be induced by methyl jasmonate, elicitors, heat-shock, anaerobic stress, or herbicide safeners.

Preferably, in the case of a multicellular organism, the promoter can also be specific to a particular tissue, organ or stage of development. Examples of such promoters include, but are not limited to, the *Zea mays* ADP-gpp and the *Zea mays* Gamma zein promoter and the *Zea mays* globulin promoter.

Expression of a gene in a transgenic plant may be desired only in a certain time period during the development of the plant. Developmental timing is frequently correlated with tissue specific gene expression. Timing the expression of carbohydrate-metabolizing enzymes advantageously takes into consideration the change in carbohydrate concentration that occurs during plant development. The importance of a carbohydrate within tissue may also change with time and, in this regard, sink tissue may undergo changes in sucrose concentrations during development. For example, sucrose concentration in certain fruits such as sweet melons changes as the fruit matures. Hexose sugars accumulate early in development, followed by high levels of sucrose at later stages (Schaffer et al., 1987, Phytochemistry 26: 1883-1887). In developing corn endosperm, sucrose concentration increases from 8 to 12 days after pollination and then drops more than ten fold 28 days after pollination (Tsai et al., 1970, Plant Phys. 46: 299-306). Additionally, sucrose concentration in soybean seed changes significantly during development as raffinose saccharides content increases dramatically, 53 days after anthesis (Amuti, 1977, Phytochemistry 16: 529-532). In pea seed, sucrose content falls dramatically with continued development (Holl and Vose, Can. 1980, J. Plant Sci. 60: 1109-1114). These examples illustrate the desirability of promoter selection for specific expression of an enzyme gene timed to take advantage of fluctuating sucrose pools. Thus, in various embodiments, the promoter is an inducible promoter which is capable of driving expression of the enzyme-encoding polynucleotide at an appropriate developmental stage of the plant. In this embodiment, the transcriptional control element is suitably a developmentally regulated promoter to control the timing of expression.

Localization Signals

The polynucleotide sequences encoding the lock and/or key enzyme of the present invention may be operably linked to polynucleotide sequences encoding localization signals or signal sequence (at the N- or C-terminus of a polypeptide), e.g., to target the enzyme to a particular compartment within a plant. Examples of such targets include, but are not limited to, the vacuole, endoplasmic reticulum, chloroplast, amyloplast, starch granule, or cell wall, or to a particular tissue, e.g., seed. The expression of a polynucleotide encoding a lock and/or key enzyme having a signal sequence in a plant, in particular, in conjunction with the use of a tissue-specific or inducible promoter, can yield high levels of localized enzyme in the plant. Targeting or signal sequences can be used to localize a lock or key enzyme such that the enzyme does not come into contact with a specific substrate during the growth and development of the plant. For instance, key enzymes expressed in plants that accumulate locked sugars may be targeted away from the plant organelle or compartment which contains the locked sugar. At the time of harvest, the plant tissue may be physically disrupted in order to combine the key enzyme with the locked sugar during the processing of the plant tissue.

Thus, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

Numerous signal sequences are known to influence the expression or targeting of a polynucleotide to a particular compartment or outside a particular compartment. Suitable signal sequences and targeting promoters are known in the art and include, but are not limited to, those provided herein.

In one embodiment, the lock enzyme carbohydrate can accumulate, and the key enzyme is targeted to the apoplast. The key enzyme can be targeted to the apoplast using, for example, the maize Gamma zein N-terminal signal sequence, which confers apoplast-specific targeting of proteins. The lock enzyme may be targeted to the amyloplast by, for example, fusion to the waxy amyloplast targeting peptide (Klosgen et al., Mol Gen Genet. 203: 237-2441986) or to a starch granule. For example, the polynucleotide encoding the lock enzyme may be operably linked to a chloroplast (amyloplast) transit peptide (CTP) and a starch binding domain, e.g., from the waxy gene. Alternatively, the maize Brittle 1 transit peptide sequence (Bt1ts, Sullivan and Kaneko, Planta 196: 477-484 (1995)) can be used for amyloplast targeting. In other embodiments, the total carbohydrate content or sweetness or the endogenous carbohydrate content of the sink tissue is increased by targeting the carbohydrate-metabolizing enzyme to a sub-cellular compartment used for carbohydrate storage in the plant cells (e.g., vacuole or apoplasmic space).

A signal sequence such as the maize Gamma zein N-terminal signal sequence for targeting to the endoplasmic reticulum and secretion into the apoplast may be operably linked to a polynucleotide encoding the key enzyme in accordance with the present invention (Torrent et al., Plant Mol. Biol. 34:139 (1997)). Another signal sequence is the amino acid sequence SEKDEL (SEQ ID NO:7) for retaining polypeptides in the endoplasmic reticulum (Munro et al. Cell 48:899 (1987)).

Enhancers

Numerous sequences have been found to enhance gene expression from within the transcriptional unit and these sequences can be used in conjunction with the genes of this invention to increase their expression in transgenic plants.

Various intron sequences have been shown to enhance expression. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., Virology 154: 9-20 (1986)); MDMV leader (Maize Dwarf Mosaic Virus); Virology 154:9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Tobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Regulatory Sequences

The polynucleotides of the present invention, in addition to processing signals, may further include other regulatory sequences, as is known in the art. "Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that are a combination of synthetic and natural sequences.

A variety of transcriptional terminators are available for use in expression cassettes. These are responsible for the termination of transcription beyond the transgene and correct mRNA polyadenylation. The termination region may be native with the transcriptional initiation region., may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Selectable Markers

Generally, the expression cassette will comprise a selectable marker gene for the selection of transformed cells. Selectable marker genes are utilized for the selection of transformed cells or tissues. Selectable markers may also be used in the present invention to allow for the selection of transformed plants and plant tissue, as is well-known in the art. One may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can select for by chemical means, i.e., through the use of a selective agent (e.g., a herbicide, antibiotic, or the like), or whether it is simply a trait that one can identify through observation or testing, i.e., by screening (e.g., the R-locus trait). Of course, many examples of suitable marker genes are known in the art and can be employed in the practice of the invention.

In one embodiment, both the lock and the key enzymes are expressed in the same plant, and the expression of the key enzyme is used as a selectable marker. In one example, the selection system is based on the expression of alpha-1,6-glucosidase in a plant accumulating isomaltulose. In such a system a means of breaking down isomaltulose into a substrate for fermentation is necessary, and may be provided in the form of sugarcane, sugarbeet, etc. plants engineered to express an alpha-1,6-glucosidase (isomaltulase, palatinase, etc.). Such a selectable marker system would be useful in screening for high level expression of alpha-1,6-glucosidase from the very earliest steps of plant transformation, this would be helpful in identifying integration events that are stable, highly expressed, and resistant to gene silencing. Also, this system could be used to select alpha-1,6-glucosidases with improved activity and in selecting for variants that increase protein or mRNA stability, localization to specific subcellular locations etc.

Also included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., β-lactamase, phosphinothricin acetyltransferase); and proteins that are inserted or trapped in the cell wall (e.g., proteins that include a leader sequence such as that found in the expression unit of extension or tobacco PR-S).

With regard to selectable secretable markers, the use of a gene that encodes a protein that becomes sequestered in the cell wall, and which protein includes a unique epitope is also encompassed herein. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extension, or hydroxyproline rich glycoprotein (HPRG). For example, the maize HPRG (Steifel et al., The Plant Cell, 2:785 (1990)) molecule is well characterized in terms of molecular biology, expression and protein structure. However, any one of a variety of extensions and/or glycine-rich wall proteins (Keller et al., EMBO Journal, 8:1309 (1989)) could be modified by the addition of an antigenic site to create a screenable marker.

Possible selectable markers for use in connection with the present invention include, but are not limited to, a neo or nptII gene (Potrykus et al., Mol. Gen. Genet., 199:183 (1985)) which codes for kanamycin resistance and can be selected for using kanamycin, G418, and the like; a bar gene which confers resistance to the herbicide phosphinothricin; a gene which encodes an altered EPSP synthase protein (Hinchee et al., Biotech., 6:915 (1988)) thus conferring glyphosate resistance; a nitrilase gene such as bxn from *Klebsiella ozaenae* which confers resistance to bromoxynil (Stalker et al., Science, 242:419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., J. Biol. Chem., 263:12500 (1988)); a dalapon dehalogenase gene that confers resistance to the herbicide dalapon; a phosphomannose isomerase (PMI) gene; a mutated anthranilate synthase gene that confers resistance to 5-methyl tryptophan; the hph gene which confers resistance to the antibiotic hygromycin; or the mannose-6-phosphate isomerase gene (also referred to herein as the phosphomannose isomerase gene), which provides the ability to metabolize mannose (U.S. Pat. Nos. 5,767,378 and 5,994,629). One skilled in the art is capable of selecting a suitable selectable marker gene for use in the present invention.

An illustrative embodiment of a selectable marker gene capable of being used in systems to select transformants are the genes that encode the enzyme phosphinothricin acetyltransferase, such as the bar gene from *Streptomyces hygroscopicus* or the pat gene from *Streptomyces* viridochromogenes. The enzyme phosphinothricin acetyl transferase (PAT) inactivates the active ingredient in the herbicide bialaphos, phosphinothricin (PPT). PPT inhibits glutamine synthetase, (Murakami et al., Mol. Gen. Genet., 205:42 (1986); Twell et al., Plant Physiol., 91:1270 (1989)) causing rapid accumulation of ammonia and cell death. The success in using this selective system in conjunction with monocots was particularly surprising because of the major difficulties which have been reported in transformation of cereals (Potrykus, Trends Biotech., 7:269 (1989)).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al., Mol. Gen. Genet., 205:42 (1986); Thompson et al., EMBO Journal, 6:2519 (1987)) as has the use of the bar gene in the context of plants other than monocots (De Block et al., EMBO Journal, 6; 2513 (1987); De Block et al., Plant Physiol., 91:694 (1989)).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in Chromosome Structure and Function, pp. 263-282 (1988)); a β-lactamase gene (Sutcliffe, PNAS USA, 75:3737 (1978)), which encodes an enzyme for which various chromogenic substrates are known (e.g., PADAC, a chromogenic cephalosporin); a xylE gene (Zukowsky et al., PNAS USA, 80:1101 (1983)) which encodes a catechol dioxygenase that can convert chromogenic catechols; a tyrosinase gene (Katz et al., J. Gen. Microbiol., 129:2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., Science, 234:856 (1986)), which allows for bioluminescence detection; or an aequorin gene (Prasher et al., Biochem. Biophys. Res. Comm., 126:1259 (1985)), which may be employed in calcium-sensitive bioluminescence detection, or a green fluorescent protein gene (Niedz et al., Plant Cell Reports, 14: 403 (1995)).

Genes from the maize R gene complex are contemplated to be particularly useful as screenable markers. The R gene complex in maize encodes a protein that acts to regulate the production of anthocyanin pigments in most seed and plant tissue. A gene from the R gene complex is suitable for maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

Additional Agronomic Traits

The plants disclosed herein may further exhibit one or more agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. Such trait may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). Various traits of interest, as well as methods for introducing these traits into a plant, are described, for example, in U.S. Pat. Nos. 5,569,823; 5,304,730; 5,495,071; 6,329,504; 6,337,431; 5,767,366; 5,928,937; 4,761,373; 5,013,659; 4,975,374; 5,162,602; 4,940,835; 4,769,061; 5,554,798; 5,879,903, 5,276,268; 5,561,236; 4,810,648; and 6,084,155; in European application No. 0 242 246; in U.S. Patent Application No. 20010016956; and on the worldwide web at wvvw.lifesci.sussex.ac.uk/home/Neil_Crickmore/Bt/.

Plant Transformation

Once a nucleic acid sequence encoding the lock and/or key enzyme has been cloned into an expression system, it is transformed into a plant cell. The word "plant" refers to any plant, particularly to seed plant, and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ. The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

Examples of methods of transformation of plants and plant cells include *Agrobacterium*-mediated transformation (De Blaere et al., 1987) and particle bombardment technology (Klein et al. 1987; U.S. Pat. No. 4,945,050). Whole plants may be regenerated from transgenic cells by methods well known to the skilled artisan (see, for example, Fromm et al., 1990).

The expression cassettes of the present invention can be introduced into the plant cell in a number of art-recognized ways. The term "introducing" in the context of a polynucleotide, for example, a nucleotide encoding an enzyme disclosed herein, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors.

Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred as discussed elsewhere herein.

Methods for regeneration of transformed plants are well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can also be utilized. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This method can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid that is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable.

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

The lock and/or key enzymes disclosed herein may also be incorporated into or maintained in plant lines through breeding or through common genetic engineering technologies. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The relevant techniques are well known in the art and include but are not limited to hybridization, inbreeding, backcross breeding, multi-line breeding, dihaploid inbreeding, variety blend, interspecific hybridization, aneuploid techniques, etc. Hybridization techniques also include the sterilization of plants to yield male or female sterile plants by mechanical, genetic (including transgenic), chemical, or biochemical means.

The following examples are offered by way of illustration and not by way of limitation.

EXPERIMENTAL

Standard recombinant DNA and molecular cloning techniques used here are well known in the art and are described by J. Sambrook, E. F. Fritsch and T. Maniatis, Molecular Cloning: A Laboratory manual, Cold Spring Harbor laboratory, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

EXAMPLE 1

Enzymes that can Produce Locked Sugars

1A: Bacterial Expression System of His-Tagged Enzymes

Selected genes coding for specific enzymes were cloned into an *Escherichia coli* expression vector, pET24b (Novagen), using restriction sites that place the coding sequence in-frame downstream of an inducible T7lac promoter. Polynucleotide sequences coding for specific enzymes were generated by back translating the polypeptide sequence of the enzyme using the codon preference for *E. coli*. The expression plasmids were introduced into an *E. coli* expression strain, BL21 Star (DE3) (Invitrogen). Recombinant *E. coli* isolates containing the modified pET24b expression vector were selected on standard LB agar containing 50 ug/mL kanamycin.

Recombinant *E. coli* isolates were grown with shaking at 37 degrees C. for 8 hours to overnight in 20 mL of LB media containing 50 ug/mL kanamycin. The 20 mL of *E. coli* culture was transferred to 1 L of autoinduction media (9.57 g trypton, 4.8 g yeast extract, 2 ml of 1 M MgSO4, 1 mL of 1000× trace metals, 20 ml of 50×5052, 20 mL of 50×M) (1000× trace metals: 36 mL sterile water, 50 mL of 0.1M FeCl3 in 0.12M HCl, 2 mL of 1M CaCl2, 1 mL of 1M MnCl2 4 H20, 1 mL of 1M ZnSO4 7 H20, 1 mL of 0.2M CoCl2 6 H20, 2 mL of 0.1M CuCl2 2 H20, 1 mL of 0.2M NiCl2 6 H20, 2 mL of 0.1M Na2MoO4 2 H20, 2 mL of 0.1M H3BO3) (50×5052: 25 g glycerol, 73 mL H20, 2.5 g glucose 10 g alpha-lactose monohydrate) (50×M: 80 mL H20, 17.75 g Na2HPO4, 17.0 g KH2PO4, 13.4 g NH4Cl, 3.55 g Na2SO4) with 25 ug/mL kanamycin and grown with shaking at 28 degrees C. overnight. The *E. coli* cells were harvested out of the autoinduction media by centrifugation at 10,000×g for 15 minutes and the collected cells were frozen at −80 degrees C.

1B: Sucrose Isomerase (E.C. 5.4.99.11)

The amino acid sequence for a sucrose isomerase expressed by *Erwinia carotovora* has been listed in GeneBank under the accession number YP049947 (SEQ ID NO: 14). The amino acid sequence of this sucrose isomerase was back translated into a polynucleotide coding sequence using the codon preference of *E. coli*. The polynucleotide sequence was generated by gene synthesis (GeneArt) and cloned into the expression vector pET24b (Novagen) using restriction sites that place the coding sequence in-frame downstream of an inducible T7lac promoter. This expression plasmid was introduced into an *E. coli* expression strain, BL21, harboring λDE3 lysogen. After growing for 3 hours in LB media containing 50 microgram/microliter kanamycin, the cells were induced to produce the *E. carotovora* sucrose isomerase enzyme with IPTG at a final concentration of 1 mM. The *E. coli* cells were harvested 3 hours after induction by centrifugation at 10,000×g for 10 min and the supernatant was removed. Cells were lysed by resuspending the cell pellet in BugBuster reagent (Novagen) containing lysozyme (1KU/1 mL BugBuster) and benzonase (25 units/1 mL BugBuster) followed by incubation for 10 mM on a shaking platform. Insoluble debris was removed by centrifugation at 16,000×g for 20 min at 4 degrees C. Supernatant containing total soluble protein and the recombinant enzyme was transferred to a fresh 1.5 mL Eppendorf tube and aliquots were stored at 4 degrees C. and −20 degrees C. for further characterization.

Sucrose isomerase enzyme activity was assayed by combining the enzyme with the substrate, sucrose, and measuring the production of isomaltulose and trehalulose. The total soluble protein extract from the recombinant *E. coli* was assayed for sucrose isomerase activity by incubating 10 microliters of supernatant *E. coli* lysate, as described above, with 90 microliters of 292 mM sucrose 50 mM sodium phosphate buffer (pH 6.0) at 30 degrees C. for 20 hours. The reaction product was screened for the presence of isomaltulose and trehalulose by thin layer chromatography (TLC) and high pressure liquid chromatography (HPLC).

TLC was performed by spotting 3 microliters of the supernatants of the growth media onto AL SIL G silica gel plates (Whatman) and developed twice in a solvent consisting of 3 parts ethylacetate: 3 parts acetic acid: 1 part distilled water. After drying, the plates were sprayed with a dye mixture consisting of 4 milliliters aniline, 4 g diphenylamine, 200 milliliters acetone, and 30 milliliters 80% phosphoric acid. Isomaltulose and trehalulose were distinguished from other sugars, such as sucrose, by their relative mobility and by the distinct colors produced when they reacted with aniline dye. Greenish yellow indicates the presence of isomaltulose, red indicates the presence of trehalulose, and brown/black indicates the presence of sucrose. The monosaccharides, glucose and fructose, produced by hydrolysis of sucrose were blue or red-orange respectively.

Identification of the sugars present in each lane of the developed TLC plate was possible by comparing both the relative mobility of the sugars present in the samples and the staining color with aniline dye to the relative mobility and staining color of sugar standards. The reaction product of sucrose isomerase incubated with sucrose as described above was three colored bands. The highest mobility band had a purple color and migrated with the same mobility as both glucose and fructose standards blue and red colored respectively and is therefore interpreted to be a mixture of co migrating glucose and fructose released by hydrolysis of one of the disaccharides: sucrose, isomaltulose, or trehalulose. The middle band corresponded with the isomaltulose standard in both coloration and relative mobility and is therefore identified as isomaltulose. The slowest migrating band had a red coloration and migrated slower than either the isomaltulose, or sucrose standards. The relative mobility of this sugar band corresponds well with published reports on the migration of trehalulose in similar TLC assays (Cho et al. Biotechnology Letters (2007) 29:453-458; an isomaltulose-producing microorganism isolated from traditional Korean food.) Therefore this sugar band was concluded to be trehalulose. No trehalulose standard was available at the time of the TLC assay, however, subsequent HPLC (Dionex) analysis of sucrose isomerase reaction products and standards obtained later indicate that this band was definitely trehalulose. Also, it is important to note that the reaction product 6 did not contain any sucrose which has a higher relative mobility than isomaltulose and trehalulose and slower mobility than the monosaccharides glucose and fructose. The absence of sucrose was expected due to the complete conversion of sucrose into isomaltulose and trehalulose due to the activity of the sucrose isomerase enzyme.

Alternatively, supernatants were screened by HPCL using 16 mM NaOH to separate sucrose isomerase reaction products followed by a linear gradient from 10 to 40 min using 200 mM NaOH at 1 ml/min on a Dionex DX-600 system with ED50 electrochemical detector (Dionex Co.).

His-Tagged Sucrose Isomerase (SEQ ID NO: 14)

Recombinant BL21[DE3] cell pellets expressing his-tagged sucrose isomerase (SEQ ID NO: 14) were generated essentially as described in Example 1A. The recombinant BL21 cell pellets were brought up to a volume of 40 mL in extraction buffer (50 mM sodium phosphate, 500 mM NaCl, 10 mM Imidazole, pH 8 containing protease inhibitors (Roche Complete EDTA-free protease inhibitor tablets)). Cells were lysed by 2 passages through a FRENCH Press (Thermo IEC). Cell lysate was centrifuged for 30 minutes at 10,000×g at 4 degrees C. Supernatant was filtered using 0.45 micron vacuum filter devices (Millipore) to generate a clarified lysate. A HisTrap FF 5 ml column (GE Healthcare) was equilibrated with extraction buffer. The clarified lysate was loaded onto the equilibrated column at 5 mL/min. Bound his-tagged sucrose isomerase was eluted in a linear imidazole gradient from 50 mM sodium phosphate, 500 mM NaCl, 10 mM Imidazole, pH 8 to 50 mM sodium phosphate, 500 mM NaCl, 200 mM Imidazole over 100 mL. Fractions containing the enzyme were collected and diluted in 50 mM Tris-HCl, pH 8. Diluted sample was loaded onto a 5 mL HiTrap Q HP anion exchange column (GE Healthcare). Bound proteins were eluted from the column by running a linear NaCl gradient from 50 mM Tris-HCl, pH 8 to 50 mM Tris-HCl, 500 mM NaCl, pH 8 over 100 mL. Active sucrose isomerase was detected in the flow through and fractions that eluted at approximately 100 mM NaCl. These fractions were pooled and concentrated to a final protein concentration of 0.8 mg/mL. Samples were aliquoted and stored at −80 degrees C.

Sucrose isomerase enzyme activity was measured in the samples by combining 6 ug/mL his-tagged sucrose isomerase, 70 mM 0.1 M Citrate-phosphate buffer, pH 6 and 584 mM sucrose at 30 degrees C. for 2 hours. Sample was analyzed by Dionex essentially as described in Example 1G. Table 1 outlines the sucrose isomerase activity detected in recombinant *E. coli* cells expressing sucrose isomerase (SEQ ID NO: 14). Activity is demonstrated by the accumulation of the locked sugars trehalulose and isomaltulose.

TABLE 1

| Sucrose isomerase (SEQ ID NO: 14) activity measured using sucrose as the substrate after 2 hr. | | | | | |
|---|---|---|---|---|---|
| Time | Glucose (mM) | Fructose (mM) | Sucrose (mM) | Trehalulose (mM) | Isomaltulose (mM) |
| Sucrose isomerase | 5.98 | 4.97 | 0.61 | 227.96 | 248.45 |
| Negative control | 0 | 0 | 512 | 0 | 0 |

1C: Dextransucrase Enzyme (E.C. 2.4.1.5)

Dextransucrases (E.C. 2.4.1.5) are glucosyl transferase enzymes capable of transferring glucose from a sucrose molecule to form glucose homopolymers known as dextrans. This type of enzymatic reaction is an example of transglycosylation. The dextran is composed of mainly 1,6 alpha D glucose linkages of varying length. The dextran can also contain a variety of 1,4 alpha D glucose linkages which form branch points in the dextran molecule. These branching points have a direct impact on the physiochemical properties (such as solubility) of the dextran molecules. The polynucleotide sequence coding for a dextransucrase enzyme will be generated that uses the codon preference for *E. coli*. This polynucleotide sequence will be synthesized, cloned into an expression vector and expressed in *E. coli* as described in Example 1A.

Dextransucrase enzyme activity will be monitored using a colorimetric assay to detect the rate of fructose release from sucrose (Kobayashi, M et al. (1980) Biochimica et Biophysica Acta vol 614, pp 46-62). Dextran accumulation will be monitored using methods similar to those described in Zhang, S., et al. (2007) Transgenic Res. 16:467-478 in combination with HPLC techniques such as size exclusion chromatography. Dextransucrase enzyme activity assays will be validated by comparing dextransucrase activity recovered from recombinant *E. coli* with commercially available dextransucrase enzyme.

Dextransucrase activity will be measured using sugarcane juice as the source of sucrose. Selected *E. coli* expressed dextransucrases will be incubated in a similar fashion as described above, however sucrose will be replaced with sugarcane juice as the substrate. These experiments will be designed to test the ability of the expressed enzymes to produce dextrans from sucrose in the presence of other proteins and unknown compounds found in sugarcane juice.

A mutant dextransucrase has been characterized by Hellmuth et al. Biochemistry 47: 6678-6684 (2008) which alters the activity of the enzyme such that it can catalyze the conversion of sucrose to isomaltulose or leucrose. This dextransucrase variant has leucrose synthase activity due to the ability of the variant enzyme to catalyze the conversion of sucrose to leucrose.

Analysis of His-Tagged Dextransucrase with Leucrose Synthase Activity (SEQ ID NO: 29).

Recombinant BL21[DE3] cell expressing a His-tagged dextransucrase with leucrose synthase activity (SEQ ID NO: 29) was generated essentially as described in Example 1A. Frozen cell pellets were brought up to a volume of 30-40 mL in extraction buffer (50 mM sodium phosphate, 500 mM NaCl, 10 mM Imidazole, pH 7.2 containing protease inhibitors (Roche Complete EDTA-free protease inhibitor tablets)). Cells were lysed by 2 passages through a FRENCH Press (Thermo IEC). Cell lysates were centrifuged for 30 minutes at 10,000×g at 4 degrees C. Supernatants were filtered using 0.45 micron vacuum filter devices (Millipore). A HisTrap FF 5 ml column (GE Healthcare) was equilibrated with extraction buffer and the clarified lysates were loaded at 5 mL/min. Bound his-tagged enzymes were eluted in 50 mM sodium phosphate, 500 mM NaCl, containing 300 mM Imidazole, pH 7.2. All samples were buffer exchanged into 50 mM HEPES, 50 mM NaCl, pH 7 using a HiPrep 26/10 desalting column (GE Healthcare). 50% Glycerol was added to such that the final buffer was 40 mM HEPES, 40 mM NaCl, 10% glycerol, pH 7. Protein concentrations were estimated by Bradford assay. Samples were stored at −80 degrees C.

As a negative control, BL21[DE3] cell pellets expressing the empty pET24b vector were processed as above except for elution from HisTrap was in 50 mM sodium phosphate, 500 mM NaCl, containing 500 mM Imidazole, pH 7.2.

His-tagged dextransucrase with leucrose synthase activity was diluted to 0.1 mg/mL in 40 mM HEPES, 40 mM NaCl, 10% glycerol, pH 7.2-100 uL reactions were set up for the leucrose synthase and the negative control with the following conditions:

| | #1 | #2 |
|---|---|---|
| Sample (0.1 mg/ml) | 10 | 10 |
| Buffer (200 mM Sorensen's Buffer + 500 mM CaCl2, pH 7) | 60.8 | 60.8 |
| 2M Sucrose | 14.6 | 14.6 |
| 2M Fructose | 0 | 14.6 |
| Water | 14.6 | 0 |
| Total Reaction Volume | 100 | 100 |

Volumes in column #1 and #2 are in microliters

Table 2 outlines data demonstrating that his-tagged dextransucrase (SEQ ID NO: 29) with leucrose synthase activity is enzymatically active and converts sucrose to leucrose and isomaltose. Dextransucrase enzymes catalyze the conversion of sucrose to locked sugars through a transglycosylation reaction. Table 2, comparing sample 1 and sample 2, demonstrates that dextransucrase with leucrose synthase activity has altered specificity toward producing leucrose versus isomaltose dependent on the addition of fructose as a secondary substrate.

TABLE 2

| Dionex analysis of carbohydrate products from microbially expressed His-tagged dextransucrase with leucrose synthase activity. Enzyme activity indicated by the change in percent sugar determined by comparing samples collected at time 0 and time 24 hours. | | | | | | |
|---|---|---|---|---|---|---|
| Sample set up | Glucose (% total sugar) | Fructose (% total sugar) | Sucrose (% total sugar) | Isomaltose (% total sugar) | Isomaltulose (% total sugar) | Leucrose (% total sugar) |
| 1 | 8.99 | 20.55 | −37.46 | 3.16 | 0.66 | 4.09 |
| 2 | 1.40 | −0.29 | −6.57 | 0.12 | 0.57 | 4.77 |

TABLE 2-continued

Dionex analysis of carbohydrate products from microbially expressed His-tagged dextransucrase with leucrose synthase activity. Enzyme activity indicated by the change in percent sugar determined by comparing samples collected at time 0 and time 24 hours.

| Sample set up | Glucose (% total sugar) | Fructose (% total sugar) | Sucrose (% total sugar) | Isomaltose (% total sugar) | Isomaltulose (% total sugar) | Leucrose (% total sugar) |
|---|---|---|---|---|---|---|
| 1 (Negative control) | 0.08 | 0.14 | −0.22 | 0 | 0 | 0 |
| 2 (Negative control) | −0.01 | 0.63 | −0.62 | 0 | 0 | 0 |

Total sugar = total amount of identifiable sugars in sample based on retention times of pure sugar standards. Extraneous peaks in samples are indeterminate and not included in sample analysis. Negative control contains bacterial fractions collected as described in Example 1A from cells containing an empty pET24 vector.

1D: Levan Sucrase, Fructosyl Transferase (E.C. 2.4.1.10, E.C. 2.4.1.99, E.C. 2.4.1.100)

Sucrose:sucrose fructosyltransferase (SST) (EC 2.4.1.99), 1,2-β-fructan 1-fructosyltransferase (FFT) (EC 2.4.1.100), and levan sucrase (EC 2.4.1.10) are enzymes within the larger class of fructosyl transferases. The fructosyl transferase enzymes catalyze the formation of fructans composed of fructose linked by β(2→1) and/or β(2→6) glucoside bonds. Fructosyl transferases may be identified and isolated from plant, bacterial, or fungal sources. These enzymes may be expressed in plants to accumulate fructans as storage carbohydrates. Accumulation of this polysaccharide (fructan) in sugarcane or other plants may allow the accumulation of excess carbohydrates.

The polynucleotide sequence coding for a fructosyltransferase enzyme will be generated that uses the codon preference for *E. coli*. This polynucleotide sequence will be synthesized, cloned into an expression vector and expressed in *E. coli* essentially as described in Example 1A.

Fructosyl transferase activity will be estimated by TLC and HPLC similar to the procedures described above for sucrose isomerase and the Dionex analysis described in Example 1B. Modifications to the protocol in order to increase the sensitivity for fructans may include development in a solution of propanol:butanol:water (12:3:4) and the use of a urea-phosphoric acid dye mixture (Wise et al., 1955, Anal Chem 27:33-36). Long polymers of fructose have low mobility in the TLC assay and will remain in the location where they are spotted on the silica gel plate. Hydrolysis of fructans to fructose by HCl solution will allow specific identification of fructose using the aniline dye described above. Alternatively a fructanase enzyme may be used to hydrolyze fructans to fructose. This technique will be useful in determining that large polymers are indeed fructans as only fructans would be hydrolyzed by a fructanase enzyme.

Fructose, as the sweetest naturally occurring sugar, also has value as a sweetener in high fructose syrups such as high fructose corn syrup. Plants engineered to produce fructans as a locked sugar may be used as a source of fructans which, after hydrolysis by a fructanase enzyme, produce a solution with a high fructose concentration. In such plants the yield of fructan may be increased by expressing an additional enzyme glucose isomerase to catalyze the conversion of glucose to fructose. The glucose isomerase (invertase) could be expressed in maize endosperm, or expressed in microbes. The purified enzyme could be used to produce fructans, glucans and alternans.

Sweeter plant products can be generated by expressing in plants a combination of enzymes that first allow for the accumulation of fructans in the plant and then convert the fructans directly or indirectly to fructose. Expressing invertase (glucose isomerase) in plants accumulating fructans will lead to a higher sweetness index in the plant.

Endogenous sucrose synthase activity in the endosperm will create additional sucrose which may be used as a substrate for further fructan synthesis.

1E: Alternansucrase

Alternan is a polysaccharide consisting of glucosyl residues linked by alternate alpha-(1-3)/alpha-(1-6) bonds. This polymer is highly soluble and has very low viscosity. Accumulation of this polysaccharide in sugarcane or other plants may allow the accumulation of excess carbohydrates. Alternansucrase is an enzyme which catalyzes the conversion of sucrose to alternan.

Alternansucrase is encoded by the Asr gene of *Leuconostoc mesenteroides* NRRL B-1355, 1498, and 1501 (Jeannes et al. Am Chem Soc 76:5041-5052, 1954). The Asr gene may be synthesized, cloned into an expression vector and expressed in *E. coli* essentially as described in Example 1A.

Alternansucrase activity may be detected by enzyme-linked immunosorbent assay (ELISA) as described by Kok-Jacor et al. J. Plant Physiol 160: 765-777 (2005) Alternans can be hydrolyzed to form fermentable sugars by the activity of a alpha-1,6-glucosidase or alpha-1,3-glucosidase or a combination of the two enzymes.

1F: Amylosucrase (E.G. 2.4.1.4)

Amylose or starch, is a polysaccharide consisting of glucosyl residues linked by alpha-(1-4) bonds and is the primary carbohydrate storage compound found in most plants. Producing starch in plants that use sucrose as their primary carbohydrate storage compound, such as sugarcane, may permit the accumulation of starch which would behave as a locked sugar.

*Neisseria polysacharea* produces an amylosucrase enzyme (GenBank Accession number Q9ZEU2) which catalyzes the conversion of sucrose to a linear alpha-1,4-linked glucan. For the purpose of producing starch in a transgenic plant, it may be advantageous to target the amylosucrase enzyme in the plant to subcellular compartments that have high concentrations of sucrose, such as the vacuole of sugarcane. Another target may be the vacuole of the maize endosperm. Targeting an enzyme capable of synthesizing starch from sucrose to the vacuole of maize endosperm cells may permit the accumulation of more starch in the maize endosperm as naturally occurring enzymes do not produce starch in the vacuoles of maize endosperms cells. Targeting such an enzyme to endosperm vacuoles may be expected to create up to 10% more starch because of starch accumulation in a subcellular compartment that normally does not accumulate starch. Alternatively targeting to the apoplast is another way to achieve conversion of sucrose into locked sugars such as starch or isomaltulose. In plants such as maize, sucrose accumulates in the leaf and is transported to the ear during grain filling which provides a carbon sink. Table 3 outlines the sugar content of maize tissue with and without removal of the ear. Note that when the ear is removed, excess sugar accumulates in the leaf tissue.

TABLE 3

Sugar content of maize with and without ears.

| Sugar, mg/mL | Earless maize | Maize with Ear |
|---|---|---|
| Sucrose | 7.42 | 2.6 |
| Glucose | 1.34 | 1.05 |
| Fructose | 1.32 | 0.95 |
| Total, mg/mL | 10.08 | 4.6 |

A codon optimized polynucleotide sequence coding for the *N. polysacharea* amylosucrase enzyme may be synthesized, cloned into an expression vector and expressed in *E. coli* essentially as described in Example 1A.

His-Tagged Amylosucrase

Recombinant BL21 cells expressing an amylosucrase will be generated essentially as described in Example 1A. Frozen BL21[DE3] cell pellets expressing amylosucrase will be recovered from a 30 mL overnight culture in autoinduction media and will be resuspended in 3 mL BugBuster HT (Novagen) containing Complete EDTA-free protease inhibitors (Roche). Samples will be incubated at room temperature for 10 minutes with occasional mixing to lyse cells. Cell lysate will be centrifuged at 10,000×g for 10 minutes at 4 degrees C. 10 uL of supernatant will be incubated in a 500 uL reaction containing 1×PBS and 100 mM sucrose overnight at 30 degrees C. The presence of a visible white precipitate indicates amylosucrase activity. Determination that this precipitate is starch can be done by washing the precipitate in 80% ethanol several times, followed by solubilization in DMSO and gel permeation chromatography. Susceptibility to digestion by amylase enzyme would further demonstrate the precipitate is composed of starch.

1G: Dionex HPAEC Analysis of Carbohydrates

Carbohydrate separation and detection was analyzed utilizing a Dionex IC3000 system with a Dionex AS autosampler, a Dionex DC detection compartment (pulsed amperometric detection (PAD) using a disposable Dionex carbohydrate certified gold surface electrode), and a Dionex SP pump system. For high resolution separation, one Carbopac PA1 4×50 mM Guard Column followed by two Carbopac PA1 4×250 mM analytical columns were used for all analysis. The electrode potentials were set to the carbohydrates standard quad with AgCl reference electrode as specified by Dionex Corporation. The eluent system utilized an isocratic mobile phase consisting of 100 mM NaOH and 2 mM NaOAc with a 38 min run time. Peak identification was based on standard retention times of glucose, fructose, sucrose (Sigma), leucrose (Carbosynth), isomaltulose (Fischer) and trehalulose. Peak analysis utilized Chromeleon version 6.80 software (Dionex Corp., Sunnyvale, Calif.).

EXAMPLE 2

Enzymes that Unlock Locked Sugars

2A: Fructanase (EC 3.2.1.80, E.C. 3.2.1.7)

Fructanases are fructosydases which catalyze the hydrolysis of fructosidic linkages in fructans to break the fructan down into simpler sugar molecules. Fructans can be hydrolyzed to fermentable sugars through the catalytic activity of fructanases. For Example, the fructanase 2,1-β-D-fructan fructanohydrolase [EC 3.2.1.7] can hydrolyze fructan polymers into fructose monosaccharides which can be fermented to form ethanol.

A codon optimized polynucleotide sequence coding for a fructanase enzyme may be synthesized, cloned into an expression vector and expressed in *E. coli* essentially as described in Example 1A.

Fructanase activity may be estimated by incubating a fructanase enzyme with a solution of fructan. Hydrolysis of fructan by the fructanase will release the monosaccharide fructose which may be detected by TLC or HPLC as described above for sucrose isomerase (Example 1B).

2B: Glucosidase

Gene sequences for alpha-1,6-glucosidases were identified using BLAST to search the NCBI database for genes homologour to a known alpha-1,6-glucosidase. The polypeptide sequences (SEQ ID NOs: 1-6) were back translated (using Vector NTI program) into polynucleotide sequences using the codon preference of *E. coli*. The *E. coli* codon optimized polynucleotide sequences were synthesized by GeneArt and expressed in *E. coli* essentially as described in Example 1B.

Alpha-1,6-glucosidase activity was assayed by measuring the production of glucose from hydrolysis of the alpha-1,6-glucoside bond of isomaltulose. 13 microliters of crude *E. coli* extract was added to 37 microliters of isomaltulose reaction buffer (100 mM isomaltulose and 30 mM HEPES (pH 7.5)) at 30 degrees, 40 degrees, 50 degrees, 60 degrees, 70 degrees, or 80 degrees C. depending on the enzyme; for 10 minutes, 20 minutes, 30 minutes, or 40 minutes. 20 microliters of the reaction product was added to a 96 well microplate, then 250 microliters of glucose oxidase reagent (Pointe Scientific) was added and the mixture was incubated at 37 degrees C. for 10 minutes. After this incubation, the Absorbance at 500 nm was read using a SpectraMax plus 384. Sample absorbance was compared with the absorbance at 500 nm of controls which were 13 microliters each of a set of glucose standards that were also allowed to react with the glucose oxidase reagent. A standard curve was created from the controls and the production of glucose from the hydrolysis of isomaltulose by the samples was estimated by comparing the absorbance at 500 nm for the samples to the standard curve.

Using this method, the alpha-1,6-glucosidase enzymes described by SEQ ID NOs: 1-6 were screened and found to have activities at temperatures ranging from 30 degrees C. to 80 degrees C. Table 4 describes the alpha-1,6-glucosidase activity measured in total cell lysate of an *E. coli* strain expressing the *Bacillus thermoamyloliquefaciens* enzyme (SEQ ID NO:5).

His Tagged Enzyme Recovery from Recombinant *E. coli*

Recombinant BL21 *E. coli* cells expressing an alpha-1,6-glucosidase (SEQ ID NOs: 1, 3, 5 and 6) were generated essentially as described in Example 1A. The frozen cell pellets expressing the his-tagged alpha-1,6-glucosidase key enzymes were brought up to a volume of 40 mL in extraction buffer (50 mM sodium phosphate, 500 mM NaCl, 10 mM Imidazole, pH 7.2-8 containing protease inhibitors (Roche Complete EDTA-free protease inhibitor tablets)). Cells were lysed by 2 passages through a FRENCH Press (Thermo IEC). Cell lysates were centrifuged for 30 minutes at 10,000×g at 4 degrees C. Supernatants were collected and filtered using 0.45 micron vacuum filter device (Millipore).

A His Trap FF column was used to recover the his-tagged enzymes from the supernatant. A HisTrap FF 5 mL column (GE Healthcare) was equilibrated with extraction buffer. The clarified lysates were loaded at 5 mL/min. Bound his-tagged enzymes were eluted in 50 mM sodium phosphate, 500 mM NaCl, containing 150-500 mM Imidazole, pH 7.2-8.

The negative control was BL21[DE3] cell pellets transformed with empty pET24b vector essentially as described in Example 1A. Negative control cell pellets were extracted essentially as described above for the his-tagged alpha-1,6-glucosidase enzymes; however, the extraction buffer and elution buffers were at pH 7.2.

All samples collected from the HisTrap FF column were buffer exchanged into 50 mM HEPES, 50 mM NaCl, pH 7 using either Bio-Rad Econo-Pac 10-DG desalting column or HiPrep 26/10 desalting column (GE Healthcare). 50% Glycerol was added such that the final buffer was 40 mM HEPES, 40 mM NaCl, 10% glycerol, pH 7. Protein concentrations were estimated by Bradford assay. Samples were stored at −80 degrees C.

*T. ethanolicus* alpha-1,6-glucosidase (SEQ ID NO: 6):

His-tagged *T. ethanolicus* alpha-1,6-glucosidase (SEQ ID NO: 6) was recovered from recombinant BL21 *E. coli* cells essentially as described above (Example 2B "His tagged enzyme recovery from recombinant *E. coli*"). Frozen samples derived from the HisTrapFF column were combined with 3 M ammonium sulfate, 50 mM ammonium phosphate, pH 7 to a final ammonium sulfate concentration of 1 M. This sample was applied to a 5 mL HiTrap Phenyl HP column (GE Healthcare). Bound proteins were eluted from the column by washing the column with a linear ammonium sulfate gradient over 100 ml from 50 mM Sodium phosphate, 1.5 M ammonium sulfate, pH 7 to 50 mM sodium phosphate buffer pH 7 containing no ammonium sulfate. Fractions containing the enzyme were pooled and concentrated using Centri-prep YM-30 concentrator device (Amicon).

*B. thurgiensis* alpha-1,6-glucosidase (SEQ ID NO: 3):

His-tagged *B. thurgiensis* alpha-1,6-glucosidase (SEQ ID NO: 3) was recovered from recombinant BL21 *E. coli* cells essentially as described above (Example 2B "His tagged enzyme recovery from recombinant *E. coli*"). Fractions containing his-tagged enzyme were pooled and diluted in 50 mM HEPES, pH 6. Sample was applied to a 5 mL HiTrap Q HP column (GE Healthcare). Bound proteins were eluted by washing the column with a linear NaCl gradient over 100 mL from 50 mM HEPES, pH 6 to 50 mM HEPES, 1 M NaCl, pH 6. The fractions containing the enzyme were pooled.

*G. thermoglucosidasius* alpha-1,6-glucosidase (SEQ ID NO: 1):

His-tagged *G. thermoglucosidasius* alpha-1,6-glucosidase (SEQ ID NO: 1) was recovered from recombinant BL21 *E. coli* cells essentially as described above (Example 2B "His tagged enzyme recovery from recombinant *E. coli*"). Fractions containing his-tagged enzyme were pooled and diluted in 50 mM Tris-HCl, pH 7. Sample was applied to a 5 mL HiTrap Q HP column (GE Healthcare). Bound proteins were eluted by washing the column with a linear NaCl gradient over 100 mL from 50 mM HEPES, 10 mM NaCl, pH7 to 50 mM HEPES, 1 M NaCl, pH 7. The fractions containing the enzyme were pooled and concentrated to 1 mL Centri-prep YM-30 concentrator device (Amicon). Sample was applied to a HiPrep 26/60 S-100 HR size exclusion column and eluted with 20 mM Tris-HCl, 250 mM NaCl, pH 7. Fractions containing the enzyme were pooled and diluted in 1.5 M Ammonium Sulfate, 50 mM Sodium phosphate, pH7. Sample was applied to a 5 mL HiTrap Phenyl HP column (GE Healthcare). Bound proteins were eluted by washing the column with a linear ammonium sulfate gradient over 100 mL from 50 mM Sodium phosphate, 1.5 M ammonium sulfate, pH 7 to 50 mM sodium phosphate buffer pH 7 containing no ammonium sulfate. Fractions containing the enzyme were pooled.

*B. thermoamyloliquefaciens* alpha-1,6-glucosidase (SEQ ID NO: 5):

His-tagged *B. thermoamyloliquefaciens* alpha-1,6-glucosidase (SEQ ID NO: 5) was recovered from recombinant BL21 *E. coli* cells essentially as described above (Example 2B "His tagged enzyme recovery from recombinant *E. coli*"). Fractions containing his-tagged enzyme were pooled and diluted in 20 mM Tris-HCl, pH 7. Sample was applied to a 5 mL HiTrap Q HP column (GE Healthcare). Bound proteins were eluted by washing the column with a linear NaCl gradient over 100 mL from 20 mM Tris-HCl, 50 mM NaCl, pH 7 to 50 mM HEPES, 1 M NaCl, pH 7. Fractions containing the enzyme were pooled and concentrated to 1 mL Centri-prep YM-30 concentrator device (Amicon). Sample was applied to a HiPrep 26/60 S-100 HR size exclusion column and eluted with 50 mM HEPES, 50 mM NaCl, pH 7.4. Fractions containing the enzyme were pooled in 1.5 M Ammonium Sulfate, 50 mM Sodium phosphate, pH7. Sample was applied to a 5 mL HiTrap Phenyl HP column (GE Healthcare). Bound proteins were eluted by washing the column with a linear ammonium sulfate gradient over 100 mL from 50 mM Sodium phosphate, 1.5 M ammonium sulfate, pH 7 to 50 mM sodium phosphate buffer pH 7 containing no ammonium sulfate. Fractions containing the enzyme were pooled.

Activity of His-Tagged alpha-1,6-glucosidase Key Enzymes

The enzyme activity of the alpha-1,6-glucosidase enzymes (SEQ ID NOs: 1, 3, 5 and 6) recovered from recombinant BL21 *E. coli* cells was measured. Samples collected from the purification schemes described above (Example 2B) were diluted to 0.2 mg/mL in 50 mM HEPES, 50 mM NaCl, pH 7. Reactions were initiated by mixing samples with an equal volume of 100 mM HEPES, 4 mM EDTA, 0.04% Tween-20, 200 mM Isomaltulose, pH 7. For buffer controls, 100 mM HEPES, 4 mM EDTA, 0.04% Tween-20, pH 7 was combined with an equal volume of 200 mM Isomaltulose. Reactions were incubated at optimal temperature for the enzyme (37, 45, or 60 degrees C.) for 40 minutes in a Biorad Tetrad 2 thermocycler for the appropriate time. Reactions were terminated by heating samples at 95 degrees C. for 5 minutes. Glucose concentrations in reactions were estimated using the GOPOD assay. Enzyme activity is detected as the conversion of isomaltulose to glucose.

The GOPOD assay was performed by combining 20 uL aliquots of reaction samples, or glucose standards of known concentrations, with 250 uL GlucoseOx Reagent (Pointe Scientific) in a 96-well assay plate (Costar 3370) and incubated for 10 minutes at 37 degrees C. Absorbance at wavelength of 500 nm was measured using SpectraMax 384 Plus plate reader. Absorbance values of sample reactions were converted to glucose concentrations using the equation from a glucose standard curve generated by plotting the absorbance value versus the known glucose standard concentration. The activity of the various alpha-1,6-glucosidase enzymes is described in Table 5.

TABLE 5

| Activity data for alpha-1,6-glucosidase enzymes | | |
|---|---|---|
| Sample (SEQ ID NO) | Glucose (mM) | Reaction temperature in degrees C. |
| *T. ethanolicus* (6) | 19.72 | 60 |
| *G. thermoglucosidasius* (1) | 29.16 | 60 |
| Negative control | 0.07 | 60 |
| Buffer only negative control | 0.03 | 60 |
| *B. thurgiensis* (3) | 23.35 | 37 |
| Negative control | 0.07 | 37 |
| Buffer only negative control | 0.01 | 37 |
| *B. thermoamyloliquefaciens* (5) | 1.17 | 45 |
| Negative control | 0.09 | 45 |
| Buffer only negative control | 0.01 | 45 |

Purification of His-Tagged alpha-1,5-glucosidase and alpha-1,1-glucosidase Key Enzymes.

Recombinant BL21[DE3] cell pellets expressing His-tagged alpha-1,5-glucosidase and alpha-1,1-glucosidase key enzymes were generated essentially as described in Example 1A. Frozen cell pellets were brought up to a volume of 30-40 mL in extraction buffer (50 mM sodium phosphate, 500 mM NaCl, 10 mM Imidazole, pH 7.2 containing protease inhibitors (Roche Complete EDTA-free protease inhibitor tablets)). Cells were lysed by 2 passages through a FRENCH Press (Thermo EC). Cell lysates were centrifuged for 30 minutes at 10,000× g at 4 degrees C. Supernatants were filtered using 0.45 micron vacuum filter devices (Millipore). A HisTrap FF 5 ml column (GE Healthcare) equilibrated with extraction buffer was used to clarify the lysates which were loaded at 5 mL/min. Bound his-tagged enzymes were eluted in 50 mM sodium phosphate, 500 mM NaCl, containing 300 mM Imidazole, pH 7.2. All samples were buffer exchanged into 50 mM HEPES, 50 mM NaCl, pH 7 using a HiPrep 26/10 desalting column (GE Healthcare). 50% Glycerol was added to such that the final buffer was 40 mM HEPES, 40 mM NaCl, 10% glycerol, pH 7. Protein concentrations were estimated by Bradford assay. Samples were stored at −80 degrees C.

As a negative control, BL21[DE3] cell pellets expressing the empty pET24b vector were processed as described above except for elution from HisTrap was in 50 mM sodium phosphate, 500 mM NaCl, containing 500 mM Imidazole, pH 7.2.

Activity Analysis of His-tagged alpha-1,5-glucosidase and alpha-1,1-glucosidase Key Enzymes Extracts of his-tagged enzymes were generated essentially as described above and were diluted to 0.08 mg/mL in 40 mM HEPES, 40 mM NaCl, 10% glycerol, pH 7. Enzyme activity assasys were initiated by mixing samples with an equal volume of 100 mM HEPES, 4 mM EDTA, 0.04% Tween-20, 200 mM leucrose (for alpha-1,5-glucosidase key enzymes (SEQ ID NOs: 30-33)) or 135 mM trehalulose/67 mM isomaltulose mixture (for alpha-1,1-glucosidase key enzyme (SEQ ID NO: 34)), pH 7. Reactions were incubated at optimal temperature (70 degrees C. for alpha-1,5-glucosidase enzymes and 80 degrees C. for alpha-1,1-glucosidase key enzyme) for 40 minutes in a Biorad Tetrad 2 thermocvcler for the appropriate time. Reactions were terminated by heating samples at 95 degrees C. for 5 minutes. Key enzyme activity was demonstrated by the conversion of a locked substrate (leucrose or trehalulose and/or isomaltulose) to glucose. Glucose concentrations in reactions were estimated using GOPOD assay essentially as described above. Table 6 outlines data which demonstrates that his-tagged alpha-1,5-glucosidase enzymes and alpha-1,1-glucosidase enzyme are active and convert locked sugar substrates to fermentable sugar.

TABLE 6

| Conversion of locked sugars to glucose by his-tagged key enzymes. | | | | | |
|---|---|---|---|---|---|
| Sample name (SEQ ID NO:) | GK24 N-del (30) | GK24 (31) | HB27 (32) | HB8 (33) | Negative Control |
| Glucose Conc. (mM) | 0.94 | 1.01 | 0.42 | 1.56 | 0.05 |
| Sample name (SEQ ID NO: | SAM1606 (34) | Negative control | | | |
| Glucose concentration (mM) | 8.67 | 0.46 | | | |

2C: Dextranase (E.C. 3.2.1.11)

Dextranases are glycosidases which catalyze the exo or endohydrolysis of 1,6 alpha D glucosidic linkages in dextrans thus converting the dextran to smaller sugar molecules. A codon optimized polynucleotide sequence coding for a dextranase enzyme may be synthesized, cloned into an expression vector and expressed in *E. coli* essentially as described in Example 1A.

Dextranase enzyme activity assays will monitor the rate of isomaltose released from a dextran molecule during a hydrolysis reaction. HPLC size exclusion chromatography will also be employed to determine the level of dextran hydrolysis achieved by measuring the release of individual sugars.

Assays will be validated using a commercially available dextranase from *Penicillium* sp I.U.B.: 3.2.1.11 (Worthington Biochemical Corporation, N.J. 08701). The dextran hydrolysis can be measured by incubating 0.1 mL of 5-20 micrograms/mL of dextranase with 1.9 mL of commercially available dextran solution (substrate). Thermostability of dextranases will be tested in experiments performed at 60 to 70 degrees C. which are temperatures relevant to sugar mill sugarcane juice processing. Validated assays will be further optimized for detection of functional dextranases cloned and expressed in *E. coli*.

EXAMPLE 3

Transgenic Plants

3A: Transgenic Sugarcane

Embryogenic callus was produced from the immature leaf tissue of sugarcane. In greenhouse, cane was harvested by cutting off immature shoots at or above ground level and outer leaves and leaf sheaths were stripped. Basal nodes and emergent leaves were trimmed. In the laboratory (laminar flow cabinet), excess leaf sheaths were unfurled, nodes were trimmed and cane was sterilized (sprayed with 70% ethanol or immersed in 20% bleach for 20 minutes). Additional outer leaf sheaths were removed to expose inner 4-6 leaf rolls and leaf roll was cut to manageable size (12-15 mm in length). Remaining basal nodes and internodes were removed to expose the leaf roll region just above the apical meristem.

Transverse sections of the leaf roll were cut to form discs 0.5-1.0 mm in thickness, using not more than a 3.0 cm length of the leaf roll material. Leaf roll discs were plated onto MS media containing 2-3 mg/L of 2,4-D and cultured in the dark for 3-4 weeks. Leaf roll discs were cut or split apart at the time of initiation or 2 weeks following initiation and the resulting pieces spread across media to promote a more consistent and prolific embryogenic/proto-embryogenic culture response. After 3-4 weeks of culture, embryogenic callus was selectively excised from leaf disc rolls and sub-cultured on same (MS+2,4-D) media. Further selective subcultures were performed every 2-3 weeks, dependent upon growth and development to produce additional cultures, until cultures reach 8-10 weeks of age.

Gene Delivery using the Biolistics PDS 2000 Particle Delivery Device for Sugarcane Transformation Target embryogenic cultures were prepared for gene delivery by selecting high quality target tissue pieces and preculturing them for 3-6 days on fresh media before gene delivery.

At 2-5 hours prior to gene delivery, target tissues were arranged in a target pattern on high osmotic potential media containing MS basal salts and B5 Vitamins supplemented with sucrose 30 g/L and 0.2 M sorbitol and 0.2 M mannitol plus 2 mg/l 2,4-D.

To prepare DNA for bombardment, gold particles (0.6 micrometer size, Bio-Rad) were re-suspended in 50% sterile glycerol by vortexing. An aliquot of the glycerol—gold particle suspension was combined by gentle mixing with $2\times10^{10}$ mol DNA of the gene encoding the selectable marker (PMI) and genes of interest outlined in Table 29 of Example 12. The mixture was combined with 2.5M CaCl2 and cold 1M spermidine to precipitate the DNA onto the gold particles. The gold particles with precipitated DNA were washed with ethanol. The gold particles were repeatedly re-suspended in ethanol and aliquots of DNA/particle suspension were placed evenly onto the center of individual macrocarrier membrane disks and allowed to dry. The macrocarrier was loaded into the gene gun above the stopping screen. Bombardment of embryos was performed with a PDS—1000 Helium gene gun. A rupture disc of 1300 psi was used and the distance from the rupture disc and the macrocarrier was set at 8 mm with a stopping screen at 10 mm. The distance between the stopping screen and the embryos was about 7 cm. The pressure on the helium tank was set at about 1400 psi. Target tissues (embryogenic cultures) were bombarded with 2 shots before being transferred to the dark at 28 degrees C. for about 12 hours.

After recovery, the bombarded cultures were transferred to maintenance medium and cultured at 28 degrees C. in the dark. After 7 days, the bombarded cultures were transferred to fresh selection medium containing mannose (7-9 grams/L), 5 g/L sucrose plus 2 mg/L 2,4-D and incubated for 4-5 weeks in dark. Growing callus pieces were then subcultured to fresh selection media every 2 weeks until they were large enough for analysis. Typically, 2 to 3 rounds of subculture were required.

Regeneration of Plants from Transgenic Callus Lines

After 4-5 weeks on mannose selection media, surviving embryogenic callus colonies are selectively isolated from original cultures and transferred onto regeneration media (MS salts and B5 vitamins, 30 g/L sucrose, supplemented with 3-6 g/L mannose and 2 mg/L BAP) at 28 degrees C. in dark in Flambeau boxes.

One week later, the cultures are transferred to a light room for shoot development under 16 hours light at 28 degrees C. After 3-4 weeks in the regeneration media, the visible green buds or shoots are sub-cultured on elongation media (MS basal salts and B5 vitamins, sucrose 30 g/L with hormone-free).

Regenerated shoots are rooted in the rooting media (Basal MS media). The rooting cultures are kept at 28 degrees C. under light for another 2 weeks before transfer to the greenhouse and soil. Any of the genes described in Example 1, Example 2 or Example 12 can be transformed into sugarcane to generate transgenic plants using the above described protocol. *Agrobacterium* mediated genetic transformation is also possible and methods are described in the literature such as Arencibia, Ariel D. and Carmona, Elva R. Sugarcane (*Saccharum* spp.) Methods in Molecular Biology (Totowa, N.J., United States) (2006), 344(*Agrobacterium* Protocols (2nd Edition), Volume 2), 227-235

3B: Transgenic Sugarcane Expressing Dextransucrase Activity

Selected dextransucrases are sequence optimized based upon the codon preference for sugarcane. The sugarcane codon optimized sequence is cloned into transformation vectors for sugarcane transformation. One of skill in the art is able to select the appropriate promoter and terminator for the dextransucrase gene as well as select an appropriate selectable marker for sugarcane transformation. Targeting sequences are incorporated into the expression construct for dextransucrases to target the enzyme to the vacuolar compartment of parenchyma cells where sucrose is stored.

Transgenic sugarcane plants are generated as described in Example 3A. Transformed plants are analyzed using routine methods for DNA analysis of transgenic plants in order to determine if the expression construct has been incorporated into the nuclear DNA of the sugarcane plant.

Transgenic sugarcane plants are evaluated for dextransucrase enzyme activity. Mature plant tissue is crushed and the juice will be collected and chilled prior to assaying for dextran accumulation using the detection methods described in Example 1C. Enzyme assay methods described in Example 1C are used to determine the functionality of the expressed enzyme in transgenic plants.

3C: Generation of Transgenic Plants Expressing Dextranase Activity.

Selected dextranases are codon optimized for expression in sugarcane using the codon preference for sugarcane. The sugarcane optimized gene sequence is cloned into a transformation vector designed for sugarcane transformation. One of skill in the art is able to select the appropriate promoter and terminator for the dextranase as well as select an appropriate selectable marker for sugarcane transformation. The dextranase enzyme is targeted to the ER subcellular compartment of parenchyma cells using the appropriate targeting sequences. The dextranase enzyme is targeted away from the sucrose and dextran storage compartment of the sugarcane plant.

Transgenic plants are generated as described in Example 3A. Enzyme activity is evaluated in mature plant tissue by crushing and extracting juice from the transgenic plant and performing the assays for dextranase activity as described in Example 2C. Enzyme assay methods described in Example 2C are used to determine the functionality of the expressed enzyme in sugarcane juice 3D: Transient expression in tobacco and sugar beet leaves Expression cassettes described in Example 12 were cloned into either a binary vector or a binary vector also containing an origin of replication from BCTV, beet curly top virus, (SEQ ID NO: 8). The binary vectors without the origin of replication from BCTV were transferred into *Agrobacterium tumefaciens* strain LBA4404 using the freeze-thaw method (An et al., Binary vector. In: Gelvin S B, Schilproot R A (eds), Plant molecular biology manual. Kluwar Academic Publishers, Dordrecht, pp A3 1-19 (1988)). The binary vectors containing the origin of replication from BCTV (BCTV binary vectors) were transferred into *Agrobacterium tumefaciens* strain LBA4404 containing a helper plasmid containing a replicase sequence from BCTV (SEQ ID NO: 9) using the freeze-thaw method (An et al., Binary vector. In: Gelvin S B, Schilproot. RA (eds), Plant molecular biology manual. Kluwar Academic Publishers, Dordrecht, pp A3 1-19 (1988)).

Leaves from sugar beet or tobacco were used for the transient expression of enzymes in plant tissue. Tobacco leaves from transgenic TEV-B tobacco plants (made in the tobacco cultivar Xanthi) containing a mutated P1/HC-Pro gene from TEV that suppresses post-transcriptional gene silencing (Mallory et al., Nat Biotechnol 20:622 (2002)) were used for transient expression of selected enzymes. Preparation of *Agrobacterium* cultures and infiltration of tobacco or sugar beet leaves was carried out as described by Azhakanandam et al., Plant Mol. Biol. 63: 393-404 (2007). In brief, the genetically modified *agrobacteria* were grown overnight in 50 mL of LB medium containing 100 μM acetosyringone and 10 μM MES (pH 5.6), and subsequently were pelleted by centrifugation at 4000×g for 10 min. The pellets were resuspended in the infection medium [Murashige and Skoog salts with vitamins, 2% sucrose, 500 μM MES (pH 5.6), 10 μM $MgSO_4$, and 100 μM acetosyringone] to $OD_{600}$=1.0 and subsequently held at 28 degrees C. for 3 hours. Infiltration of individual leaves was carried out on sugar beet (about 3 weeks old) and TEV-B tobacco plants (about 4 weeks old) using a 5 mL syringe by pressing the tip of the syringe (without a needle) against the abaxial surface of the leaf. Infiltrated plants were maintained at 22-25 degrees C. with a photoperiod of 16 hours light and 8 hours dark. Plant tissue was harvested after 5 days post infiltration for subsequent analysis.

To ensure that enzyme activity measured was due to plant expression of the enzymes, the expression constructs also incorporated an intron in the polynucleotide sequence coding for the enzyme. The presence of the intron ensures that expression of the enzyme is due to plant expression (able to process out the intron and therefore express a fully processed enzyme) versus *agrobacterium* expression (unable to process the intron and thus not able to express a functional enzyme).

3D: Transient Expression in Tobacco and Sugar Beet Leaves

Expression cassettes described in Example 12 were cloned into either a binary vector or a binary vector also containing an origin of replication from BCTV, beet curly top virus (SEQ ID NO: 8). The binary vectors without the BCTV origin of replication were transferred into *Agrobacterium tumefaciens* strain LBA4404 using the freeze-thaw method (An et al., Binary vector. In: Gelvin S B, Schilproot R A (eds), Plant molecular biology manual. Kluwar Academic Publishers, Dordrecht, pp A3 1-19 (1988)). The BCTV containing binary vectors were transferred into *Agrobacterium tumefaciens* strain LBA4404 containing a helper plasmid containing a BCTV replicase sequence (SEQ ID NO: 9) using the freeze-thaw method (An et al., Binary vector. In: Gelvin S B, Schilproot R A (eds), Plant molecular biology manual. Kluwar Academic Publishers, Dordrecht, pp A3 1-19 (1988)).

Leaves from sugar beet or tobacco were used for transient expression of enzymes. Transgenic TEV-B tobacco plants (made in the tobacco cultivar Xanthi) containing a mutated P1/HC-Pro gene from TEV that suppresses post-transcriptional gene silencing (Mallory et al., Nat Biotechnol 20:622 (2002)) were used for transient expression of selected enzymes in tobacco leaves. Preparation of *Agrobacterium* cultures and infiltration of tobacco or sugar beet plants was carried out as described by Azhakanandam et al., Plant Mol. Biol. 63: 393-404 (2007). In brief, the genetically modified agrobacteria were grown overnight in 50 mL of LB medium containing 100 μM acetosyringone and 10 μM MES (pH 5.6), and subsequently were pelleted by centrifugation at 4000×g for 10 min. The pellets were resuspended in the infection medium [Murashige and Skoog salts with vitamins, 2% sucrose, 500 μM MES (pH 5.6), 10 μM $MgSO_4$, and 100 μM acetosyringone] to $OD_{600}$=1.0 and subsequently held at 28 degrees C. for 3 hours. Infiltration of individual leaves was carried out on sugar beet (about 3 weeks old) and TEV-B tobacco plants (about 4 weeks old) using a 5 mL syringe by pressing the tip of the syringe (without a needle) against the abaxial surface of the leaf. Infiltrated plants were maintained at 22-25 degrees C. with a photoperiod of 16 hours light and 8 hours dark. Plant tissue was harvested after 5 days post infiltration for subsequent analysis.

3E. Maize Transient Expression System

Expression cassettes described in Example 12 were cloned into a binary vector. The constructs were transferred into *Agrobacterium tumefaciens* strain LBA4404 containing helper plasmid (pSBI) using a freeze-thaw method (An et al., Binary vector. In: Gelvin S B, Schilproot R A (eds), Plant molecular biology manual. Kluwar Academic Publishers, Dordrecht, pp A3 1-19 (1988)).

The maize transient expression system was established using young maize seedlings (5-12 d old). Preparation of *Agrobacterium* cultures and infiltration of maize leaves was carried out as described by Azhakanandam et al., Plant Mal. Biol. 63: 393-404 (2007). In brief, the genetically modified *agrobacteria* were grown overnight in 50 mL of LB medium containing 100 μM acetosyringone and 10 μM MES (pH 5.6), and subsequently were pelleted by centrifugation at 4000×g for 10 min. The pellets were resuspended in the infection medium (Murashige and Skoog salts with vitamins, 2% sucrose, 500 μM MES (pH 5.6), 10 μM $MgSO_4$, and 100 μM acetosyringone) to $OD_{600}$=1.0 and subsequently held at 28 degrees C. for 3 hours. Infiltration of individual leaves was carried out on maize seedlings using a 5 mL syringe, without a needle, by pressing the tip of the syringe against the abaxial surface of the leaf. Infiltrated plants were maintained at 22-25 degrees C. with a photoperiod of 16 hours light and 8 hours dark. Plant tissue was harvested after 5-7 days post infiltration for subsequent analysis.

To ensure that enzyme activity measured was due to plant expression of the enzymes, the expression constructs also incorporated an intron in the polynucleotide sequence coding for the enzyme. The presence of the intron ensures that expression of the enzyme is due to plant expression (able to process out the intron and therefore express a fully processed enzyme) versus agrobacterium expression (unable to process the intron and thus not able to express a functional enzyme).

3F. Transgenic Maize Callus and Plants

Transformation of maize callus was performed using a biolistic transformation method. Maize embryos were collected from maize kernels about 8 to 11 days after pollination. The ears were collected and sterilized in 20% Germicidal Clorox for 20 minutes on an orbital shaker set at 120 rpm followed by extensive rinsing of the ear in sterile water. Embryos were collected from the kernels and kept on culture media in the dark for 3 to 7 days.

To prepare DNA for bombardment, gold particles (0.6 to 1 micrometer size, Bio-Rad) were resuspended in 50% sterile glycerol by vortexing. An aliquot of the glycerol—gold particle suspension was combined by gentle mixing with $2\times10^{10}$ mol DNA of the gene encoding the selectable marker (PM) and gene of interests outlined in. Table 29 of Example 12. The mixture was combined with 2.5M CaCl2 and cold 1M spermidine to precipitate the DNA onto the gold particles. The gold particles with precipitated DNA were washed in ethanol. The washed gold particles were re-suspended in ethanol and aliquots of DNA suspension were placed evenly onto the center of individual macrocarrier membrane disks and allowed to dry. The macrocarrier was loaded into the gene gun above the stopping screen. Bombardment of embryos was performed with a PDS Helium—1000 gene gun. A rupture disc in the range of 650-1800 psi was used and the distance from the rupture disc and the macrocarrier was set at 8 mm with a stopping screen at 10 mm. The distance between the stopping screen and the embryos was about 7 cm. The pressure on the helium tank was set at about 1200 psi. Target tissues (embryos) were bombarded 3 times before being transferred to the dark at 28 degrees C. to recover for 3 days.

After recovery, the bombarded embryos were transferred to maintenance medium and cultured at 28 degrees C. in the dark. After 3 days, the bombarded embryo tissue was transferred to fresh callus induction medium and incubated for 1 week to induce callus formation. The calli were then transferred to selection medium containing mannose for three weeks at 28 degrees C. in the dark.

Selection of transgenic calli was performed by transferring living callus tissue to selection medium and cultured at 28 degrees C. in the dark for 3 weeks. Surviving calli were transferred to fresh selection medium and cultured an additional 2 weeks at 28 degrees C. in the dark. Surviving calli were then transferred to regeneration medium and cultured at 28 degrees C. in the dark for 2 weeks.

Callus tissues will be incubated under 16 hours of light at 24 degrees C. to encourage shoot development. Once shoot development starts, callus with shoots will be transferred to rooting medium and cultured at 24 degrees C. with light for another week prior to transplanting to soil for the remainder of the maize growing cycle.

3G: Analysis of Key Enzymes in Plant Tissue

Whole leaves from tobacco or sugar beet transiently expressing an enzyme were frozen at −80 degrees C. in 24-well blocks containing 3⁄16" chrome ball bearings. The frozen material was shaken at setting 9 for 2 min in a Kleco Titer plate/Microtube Grinding Mill creating a powder. Buffer (50 mM HEPES, 2 mM EDTA, 0.02% Tween-20, 100 mM locked sugar (isomaltulose, leucrose, or trehalulose depending upon the enzyme), pH 7) was added to the powdered samples to give a thick slurry. Samples were incubated in a Glas-Col rotator at 80% speed for 30 min. Samples were transferred by wide-bore P200 pipet to PCR tubes at 100 uL per tube and incubated at the appropriate temperature for the enzyme (50, 60, 70, 80 degrees C. depending on enzyme) in a Biorad Tetrad 2 thermocycler. The sample was transferred to either a Millipore Biomax 5KD MW membrane spin filter and centrifuged at 12,000×g for 20 min or a Millipore Multiscreen-HV filter plate and filtered at 20 InHg vacuum. After filtration, the samples were diluted in Milli-Q water as necessary and placed into either 0.3 or 1.5 mL sample vials with split caps for carbohydrate analysis by Dionex HPAEC.

3H: Analysis of Locking Enzymes in Plant Tissue

Whole leaves from tobacco, sugar beet, or maize were rolled and placed into filtration baskets (DNA IQ Spin Basket) and the filled filtration baskets placed into 1.5 mL eppendorf tubes. The filled filtration baskets and eppendorf tubes were frozen on dry ice for 5-8 min (or until frozen) followed by thawing on ice for 5-8 min (or until thawed). The thawed filled filtration baskets and eppendorf tubes were then centrifuged at 10,000×g for 15 min at 4 degrees C. and the filtrate collected.

The filtrate was boiled at 100 degrees C. for 5 min followed by centrifugation at 16,000×g for 20 min. The boiled filtrate was further filtered by transferring the boiled filtrate to either a Millipore Biomax 5 KD MW membrane spin filter and centrifuged at 12,000×g for 20 min or a Millipore Multiscreen-HV filter plate and filtered at 20 InHg. The filtrate was collected and diluted in Milli-Q water as necessary and placed into either 0.3 or 1.5 mL sample vials with split caps for analysis.

EXAMPLE 4

Plant Expressed Sucrose Isomerase Enzyme

4A: Transient Expression of Sucrose Isomerase in Sugar Beet and Tobacco Leaves

The transformation vector 17588, as described in Example 12, was used to transiently expressing enzymes in tobacco or sugar beet leaves essentially as described in Example 3D. Tobacco or sugar beet leaves transiently expressing a sucrose isomerase were generated using the vector 17588 which contains a dicot optimized polynucleotide sequence encoding a sucrose isomerase (SEQ ID NO: 16). Leaves transiently expressing sucrose isomerase were harvested and extracted essentially as described in Example 3H and analyzed by Dionex for carbohydrates essentially as described in Example 1G.

Dionex HPAE chromatography utilized pure sugar standards as a reference for retention time and standard curve production for determining sugar concentrations. Sugar concentrations were based on the total sugar consisting of glucose, fructose, sucrose, trehalulose and isomaltulose when present. These five sugars represent >98% of the total peak area of the chromatograms with the remainder coming from minor unknown peaks from the biological extraction milieu of the leaf.

Sucrose isomerase activity in transiently infiltrated leaves was directly detected by the formation of the two major products of the enzymatic conversion of sucrose to the locked sugars, trehalulose and isomaltulose. Neither of the locked sugars were present in control leaves. Tables 7-10 summarize the analysis of tobacco and sugar beet transiently expressing a sucrose isomerase (vector 17588) and demonstrate that tobacco and sugar beet plants are able to express an active sucrose isomerase which catalyzes the conversion of sucrose to the locked sugars isomaltulose and trehalulose and accumulate the locked sugars in the leaves.

TABLE 7

Carbohydrate analysis (HPAEC) of tobacco leaves expressing a sucrose isomerase (SEQ ID NO: 16).

| sample | Sucrose (mM) | Trehalulose (mM) | Isomaltulose (mM) | Total Disaccharide (mM) |
|---|---|---|---|---|
| 17588 | 3.6 | 17.7 | 6.4 | 27.7 |
| 17588 | 6.8 | 34.3 | 14.1 | 55.2 |
| 17588 | 4.2 | 23.9 | 8.1 | 36.2 |
| 17588 | 14.7 | 33.1 | 13.8 | 61.6 |
| Negative control | 11.9 | 0.0 | 0.0 | 11.9 |
| Negative control | 11.8 | 0.0 | 0.0 | 11.8 |
| Negative control | 6.3 | 0.0 | 0.0 | 6.3 |
| Negative control | 4.2 | 0.0 | 0.0 | 4.2 |

TABLE 8

Carbohydrate analysis (HPAEC) of tobacco leaves transiently expressing sucrose isomerase.

| sample | Glucose + Fructose (% total sugar) | Sucrose (% total sugar) | Trehalulose (% total sugar) | Isomaltulose (% total sugar) |
|---|---|---|---|---|
| 17588 | 39.2 | 7.9 | 38.8 | 14.1 |
| 17588 | 51.4 | 6.0 | 30.2 | 12.4 |

TABLE 8-continued

Carbohydrate analysis (HPAEC) of tobacco leaves transiently expressing sucrose isomerase.

| sample | Glucose + Fructose (% total sugar) | Sucrose (% total sugar) | Trehalulose (% total sugar) | Isomaltulose (% total sugar) |
|---|---|---|---|---|
| 17588 | 47.9 | 6.0 | 34.4 | 11.7 |
| 17588 | 51.7 | 11.5 | 26.0 | 10.8 |
| Negative control | 40.6 | 59.4 | 0.0 | 0.0 |
| Negative control | 58.5 | 41.5 | 0.0 | 0.0 |
| Negative control | 45.7 | 54.3 | 0.0 | 0.0 |
| Negative control | 53.3 | 46.7 | 0.0 | 0.0 |

TABLE 9

Carbohydrate analysis (HPAEC) of sugar beet leaves transiently expressing sucrose isomerase (SEQ ID NO: 16).

| Sample | Sucrose (mM) | Trehalulose (mM) | Isomaltulose (mM) | Total disaccharide (mM) |
|---|---|---|---|---|
| 17588 | 8.5 | 9.9 | 3.1 | 21.5 |
| 17588 | 16.6 | 0.7 | 0.1 | 17.3 |
| 17588 | 15.1 | 2.5 | 1.3 | 18.9 |
| 17588 | 31.8 | 0.5 | 0.3 | 32.6 |
| Negative control | 10.0 | 0.0 | 0.0 | 10.0 |
| Negative control | 15.3 | 0.0 | 0.0 | 15.3 |
| Negative control | 17.6 | 0.0 | 0.0 | 17.6 |
| Negative control | 7.8 | 0.0 | 0.0 | 7.8 |

TABLE 10

Carbohydrate analysis (HPAEC) of sugar beet leaves transiently expressing sucrose isomerase (SEQ ID NO: 16).

| Sample | Glucose + fructose (% total sugar) | Sucrose (% total sugar) | Trehalulose (% total sugar) | Isomaltulose (% total sugar) |
|---|---|---|---|---|
| 17588 | 28.2 | 28.5 | 33.1 | 10.2 |
| 17588 | 43.2 | 54.2 | 2.3 | 0.3 |
| 17588 | 56.5 | 34.7 | 5.8 | 3.0 |
| 17588 | 42.4 | 56.1 | 0.9 | 0.6 |
| Negative control | 50.4 | 49.6 | 0.0 | 0.0 |
| Negative control | 42.9 | 57.1 | 0.0 | 0.0 |
| Negative control | 39.8 | 60.2 | 0.0 | 0.0 |
| Negative control | 74.4 | 25.6 | 0.0 | 0.0 |

4B: Transient Expression of Enzymes in Maize Leaves

Transient expression of enzymes in maize leaves was performed essentially as described in Example 3E using the binary vector pEB47 (described in Example 12) comprising a monocot optimized polynucleotide sequence encoding a sucrose isomerase (SEQ ID NO: 24). Maize leaves were harvested and analyzed for the presence of isomaltulose and trehalulose (products of sucrose isomerase activity within the maize leaf) essentially as described above for tobacco and sugar beet leaves transiently expressing sucrose isomerase. Table 11 outlines data that demonstrates sucrose isomerase is actively expressed in maize leaves transiently expressing sucrose isomerase and leads to the accumulation of the locked sugars, isomaltulose and trehalulose within the maize leaf.

TABLE 11

Carbohydrate analysis (HPAEC) of maize leaves transiently expressing sucrose isomerase (SEQ ID NO: 24).

| Sample | Glucose + fructose (% total sugar) | Sucrose (% total sugar) | Trehalulose (% total sugar) | Isomaltulose (% total sugar) |
|---|---|---|---|---|
| 47-6 (pEB47) | 78.9 | 17.2 | 2.4 | 1.5 |
| 47-7 (pEB47) | 63.7 | 33.3 | 2.1 | 0.9 |
| 47-8 (pEB47) | 73.1 | 16.0 | 7.3 | 3.6 |
| Negative control (GUS containing construct) | 69.4 | 30.6 | 0.0 | 0.0 |
| Negative control leaf tissue | 58.2 | 41.8 | 0.0 | 0.0 |

4C: Transgenic Maize Callus Expressing Sucrose Isomerase

Transgenic maize callus expressing sucrose isomerase was generated by bombarding maize embryos with linear polynucleotide sequence. The method of embryo transformation and generation of callus was essentially as described in Example 3F; however, two polynucleotide sequences were bombarded at the same time. One of the polynucleotide sequences contained the selectable marker, PMI, which allows for selection of transgenic maize cells by growth on mannose. The second polynucleotide sequence, pEB38, contained a maize optimized polynucleotide sequence encoding a sucrose isomerase (SEQ ID NO: 20). The sucrose isomerase was targeted to the vacuole. Table 12 outlines data which demonstrates that transgenic maize callus which expresses sucrose isomerase accumulated the locked sugars trehalulose and isomaltulose.

TABLE 12

Carbohydrate analysis (HPAEC) of transgenic maize callus tissue expressing sucrose isomerase.

| Sample | Glucose + Fructose % total sugar | Sucrose % total sugar | Trehalulose % total sugar | Isomaltulose % total sugar |
|---|---|---|---|---|
| 1 pEB38 | 14.8 | 0.95 | 38.2 | 46.0 |
| 2 pEB38 | 25.0 | 0.69 | 35.3 | 39.0 |
| 3 pEB38 | 32.0 | 5.13 | 34.8 | 28.1 |
| Negative control | 70.0 | 30.0 | 0.0 | 0.0 |

Total sugar = total amount of identifiable sugars in sample based on retention times of pure sugar standards. Extraneous peaks in samples are indeterminate and not included in sample analysis. The negative control is transgenic maize callus generated by bombardment with the polynucleotide sequence encoding PMI only.

4D: Transgenic Sugarcane Callus Expressing Sucrose Isomerase

Transgenic sugarcane callus expressing sucrose isomerase was generated essentially as described in Example 3A; however, two polynucleotide sequences were bombarded at the same time. One of the polynucleotide sequences contained the selectable marker, PMI, which allows for selection of transgenic sugarcane cells by growth on mannose. The second polynucleotide sequence, pEB38, contained a monocot optimized polynucleotide sequence encoding a sucrose isomerase (SEQ ID NO: 20). The sucrose isomerase was targeted to the vacuole. Table 13 outlines data which demonstrates that transgenic sugarcane callus which expresses sucrose isomerase accumulated the locked sugars trehalulose and isomaltulose.

TABLE 13

Carbohydrate analysis (HPAEC) of transgenic sugarcane callus tissue expressing sucrose isomerase.

| Sample | Glucose + Fructose % total sugar | Sucrose % total sugar | Trehalulose % total sugar | Isomaltulose % total sugar |
|---|---|---|---|---|
| 1 pEB38 | 44.13 | 37.70 | 8.87 | 9.30 |
| Negative control | 34.61 | 65.39 | 0.0 | 0.0 |

Total sugar = total amount of identifiable sugars in sample based on retention times of pure sugar standards. Extraneous peaks in samples are indeterminate and not included in sample analysis. Negative control is transgenic sugarcane callus generated by bombardment with a polynucleotide sequence encoding the selectable marker PMI.

4E: Transgenic Sugar Beet Expressing Sucrose Isomerase (SEQ ID NO: 16)

Transgenic sugar beet plants containing the expression cassette 17588 (described in Example 12) were generated essentially as described in patent application WO02/14523 which is a multiple shoot method of transformation. The transgenic sugar beet callus was selected using mannose selection (the selectable marker gene was PMI) which was performed essentially as described in patent application WO94/20627.

The transgenic sugar beet plants were analyzed by PCR to determine if the selectable marker (PMI) and the sucrose isomerase gene (SEQ ID NO: 16) were present in the plant. In addition, the transgenic sugar beet plants were analyzed for the accumulation of locked sugars.

To analyze the sugar content of the transgenic sugar beet plants, leaves from the transgenic sugar beet plants were sampled into a Costar 96-well box. The box was placed on ice during the sampling procedure. After filling the box with glass balls the leaf samples were placed into the wells and 100 μL sterile $ddH_20$ was added. The wells were closed using strip caps or a lock and the box shaken in a Tissue laser (25-30 s, 30 Hz.) to pulverize the tissue in the water. The locks covering the wells were pierced and the samples were boiled on a water bath for 10 min. After boiling, an additional 100 μL sterile $ddH_20$ was added followed by centrifugation (10 min, 3000 rpm). The supernatants were transferred to Millipore spin filter and centrifuged at 12000 rpm, 5 min. The filtered supernatants were stored at −20 degrees C. or in 4 degrees C. if the analysis was performed directly.

The samples were diluted 100 times with distilled water prior to analysis using the Dionex HPAE-system. The Dionex HPAE-system, ICS-3000 was used to separate the carbohydrates. The instrument was equipped with a temperature regulated auto sampler, CarboPac PA20 3×30 mm guard column, CarboPac PA20 3×15 mm analytical column and pulsed amperometric detector (PAD). The mobile phase used was 200 mM NaOH solution and water in following gradient program: 8 min/16% NaOHsolution/2 min 16-100% NaOHsolution/3 min 100% NaOHsolution/2 min 100-16%/7 min 16% NaOHsolution. The column temperature was set at 30 degrees C. and the flow 0.43 mL/min. The approximate retention times were glucose 7.7 min, fructose 9.3 min, sucrose 11.0 min, trehalulose 13.1 min and isomaltulose 14.5 min. The peaks were identified using the standard solutions. Table 14 outlines data which demonstrates transgenic sugar beet plants expressing a sucrose isomerase enzyme and the subsequent accumulation of the locked sugars, isomaltulose and trehalulose. Locked sugars are detected in transgenic sugar beet plants expressing sucrose isomerase indicating that the enzyme is both expressed and is able to perform the enzymatic activity which converts sucrose to isomaltulose and trehalulose.

TABLE 14

Transgenic sugar beet plants expressing sucrose isomerase.

| Event | PCR PMI | PCR GOI | Dionex-isomaltulose | Dionex-trehalulose |
|---|---|---|---|---|
| 0851B:1 A biennial | + | + | + | ++ |
| 0851B:2 A biennial | | + | + | ++ |
| 0851F:2 A biennial | + | + | − | + |
| 0851I:1 B biennial | + | − | + | ++ |
| 0851K:2 A biennial | + | + | ++ | +++ |
| 0851K:2 B biennial | + | − | − | − |
| 0851K:2 C biennial | + | − | − | − |
| 0851K:4 A biennial | + | + | − | + |
| 0851N:1 A biennial | | + | − | + |
| 0851O:1 A biennial | + | + | + | ++ |
| 0851O:2 A biennial | + | + | + | ++ |
| 0851O:3 A biennial | + | + | + | +++ |
| 0851O:4 A biennial | | + | + | ++ |
| 0851O:5 A biennial | + | + | + | ++ |
| 0903B:5 A annual | | − | + | ++ |
| 0903B:7 A annual | | + | + | + |
| 0903D:1 A annual | + | + | − | + |
| 0903F:1 B annual | + | + | + | ++ |
| 0903F:1 C annual | + | + | + | ++ |
| 0903G:1 A annual | + | + | − | + |
| 0903I:1 A annual | + | + | + | ++ |

EXAMPLE 5

Transgenic Plants Expressing Dextransucrase with Leucrose Synthase Activity

5A: Transient Expression of Dextransucrase (SEQ ID NO: 35) in Tobacco Leaves

The transformation vector 902195, as described in Example 12, was used to generate tobacco leaves transiently expressing dextransucrase essentially as described in Example 3D. Transient expression of dextransucrase in tobacco leaves was performed using the vector 902195 which contains a dicot optimized polynucleotide sequence encoding a dextransucrase with leucrose synthase activity (SEQ ID NO: 35). Transiently expressing leaves were harvested and extracted essentially as described in Example 3H and analyzed by Dionex for carbohydrates essentially as described in Example 1G.

Dionex HPAE chromatography utilized pure sugar standards as a reference for retention time and standard curve production for determining sugar concentrations. Sugar concentrations were based on the total sugar consisting of glucose, fructose, sucrose, and locked sugars when present. These sugars represent >98% of the total peak area of the chromatograms with the remainder coining from minor unknown peaks from the biological extraction milieu of the leaf.

Dextransucrase with leucrose synthase activity transiently expressed in leaves was directly detected by the formation of the locked sugar leucrose. Leucrose was not present in control leaves. Table 15 summarizes the analysis of tobacco leaves transiently expressing a dextransucrase with leucrose synthase activity (vector 902195) and demonstrates that tobacco leaves are able to express an active dextransucrase which catalyzes the conversion of sucrose to the locked sugar leucrose which accumulates in the leaf.

5B: Transient Expression of Dextransucrase (SEQ ID NO: 24) in Maize Leaves.

Maize leaves transiently expressing dextransucrase with leucrose synthase activity were generated essentially as described in Example 3E using the vector pEB47 (described in Example 12) comprising a monocot optimized polynucleotide sequence encoding a dextransurase (SEQ ID NO: 47). Maize leaves were harvested and extracted essentially as described in Example 3H. The extract was analyzed for carbohydrate content essentially as described in Example 1G. Table 15 outlines data that demonstrates dextranase is actively expressed in maize leaves and leads to the accumulation of the locked sugar leucrose within the maize leaf.

5C: Transgenic Sugarcane Callus Expressing Dextransucrase (SEQ ID NO: 37)

Transgenic sugarcane callus expressing dextransucrase with leucrose synthase activity (SEQ ID NO: 37) was generated essentially as described in Example 3A; however, two polynucleotide sequences were bombarded at the same time. One of the polynucleotide sequences contained the selectable marker, PMI, which allows for selection of transgenic sugarcane cells by growth on mannose. The second polynucleotide sequence, pEB28, contained a monocot optimized polynucleotide sequence encoding a dextransucrase (SEQ ID NO: 37). The dextransucrase was targeted to the vacuole. Table 15 outlines data which demonstrates that transgenic sugarcane callus which expresses sucrose isomerase accumulated the locked sugar leucrose.

TABLE 15

Plant tissue expressing dextransucrase accumulates leucrose and/or isomaltose.

| | tobacco | maize | sugar cane |
|---|---|---|---|
| dextransucrase | Leucrose | Leucrose | Leucrose and isomaltose |
| Negative control | — | — | — |

Leucrose synthase activity is determined by the accumulation of leucrose above 10x signal: noise on a Dionex IC.

EXAMPLE 6

Transgenic Plants Expressing Amylosucrase

6A: Total Starch Analysis of Amylosucrase-Expressing Maize and Sugarcane Callus

The effectiveness of the amylosucrase gene, when expressed in either maize or sugar cane callus, can be evaluated by comparing the total starch content of the amylosucrase expressing calli to control calli that have not been transformed with the gene. The total starch content of any plant tissue of interest can be measured using a protocol similar to that of the Megazyme Total Starch Assay kit. In this assay, the starch contained in a plant sample is broken down into glucose monomers through digestion by both an alpha-amylase and an amyloglucosidase. The resulting solution of glucose can be enumerated by a glucose oxidase-peroxidase (GOPOD) reaction essentially as is described in Example 2B. In this reaction, the glucose oxidase enzymes break down glucose to hydrogen peroxide which the peroxidase then digests, releasing oxygen which reacts with the 4-aminoantipyrine in solution to evolve a pink color. The pink color can be measured with a spectrophotometer and, when compared with the absorbance of a glucose standard, can give a measure of the amount of glucose and therefore, the amount of starch in a given sample.

To accurately measure the production of carbohydrate polymers by the amylosucrase gene in callus, several controls and conditions will need to be established. For every calli that is transformed with the amylosucrase gene, a duplicate calli should be transformed with an empty vector that can act as a control sample. Both transformed and control calli should initially be grown on sucrose media to provide amylosucrase with its natural substrate and raise the overall starch content in the calli. After sufficient growth, some calli (both AMS and control) should be transferred to sorbitol media where the natural metabolism of the tissue will lower the background of transient starch and, theoretically, leave the amylosucrase produced carbohydrate polymer. In tissue culture, sorbitol is assimilated and metabolized by plants to a much lesser degree than sucrose. With sorbitol as a carbon source, plant cells are expected to deplete transient and storage starch reserves leaving an amylosucrase derived starch to accumulate.

Once the calli are harvested from the media, similar events can be pooled into wells of a 24-well block to bulk up the amount of tissue and lyophilized so that calculations can be made on a dry weight basis. Lyophilized tissue can be easily ground in the 24-well blocks using a Kleco. As mentioned previously, the Megazyme total starch protocol can be used to effectively measure the total starch content of tissue samples. The following is an example of a slightly modified protocol that could be employed to analyze lyophilized callus material. Approximately 30-70 mg of the ground tissue should be washed with 5 mL of 80-90% ethanol for 30-60 minutes and centrifuged for 5 minutes at 3000 rpm to wash away any soluble sugars or other soluble compounds. Additional ethanol washes may be added as necessary, as long as all samples are treated identically. The pelleted material should then be washed in 5 mL of cold water and centrifuged again for 5 minutes at 3000 rpm to remove any remaining ethanol. At this stage, the pellet should be completely resuspended in 3 mL of a 1:30 dilution of alpha-amylase (Megazyme) in 50 mM MOPS buffer pH=7 and incubated for 6 minutes in a 100 degree C. water bath. Samples should then be transferred to a 50 degree C. water bath where 4 mL of NaOAc buffer pH=4.5 and 0.1 mL of amyloglucosidase (Megazyme) will be added and then incubated for 30 minutes at 50 degree C. After incubation, all samples should be brought to 10 mL with water, vortexed, and centrifuged for 10 minutes at 3000 rpm. This supernatant contains the solubilized glucose monomers that remain from the digestion of the carbohydrate polymers that were extracted from the lyophilized tissue samples. To enumerate the glucose in this mixture, 2 mL should be added in duplicate to glass test tubes, mixed with 3 mL of GOPOD reagent, and incubated for 20 minutes at 50 degree C. Once cooled to room temperature, the optical density of the samples can be read at 510 nm. Based on the OD reading of the samples and its comparison to a known standard, the amount of glucose, and therefore starch, in the original dry weight sample can be calculated.

Upon completion of total starch content analysis, it is expected that calli expressing the amylosucrase gene will show an increased level of total starch over the negative control calli due to the additional production of carbohydrate polymers by the enzyme. Additionally, targeted expression of the amylosucrase enzyme to the vacuole or apoplast of transgenic plant cells would serve to isolate the de novo starch from the endogenous starch metabolizing enzymes allowing for accumulation of a locked carbohydrate. Therefore, when the calli are depleted of transient starch after growth on sorbitol media, the total starch content would be expected to fall slightly, but remain at an increased level over the negative controls.

6B: Starch Structure: Amylose/Amylopectin Differentiation by Iodine Binding

The structure of the carbohydrate polymers produced by the amylosucrase enzyme can potentially be identified by developing a method to enumerate the proportions of amylose and amylopectin in plant material. The comparison of control samples with samples expressing the amylosucrase gene could identify structural composition changes that may be present in the polymers produced by amylosucrase expressing events, suggesting that a carbohydrate polymer lock is being produced. One possible method for accomplishing this is through an iodine binding assay. In this assay, the plant produced carbohydrate polymers are solubilized from the tissue and then stained with iodine. The resulting iodine-starch complexes will absorb at different wavelengths depending on the proportions of amylose and amylopectin present in the extract. Through comparison with known standards and mixtures of amylose and amylopectin, both the total amount of starch present and the proportions of amylose and amylopectin present in the starch produced in the tissue can be calculated.

The following is an example of a starch extraction and iodine staining procedure that could be used to analyze lyophilized, ground tissue samples. Approximately 100-200 mg of ground, lyophilized tissue should be washed with 5 mL of 90% ethanol, incubated for 15 minutes in a 100 degree C. water bath, and centrifuged for 5 minutes at 3000 rpm to remove the supernatant. This wash step should be repeated at least two more times to ensure sufficient removal of soluble sugars and other potential iodine binding compounds from the samples. To the sample material, 5 mL of 100% ethanol should be added and incubated again for 15 minutes at 100 degree C. Prior to centrifuging the sample, 5 mL of acetone should be added to the mixture. The pellet should then be suspended once more in 5 mL of acetone to ensure the complete removal of any residual ethanol, centrifuged for 5 minutes at 3000 rpm, and the pellet allowed to dry overnight. To solubilize the starch from the dried pellet, 5 mL of 0.5M KOH should be added and incubated for 2-3 hours at 100 degree C. Debris may be pelleted by centrifugation for 10 min at 3000 rpm. For the staining of the solubilized carbohydrate polymers, 1 mL of the KOH extract should first be neutralized with 5 mL of 0.1M HCl, then 0.5 mL of Lugol's Iodine solution should be added and diluted to between 25 and 50 mL with water to bring the absorbance into an appropriate range. The color should be allowed to develop for about 15 minutes and then samples can be added to a microtiter plate for measuring the optical density along with pure amylose and pure amylopectin stained standards. The spectra of the samples and standards should be measured first to determine at which wavelength the maximum absorbance occurs for each sample, since this is indicative of the proportions of amylose and amylopectin in the samples. To analyze the sample spectra, a system of equations will be set up using Beer's law based on the absorbance values at 6 different wavelengths. Measurements of the absorbance will be recorded at 504 nm, the wavelength of greatest difference between the amylose and amylopectin peaks where amylopectin's absorbance is greater than amylase's absorbance; 548 nm, the wavelength of the pure amylopectin peak; 630 nm, the wavelength of the pure amylose peak; 700 nm, the wavelength of greatest difference between the amylose and amylopectin peaks where amylase's absorbance is greater than amylopectin's absorbance; 800 nm, the wavelength of greatest absorbance due to amylase where amylopectin's absorbance approaches zero; and the wavelength determined to be the location of the sample spectra's maximum (Jarvis and Walker J. Sci. Food Agric. 63: 53-57 (1993)). The results of this system of equations will give a concentration value of the amount of amylose and the amount of amylopectin present in the sample extract, from which a ratio of the two starch forms can be determined.

Upon successful completion of the iodine binding assay, it is expected that the assay data will support the total starch assay data in showing an overall starch increase in the samples expressing the amylosucrase gene. In addition, it is expected that the amylosucrase expressing events will produce a carbohydrate polymer that is more closely related to amylose than amylopectin, therefore a larger proportion of amylose when compared to control samples should be observed. This shift in composition of the starch produced in amylosucrase expressing events will also support the successful production of a locked substrate in plant tissue.

6C: Digestion of Plant Produced Carbohydrate Polymers with Plant-Expressed Enzymes The ability of a plant produced key enzyme to digest a plant produced locked substrate can be exemplified using the principle underlying the glucose oxidase-peroxidase (GOPOD) reaction. If the plant purified key enzyme acts on the plant produced locked sugar, glucose monomers should be liberated from the locked sugar which can be enumerated by the GOPOD reaction. In order to complete this digestion, however, an appropriate plant expressed ky enzyme must be purified and a carbohydrate polymer produced by the amylosucrase enzyme must be solubilized in an appropriate buffer. Alpha-amylase can be collected from transgenic maize plants expressing alpha-amylase in the seed through laboratory established FPLC methods yielding a purified plant-expressed key enzyme (alpha-amylase). Locked sugars produced in tobacco or another plant system by the amylosucrase gene can be extracted in boiling water from lyophilized plant material after washing with 80-90% ethanol to remove any soluble sugars or compounds (Spoehr and Milner J. Biol. Chem. 111 (3): 679-687. (1935)). The alpha-amylase will not yield strictly glucose in its digest, the amount of glucose produced should be sufficient to be detected by the GOPOD reaction assay when compared to a control sample of the undigested locked sugar. It is expected that a difference in glucose levels would be detected in this type of digestion assay, verifying that plant expressed key enzymes are, indeed, capable of digesting plant produced locks.

Additionally, in the process of performing HPSEC on debranched amylosucrose polymer mixture, sample fractions could be collected, and a plant expressed alpha amylase or glucoamylase key enzyme could be used to hydrolyze the starch in the collected fractions to glucose. A GOPOD reaction assay could be used to detect the glucose liberated from the amylosucrose locked-carbohydrate fraction.

6D: Detection of Amylosucrase Activity in Stably Transformed Plants or Plants Transiently Expressing Amylosucrase.

Amylosucrase may be expressed either transiently or through stable transformation of maize, cane, beets, tobacco or other plants with a promoter that drives expression in the appropriate target tissue (leaf, endosperm, embryo, etc.) and with targeting sequences that direct the amylosucrase to the desired subcellular location (vacuole, chloroplast, cytoplasm, apoplast, etc.). A variety of techniques may be used to detect the activity of the amylosucrase gene in plants.

For instance, plant tissue samples expressing the amylosucrase polypeptide may be incubated in the dark for 24 to 48 hours in order for transient starch produced in the chloroplast to be broken down by the plant. Leaf or other tissue may be excised from the plant and dipped into boiling water for one minute to heat kill the tissue. After heat killing plant tissue samples may be incubated in hot ethanol to remove the chlorophyll, repeated washing with hot ethanol may be necessary to remove all the chlorophyll. Once the chlorophyll has been removed, the tissue can be rinsed with cold water and placed on a petri dish. Lugol's solution (5 g iodine ($I_2$) and 10 g potassium iodide (KI) mixed with 85 ml distilled water), may then be poured over the sample an allowed to incubate at room temperature. Control samples that have been in the dark for 24 hours should contain no starch and should not stain black in Lugols solution. Samples expressing the amylosucrase gene should stain black due to starch that is produced in the vacuole or other organelles targeted for expression of the Amylosucrase enzyme.

Leaves contain a variety of unique cell types such as the pavement cells that are highly specialized cells making up the majority of the leaf surface. These are easily identified by their puzzle piece shapes (in dicots) and are only found at the leaf surface. They contain no chloroplasts or amyloplasts, so if pavement cells are found to have what appeared to be dark staining "amyloplasts" and these are not observed in pavement cells from "vector only" controls, this would be good evidence that the construct is working and that starch is being produced.

6E: Analysis of Locked Amylosucrose Carbohydrates by HPSEC

Another means of analyzing structural composition changes that may be present in the polymers produced by amylosucrase expressing events is by the use of High-performance size exclusion chromatography, HPSEC. Using HPSEC, a locked amylosucrase carbohydrate polymer could be identified and characterized based on its molecular weight or chain length distribution.

The extraction of starch from plant material for analysis by HPSEC could be carried out essentially as described by Santacruz et al J. Agric. Food Chem. 2004, 52 (7): 1985-1989. Starch could be extracted from plant material such as leaf or callus by lyophilizing and grinding plant material. Powdered lyophilized plant tissue could be mixed with 90% ethanol (v/v) and placed in a boiling water bath for 15 minutes. After centrifugation at 1000 g for 10 minutes, the pellet could be washed three more times with hot 90% ethanol. The pellet can be washed again with 100% ethanol, boiled for 15 minutes. After centrifugation, the supernatant can be discarded and the pellet washed further with acetone, centrifuged and supernatant discarded. The pellet can be dried overnight at room temperature. The dried plant material can be further extracted by addition of 0.2% EDTA to the dried residual pellet and mixed overnight with shaking at room temperature. After centrifugation, the resulting starch pellet can be further extracted by addition of 90% ethanol and boiled for 30 minutes. After centrifugation, the supernatant can be saved and the pellet extracted again with 90% ethanol. The supernatants can be combined and mixed with 100% ethanol in a ratio of 1 part DMSO to 9 parts ethanol. The solution can be incubated at room temperature for 15 minutes, centrifuged to obtain a starch pellet. The starch pellet can then be solubilized in 90% DMSO with boiling for 15 minutes. The starch could be done debranched for GPC analysis essentially as described by Yao et al Carbo. Research. 2005, 340:701-710. Debranching of starch can be carried out in a 50 mM Sodium Acetate, pH 4.0 buffer which has been warmed to 42-SOC. A reaction which combines 880 ul of warm NaAc buffer, 120 ul of the DMSO solubilized starch pellet can be prepared. To keep the starch solubilized, the reaction can be heated to 100 C for 10 minutes and then cooled to 22-42 C before addition of 1 U/ml of isoamylase (Megazyme Inc., Ireland.) The digestion reaction can be incubated at 37-42 C with constant agitation for 16-24 hours. After digestion, the debranching reaction can be heated in a boiling water bath for 10 minutes. The starch dispersion can then be concentrated in a Speed-Vac vacuum evaporator. Gel permeation chromatography or HPSEC could be carried out on this concentrated starch sample to characterize the starch structure of the locked amylosucrose carbohydrate. Starch samples can be diluted up to 30 fold in DMSO in preparation for analysis by the HPSEC system.

Using an HPSEC system such as a Waters Breeze 717 system. 50 ul of debranched starch polymer could be injected into a Ultrahydrogel-6×40 mm Guard column (WAT 011565) and Ultrahydrogel 250 A—7.8×300 mm column (WAT011525) with Waters 1515 isocratic HPLC pump and a differential refractometer such as Waters Model 410 for detection. A flow rate of 0.5 mL/min at a column, column temperature of 35 C and detector temperature of 40 C may be used. The molecular weight standards for column calibration could be maltotriose (Sigma), maltohepatose (Sigma), and pullulan standards (P-5, MW 5800; P-10, MW 12,200; P-20, MW 23,700; P-50, MW 48,000, from Shodex, Japan). On the chromatogram the differential refractive index (DRI) value on the y-axis will be the mass response to the carbohydrate at a particular retention time (RT).

Within the separation range of the HPSEC media, the RT on the x-axis will be approximately proportional to the logarithm of the molecular weight (or chain length), and using standards the precise relationship may be determined to generate a standard curve. In this way, the chain length of an amylosucrose polymer may be determined and characterized.

EXAMPLE 7

Transgenic Plants Expressing Key Enzymes

7A: Transient Transgenic Tobacco and Sugar Beet Expressing alpha-1,6-glucosidase Tobacco and sugar beet leaves transiently expressing an alpha-1,6-glucosidase enzyme were generated essentially as described in Example 3D. Leaves transiently expressing alpha-1,6-glucosidase were generated using the binary vector 902525 or the BCTV binary vector 902526. Both of the binary vectors contain expression cassettes encoding an alpha-1,6-glucosidase (SEQ ID NO: 11) which has been targeted through the ER and is expected to accumulate in the apoplast. Infiltrated tobacco and sugar beet leaves were harvested, extracted and enzyme activity assayed essentially as described in Example 3G. The key enzyme, alpha-1,6-glucosidase, catalyzes the conversion of isomaltulose to the fermentable sugars fructose and glucose and was assayed at 60 degrees C. Carbohydrate analysis of the final filtrate was performed using the Dionex system essentially as described in Example 1G. Tables 16-17 outline data demonstrating transient expression of an alpha-1,6-glucosidase in tobacco and sugar beet leaves.

TABLE 16

Carbohydrate analysis of tobacco leaves transiently expressing an alpha-1,6-glucosidase enzyme (SEQ ID NO: 11). Enzyme activity is indicated by the change in abundance of each sugar as a percentage of the total sugars over a 24 hour period.

| sample | Glucose (% total sugar) | Fructose (% total sugar) | Isomaltulose (% total sugar) |
|---|---|---|---|
| 902525 binary | 11.97 | 12.46 | −24.43 |
| 902526 BCTV | 22.66 | 26.95 | −49.61 |
| Negative control | −1.67 | 3.75 | −2.08 |

Total sugar = total amount of identifiable sugars in sample based on retention times of pure sugar standards. Extraneous peaks in samples are indeterminate and not included in sample analysis. The negative control is tobacco leaves transiently expressing a binary vector containing an origin of replication from beet curly top.

TABLE 17

HPAEC analysis of carbohydrate products from sugar beet leaves transiently expressing an alpha-1,6-glucosidase enzyme (SEQ ID NO: 11). Enzyme activity is indicated by the change in abundance of each sugar as a percentage of the total sugars over a 24 hour period.

| sample | Glucose (% total sugar) | Fructose (% total sugar) | Isomaltulose (% total sugar) |
|---|---|---|---|
| 902525 binary | 19.73 | 19.10 | −38.83 |
| 902526 BCTV | 14.05 | 11.91 | −25.96 |
| Negative control | 6.14 | 6.61 | −12.74 |

Total sugar = total amount of identifiable sugars in sample based on retention times of pure sugar standards. Extraneous peaks in samples are indeterminate and not included in sample analysis. The negative control is sugar beet leaves transiently expressing a binary vector containing an origin of replication from beet curly top.

7B: Transgenic Maize Callus Expressing alpha-1,6-glucosidase

Transgenic maize callus expressing an alpha-1,6-glucosidase enzyme was generated by bombarding maize embryos with linear polynucleotide sequence. The method of embryo transformation and generation of callus was essentially as described in Example 3F; however, two polynucleotide sequences were bombarded at the same time. One of the polynucleotide sequences contained the selectable marker, PMI, which allows for selection of transgenic maize cells by growth on mannose. The second polynucleotide sequence, 902435 or 902425, contained a maize optimized polynucleotide sequence encoding an alpha-1,6-glucosidase (SEQ ID NO: 54 or SEQ ID NO: 56). The alpha-1,6-glucosidase was targeted to the endoplasmic reticulum (902435) or to the chloroplast (902425).

Analysis of alpha-1,6-glucosidase enzyme activity in transgenic maize calli was performed by extracting the enzyme from the transgenic calli and incubating the extract with isomaltulose. If alpha-1,6-glucosidase enzyme activity is present, the isomaltulose is converted to glucose and fructose. Essentially, maize calli expressing the alpha-1,6-glucosidase were collected 8 calli per well in Slicprep 96 device. Samples were frozen at −80 degrees C. and thawed at room temperature. Thawed samples were centrifuged at 1770×g and flow-through extract collected. Extracts were heated at 60 degrees C. for 10 minutes. Extracts were centrifuged at 1770×g 30 minutes at 4 degrees C. to pellet denatured proteins in samples. Equal volumes of clarified extract and reaction buffer (200 mM Isomaltulose, 100 mM HEPES, 0.04% Tween-20, 4 mM EDTA, 40 mM NaOH, 2× protease inhibitor [Roche Complete EDTA-free]) were combined and incubated at 60 degrees C. in. BioRad Tetrad 2 thermocycler. Samples were collected at times 0 and 24 hours. Collected samples were incubated at 95 degrees C. for 5 minutes before freezing at −20 degrees C. Samples were analyzed by Dionex. Table 18 outlines data which demonstrates that transgenic maize callus expresses an active alpha-1,6-glucosidase enzyme.

TABLE 18

HPAEC analysis of carbohydrate products from transformed maize callus tissue expressing alpha-1,6-glucosidase enzymes. Enzyme activity is indicated by the change in abundance of each sugar as a percentage of the total sugars over a 24 hour period.

| Sample | Glucose (% total sugar) | Fructose (% total sugar) | Isomaltulose (% total sugar) |
|---|---|---|---|
| 902435 ER | 14.28 | 18.03 | −32.31 |
| 902425 (plastid) | 7.24 | 9.26 | −16.50 |
| Negative control | 0.49 | −0.18 | −0.31 |

Total sugar = total amount of identifiable sugars in sample based on retention times of pure sugar standards. Extraneous peaks in samples are indeterminate and not included in sample analysis. Negative control is maize callus transformed with a vector that contains the PMI selectable marker only.

7C: Transgenic Sugarcane Callus Expressing alpha-1,6-glucosidase

Transgenic sugarcane callus expressing an alpha-1,6-glucosidase enzyme was generated essentially as described in Example 3A; however, two polynucleotide sequences were bombarded at the same time. One of the polynucleotide sequences contained the selectable marker, PMI, which allows for selection of transgenic sugarcane cells by growth on mannose. The second polynucleotide sequence, 902425, contained a polynucleotide sequence encoding an alpha-1,6-glucosidase (SEQ ID NO: 56). The alpha-1,6-glucosidase was targeted to the chloroplast.

Sugarcane calli expressing the alpha-1,6-glucosidase were collected 1 callus per well in 96-well 2 mL plates (Whatman) containing one 3/16" chrome ball bearing per well. The plate was shaken at setting 9 for 2 min in a Kleco Titer plate/Microtube Grinding Mill creating a powder. Buffer (100 mM HEPES, 4 mM EDTA, 0.04% Tween-20, pH 7) was added to the powdered samples to give a thick slurry. Samples were incubated in a Glas-Col rotator at 80% speed for 30 min. Samples were transferred by wide-bore P200 pipet to a 96 well PCR at 100 uL per well and incubated at 60 degrees C. for 20 minutes. Extracts were centrifuged at 1770×g for 30 mins to pellet denatured proteins in samples. Equal volumes of clarified extract and 271 mM trehalulose/134 mM isomaltulose were combined and incubated at 60 degrees C. in BioRad Tetrad 2 thermocycler. Samples were collected at times 0 and 24 hours. Collected samples were incubated at 95 degrees C. for 5 minutes before freezing at −20 degrees C. Samples were analyzed by HPAE chromatography essentially as described in Example 1G. Table 19 demonstrates that sugarcane callus expresses an active alpha-1,6-glucosidase that also shows alpha-1,1-glucosidase activity.

TABLE 19

Carbohydrate analysis (HPAE chromatography) of products from transformed sugarcane callus tissue expressing an alpha-1,6-glucosidase enzyme. Enzyme activity is indicated by the change in abundance of each sugar as a percentage of the total sugars over a 24 hour period.

| Sample | Glucose (% total sugar) | Fructose (% total sugar) | Isomaltulose (% total sugar) | Trehalulose (% total sugar) |
|---|---|---|---|---|
| 902425 (plastid) | 8.98 | 9.59 | −6.86 | −9.60 |
| Negative control | 2.53 | 3.70 | −2.82 | −2.15 |

Total sugar = total amount of identifiable sugars in sample based on retention times of pure sugar standards. Extraneous peaks in samples are indeterminate and not included in sample analysis. Negative control is wildtype sugarcane callus.

7D: Transient Expression of alpha-1,1-glucosidase (SEQ ID NO: 27) Enzyme in Sugar Beet or Tobacco Leaves Tobacco and sugar beet leaves transiently expressing an alpha-1,1-glucosidase (SEQ ID NO: 27) enzyme were generated essentially as described in Example 3D. The vector for transient expression was 901612 or 902522 which are described in Example 12. The binary vector 901612 contains an expression cassette encoding an alpha-1,1-glucosidase (SEQ ID NO: 27) targeted to the chloroplast. The binary vector 902522 contains an expression cassette encoding an alpha-1,1-glucosidase (SEQ ID NO: 27) targeted to pass through the endoplasmic reticulum and accumulate in the apoplast. Infiltrated tobacco and sugar beet leaves were harvested, extracted and enzyme activity assayed essentially as described in Example 3G. The key enzyme, alpha-1,1-glucosidase, catalyzes the conversion of isomaltulose or trehalulose to the fermentable sugars fructose and glucose and was assayed at 70 degrees C. Carbohydrate analysis of the final filtrate was performed using the Dionex system essentially as described in Example 1G. Tables 20-21 outline data demonstrating transient expression of an alpha-1,1-glucosidase in tobacco and sugar beet leaves.

TABLE 20

HPAEC analysis of carbohydrate products from tobacco leaves transiently expressing an alpha-1,1-glucosidase enzyme. Enzyme activity is indicated by the change in abundance of each sugar as a percentage of the total sugars over a 24 hour period.

| Sample | Glucose (% total sugar) | Fructose (% total sugar) | Trehalulose (% total sugar) | Isomaltulose (% total sugar) |
|---|---|---|---|---|
| 901612 | 21.61 | 23.38 | −22.57 | −22.41 |
| Negative control | 1.47 | 1.55 | 1.93 | −4.95 |

Total sugar = total amount of identifiable sugars in sample based on retention times of pure sugar standards. Extraneous peaks in samples are indeterminate and not included in sample analysis. The negative control is tobacco leaves transiently expressing empty binary vector.

TABLE 21

HPAEC analysis of carbohydrate products from sugar beet leaves transiently expressing alpha-1,1-glucosidase enzymes. Enzyme activity is indicated by the change in abundance of each sugar as a percentage of the total sugars over a 24 hour period.

| sample | Glucose (% total sugar) | Fructose (% total sugar) | Trehalulose (% total sugar) |
|---|---|---|---|
| 901612 chloroplast | 12.48 | 13.70 | −13.59 |
| 902522 apoplast | 18.73 | 19.51 | −22.46 |
| Negative control | 6.94 | 7.45 | −5.49 |

Total sugar = total amount of identifiable sugars in sample based on retention times of pure sugar standards. Extraneous peaks in samples are indeterminate and not included in sample analysis. The negative control is sugar beet leaves transiently expressing empty binary vector 7E: Transgenic Maize Callus Expressing alpha-1,1-glucosidase Transgenic maize callus expressing alpha-1,1-glucosidase enzyme was generated by bombarding maize embryos with two binary vectors. The method of embryo transformation and generation of callus was essentially as described in Example 3F; however, two polynucleotide sequences were bombarded at the same time. One of the polynucleotide sequences contained the selectable marker, PMI, which allows for selection of transgenic maize cells by growth on mannose. The second polynucleotide sequence, 902429, contained a maize optimized polynucleotide sequence encoding an alpha-1,1-glucosidase (SEQ ID NO: 49). The alpha-1,1-glucosidase was targeted to be retained by the endoplasmic reticulum.

Maize calli expressing the alpha-1,1-glucosidase was collected 1 callus per well in 96-well 2 mL plates (Whatman) containing one 3/16" chrome ball bearing per well. The plate was shaken at setting 9 for 2 min in a Kleco Titer plate/Microtube Grinding Mill. Sets of 4 pulverized callus tissue samples were combined and transferred to microfuge tubes. The samples were centrifuged at 20,000×g 30 minutes at 4 degrees C. The supernatants containing protein extract were transferred to new tubes and extracts with volumes <20 uL were pooled such that all samples were >30 uL in volume. Equal volume of extract and reaction buffer (~185 mM trehalulose, 93 mM isomaltulose, 100 mM HEPES, 0.04% Tween-20, 4 mM EDTA, 40 mM NaOH, Roche protease inhibitors) were combined and incubated at 70 degrees C. in BioRad Tetrad 2 thermocycler. Samples were collected at times 0 and 24 hours. Collected samples were incubated at 95 degrees C. for 5 minutes before freezing at −20 degrees C. Samples were analyzed by Dionex essentially as described in Example 1G. Table 22 demonstrates that maize callus expresses an active alpha-1,1-glucosidase.

TABLE 22

HPAEC analysis of carbohydrate products from transformed maize callus tissue expressing an alpha-1,1-glucosidase enzyme. Enzyme activity is indicated by the change in abundance of each sugar as a percentage of the total sugars over a 24 hour period.

| Sample | Glucose (% total sugar) | Fructose (% total sugar) | Trehalulose (% total sugar) |
|---|---|---|---|
| 902429 | 10.02 | 11.32 | −6.47 |
| Negative control | 3.51 | 3.46 | 1.50 |

Total sugar = total amount of identifiable sugars in sample based on retention times of pure sugar standards. Extraneous peaks in samples are indeterminate and not included in sample analysis. The negative control was transgenic maize callus generated by transformation with the binary vector expressing the selectable marker (PMI) only.

7F: Transient Expression of alpha-1,5-glucosidase by Tobacco Leaves

Tobacco leaves transiently expressing an alpha-1,5-glucosidase (SEQ ID NO: 46) enzyme were generated essentially as described in Example 3D. The vector for transient expression was BCTV binary vector 902550 which is described in Example 12. BCTV binary vector 902550 contains an expression cassette encoding an alpha-1,5-glucosidase (SEQ ID NO: 46) which is targeted to the chloroplast. Infiltrated tobacco and sugar beet leaves were harvested, extracted and enzyme activity assayed essentially as described in Example 3G. The key enzyme, alpha-1,5-glucosidase, catalyzes the conversion of leucrose to the fermentable sugars glucose and fructose and was assayed at 80 degrees C. Table 23 outlines data demonstrating tobacco leaves transiently expressed the alpha-1,5-glucosidase enzyme.

TABLE 23

HPAEC analysis of carbohydrate products from tobacco leaves transiently expressing an alpha-1,5-glucosidase enzyme. Enzyme activity is indicated by the change in abundance of each sugar as a percentage of the total sugars over a 24 hour period.

| sample | Glucose (% total sugar) | Fructose (% total sugar) | Leucrose (% total sugar) |
|---|---|---|---|
| 902550 | 18.07 | 20.36 | −38.43 |
| Negative control | 3.30 | 1.50 | −4.80 |

Total sugar = total amount of identifiable sugars in sample based on retention times of pure sugar standards. Extraneous peaks in samples are indeterminate and not included in sample analysis. The negative control is tobacco leaves transiently expressing empty BCTV vector.

7G: Transgenic Maize Callus Expressing alpha-1,5-glucosidase (SEQ ID NO: 43)

Transgenic maize callus expressing alpha-1,5-glucosidase enzyme was generated by bombarding maize embryos with two binary vectors. The method of embryo transformation and generation of callus was essentially as described in Example 3F; however, two polynucleotide sequences were bombarded at the same time. One of the polynucleotide sequences contained the selectable marker, PMI, which allows for selection of transgenic maize cells by growth on mannose. The second polynucleotide sequence, 902423, contained a maize optimized polynucleotide sequence encoding an alpha-1,5-glucosidase (SEQ ID NO: 43). The alpha-1,5-glucosidase was targeted to the chloroplast.

Maize calli expressing an alpha-1,5-glucosidase (SEQ ID NO: 43) was collected 1 callus per well in 96-well 2 mL plates (Whatman) containing one 3/16" chrome ball bearing per well. Samples were frozen at −80 degrees C. The frozen material was shaken at setting 9 for 4 min in a Kleco Titer plate/Microtube Grinding Mill. 200 uL of extraction buffer (100 mM HEPES, 4 mM EDTA, 0.04% Tween-20, pH 7) was added to each sample. Extracts were incubated in a Glas-Col rotator at 80% speed for 10 min. Extract was centrifuged at 1770×g for 10 minutes at 4 degrees C. in Eppendorf 5810R swing bucket centrifuge. Extract was frozen at −80 degrees C. Extract was later thawed and transferred to a 96-well PCR plate (Thermo Sci). Samples were heated at 80 degrees C. for 15 minutes in BioRad Tetrad 2 thermocycler. Plates were again centrifuged at 1770×g for 10 minutes at 4 degrees C. in Eppendorf 5810R swing bucket centrifuge. Supernatants were filtered using a Millipore Multiscreen-HV filter plate. Filtered extracts of 8 callus samples were combined. Combined samples were concentrated from ~1.6 mL to 100-500 uL using Microcon concentrators with MWCO 3 k membrane filters (Amicon). An equal volume of 200 mM leucrose and extract was added to 96-well PCR plate and incubated at 80 degrees C. in the thermocycler. Samples were collected at times 0 and 24 hours. Collected samples were incubated at 95 degrees C. 5 minutes before freezing at −20 degrees C. Samples were analyzed by Dionex essentially as described in Example 1G. Alpha-1,5-glucosidase activity was confirmed by measuring the conversion of the locked sugar, leucrose, to the fermentable sugars glucose and fructose. Table 24 demonstrates that maize callus expressed an active alpha-1,5-glucosidase enzyme.

TABLE 24

HPAEC analysis of carbohydrate products from transformed maize callus tissue expressing an alpha-1,5-glucosidase enzyme. Enzyme activity is indicated by the change in abundance of each sugar as a percentage of the total sugars over a 24 hour period.

| sample | Glucose (% total sugar) | Fructose (% total sugar) | Leucrose (% total sugar) |
|---|---|---|---|
| 902423 | 6.86 | 12.71 | −19.57 |
| Negative control | 0.48 | 0.73 | −1.21 |

Total sugar = total amount of identifiable sugars in sample based on retention times of pure sugar standards. Extraneous peaks in samples are indeterminate and not included in sample analysis. Negative control consisted of maize callus transformed with the binary vector containing the selectable marker (PMI) only.

EXAMPLE 8

Combining Plant Expressed Locking and Key Enzymes

Tobacco leaves transiently expressing enzymes were generated essentially as described in Example 3D. Leaves were generated by transiently expressing two binary vectors simultaneously. One of the binary vectors was 17588 (described in Example 12) which contains a polynucleotide sequence encoding a sucrose isomerase (SEQ ID NO: 16). The second binary vector was 902526 (described in Example 12) which contains a polynucleotide sequence encoding an alpha-1,6-glucosidase (SEQ ID NO: 11). Both binary vectors were infiltrated into the same tobacco leaf.

Essentially as described in Example 3D, whole leaves from tobacco were co-infiltrated with both binary vectors 17588 and 092526. Co-infiltration was performed essentially as described in Example 3D except that two strains of *Agrobacterium*, each containing one of the two vectors, were infiltrated into the tobacco leaf. Infiltrated leaves were collected and frozen at −80 degrees C. in 24-well blocks containing 3/16" chrome ball bearings. The frozen material was shaken at setting 9 for 2 min in a Kleco Titer Plate/Microtube Grinding Mill creating a powder. Powder samples were transferred to 30 mL centrifuge tubes and centrifuged at 20,000×g for 20 minutes at 4 degrees C. The supernatants were transferred to new tubes and adjusted to 50 mM HEPES, 0.02% Tween-20, 2 mM EDTA and 20 mM NaOH resulting in a mixture with pH between 7 and 8. Samples were then transferred to PCR tubes and incubated at 60 degrees C. in a Biorad Tetrad 2 thermocycler. Samples were collected from the thermocycler at times 0, 18, and 48 hours and heated at 95 degrees C. before freezing at −20 degrees C. The sugar contents of the samples thawed after the −20 degree C. freeze were analyzed by Dionex.

Table 25 demonstrates that plants transiently expressing both sucrose isomerase and alpha-1,6-glucosidase expressed an active sucrose isomerase. Sucrose isomerase activity was demonstrated by the accumulation of trehalulose and isomaltulose in both the negative control (17588) and the sample (17588 and 902526). It is noted that the sample (17588 and 902526) accumulated less trehalulose and isomaltulose than the negative control (17588). While not to be limited by theory, this observation suggests that the alpha-1,6-glucosidase enzyme is active in the sample (17588 and 902526) and thus leads to the conversion of the trehalulose and isomaltulose to fermentable sugars.

Tables 25-26 demonstrate that plants transiently expressing both sucrose isomerase and alpha-1,6-glucosidase expressed active enzymes. Alpha-1,6-glucosidase activity was demonstrated by comparing time 0 samples with samples collected at 48 hours which demonstrated the conversion of the locked sugars, trehalulose and isomaltulose, to the fermentable sugars, glucose and fructose.

Data outlined in Table 25-26 demonstrates the co-expression of a locking enzyme (sucrose isomerase) and an key enzyme (alpha-1,6-glucosidase) in a plant.

TABLE 25

HPAEC analysis of carbohydrate products from tobacco leaves transiently expressing both sucrose isomerase and an alpha-1,6-glucosidase enzyme. Accumulation of sucrose isomers in a plant co-expressing both lock and key enzymes before incubating for key activity. (*T. ethanolicus*)

| sample | Glucose + Fructose % total sugar | Sucrose % total sugar | Trehalulose % total sugar | Isomaltulose % total sugar |
|---|---|---|---|---|
| 17588 and 902526 | 75.88 | 0 | 15.91 | 8.21 |
| Negative control | 80.99 | 19.01 | 0 | 0 |

Total sugar = total amount of identifiable sugars in sample based on retention times of pure sugar standards. Extraneous peaks in samples are indeterminate and not included in sample analysis. Negative control consisted of non-infiltrated tobacco leaves.

TABLE 26

HPAEC analysis of carbohydrate products from tobacco leaves transiently expressing both sucrose isomerase and an alpha-1,6-glucosidase enzyme. Table 254 convers hydrolysis of the lock sugars by key activity after incubation. Enzyme activity is indicated by the change in abundance of each sugar as a percentage of the total sugars over a 24 hour period.

| sample | Glucose (% total sugar) | Fructose (% total sugar) | Isomaltulose (% total sugar) | Trehalulose (% total sugar) |
|---|---|---|---|---|
| 17588 and 902526 | 0.15 | 10.34 | −4.20 | −6.30 |
| Negative control | −8.18 | 3.58 | 1.19 | 3.41 |

Total sugar = total amount of identifiable sugars in sample based on retention times of pure sugar standards. Extraneous peaks in samples are indeterminate and not included in sample analysis. Negative control consisted tobacco leaves transiently expressing sucrose isomerase and an empty control vector.

EXAMPLE 9

Production of Fermentable Sugars and/or Ethanol

9A: Glucose Production Using Both Dextransucrase and Dextranase

Dextransucrase and dextranase form a pair of enzymes that are a lock and key combination. The dextransucrase catalyzes the formation of dextrans which are a locked form of sugar or carbohydrate. The dextranase is a key enzyme which can be used to convert the dextran back to a fermentable form of sugar.

The dextransucrase is expressed in transgenic sugarcane plants such that dextrans accumulate in the sugarcane plant. Dextrans produced from dextransucrase reactions in sugarcane juice (Example 1C) or dextrans produced by transgenic plants expressing dextransucrases (Example 3B) are harvested. These dextrans are used as substrate for dextranase activity assays to demonstrate the ability of the selected dextranases to convert the dextrans back into glucose, maltose and other small reducing sugars. The dextranase is provided as either transgenic plant produced enzyme (Example 3C) or as microbially produced enzyme (Example 2C).

9B: Isomaltulose Fermented to Produce Ethanol

Yeast, *Saccharomyces cerevisiae*, strains were screened for the ability to ferment isomaltulose into ethanol. Strains were grown in a media containing 10 g yeast extract, and 20 g peptone per liter of media. This media was supplemented with glucose or isomaltulose to the appropriate final concentration.

Single yeast colonies were inoculated into 5 mL 2% glucose media and incubated for 24 hours at 30 degrees C. cells were centrifuged at 3000×g for 5 minutes, supernatant was discarded, cells were washed by resuspending the cells in 5 mLs of distilled water, washed cells were centrifuged at 3000×g for 5 minutes, supernatant was discarded, cells were resuspend in 5 mLs of yeast media containing 1% isomaltulose media and incubated for 12 hours at 30 degrees C. After 12 hours cells were centrifuged at 3000×g for 5 minutes, supernatant was discarded, cells were washed by resuspending in 5 mLs of distilled water, washed cells were centrifuged at 3000×g for 5 minutes, supernatant was discarded, cells were resuspend in 5 mLs of 4% isomaltulose media or 4% glucose media for fermentation. Samples for ethanol and sugar analysis were removed every hour for six hours and stored at −20 degrees C. After all samples were collected they were thawed and filtered in 0.45 Micron nylon SpinX columns by centrifugation at 7000 rpm for 5 minutes. Filtered solution was then subjected to HPLC to determine the concentration of ethanol and the sugar composition of the solution which is shown in table 27. The graph below outlines the ethanol produced by various yeast strains grown in the presence of glucose or isomaltulose over time.

TABLE 27

Ethanol yield from yeast strains grown with isomaltulose or glucose

| Yeast Strain | Sugar | Percentage Ethanol Yield | Percentage of Theoretical Yield |
|---|---|---|---|
| B | Glucose | 2.1 | 80.1 |
| B | Isomaltulose | 1.49 | 57.4 |
| C | Glucose | 2.14 | 82.0 |
| C | Isomaltulose | 0.35 | 13.6 |
| A | Glucose | 1.9 | 72.4 |
| A | Isomatlulose | 0 | |

EXAMPLE 10

Transfer of Ethanol Producing Genes Between Yeast Strains

Not all yeast strains, including commercial yeast strains used in the ethanol industry, possess the capacity for isomaltulose fermentation. Genes needed for isomaltulose fermentation can be introduced into commercial strains by mating, mutagenesis or transformation. These genes may include an alpha glucosidase enzyme in addition to a receptor which senses the presence of isomaltulose and induces the expression of an alpha-glucoside transporter which transports isomaltulose and other alpha glucosides into the cell. Genes involved with these functions occur at the melezitose locus in *S. cerevisiae* and may be introduced into other strains of yeast by mating techniques known to skilled practitioners in the art (Hwang & Lindegren Nature vol 203 no 4946, pp 791-792 (1964)). Alternatively, the coding sequence of a highly efficient alpha-1,6-glucosidase enzyme may be introduced into yeast in place of the alpha glucosidase gene at the melezitose locus by homologous recombination or they may be inserted elsewhere in the genome. By replacing the endogenous alpha-glucosidase gene with a gene that more efficiently hydrolyzes isomaltulose or other locked sugars it may be possible to improve the rate of fermentation of these sugars. Similarly, genes for alpha-glucoside transporters and receptors may be overexpressed or altered by site directed mutagenesis in order to increase the rate of isomaltulose uptake by yeast strains to improve the efficiency of isomaltulose fermentation. Another approach may be to identify strains which constitutively express the genes necessary for isomaltulose fermentation or to mutagenize or engineer yeast strains so that they constitutively express the genes necessary for isomaltulose fermentation. The techniques necessary for these approaches are widely known to skilled practitioners of the art.

10A: Transgenic Yeast Expressing Key Enzymes

A yeast codon optimized gene for *Bacillus* SAM1606 (Sc_SAM1606) glucosidase (GeneBank Accession CAA54266) was cloned into the XhoI/XbaI sites of pGEM30 (ATCC 53345), which contains an N-terminus DEX4 secretion signal. This created a DEX4-Sc_SAM1606 glucosidase fusion protein.

The URA3 marker was replaced with the kanMX locus, which confers resistance to the antibiotic Geneticin (G418) (Wach et al. Yeast 10: 1793-1808 (1994)). The URA3 cassette was excised with SmaI and ClaI and the backbone was gel-purified. The kanMX cassette was amplified from a yeast insertional library (ATCC number GSA-7) using Phusion High Fidelity DNA polymerase (Finnzymes) with primers bearing 30 bp of homology to the ends of the SmaI/ClaI backbone fragment.

The SmaI/ClaI backbone fragment and the kanMX cassette were recombined using SLIC recombination (Li and Elledge, Nature Methods 4: 251-256 (2007)). Briefly, both fragments were treated with T4 DNA polymerase at room temperature to create single stranded DNA, the reaction was stopped after 15 minutes with dCTP, and the fragments were co-transformed into *E. coli* TOP10 competent cells (Invitrogen). Plasmids isolated from recombinant *E. coli* cells were sequenced and analyzed by restriction enzymes. The resulting vector was named pEB68.

A second yeast vector containing the *Bacillus thuringiensis* alpha-1,6-glucosidase gene was generated by cloning a yeast codon optimized polynucleotide sequence encoding the alpha-1,6-glucosidase into the pEB68 backbone by SLIC recombination to create pEB77.

An ‘empty-vector’ control consisting of the pEB68 backbone but lacking any gene behind the TP1 promoter was made by cutting pEB68 with XhoI/XbaI, purification of the backbone, blunting the ends, and self-ligation. This vector was named pEB70.

*Saccharomyces cerevisiae* strain X1049-9C (ATCC number 204802) was transformed with the vectors pEB68, pEB77, and pEB70. Yeast competent cells were made and transformed using the S. c. EasyComp™ Transformation kit (Invitrogen). Transformed yeast cells were recovered by holding them at 30 degreesC for 4-5 hours after transformation and then plated on YPD medium containing 200 ug/mL of G418.

Glucosidase enzyme activity associated with vector pEB69 was measured in transformed yeast cells by selected three yeast clones expressing DEX4-Sc_SAM1606 fusion protein and three untransformed yeast clones which were inoculated on 5 mL of YPD with G418 (untransformed yeast was inoculated in YPD without selection). After 24 hours of growth, cells were pelleted and the media was separated and used for enzyme analyses.

Sc-SAM1606 activity was measured at 70 degreesC for 16 hours by combining 10 uL of yeast media, 25 uL of buffer (100 mM Hepes, 4 mM EDTA, 0.04% Tween-20, pH 7.0), and 15 uL of a sugar solution containing 280 mM trehalulose, 100 mM isomaltulose, 70 mM citrate. Enzyme activity was estimated by measuring the amount of glucose released from the conversion of locked sugar (trehalulose and isomaltulose) to glucose using a GO-POD assay essentially as described in Example 2B. Table 27 outlines data demonstrating the transformed yeast expressed an active glucosidase enzyme.

Glucosidase enzyme activity associated with vector pEB77 was demonstrated by isolating two clones of each transformation (pEB77 and pEB70) and inoculated into medium containing 10 g yeast extract, 20 g peptone, 4 g isomaltulose, and 0.5% glucose per liter of medium. Cultures were grown until glucose was exhausted (24 hours). After 24 hours, the cells were spun and 1 mL of medium was saved for enzyme activity. To evaluate glucosidase activity on isomaltulose the following reaction was set up: 25 ul of 2× Buffer (100 mM Hepes pH: 7.0, 4 mM EDTA, 0.04% Tween-20, protease inhibitors), 10 ul isomaltulose (500 mM), and 15 ul medium obtained as described above. The 50 uL reaction was incubated overnight at 37 degrees C. 20 uL of the above reaction were added to 250 μL of Glucose oxidase reagent (GOPOD assay essentially as described in Example 2B) and incubated at 37 degrees C. for 10 minutes. The reactions consisted of three technical replicates. The glucose concentration measured was termed GlucoseA. To account for any glucose left in the medium after 24 hours of yeast growth, the same GOPOD assay was conducted by diluting 15 uL of medium with 35 uL of water (no isomaltulose) and using 20 uL of this dilution to the Glucose oxidase reagent. All the glucose measured this way is considered background noise and must come from the medium. This was termed GlucoseB.

The amount of glucose produced by hydrolysis of isomaltulose was calculated as GlucoseA minus GlucoseB and correspond to the values shown in Table 29.

TABLE 28

Glucose Conc of samples (mM): Transformed raw data from yeast expressing glucosidase using equation from glucose standard curve.

| | Sample # | | | | |
|---|---|---|---|---|---|
| Sample Replicate | pEB68 | pEB68 | pEB68 | pEB68 | Negative control |
| A | 4.74 | 7.19 | 4.21 | 4.73 | 1.49 |
| B | 4.81 | 3.86 | 4.26 | 4.59 | 1.65 |
| C | 4.83 | 4.50 | 4.47 | 4.90 | 1.63 |

EXAMPLE 11

Improvement of Molecules to Increase Activity, Thermostability, and Catalytic Efficiency and Product Specificity Improvement of sucrose isomerase enzymes can be achieved through rational design of the enzyme. For example, the product of the pall gene (GenBank accession number AY040843) contains a product specificity domain $^{325}$RLDRD$^{329}$ which influences the proportion of trehalulose or isomaltulose produced by the enzyme. By mutating these four charged amino acid residues (Arg325, Arg328, Asp327 and Asp329) trehalulose formation can be increased by 17-61% and formation of isomaltulose can be decreased by 26-67% (Zhang et al. FEBS Letters 534 (2003) 151-155). An aromatic clamp formed by Phe 256 and Phe280 has also been identified as important in substrate recognition and product specificity. (Ravaud et al. The Journal of Biological Chemistry VOL. 282, NO. 38, pp. 28126-28136, Sep. 21, 2007).

EXAMPLE 12

Constructs for Transient Expression

Table 1 outlines expression constructs used for generation of stable, transgenic plants as well as for the expression of enzymes transiently in plant tissues. The DNA sequences encoding proteins were codon optimized for the appropriate host; for example, expression constructs designed for tobacco and sugarbeet transient and stable transgenic plant expression were codon optimized for dicots while expression constructs designed for sugarcane or maize transient and stable transgenic plant expression were codon optimized for monocots. Codon optimization tables are available through commercial software applications such as Vector NTI 9.0.

Standard cloning techniques such as restriction enzyme digestion, gel electrophoresis and subsequence fragment purification, DNA ligation, bacterial cell transformation and selection, and the like were used to generate the vectors described in Table 29. Some of the components of the expression vectors described in Table 1 were synthesized by GeneArt (Germany), additionally, some of the vectors were cloned by GeneArt (Germany).

The binary vector 17588 contains an expression cassette with the following components operatively linked together in this order: the *Arabidopsis* ubiquitin promoter (SEQ ID NO: 7); GY1 ER targeting sequence (SEQ ID NO: 13), which targets the polypeptide encoded by the sucrose isomerase coding region through the endoplasmic reticulum; the sporamin vacuolar targeting sequence (SEQ ID NO 15) which directs the sucrose isomerase polypeptide from the endoplasmic reticulum to the vacuole; a dicot optimized polynucleotide sequence encoding a sucrose isomerase (SEQ ID NO: 16); and a NOS termination sequence.

The binary vector pEB47 contains an expression cassette with the following components operatively linked together in this order: an FMV enhancer (SEQ ID NO: 22); a 35S enhancer (SEQ ID NO: 23); a maize ubiquitin promoter (SEQ ID NO: 18); a maize gamm-zein ER targeting sequence (SEQ ID NO: 19) which directs the sucrose isomerase polypeptide to the ER; a sporamin vacuolar targeting sequence (SEQ ID NO: 15) which directs the sucrose isomerase polypeptide from the ER to the vacuole; a maize optimized polynucleotide sequence encoding a sucrose isomerase (SEQ ID NO: 24); a NOS terminator.

The vector pEB38 contains an expression cassette with the following components operatively linked together in this order: maize ubiquitin promoter (SEQ ID NO: 18); maize gamma zein signal sequence (SEQ ID NO: 19) which targets the polypeptide encoded by the sucrose isomerase polynucleotide sequence to the endoplasmic reticulum; sporamin vacuolar targeting sequence (SEQ ID NO: 15) which directs the polypeptide encoded by the sucrose isomerase polynucleotide sequence from the endoplasmic reticulum to the vacuole; monocot optimized polynucleotide sequence encoding sucrose isomerse (SEQ ID NO: 20); and the NOS terminator.

The binary vector 902525 contains an expression cassette with the following components operatively linked together in this order: *Arabidopsis* ubiquitin promoter (SEQ ID NO: 7); GY1 ER targeting sequence (SEQ ID NO: 13), which targets the polypeptide encoded by the sucrose isomerase coding region through the endoplasmic reticulum; dicot optimized polynucleotide sequence encoding sucrose isomerase polypeptide (SEQ ID NO: 11); NOS terminator. The sucrose isomerase enzyme expressed by this expression cassette is expected to accumulate in the apoplast of the transgenic plant cell comprising the expression cassette.

The BCTV binary vector 902526 contains an expression cassette with the following components operatively linked together in this order: *Agrobacterium* NOS promoter (SEQ ID NO: 10); GY1 ER targeting sequence (SEQ ID NO: 13), which targets the polypeptide encoded by the sucrose isomerase coding region through the endoplasmic reticulum; dicot optimized polynucleotide sequence encoding sucrose isomerase polypeptide (SEQ ID NO: 11); NOS terminator. The sucrose isomerase enzyme expressed by this expression cassette is expected to accumulate in the apoplast of the transgenic plant cell comprising the expression cassette.

The binary vector 901612 contains an expression cassette with the following components operatively linked together in this order: *Arabidopsis* ubiquitin promoter (SEQ ID NO: 7); FNR plastid targeting sequence (SEQ ID NO: 26) which directs the alpha-1,1-glucosidase polypeptide to the chloroplast; dicot optimized polynucleotide sequence encoding alpha-1,1-glucosidase (SEQ ID NO: 27); NOS terminator. The alpha-1,1-glucosidase enzyme expressed by this expression cassette is expected to accumulate in the chloroplast of the transgenic plant cell comprising the expression cassette.

The binary vector 902195 contains an expression cassette with the following components operatively linked together in this order: *Agrobacterium* NOS promoter (SEQ ID NO: 10); GY1 ER targeting sequence (SEQ ID NO: 13) which targets the dextransucrase polypeptide to the endoplasmic reticulum; sporamin vacuolar targeting sequence (SEQ ID NO: 15) which directs the polypeptide encoded by the dextransucrase polynucleotide sequence from the endoplasmic reticulum to the vacuole; dicot optimized polynucleotide sequence encoding a dextransucrase with leucrose synthase activity (SEQ ID NO: 35); NOS terminator.

The vector pEB28 contains an expression cassette with the following components operatively linked together in this order: maize ubiquitin promoter (SEQ ID NO: 18); maize gamma zein signal sequence (SEQ ID NO: 19) which targets the polypeptide encoded by the dextransucrase polynucleotide sequence to the endoplasmic reticulum; sporamin vacuolar targeting sequence (SEQ ID NO: 15) which directs the polypeptide encoded by the dextransucrase polynucleotide sequence from the endoplasmic reticulum to the vacuole; monocot optimized polynucleotide sequence encoding a dextransucrase with leucrose synthase activity (SEQ ID NO: 37); NOS terminator.

The binary vector 902550 contains an expression cassette with the following components operatively linked together in this order: *Arabidopsis* ubiquitin promoter (SEQ ID NO: 7); chloroplast targeting sequence (SEQ ID NO: 42); dicot optimized polynucleotide sequence encoding an alpha-1,5-glucosidase (SEQ ID NO: 46); NOS terminator.

The vector 902423 contains an expression cassette with the following components operatively linked together in this order: maize ubiquitin promoter (SEQ ID NO: 39); TMV enhancer (SEQ ID NO: 40); chloroplast targeting sequence (SEQ ID NO: 41) which directs the alpha-1,5-glucosidase polypeptide encoded by the polynucleotide sequence (SEQ ID NO: 43) to the chloroplast; maize optimized polynucleotide sequence encoding alpha-1,5-glucosidase (SEQ ID NO: 43); terminator from maize ubiquitin (SEQ ID NO: 45).

The binary vector 90522 contains an expression cassette with the following components operatively linked together in this order: *Arabidopsis* ubiquitin promoter (SEQ ID NO: 7); GY1 ER targeting sequence (SEQ ID NO: 13) which targets the alpha-1,1-glucosidase polypeptide to the endoplasmic reticulum; dicot optimized polynucleotide sequence encoding an alpha-1,1-glucosidase (SEQ ID NO: 52); NOS terminator. The expectation is that the alpha-1,1-glucosidase polypeptide will be processed through the endoplasmic reticulum and accumulate in the apoplast.

The vector 902435 contains an expression cassette with the following components operatively linked together in this order: maize ubiquitin promoter (SEQ ID NO: 29); TMV enhancer sequence (SEQ ID NO: 40); maize optimized polynucleotide sequence encoding an alpha-1,6-glucosidase (SEQ ID NO: 54); ER retention sequence (SEQ ID NO: 51); maize ubiquitin termination sequence (SEQ ID NO: 45).

The vector 902425 contains an expression, cassette with the following components operatively linked together in this order: maize ubiquitin promoter (SEQ ID NO: 29); TMV enhancer sequence (SEQ ID NO: 40); chloroplast targeting sequence (SEQ ID NO: 26); monocot optimized polynucleotide sequence encoding an alpha-1,6-glucosidase (SEQ ID NO: 56); maize ubiquitin termination sequence (SEQ ID NO: 45).

TABLE 29

Expression constructs

| Vector number | Promoter | Regulatory elements | Enzyme | crop |
|---|---|---|---|---|
| 17588 (binary vector) | *Arabidopsis* ubiquitin promoter (SEQ ID NO: 7) | GY1 ER targeting sequence (SEQ ID NO: 13); sporamin vacuolar targeting sequence (SEQ ID NO: 15) | Sucrose isomerase (SEQ ID NO: 16) | Sugar beet and tobacco |
| pEB47 (binary vector) | maize ubiquitin promoter (SEQ ID NO: 18) | FMV enhancer (SEQ ID NO: 22); 35S enhancer (SEQ ID NO: 23); Maize ? gamma zein ER targeting sequence (SEQ ID NO: 19); sporamin vacuolar targeting sequence (SEQ ID NO: 15) | Sucrose isomerase (SEQ ID NO: 24) | Maize and sugarcane |
| pEB38 | maize ubiquitin promoter (SEQ ID NO: 18) | Maize gamma zein ER targeting sequence (SEQ ID NO: 19); sporamin vacuolar targeting sequence (SEQ ID NO: 15) | Sucrose isomerase (SEQ ID NO: 20) | Maize and sugarcane |
| 902525 binary | *Arabidopsis* ubiquitin promoter (SEQ ID NO: 7) | GY1 ER targeting sequence (SEQ ID NO: 13) | *T. ethanolicus* alpha-1,6-glucosidase (SEQ ID NO: 11) | Sugar beet and tobacco |
| 902526 (BCTV binary) | NOS promoter (SEQ ID NO: 10) | GY1 ER targeting sequence (SEQ ID NO: 13) | *T. ethanolicus* alpha-1,6-glucosidase (SEQ ID NO: 11) | Sugar beet and tobacco |
| 902195 | NOS promoter (SEQ ID NO: 10) | GY1 ER targeting sequence (SEQ ID NO: 13); sporamin vacuolar targeting sequence (SEQ ID NO: 15) | Dextransucrase (SEQ ID NO: 35) | Tobacco and sugarbeet |
| pEB28 | maize ubiquitin promoter (SEQ ID NO: 18) | Maize gamma zein ER targeting sequence (SEQ ID NO: 19); sporamin vacuolar targeting sequence (SEQ ID NO: 15) | Dextransucrase (SEQ ID NO: 37) | Maize and sugarcane |
| 902435 | maize ubiquitin promoter (SEQ ID NO: 39) | ER retention sequence (51); maize ubiquitin terminator (SEQ ID NO: 45); TMV enhancer (SEQ ID NO: 40) | Alpha-1,6-glucosidase (SEQ ID NO: 54) | Maize and sugarcane |
| 902425 | maize ubiquitin promoter (SEQ ID NO: 39) | TMV enhancer (SEQ ID NO: 40); FNR chloroplast targeting sequence (SEQ ID NO: 41); maize ubiquitin terminator (SEQ ID NO: 45) | Alpha-1,6-glucosidase (SEQ ID NO: 56) | Maize and sugarcane |

TABLE 29-continued

| Expression constructs | | | | |
|---|---|---|---|---|
| Vector number | Promoter | Regulatory elements | Enzyme | crop |
| 901612 | *Arabidopsis* ubiquitin promoter (SEQ ID NO: 7) | Plastid targeting sequence FNR (SEQ ID NO: 26) | *Bacillus* alpha-1,1-glucosidase (SEQ ID NO: 27) | Sugar beet and tobacco |
| 902522 | *Arabidopsis* ubiquitin promoter (SEQ ID NO: 7) | GY1 ER targeting sequence (SEQ ID NO: 13) | Alpha-1,1-glucosidase (SEQ ID NO: 52) | Sugar beet and tobacco |
| 902429 | maize ubiquitin promoter (SEQ ID NO: 39) | TMV enhancer (SEQ ID NO: 40); ER targeting sequence (SEQ ID NO: 48); ER retention sequence (51); maize ubiquitin terminator (SEQ ID NO: 45) | Alpha-1,1-glucosidase (SEQ ID NO: 49) | Maize and sugarcane |
| 902550 | *Arabidopsis* ubiquitin promoter (SEQ ID NO: 7) | Plastid targeting sequence FNR (SEQ ID NO: 26) | Alpha-1,5-glucosidase (SEQ ID NO: 46) | Sugarbeet and tobacco |
| 902423 | maize ubiquitin promoter (SEQ ID NO: 39) | TMV enhancer (SEQ ID NO: 40); FNR chloroplast targeting sequence (SEQ ID NO: 41); maize ubiquitin terminator (SEQ ID NO: 45) | Alpha-1,5-glucosidase (SEQ ID NO: 43) | Maize and sugarcane |

The following embodiments are encompassed by the present invention:

1. A method for producing fermentable sugar comprising:
   a) providing transgenic plant material comprising one or more locked carbohydrates; and
   b) contacting said transgenic plant material with one or more key enzymes wherein said contacting is under conditions sufficient for conversion of said locked carbohydrate to fermentable sugar.

2. The method of claim 1, wherein the one or more locked carbohydrate is selected from the group consisting of isomaltulose, trehalulose, leucrose, starch, dextrans, fructans, maltulose, turanose and isomaltose.

3. The method of claim 1, wherein the one or more key enzyme is selected from the group consisting of dextranase, alpha-amylase, glucoamylase, alpha-1,5-glucosidase, alpha-1,1-glucosidase and alpha-1,6-glucosidase.

4. The method of claim 1, wherein the one or more key enzyme is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

5. The method of claim 1, wherein the transgenic plant is selected from the group consisting of maize, sugar beet, sorghum and sugarcane.

6. A method for producing fermentable sugar comprising:
   a) providing transgenic plant material comprising one or more lock enzymes and one or more locked carbohydrates; and
   b) contacting said transgenic plant material with one or more key enzymes wherein said contacting is under conditions sufficient for conversion of said locked carbohydrate to fermentable sugar.

7. The method of claim 6, wherein the one or more locked carbohydrate is selected from the group consisting of isomaltulose, trehalulose, leucrose, starch, dextran, fructan, maltulose, turanose and isomaltose.

8. The method of claim 6, wherein the one or more lock enzymes is selected from the group consisting of dextransucrase, levan sucrose, alternansucrase, sucrose isomerase and amylosucrase.

9. The method of claim 6, wherein the one or more key enzymes is selected from the group consisting of dextranase, alpha-amylase, glucoamylase, alpha-1,5-glucosidase, alpha-1,1-glucosidase and alpha-1,6-glucosidase.

10. The method of claim 6, wherein the one or more key enzymes is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

11. The method of claim 6, wherein the transgenic plant is selected from the group consisting of maize, sugar beet, sorghum and sugarcane.

12. A method for producing alcohol comprising:
   a) providing transgenic plant material comprising one or more locked carbohydrates;
   b) contacting said transgenic plant material with one or more key enzymes wherein said contacting is under conditions sufficient for conversion of said one or more locked carbohydrates to fermentable sugar; and
   c) fermenting said fermentable sugar to form alcohol.

13. The method of claim 12, wherein the locked carbohydrate is selected from the group consisting of isomaltulose, trehalulose, leucrose, starch, dextran, fructan, maltulose, turanose and isomaltose.

14. The method of claim 12, wherein the one or more key enzyme is selected from the group consisting of dextranase, alpha-amylase, glucoamylase, alpha-1,5-glucosidase, alpha-1,1-glucosidase and alpha-1,6-glucosidase.

15. The method of claim 12, wherein the one or more key enzyme is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

16. The method of claim 12, wherein the alcohol is selected from the group consisting of ethanol and butanol.

17. The method of claim 12, wherein the transgenic plant is selected from the group consisting of maize, sugar beet, sorghum and sugarcane.

18. A method for producing alcohol comprising:

a) providing transgenic plant material comprising one or more lock enzymes and one or more locked carbohydrates;

b) contacting said transgenic plant material with one or more key enzymes wherein said contacting is under conditions sufficient for conversion of said one or more locked carbohydrates to fermentable sugar; and c) fermenting said fermentable sugar to form alcohol.

19. The method of claim 18, wherein the one or more locked carbohydrates is selected from the group consisting of isomaltulose, trehalulose, leucrose, starch, dextran, fructan, maltulose, turanose and isomaltose.

20. The method of claim 18, wherein the one or more lock enzymes is selected from the group consisting of dextransucrase, levan sucrose, alternansucrase, sucrose isomerase and amylosucrase.

21. The method of claim 18, wherein the one or more key enzymes is selected from the group consisting of dextranase, alpha-amylase, glucoamylase, alpha-1,5-glucosidase, alpha-1,1-glucosidase and alpha-1,6-glucosidase.

22. The method of claim 18, wherein the one or more key enzymes is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

23. The method of claim 18, wherein the alcohol is selected from the group consisting of ethanol and butanol.

24. The method of claim 18, wherein the transgenic plant is selected from the group consisting of maize, sugar beet, sorghum and sugarcane.

25. A method for producing fermentable sugar comprising:

a) providing transgenic plant material comprising one or more locked carbohydrates and one or more key enzymes; and b) processing said transgenic plant material under conditions sufficient for one or more key enzymes to convert one or more locked carbohydrates to fermentable sugar.

26. The method of claim 25, wherein the one or more key enzymes is targeted away from the one or more locked carbohydrates.

27. The method of claim 25, wherein the one or more key enzymes is targeted to an organelle selected from the group consisting of chloroplast, vacuole, cytoplasm, apoplast and endoplasmic reticulum.

28. The method of claim 25, wherein the one or more locked carbohydrates is selected from the group consisting of isomaltulose, trehalulose, leucrose, starch, dextran, fructan, maltulose, turanose and isomaltose.

29. The method of claim 25, wherein the one or more key enzymes is selected from the group consisting of dextranase, alpha-amylase, glucoamylase, alpha-1,5-glucosidase, alpha-1,1-glucosidase and alpha-1,6-glucosidase.

30. The method of claim 25, wherein the one or more key enzymes is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

31. The method of claim 25, wherein the transgenic plant is selected from the group consisting of maize, sugar beet, sorghum and sugarcane.

32. A method for producing fermentable sugar comprising:

a) providing transgenic plant material comprising one or more lock enzymes, one or more locked carbohydrates and one or more key enzymes; and b) processing said transgenic plant material under conditions sufficient for said one or more key enzymes to convert said one or more locked carbohydrates to fermentable sugar.

33. The method of claim 32, wherein the one or more lock enzymes is selected from the group consisting of dextransucrase, levan sucrose, alternansucrase, sucrose isomerase and amylosucrase.

34. The method of claim 32, wherein the one or more key enzymes is targeted away from the one or more locked carbohydrates.

35. The method of claim 32, wherein the one or more key enzymes is targeted to an organelle selected from the group consisting of chloroplast, vacuole, cytoplasm, apoplast and endoplasmic reticulum.

36. The method of claim 32, wherein the one or more locked carbohydrates is selected from the group consisting of isomaltulose, trehalulose, leucrose, starch, dextran, fructan, maltulose, turanose and isomaltose.

37. The method of claim 32, wherein the one or more key enzymes is selected from the group consisting of dextranase, alpha-amylase, glucoamylase, alpha-1,5-glucosidase, alpha-1,1-glucosidase and alpha-1,6-glucosidase.

38. The method of claim 32, wherein the one or more key enzymes is provided by a source selected from the group consisting of transgenic plant material expressing a key enzyme, recombinant microbe expressing a key enzyme, transgenic yeast expressing a key enzyme, microbe expressing a key enzyme and yeast expressing a key enzyme.

39. The method of claim 32, wherein the transgenic plant is selected from the group consisting of maize, sugar beet, sorghum and sugarcane.

40. A transgenic plant comprising one or more heterologous lock enzymes and one or more heterologous key enzymes.

41. The transgenic plant of claim 40, wherein the one or more lock enzymes is selected from the group consisting of dextransucrase, levan sucrose, alternansucrase, sucrose isomerase and amylosucrase.

42. The transgenic plant of claim 40, wherein the one or more key enzymes is targeted away from the locked carbohydrate.

43. The transgenic plant of claim 40, wherein the one or more key enzymes is targeted to an organelle selected from the group consisting of chloroplast, vacuole, cytoplasm, apoplast and endoplasmic reticulum.

44. The transgenic plant of claim 40, wherein the locked carbohydrate is selected from the group consisting of isomaltulose, trehalulose, leucrose, starch, dextran, fructan, maltose, turanose and isomaltose.

45. The transgenic plant of claim 40, wherein the one or more key enzyme is selected from the group consisting of dextranase, alpha-amylase, glucoamylase, alpha-1,5-glucosidase, alpha-1,1-glucosidase and alpha-1,6-glucosidase.

46. The transgenic plant of claim 40, wherein the transgenic plant is selected from the group consisting of maize, sugar beet, sorghum and sugarcane.

47. A transgenic plant comprising one or more locked carbohydrates and one or more key enzymes.

48. The transgenic plant of claim 47, wherein the one or more key enzymes is targeted away from the one or more locked carbohydrates.

49. The transgenic plant of claim 47, wherein the key enzyme is targeted to an organelle selected from the group consisting of chloroplast, vacuole, cytoplasm, apoplast and endoplasmic reticulum.

50. The transgenic plant of claim 47, wherein the one or more locked carbohydrates is selected from the group consisting of isomaltulose, trehalulose, leucrose, starch, dextran, fructan, maltose, turanose and isomaltose.

51. The transgenic plant of claim 47, wherein the one or more key enzyme is selected from the group consisting of dextranase, alpha-amylase, glucoamylase, alpha-1,5-glucosidase, alpha-1,1-glucosidase and alpha-1,6-glucosidase.

52. The transgenic plant of claim 47, wherein the transgenic plant is selected from the group consisting of maize, sugar beet, sorghum and sugarcane.

53. A method for producing fermentable sugar comprising:
  - a) providing transgenic plant material wherein said transgenic plant material is selected from the group consisting of sugar beet, sorghum, maize, and sugarcane, and wherein said transgenic plant material comprises:
    - i) one or more lock enzymes wherein said one or more lock enzymes is selected from the group consisting of dextransucrase, levan sucrose, alternansucrase, sucrose isomerase and amylosucrase,
    - ii) one or more locked carbohydrates wherein said one or more locked carbohydrates is selected from the group consisting of isomaltulose, trehalulose, leucrose, starch, dextrans, fructans, maltose, turanose and isomaltose,
    - iii) one or more key enzymes wherein said one or more key enzymes is selected from the group consisting of dextranase, alpha-amylase, glucoamylase, alpha-1,5-glucosidase, alpha-1,1-glucosidase and alpha-1,6-glucosidase; and wherein said one or more key enzymes is targeted away from said one or more locked carbohydrates; and
  - b) processing said transgenic plant material under conditions sufficient for said one or more key enzymes to convert said one or more locked carbohydrates to fermentable sugar.

54. A transgenic plant comprising:
  - a) one or more lock enzymes wherein said one or more lock enzymes is selected from the group consisting of dextransucrase, levan sucrose, alternansucrase, sucrose isomerase and amylosucrase,
  - b) one or more locked carbohydrates wherein said one or more locked carbohydrates is selected from the group consisting of isomaltulose, trehalulose, leucrose, starch, dextrans, fructans, maltose, turanose and isomaltose,
  - c) one or more key enzymes wherein said one or more key enzymes is selected from the group consisting of dextranase, alpha-amylase, glucoamylase, alpha-1,5-glucosidase, alpha-1,1-glucosidase and alpha-1,6-glucosidase; and wherein said one or more key enzymes is targeted away from the one or more locked carbohydrates, and
  - d) wherein said transgenic plant is selected from the group consisting of maize, sugar beet, sorghum and sugarcane.

55. A method for producing fermentable sugar derived from a plant comprising:
  - a) providing plant material comprising locked carbohydrate; and,
  - b) contacting said plant material with one or more enzymes capable of converting the locked carbohydrate into fermentable sugar (key enzyme), wherein said contacting is under conditions sufficient for said conversion.

56. The method of embodiment 55, wherein said plant material comprising locked carbohydrate is derived from a transgenic plant expressing one or more enzymes capable of converting an endogenous carbohydrate of said transgenic plant into said locked carbohydrate (lock enzyme).

57. The method of embodiment 55 or 56, wherein the key enzyme is provided as a purified or semi-purified enzyme preparation.

58. The method of embodiment 55 or 56, wherein at least one of the key enzymes is provided as plant material derived from a plant expressing said key enzyme.

59. The method of embodiment 58, wherein at least one of the key enzymes is expressed in the same plant as the plant comprising the locked carbohydrate.

60. The method of embodiment 55, wherein the locked carbohydrate is selected from the group consisting of isomaltulose, trehalulose, dextran, fructan, amylose, leucrose and alternan.

61. The method of embodiment 56, wherein the transgenic plant expresses at least two sucrose isomerase enzymes, wherein at least the first sucrose isomerase enzyme catalyzes the conversion of sucrose primarily into isomaltulose, and wherein at least the second sucrose isomerase enzyme catalyzes the conversion of sucrose primarily into trehalulose.

62. The method of embodiment 55, wherein said plant material comprising the locked carbohydrate is derived from a plant selected from the group consisting of maize, wheat, rice, barley, soybean, cotton, sorghum, oats, tobacco, *Miscanthus* grass, Switch grass, trees, beans, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

63. The method of embodiment 62, wherein said plant material comprising the locked carbohydrate is derived from sugarcane, sugar beet, or sweet sorghum.

64. The method of embodiment 55, wherein the key enzyme is derived from a microorganism.

65. The method of embodiment 64, wherein the key enzyme is endogenous to said microorganism.

66. The method of embodiment 64, wherein the key enzyme is a recombinant enzyme expressed in the microorganism.

67. The method of embodiment 65, wherein the microorganism is a *Saccharomyces* strain capable of fermenting isomaltulose.

68. A method of selecting a transformed plant comprising:
  - a) introducing into said plant or part thereof:
    - i) an expression cassette comprising a nucleotide sequence encoding an enzyme capable of converting an endogenous sugar in said plant to a locked carbohydrate; and,
    - ii) an expression cassette comprising a nucleotide sequence encoding an enzyme capable of converting the locked carbohydrate into a fermentable sugar;
  - b) maintaining said plant or part thereof under conditions sufficient for the expression of the lock enzyme and the key enzyme; and,
  - c) evaluating the sugar profile of said plant;

wherein the presence of one or more of the fermentable sugars produced by said key enzyme is indicative of a transformed plant.

69. A transgenic plant useful for the production of ethanol, wherein said plant comprises:
   a) a nucleotide sequence encoding an enzyme capable of converting an endogenous sugar in said plant to said locked carbohydrate; and,
   b) a nucleotide sequence encoding an enzyme capable of converting the locked carbohydrate into a fermentable sugar.

70. The plant of embodiment 69, wherein the locked carbohydrate is selected from the group consisting of isomaltulose, trehalulose, dextran, fructan, amylose, leucrose and alternan.

71. The plant of embodiment 70, wherein the transgenic plant expresses at least two sucrose isomerase enzymes, wherein at least the first sucrose isomerase enzyme catalyzes the conversion of sucrose primarily into isomaltulose, and wherein at least the second sucrose isomerase enzyme catalyzes the conversion of sucrose primarily into trehalulose.

72. The transgenic plant of embodiment 69 selected from the group consisting of maize, wheat, rice, barley, soybean, cotton, sorghum, oats, tobacco, *Miscanthus* grass, Switch grass, trees, beans, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

73. The plant of embodiment 62, wherein said plant is sugarcane, sugar beet, or sorghum.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method comprising the steps of:

a) providing transgenic plant material comprising one or more locked carbohydrates and one or more key enzymes, wherein the one or more key enzymes is targeted away from the one or more locked carbohydrates; and b) processing said transgenic plant material under conditions sufficient for one or more key enzymes to convert one or more locked carbohydrates to fermentable sugar.

2. The method of claim 1, wherein the one or more key enzymes is targeted to an organelle selected from the group consisting of chloroplast, vacuole, cytoplasm, apoplast and endoplasmic reticulum.

3. The method of claim 1, wherein the one or more locked carbohydrates is selected from the group consisting of isomaltulose, trehalulose, leucrose, starch, dextran, fructan, maltulose, turanose and isomaltose.

4. The method of claim 1, wherein the one or more key enzymes is selected from the group consisting of dextranase, alpha-amylase, glucoamylase, and alpha-1,6-glucosidase.

5. The method of claim 1, wherein the transgenic plant is selected from the group consisting of maize, sugar beet, sorghum and sugarcane.

6. A method comprising the steps of:

a) providing transgenic plant material comprising one or more lock enzymes, one or more locked carbohydrates and one or more key enzymes, wherein the one or more key enzymes is targeted away from the one or more locked carbohydrates; and b) processing said transgenic plant material under conditions sufficient for said one or more key enzymes to convert said one or more locked carbohydrates to fermentable sugar.

7. The method of claim 6, wherein the one or more lock enzymes is selected from the group consisting of dextransucrase, levan sucrase, alternansucrase, sucrose isomerase and amylosucrase.

8. The method of claim 6, wherein the one or more key enzymes is targeted to an organelle selected from the group consisting of chloroplast, vacuole, cytoplasm, apoplast and endoplasmic reticulum.

9. The method of claim 6, wherein the one or more locked carbohydrates is selected from the group consisting of isomaltulose, trehalulose, leucrose, starch, dextran, fructan, maltulose, turanose and isomaltose.

10. The method of claim 6, wherein the one or more key enzymes is selected from the group consisting of dextranase, alpha-amylase, glucoamylase, and alpha-1,6-glucosidase.

11. The method of claim 6, wherein the transgenic plant is selected from the group consisting of maize, sugar beet, sorghum and sugarcane.

12. A transgenic plant comprising one or more heterologous lock enzymes, one or more locked carbohydrates and one or more heterologous key enzymes, wherein the one or more key enzymes is targeted away from the locked carbohydrate.

13. The transgenic plant of claim 12, wherein the one or more lock enzymes is selected from the group consisting of dextransucrase, levan sucrase, alternansucrase, sucrose isomerase and amylosucrase.

14. The transgenic plant of claim 12, wherein the one or more key enzymes is targeted to an organelle selected from the group consisting of chloroplast, vacuole, cytoplasm, apoplast and endoplasmic reticulum.

15. The transgenic plant of claim 12, wherein the locked carbohydrate is selected from the group consisting of isomaltulose, trehalulose, leucrose, starch, dextran, fructan, maltose, turanose and isomaltose.

16. The transgenic plant of claim 12, wherein the one or more key enzyme is selected from the group consisting of dextranase, alpha-amylase, glucoamylase, and alpha-1,6-glucosidase.

17. The transgenic plant of claim 12, wherein the transgenic plant is selected from the group consisting of maize, sugar beet, sorghum and sugarcane.

18. A transgenic plant comprising one or more locked carbohydrates and one or more key enzymes, wherein the one or more key enzymes is targeted away from the one or more locked carbohydrates.

19. The transgenic plant of claim 18, wherein the key enzyme is targeted to an organelle selected from the group consisting of chloroplast, vacuole, cytoplasm, apoplast and endoplasmic reticulum.

20. The transgenic plant of claim 18, wherein the one or more locked carbohydrates is selected from the group consisting of isomaltulose, trehalulose, leucrose, starch, dextran, fructan, maltose, turanose and isomaltose.

21. The transgenic plant of claim 18, wherein the one or more key enzyme is selected from the group consisting of dextranase, alpha-amylase, glucoamylase, and alpha-1,6-glucosidase.

22. The transgenic plant of claim 18, wherein the transgenic plant is selected from the group consisting of maize, sugar beet, sorghum and sugarcane.

* * * * *